United States Patent
Saito et al.

(10) Patent No.: US 10,590,492 B2
(45) Date of Patent: *Mar. 17, 2020

(54) METHOD FOR DETERMINING DESIRED CELL TYPE USING EXPRESSION OF MIRNA AS INDICATOR

(71) Applicant: KYOTO UNIVERSITY, Kyoto (JP)

(72) Inventors: Hirohide Saito, Kyoto (JP); Kei Endo, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/110,503

(22) PCT Filed: Jan. 9, 2015

(86) PCT No.: PCT/JP2015/050467
§ 371 (c)(1),
(2) Date: Oct. 5, 2016

(87) PCT Pub. No.: WO2015/105172
PCT Pub. Date: Jul. 16, 2015

(65) Prior Publication Data
US 2017/0016077 A1    Jan. 19, 2017

(30) Foreign Application Priority Data
Jan. 10, 2014 (JP) ................................. 2014-003726

(51) Int. Cl.
*C12Q 1/6897* (2018.01)
*G01N 15/14* (2006.01)
*G01N 21/64* (2006.01)
*G01N 15/10* (2006.01)
*G01N 15/00* (2006.01)

(52) U.S. Cl.
CPC ....... *C12Q 1/6897* (2013.01); *G01N 15/1459* (2013.01); *G01N 21/6428* (2013.01); *G01N 21/6456* (2013.01); *C12Q 2600/178* (2013.01); *G01N 2015/0065* (2013.01); *G01N 2015/1006* (2013.01); *G01N 2015/1402* (2013.01); *G01N 2015/1477* (2013.01); *G01N 2021/6439* (2013.01)

(58) Field of Classification Search
CPC .............. C12Q 1/6897; G01N 21/6428; C12N 2310/141
See application file for complete search history.

(56) References Cited

U.S. PATENT DOCUMENTS

2005/0042641 A1 * 2/2005 Mittal ................ G01N 33/5023
435/6.11
2009/0286242 A1 11/2009 Hannon et al.
2010/0286044 A1 * 11/2010 Litman ................ C12Q 1/6813
514/9.7
2010/0317532 A1 * 12/2010 Liu ..................... C12N 15/1086
506/7
2010/0323356 A1 * 12/2010 Inoue .................... C12N 15/111
435/6.14

FOREIGN PATENT DOCUMENTS

| WO | WO2008/061537 A2 * | 5/2008 | |
| WO | WO-2009066758 A1 * | 5/2009 | ........... C12N 15/111 |
| WO | WO-2011154553 A2 * | 12/2011 | ........... C12N 15/113 |
| WO | WO 2013/027427 A1 | 2/2013 | |

OTHER PUBLICATIONS

Colin et al. GLIA 57:667-679, 2009.*
Diekmann et al. Stem Cell Rev and Rep 2013 9:555-568.*
Sachdeva et al. PNAS 107: 11602-11607, 2010.*
Warren et al. Cell Stem Cell 7: 618-630 (Year: 2010).*
Kato et al. The International Journal of Biochemsitry & Cell Biology 41, pp. 2225-2231 (Year: 2009).*
Extended European Search Report corresponding to European Patent Application No. 15735429.1 (7 pages) (dated Jul. 28, 2017).
Haas et al. "MicroRNA-mediated regulation of gene expression is affected by disease-associated SNPs within the 3'-UTR via altered RNA structure" *RNA Biology* 9(6):924-937 (2012).
Japanese Office Action corresponding to Japanese Patent Application No. JP2015-556843 dated Jan. 25, 2019, 10 pages with Machine Translation.
Chinese Office Action corresponding to Chinese Application No. CN201580013525.1, dated Sep. 25, 2019 (16 pages to include English translation).
Brown et al. "Endogenous microRNA can be broadly exploited to regulate transgene expression according to tissue, lineage and differentiation state" Nature Biotechnology, 25(12):1457-1467 (2007).
Papoutsidakis et al. "MicroRNAs and the Heart: Small Things Do Matter", *Current Topics in Medicinal Chemistry* 13:216-230 (2013).
Mizutani "MicroRNAs in a variety of life phenomena" *Fukuoka Acta Medica* 100(8):265-273 (2009).
Miki et al. "Efficient detection and purification of cells by synthetic microRNA switches", *Regenerative Medicine* 14:188 (2015).
International Search Report corresponding to International Application No. PCT/JP2015/050467 dated Apr. 14, 2015.

* cited by examiner

*Primary Examiner* — Brian Whiteman
(74) *Attorney, Agent, or Firm* — Myers Bigel, P.A.

(57) ABSTRACT

A method for distinguishing living cells in a living state with high accuracy. A method for distinguishing a desired cell type from a cell group comprising two or more types of cells, using the expression of miRNA as an indicator, wherein the method comprises the following steps:
(1) a step of introducing mRNA comprising a marker gene operably linked to the target sequence of miRNA used as an indicator into a cell group; and
(2) a step of distinguishing a cell type, using the translation level of the marker gene as an indicator.

24 Claims, 29 Drawing Sheets

Specification includes a Sequence Listing.

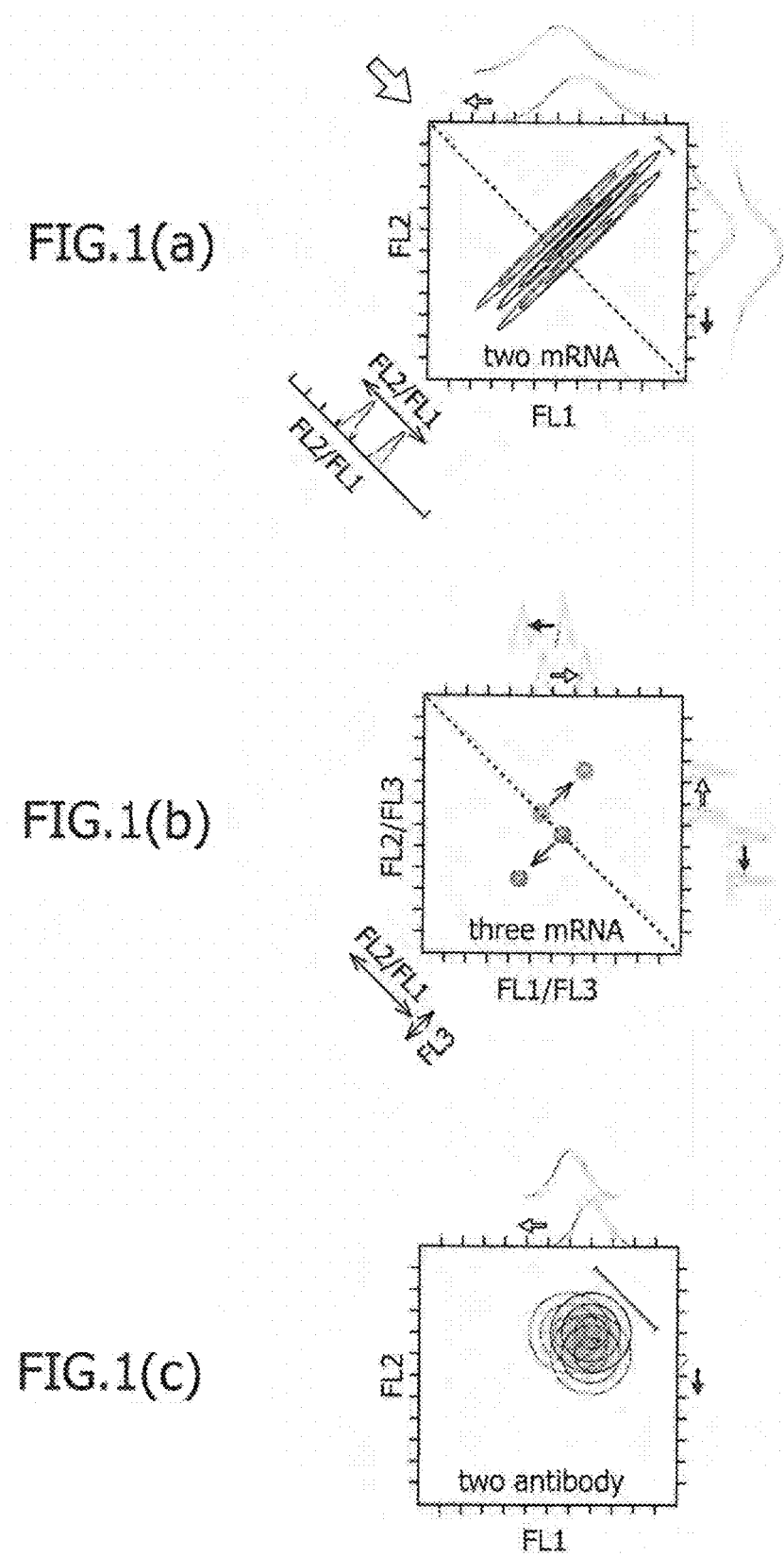

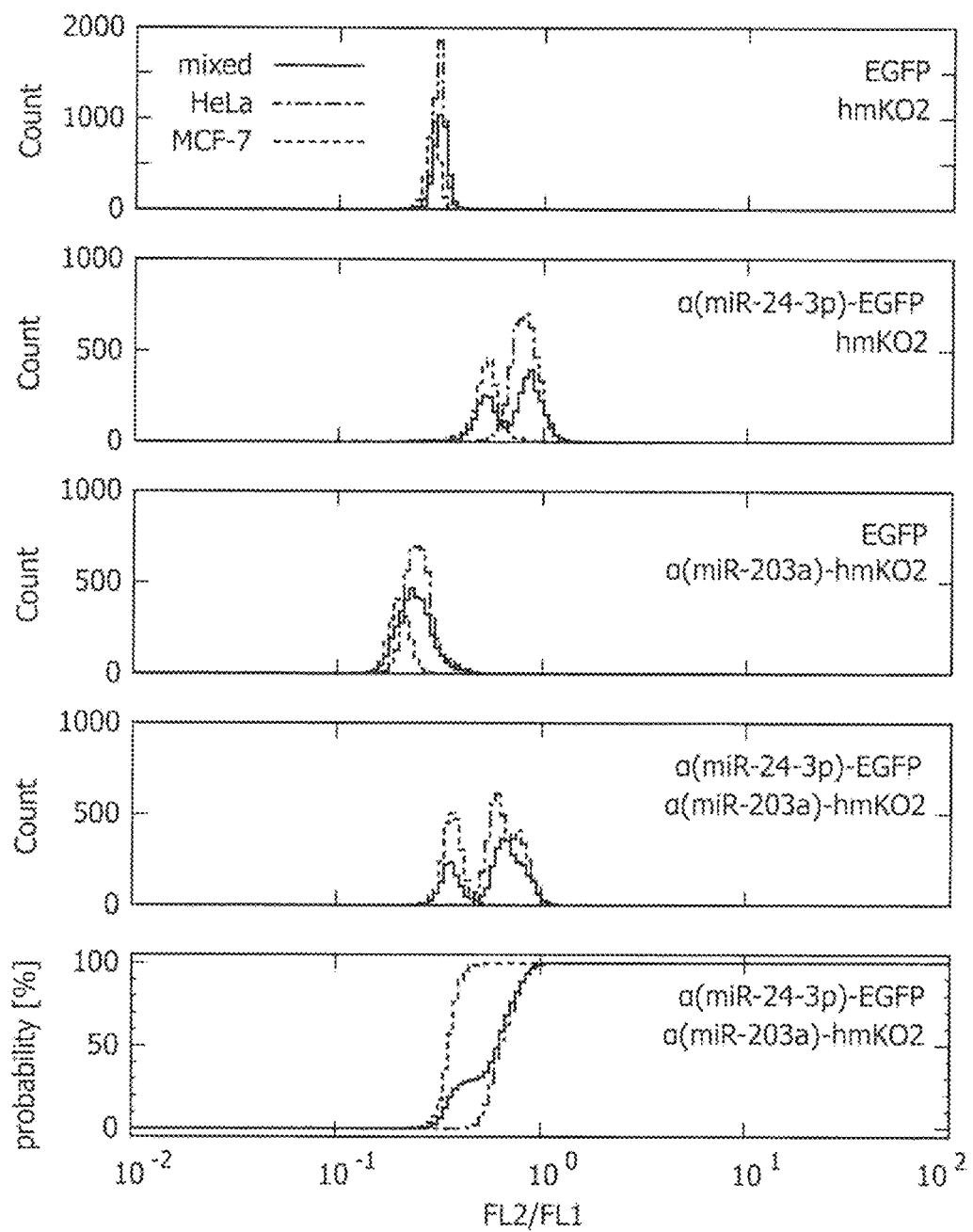

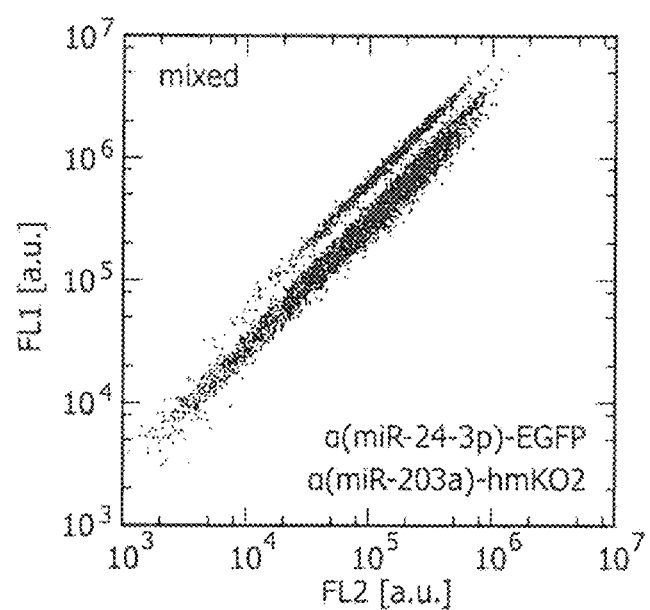

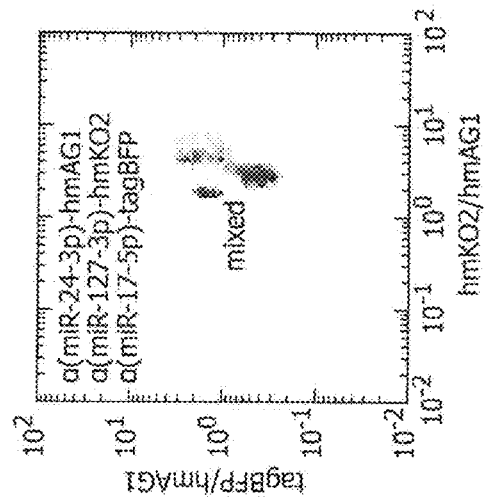
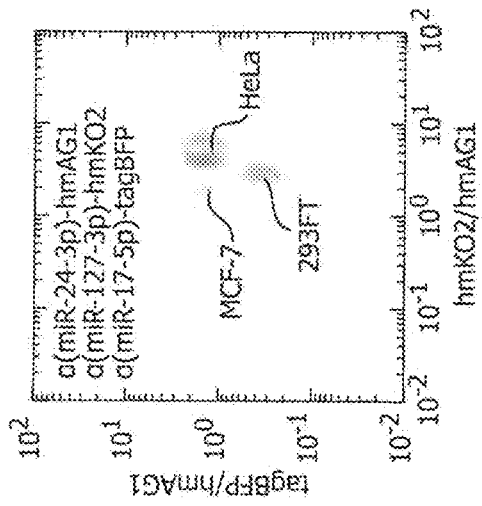
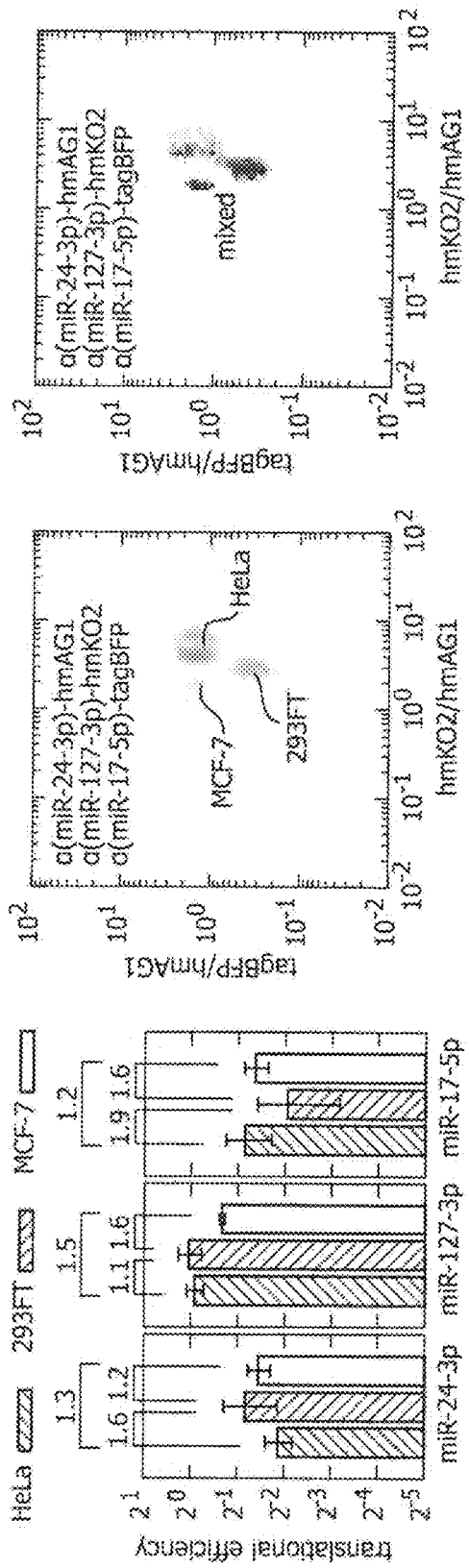
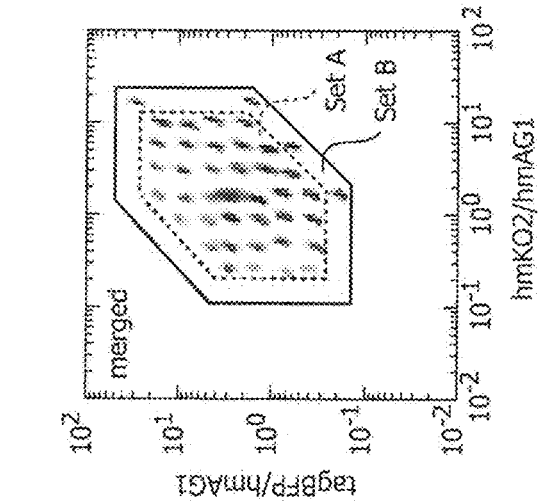
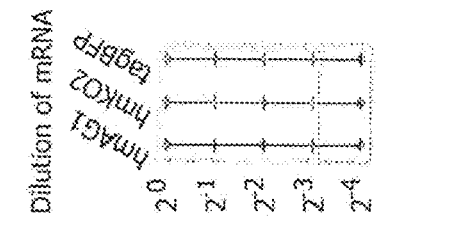
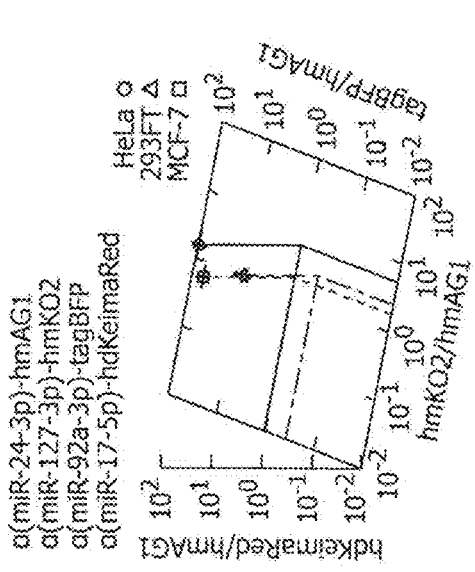

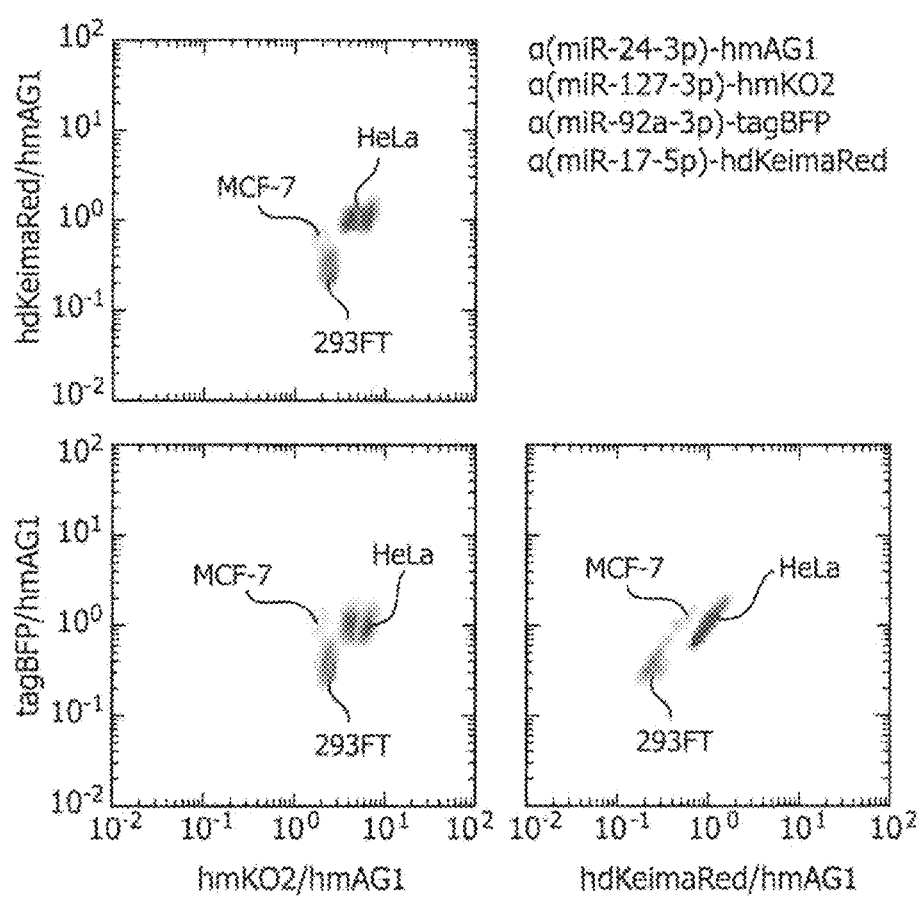

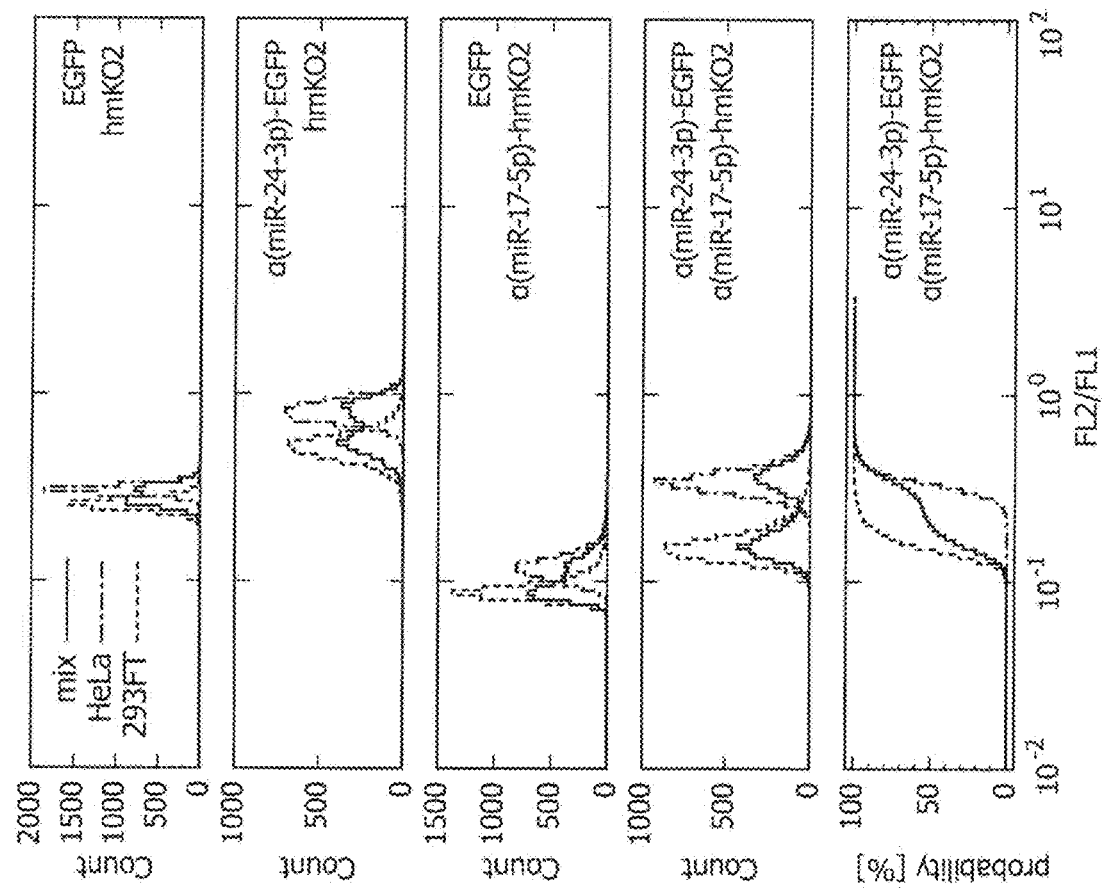
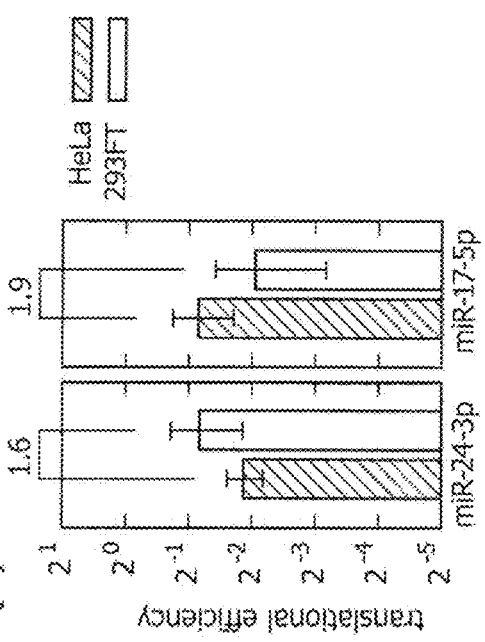
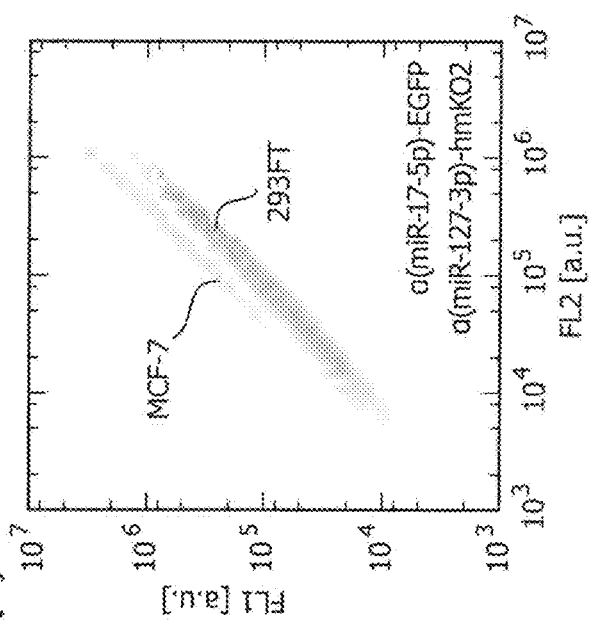
FIG. 9A(a)   FIG. 9A(b)   FIG. 9A(c)

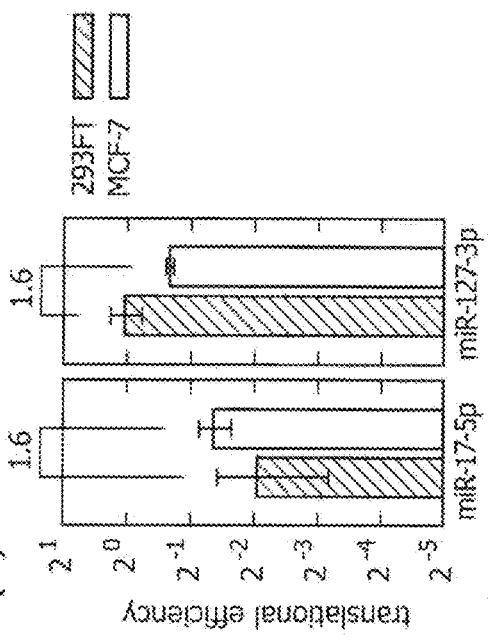
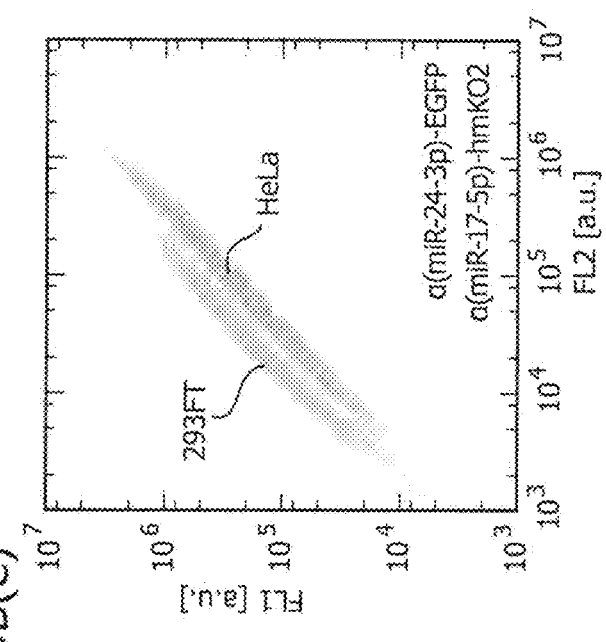
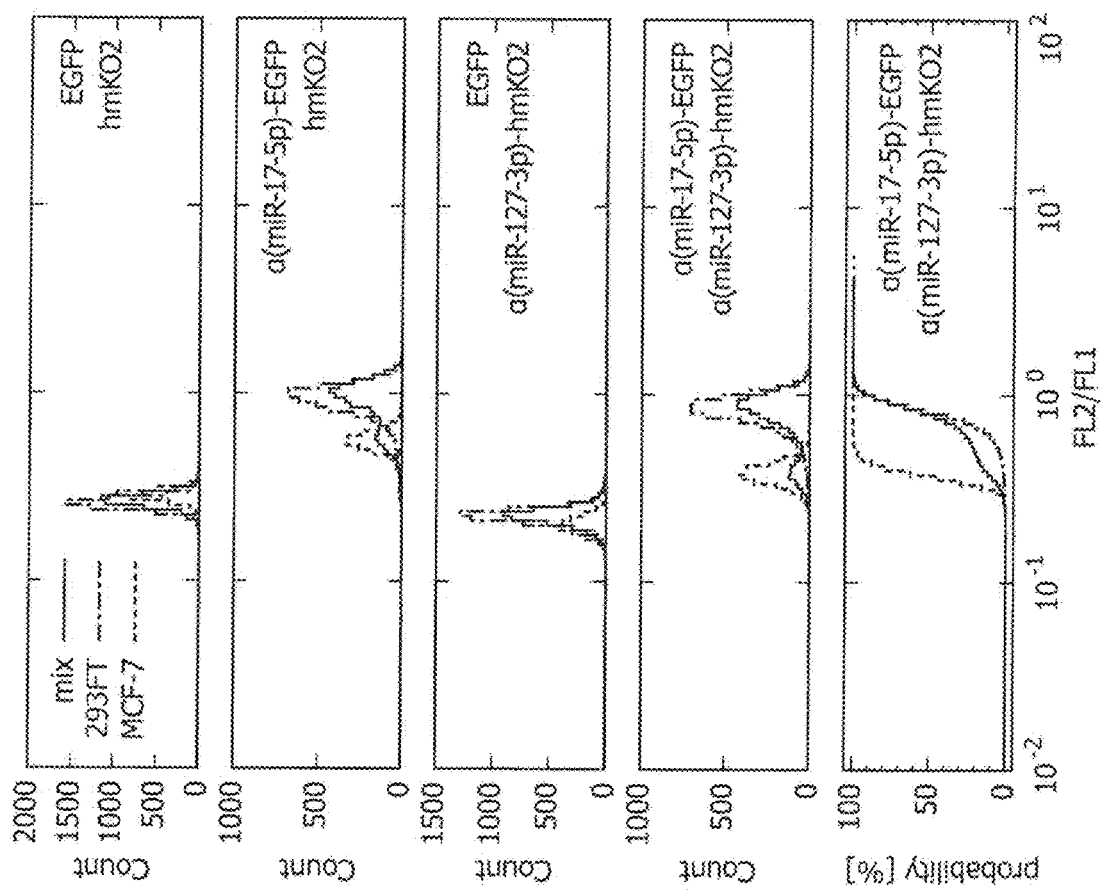

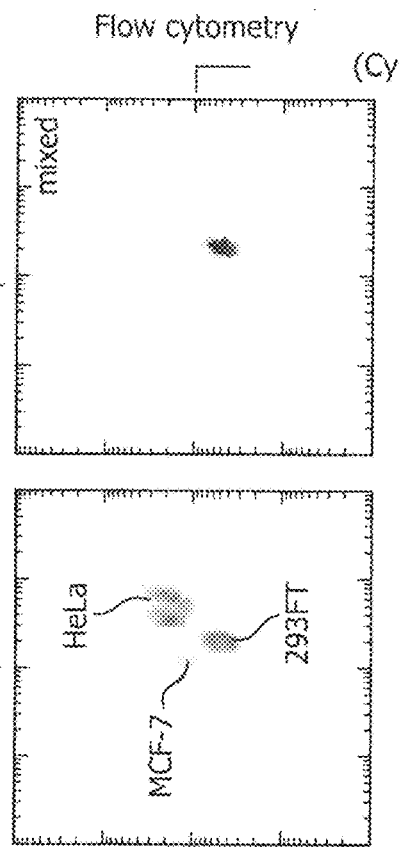
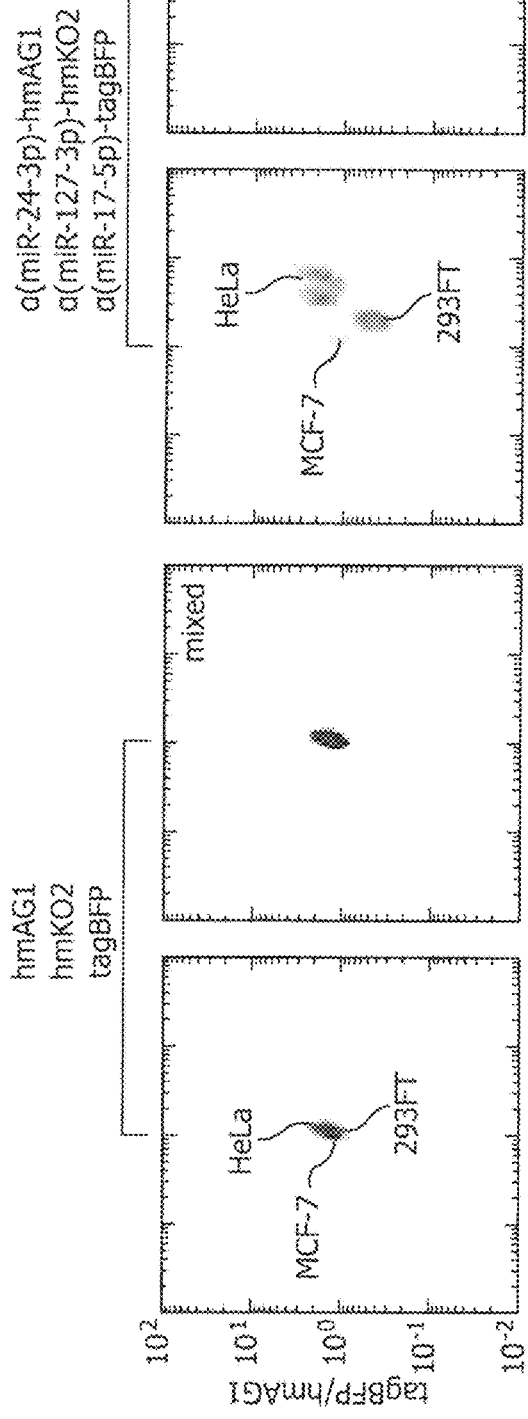
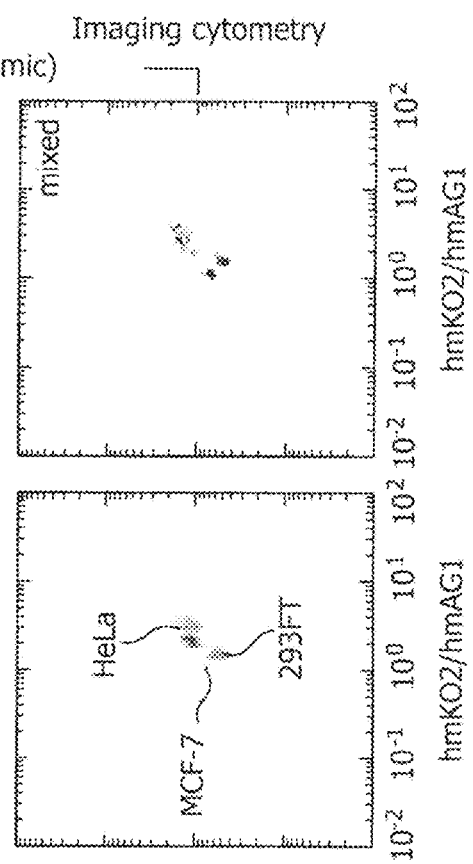
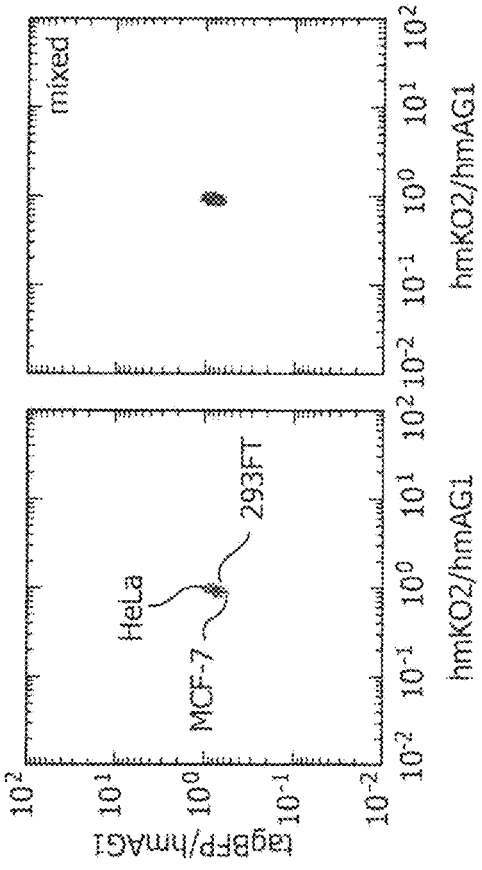
FIG.11A(a) FIG.11A(b) FIG.11A(c) FIG.11A(d)

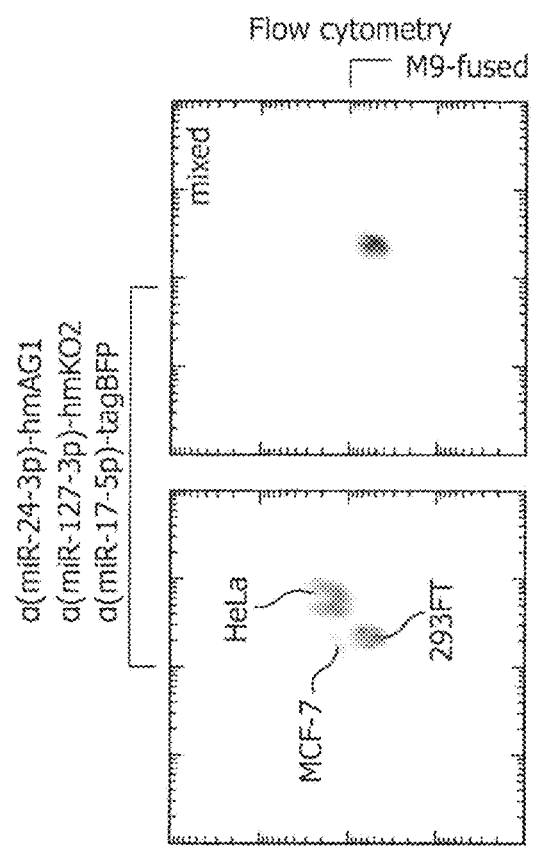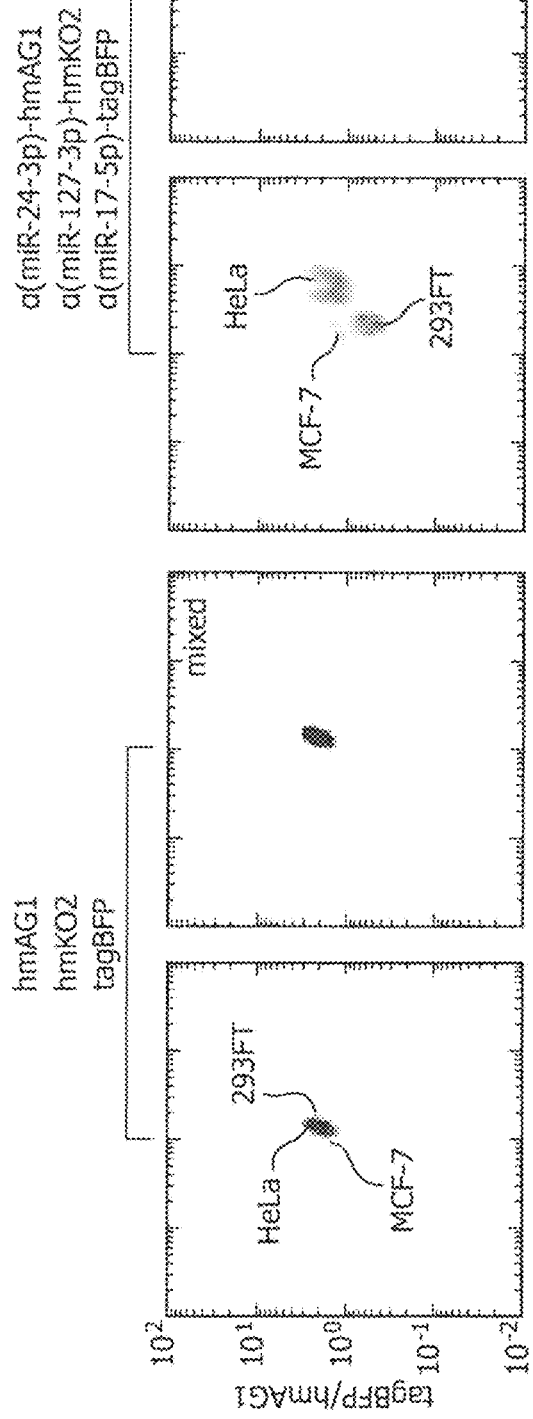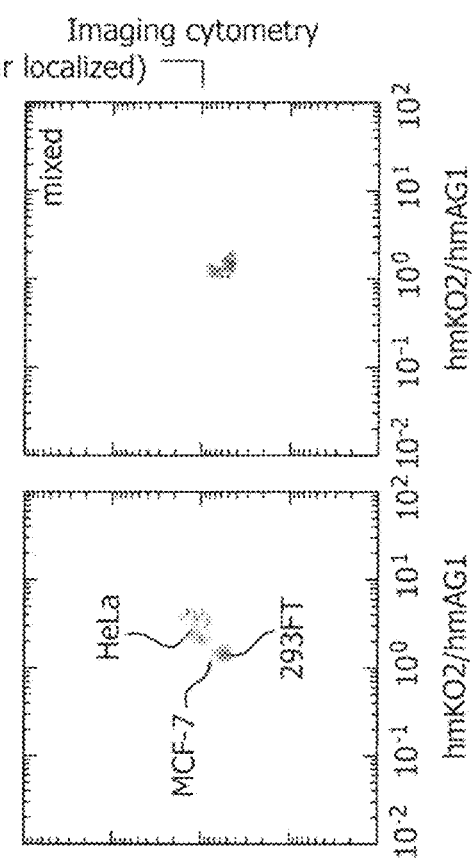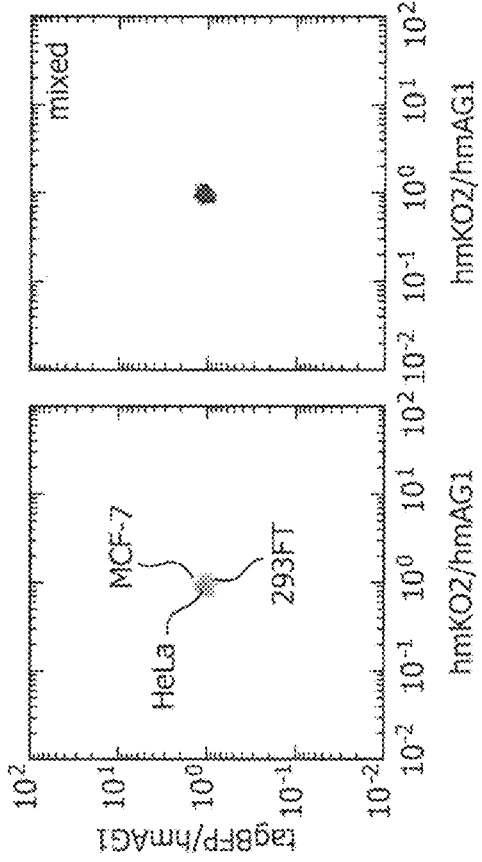
FIG. 11B(e)
FIG. 11B(f)
FIG. 11B(g)
FIG. 11B(h)

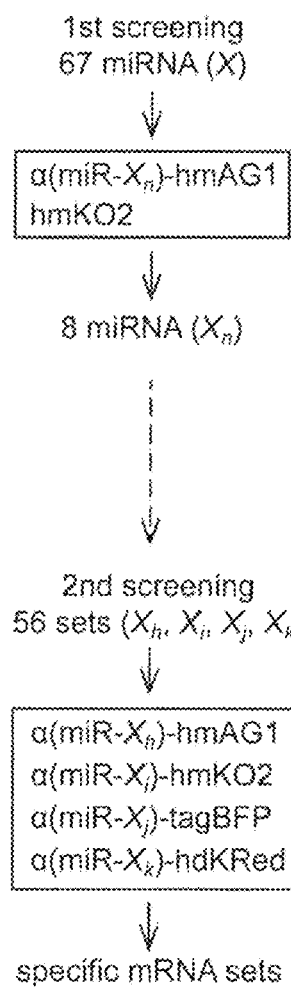
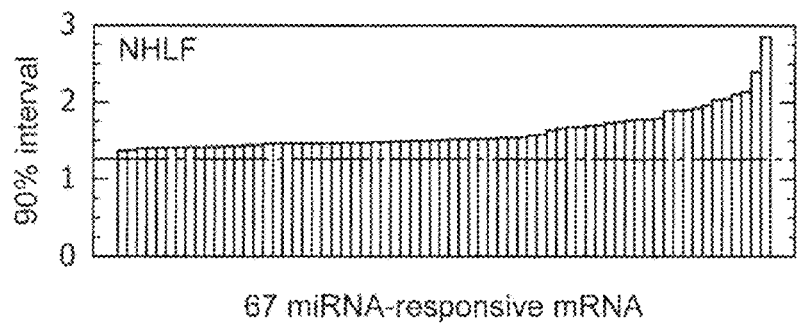
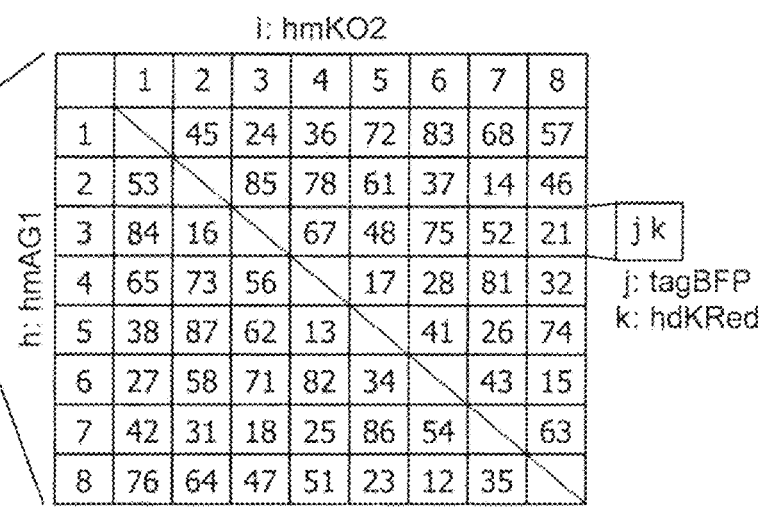
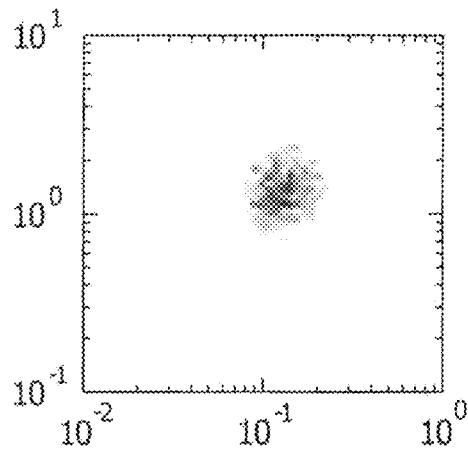
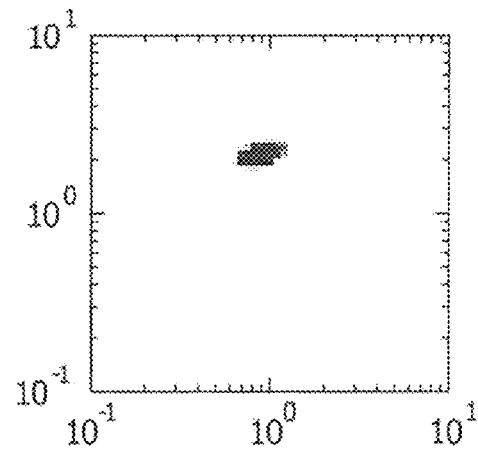
FIG.13(a)
FIG.13(b)
FIG.13(c)
FIG.13(d)
FIG.13(e)

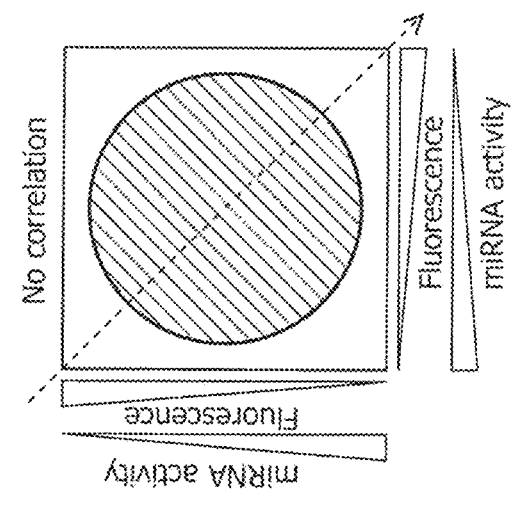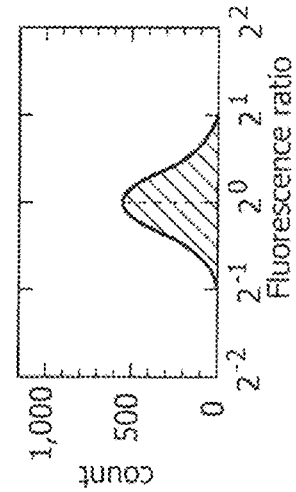
FIG.15(a) Positive correlation
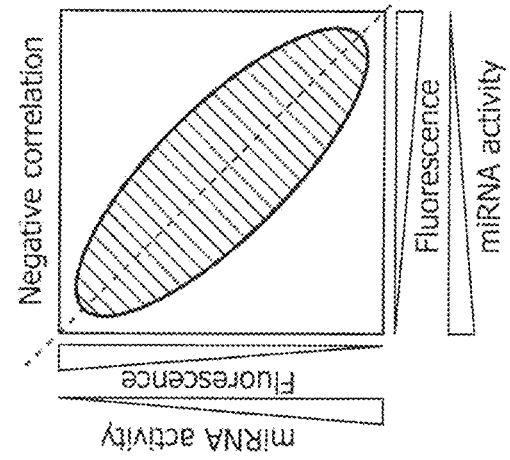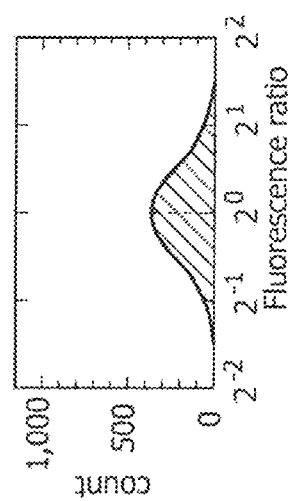
FIG.15(b) Negative correlation
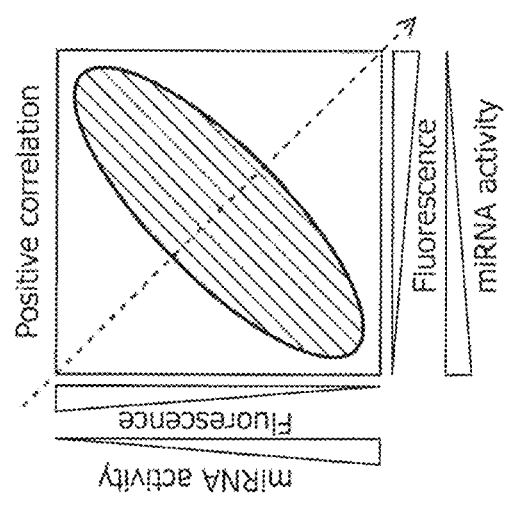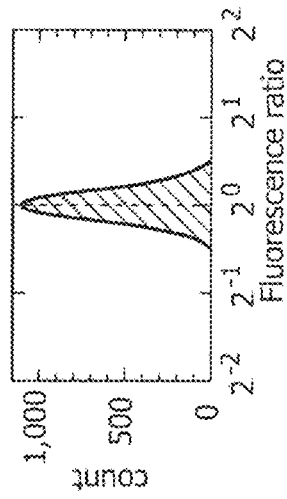
FIG.15(c) No correlation

SEQUENCE LISTING

```
<160> NUMBER OF SEQ ID NOS: 212

<210> SEQ ID NO 1
<211> LENGTH: 1023
<212> TYPE: RNA
<213> ORGANISM: Artificial
<220> FEATURE:
<223> OTHER INFORMATION: alpha(miR-21-5p)-EGFP

<400> SEQUENCE: 1
ggucagaucc gcuaggaucc ucaacaucag ucugauaagc uaagaucuac cggucgccac      60
caugggaucc gugagcaagg gcgaggagcu guucaccggg guggugccca uccuggucga     120
gcuggacggc gacguaaacg gccacaaguu cagcgugucc ggcgagggcg agggcgaugc     180
caccuacggc aagcugaccc ugaaguucau cugcaccacc ggcaagcugc ccgugcccug     240
gcccacccuc gugaccaccc ugaccuacgg cgugcagugc uucagccgcu acccgacca      300 caugaagcag cacgacuucu ucaagucgc caugcccgaa ggcuacgucc aggagcgcac      360
caucuucuuc aaggacgacg gcaacuacaa gacccgcgcc gaggugaagu ucgagggcga     420
cacccuggug aaccgcaucg agcugaaggg caucgacuuc aaggaggacg gcaacauccu     480
ggggcacaag cuggaguaca acuacaacag ccacaacguc uauaucaugg ccgacaagca     540
gaagaacggc aucaagguga acuucaagau ccgccacaac aucgaggacg gcagcgugca     600
gcucgccgac cacuaccagc agaacacccc caucggcgac ggccccgugc ugcugcccga     660
caaccacuac cugagcaccc aguccgcccu gagcaaagac cccaacgaga gcgcgauca      720 caugguccug cuggaguucg ugaccgccgc cgggaucacu cucggcaugg acgagcugua     780
caagagaucu cauaugcauc ucgagugaua gucuagaccu ucugcgggc uugccuucug      840 gccaugcccu ucuucucucc cuugcaccug uaccucuugg ucuuugaaua aagccugagu     900
aggaaaaaaa aaaaaaaaa aaaaaaaaaa aaaaaaaaaa aaaaaaaaaa aaaaaaaaa      960 aaaaaaaaa aaaaaaaaa aaaaaaaaa aaaaaaaaa aaaaaaaaa aaaaaaaaa         1020 aaa                                                                 1023

<210> SEQ ID NO 2
<211> LENGTH: 1075
<212> TYPE: RNA
<213> ORGANISM: Artificial
<220> FEATURE:
<223> OTHER INFORMATION: EGFP-4xalpha(4xmiR-21-5p)

<400> SEQUENCE: 2
gggcgaauua agagagaaaa gaagaguaag aagaauaua agacaccggu cgccaccaug       60
ggauccguga gcaagggcga ggagcuguuc accggguggu gcccauccu ggucgagcug      120
```

| | |
|---|---|
| gacggcgacg uaaacggcca caaguucagc guguccggcg agggcgaggg cgaugccacc | 180 |
| uacggcaagc ugacccugaa guucaucugc accaccggca agcugccgu gcccuggcc | 240 |
| acccucguga ccacccugac cuacggcgug cagugcuuca gccgcuaccc cgaccacaug | 300 |
| aagcagcacg acuucuucaa guccgccaug cccgaaggcu acguccagga gcgccaucu | 360 |
| uucuucaagg acgacggcaa cuacaagacc cgcgccgagg ugaaguucga gggcgacacc | 420 |
| cuggugaacc gcaucgagcu gaagggcauc gacuucaagg aggacggcaa cauccugggg | 480 |
| cacaagcugg aguacaacua caacagccac aacgucuaua ucauggccga caagcagaag | 540 |
| aacggcauca aggugaacuu caagauccgc cacaacaucg aggacggcag cgugcagcuc | 600 |
| gccgaccacu accagcagaa caccccccauc ggcgacggcc ccgugcugcu gcccgacaac | 660 |
| cacuaccuga gcacccaguc cgcccugagc aaagaccccca acgagaagcg cgaucaug | 720 |
| guccugcugg aguucgugac cgccgccggg aucacucucg gcauggacga gcuguacaag | 780 |
| agaucucaua ugcaucucga gugauagucu agaccuucug cggggcgacg agcgucaac | 840 |
| aucagucuga uaagcuacuc aacaucaguc ugauaagcua cucaacauca gucugauaag | 900 |
| cuacucaaca ucagucugau aagcuacgcg gccgcgugaa uaaagccuga guaggaaaaa | 960 |
| aaaaaaaaaa aaaaaaaaaa aaaaaaaaaa aaaaaaaaa aaaaaaaaaa aaaaaaaaa | 1020 |
| aaaaaaaaaa aaaaaaaaaa aaaaaaaaaa aaaaaaaaaa aaaaaaaaaa aaaaa | 1075 |

<210> SEQ ID NO 3
<211> LENGTH: 1023
<212> TYPE: RNA
<213> ORGANISM: Artificial
<220> FEATURE:
<223> OTHER INFORMATION: alpha(miR-24-3p)-EGFP

<400> SEQUENCE: 3

| | |
|---|---|
| ggucagaucc gcuaggaucc cuguuccugc ugaacugagc caagaucuac cggucgccac | 60 |
| caugggaucc gugagcaagg gcgaggagcu guucaccggg guggugccca uccuggucga | 120 |
| gcuggacggc gacguaaacg ccacaaguu cagcgugucc ggcgagggcg agggcgaugc | 180 |
| caccuacggc aagcugaccc ugaaguucau cugcaccacc ggcaagcugc ccgugcccug | 240 |
| gcccacccuc gugaccaccc ugaccuacgg cgugcagugc uucagccgcu accccgacca | 300 |
| caugaagcag cacgacuucu ucaaguccgc caugcccgaa ggcuacgucc aggagcgcac | 360 |
| caucuucuuc aaggacgacg gcaacuacaa gacccgcgcc gaggugaagu ucgagggcga | 420 |
| cacccugguc aaccgcaucg agcugaaggg caucgacuuc aaggaggacg gcaacauccu | 480 |
| ggggcacaag cuggaguaca acuacaacag ccacaacguc uauaucaugg ccgacaagca | 540 |
| gaagaacggc aucaaggug acuucaagau ccgccacaac aucgaggacg gcagcguca | 600 |
| gcucgccgac cacuaccagc agaacacccc caucggcgac ggccccgugc ugcugcccga | 660 |
| caaccacuac cugagcaccc aguccgcccu gagcaaagac cccaacgaga gcgcgauca | 720 |
| caugguccug cuggaguucg ugaccgccgc cgggaucacu cucggcaugg acgagcugua | 780 |
| caagagaucu cauaugcauc ucgagugaua gucuagaccu ucugcggggc uugccuucug | 840 |
| gccaugcccu ucuucucucc cuugcaccug uaccucuugg ucuuugaaua aagccugagu | 900 |
| aggaaaaaaa aaaaaaaaaa aaaaaaaaaa aaaaaaaaaa aaaaaaaaa aaaaaaaaa | 960 |
| aaaaaaaaaa aaaaaaaaaa aaaaaaaaaa aaaaaaaaaa aaaaaaaaaa aaaaaaaaaa | 1020 |
| aaa | 1023 |

<210> SEQ ID NO 4
<211> LENGTH: 955
<212> TYPE: RNA
<213> ORGANISM: Artificial
<220> FEATURE:
<223> OTHER INFORMATION: alpha(miR-24-3p)-hmAG1

<400> SEQUENCE: 4

```
ggucagaucc gcuaggaucc cuguuccugc ugaacugagc caagaucuac cggucgccac      60
caugugagc gugaucaagc ccgagaugaa gaucaagcug ugcaugaggg gcaccgugaa     120
cggccacaac uucgugaucg agggcgaggg caagggcaac cccuacgagg gcacccagau     180
ccuggaccug aacgugaccg agggcgcccc ccugcccuuc gccuacgaca uccugaccac     240
cguguuccag uacggcaaca gggccuucac caaguacccc gccgacaucc aggacuacuu     300
caagcagacc uuccccgagg cuaccacugg gagaggagc augaccuacg aggaccaggg     360
caucugcacc gccaccagca acaucagcau gagggggcgac ugcuucuucu acgacaucag     420
guucgacggc accaacuucc cccccaacgg ccccgugaug cagaagaaga cccugaagug     480
ggagcccagc accgagaaga guacgugga gacggcgug cugaagggcg acguaacau     540
gaggcugcug cuggagggcg gcggccacua caggugcgac uucaagacca ccuacaaggc     600
caagaaggag gugaggcugc ccgacgccca caagaucgac cacaggaucg agauccugaa     660
gcacgacaag gacuacaaca aggugaagcu guacgagaac gccgggggcca gguacuccau     720
gcugcccagc caggccaagu gaaucuagac cuucgcgggg gcuugccuuc uggccaugcc     780
cuucuucucu cccuugcacc uguaccucuu ggucuuugaa uaaagccuga guaggaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaa          955
```

<210> SEQ ID NO 5
<211> LENGTH: 1023
<212> TYPE: RNA
<213> ORGANISM: Artificial
<220> FEATURE:
<223> OTHER INFORMATION: alpha(miR-203a)-EGFP

<400> SEQUENCE: 5

```
ggucagaucc gcuaggaucc cuaguggucc uaaacauuuc acagaucuac cggucgccac      60
caugggaucc gugagcaagg gcgaggagcu guucaccggg guggugccca uccuggucga     120
gcuggacggc gacguaaacg gccacaaguu cagcgugucc ggcgagggcg agggcgaugc     180
caccuacggc aagcugaccc ugaaguucau cugcaccacc ggcaagcugc ccgugcccug     240
gcccacccuc gugaccaccc ugaccuacgg cgugcagugc uucagccgcu accccgacca     300
caugaagcag cacgacuucu ucaaguccgc caugcccgaa ggcuacgucc aggagcgcac     360
caucuucuuc aaggacgacg gcaacuacaa gacccgcgcc gaggugaagu ucgagggcga     420
cacccuggug aaccgcaucg agcugaaggg caucgacuuc aaggaggacg gcaacauccu     480
ggggcacaag cuggaguaca acuacaacag ccacaacguc uauaucaugg ccgacaagca     540
gaagaacggc aucaaggugaa acuucaagau ccgccacaac aucgaggacg gcagcgugca     600
gcucgccgac cacuaccagc agaacacccc caucggcgac ggccccgugc ugcugcccga     660
caaccacuac cugagcaccc aguccgcccu gagcaaagac cccaacgaga agcgcgauca     720
caugguccug cuggaguucg ugaccgccgc cgggaucacu cucggcaugg acgagcugua     780
caagagaucu cauaugcauc ucgagugaua gucuagaccu ucugcggggc uugccuucug     840
```

```
gccaugcccu ucuucucucc cuugcaccug uaccucuugg ucuuugaaua aagccugagu    900
aggaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaa                                                                 1023

<210> SEQ ID NO 6
<211> LENGTH: 931
<212> TYPE: RNA
<213> ORGANISM: Artificial
<220> FEATURE:
<223> OTHER INFORMATION: alpha(miR-203a)-hmKO2

<400> SEQUENCE: 6
ggucagaucc gcuaggaucc cuaguggucc uaaacauuuc acagaucuac cggucgccac     60 caugugagu gugauuaaac cagagaugaa gaugagguac uacauggacg gcuccgucaa    120
ugggcaugag uucacaauug aaggugaagg cacaggcaga ccuuacgagg acaucaaga    180 gaugacacua cgcgucacaa uggccgaggg cgggccaaug ccuuucgcgu ugacuuagu    240 gucacacgug uucuguuacg gccacagagu auuuacuaaa uaccagaag agauaccaga    300 cuauuucaaa caagcauuuc cugaaggccu gcaugggaa aggucguugg aguucgaaga    360 ugguggguc gcuucaguca gugcgcauau aagccuuaga ggaaacaccu ucuaccacaa    420
auccaaauuu acuggggua acuuccugc cgauggccu aucaugcaaa accaaagugu    480
ugauugggag ccaucaaccg agaaaauuac ugccagcgac ggaguucuga agggugaugu    540
uacgauguac cuaaaacuug aaggaggcgg caaucacaaa ugccaaauga agacuacuua    600
caaggcggca aaagagauuc uugaaaugcc aggagaccau uacaucggcc aucgccucgu    660
caggaaaacc gaaggcaaca uuacugagca gguagaagau gcaguagcuc auuccugaau    720
cuagaccuuc ugcggggcuu gccuucggc caugcccuuc uucucucccu ugcaccugua    780 ccucuuggu uuugaauaaa gccugaguag gaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa a                                  931

<210> SEQ ID NO 7
<211> LENGTH: 1023
<212> TYPE: RNA
<213> ORGANISM: Artificial
<220> FEATURE:
<223> OTHER INFORMATION: alpha(miR-127-3p)-EGFP

<400> SEQUENCE: 7
ggucagaucc gcuaggaucc agccaagcuc agacggaucc gaagaucuac cggucgccac     60
caugggaucc gugagcaagg gcgaggagcu guucaccggg gugguugccca uccuggucga    120 gcuggacggc gacguaaacg gccacaaguu cagcgugucc ggcgagggcg agggcgaugc    180
caccuacggc aagcugaccc ugaaguucau cugcaccacc ggcaagcugc ccgugcccug    240
gcccacccuc gugaccaccc ugaccuacgg cgugcagugc uucagccgcu acccgacca    300 caugaagcag cacgacuucu ucaagccgc caugcccgaa ggcuacgucc aggagcgcac    360
caucuucuuc aaggacgacg gcaacuacaa gacccgcgcc gagugaagu cgagggcga    420 cacccugguug aaccgcaucg agcugaaggg caucgacuuc aaggaggacg gcaacauccu    480 gggcacaag cuggagucaca acuacaacag ccacaacguc uauaucaugg ccgacaagca    540
```

| | |
|---|---|
| gaagaacggc aucaagguga acuucaagau ccgccacaac aucgaggacg gcagcgugca | 600 |
| gcucgccgac cacuaccagc agaacacccc caucggcgac ggccccgugc ugcugcccga | 660 |
| caaccacuac cugagcaccc aguccgcccu gagcaaagac cccaacgaga agcgcgauca | 720 |
| caugguccug cuggaguucg ugaccgccgc cgggaucacu cucggcaugg acgagcugua | 780 |
| caagagaucu cauaugcauc ucgagugaua gucuagaccu cugcggggc uugccuucug | 840 |
| gccaugcccu ucuucucucc cuugcaccug uaccucuugg ucuuugaaua aagccugagu | 900 |
| aggaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaa | 1023 |

<210> SEQ ID NO 8
<211> LENGTH: 931
<212> TYPE: RNA
<213> ORGANISM: Artificial
<220> FEATURE:
<223> OTHER INFORMATION: alpha(miR-127-3p)-hmKO2

<400> SEQUENCE: 8

| | |
|---|---|
| ggucagaucc gcuaggaucc agccaagcuc agacggaucc gaagaucuac cggucgccac | 60 |
| cauggugagu gugauuaaac cagagaugaa gaugagguac uacauggacg gcuccgucaa | 120 |
| ugggcaugag uucacaauug aaggugaagg cacaggcaga ccuuacgagg acaucaaga | 180 |
| gaugacacua cgcgucacaa uggccgaggg cgggccaaug ccuuucgcgu ugacuuagu | 240 |
| gucacacgug uucuguuacg gccacagagu auuuacuaaa uauccagaag agauaccaga | 300 |
| cuauuucaaa caagcauuuc cugaaggccu gucaugggaa aggucguugg aguucgaaga | 360 |
| ugguggguucc gcuucaguca gugcgcauau aagccuuaga ggaaacaccu ucuaccacaa | 420 |
| auccaaauuu acuggggnuua acuuuccugc cgauggccuu aucaugcaaa accaaagugu | 480 |
| ugauugggag ccaucaaccg agaaaauuac ugccagcgac ggaguucuga agggugaugu | 540 |
| uacgauguac cuaaaacuug aaggaggcgg caaucacaaa ugccaaauga agacuacuua | 600 |
| caaggcggca aaagagauuc uugaaaugcc aggagaccau acaucggcc aucgccucgu | 660 |
| caggaaaacc gaaggcaaca uuacugagca gguagaagau gcaguagcuc auuccugaau | 720 |
| cuagaccuuc ucgggggcuu gccuucggc caugcccuuc uucucucccu ugcaccugua | 780 |
| ccucuugguc uuugaauaaa gccugaguag gaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa a | 931 |

<210> SEQ ID NO 9
<211> LENGTH: 1024
<212> TYPE: RNA
<213> ORGANISM: Artificial
<220> FEATURE:
<223> OTHER INFORMATION: alpha(miR-17-5p)-EGFP

<400> SEQUENCE: 9

| | |
|---|---|
| ggucagaucc gcuaggaucc cuaccugcac uguaagcacu uugagaucua ccggucgcca | 60 |
| ccaugggauc cgugagcaag ggcgaggagc uguucaccgg ggugugcccc auccuggucg | 120 |
| agcuggacgg cgacguaaac ggccacaagu ucagcgugcc cggcgagggc gagggcgaug | 180 |
| ccaccuacgg caagcugacc cugaaguuca ucugcaccac cggcaagcug cccgugcccu | 240 |
| ggcccacccu cgugaccacc cugaccuacg gcgugcagug cuucagccgc uaccccgacc | 300 |

```
acaugaagca gcacgacuuc uucaagugccg ccaugcccga aggcuacguc caggagcgca    360
ccaucuucuu caaggacgac ggcaacuaca agacccgcgc cgaggugaag uucgagggcg    420
acacccuggu gaaccgcauc gagcugaagg gcaucgacuu caaggaggac ggcaacaucc    480
uggggcacaa gcuggaguac aacuacaaca gccacaacgu cuauaucaug gccgacaagc    540
agaagaacgg caucaaggug aacuucaaga uccgccacaa caucgaggac ggcagcgugc    600
agcucgccga ccacuaccag cagaacaccc ccaucgcgca cggccccgug cugcugcccg    660
acaaccacua ccugagcacc cagcucgccc ugagcaaaga ccccaacgag aagcgcgauc    720
acaugguccu gcuggaguuc gugaccgccg ccgggaucac ucucggcaug gacgagcugu    780
acaagagauc ucauaugcau cucgagugau agucuagacc uucugcgggg cuugccuucu    840
ggccaugccc uucuucucuc ccuugcaccu guaccucuug gucuuugaau aaagccgag    900 uaggaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaa                                                                 1024

<210> SEQ ID NO 10
<211> LENGTH: 1075
<212> TYPE: RNA
<213> ORGANISM: Artificial
<220> FEATURE:
<223> OTHER INFORMATION: EGFP-4xalpha(miR-17-5p)

<400> SEQUENCE: 10
gggcgaauua agagagaaaa gaagaguaag aagaaauaua agacaccggu cgccaccaug     60
ggauccguga gcaagggcga ggagcuguuc accggggugg ugcccauccu ggucgagcug    120
gacggcgacg uaaacggcca caaguucagc guguccggcg agggcgaggg cgaugccacc    180
uacggcaagc ugacccugaa guucaucugc accaccggca agcugcccgu gcccuggccc    240
acccucguga ccacccugac cuacggcgug cagugcuuca gccgcuaccc cgaccacaug    300
aagcagcacg acuucuucaa guccgccaug cccgaaggcu acguccagga gcgcaccauc    360
uucuucaagg acgacggcaa cuacaagacc cgcgccgagg ugaaguucga gggcgacacc    420
cuggugaacc gcaucgagcu gaagggcauc gacuucaagg aggacggcaa cauccugggg    480
cacaagcugg aguacaacua caacagccac aacgucuaua ucauggccga caagcagaag    540
aacggcauca aggugaacuu caagauccgc cacaacaucg aggacggcag cgugcagcuc    600
gccgaccacu accagcagaa cacccccauc ggcgacggcc ccgugcugcu gcccgacaac    660
cacuaccuga gcacccaguc cgcccugagc aaagacccca acgagaagcg cgaucacaug    720
guccugcugg aguucgugac cgccgccggg aucacucucg gcauggacga gcuguacaag    780
agaucucaua ugcaucucga gugauagucu agaccuucug cggggcgacg agcugcuacc    840
ugcacuguaa gcacuuugcu accugcacug uaagcacuuu gcuaccugca cuguaagcac    900
uuugcuaccu gcacuguaag cacuuuggcg gccgcgugaa uaaagccuga guaggaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaa        1075

<210> SEQ ID NO 11
<211> LENGTH: 956
<212> TYPE: RNA
<213> ORGANISM: Artificial
<220> FEATURE:
```

<223> OTHER INFORMATION: alpha(miR-17-5p)-hmAG1

<400> SEQUENCE: 11

| | | |
|---|---|---|
| ggucagaucc gcuaggaucc cuaccugcac uguaagcacu uugagaucua ccggucgcca | 60 | |
| ccauggugag cgugaucaag cccgagauga agaucaagcu gugcaugagg ggcaccguga | 120 | |
| acggccacaa cuucgugauc gagggcgagg gcaagggcaa ccccuacgag ggcacccaga | 180 | |
| uccuggaccu gaacgugacc gagggcgccc ccugcccuu cgccuacgac auccugacca | 240 | |
| ccguguucca guacggcaac agggccuuca ccaaguaccc cgccgacauc caggacuacu | 300 | |
| ucaagcagac cuuccccgag ggcuaccacu gggagaggag caugaccuac gaggaccagg | 360 | |
| gcaucugcac cgccaccagc aacaucagca ugaggggcga cugcuucuuc uacgacauca | 420 | |
| gguucgacgg caccaacuuc cccccaacg gccccgugau gcagaagaag acccugaagu | 480 | |
| gggagcccag caccgagaag auguacgugg aggacgcgu gcugaagggc gacgugaaca | 540 | |
| ugaggcugcu gcuggagggc ggcggccacu acaggugcga cuucaagacc accuacaagg | 600 | |
| ccaagaagga ggugaggcug cccgacgccc acaagaucga ccacaggauc gagauccuga | 660 | |
| agcacgacaa ggacuacaac aaggugaagc uguacgagaa cgccguggcc agguacucca | 720 | |
| ugcugcccag ccaggccaag ugaaucuaga ccuucgcgg ggcuugccuu cuggccaugc | 780 | |
| ccuucuucuc ucccuugcac cuguaccucu uggucuuuga auaaagccug aguaggaaaa | 840 | |
| aaaaaaaaaa aaaaaaaaaa aaaaaaaaaa aaaaaaaaaa aaaaaaaaaa aaaaaaaaaa | 900 | |
| aaaaaaaaaa aaaaaaaaaa aaaaaaaaaa aaaaaaaaaa aaaaaaaaaa aaaaaa | 956 | |

<210> SEQ ID NO 12
<211> LENGTH: 932
<212> TYPE: RNA
<213> ORGANISM: Artificial
<220> FEATURE:
<223> OTHER INFORMATION: alpha(miR-17-5p)-hmKO2

<400> SEQUENCE: 12

| | | |
|---|---|---|
| ggucagaucc gcuaggaucc cuaccugcac uguaagcacu uugagaucua ccggucgcca | 60 | |
| ccauggugag ugugauuaaa ccagagauga agaugaggua cuaccuggac ggcuccguca | 120 | |
| augggcauga guucacaauu gaaggugaag gcacaggcag accuuacgag ggacaucaag | 180 | |
| agaugacacu acgcgucaca auggccgagg gcgggccaau gccuucgcg uuugacuuag | 240 | |
| ugucacacgu guucuguuac ggccacagag uauuuacuaa auaccagaa gagauaccag | 300 | |
| acuauuucaa acaagcauuu ccugaaggcc ugucauggga aggucguug gaguucgaag | 360 | |
| auggugggguc cgcuucaguc agugcgcaua uaagccuuag aggaaacacc uucuaccaca | 420 | |
| aauccaaauu uacugggguu aacuuuccug ccgaugaucc uaucaugcaa aaccaaagug | 480 | |
| uugauuggga gccaucaacc gagaaaauua cugccagcga cggaguucug aagggugaug | 540 | |
| uuacgaugua ccuaaaacuu gaaggaggcg gcaaucacaa augccaaaug aagacuacuu | 600 | |
| acaaggcggc aaaagagauu cuugaaaugc caggagacca uuacaucggc caucgccucg | 660 | |
| ucaggaaaac cgaaggcaac auuacugagc agguagaaga ugcaguagcu cauuccugaa | 720 | |
| ucuagaccuu cugcggggcu ugccuucugg ccaugcccuu cucucuccc uugcaccugu | 780 | |
| accucuuggu cuuugaauaa agccugagua ggaaaaaaaa aaaaaaaaaa aaaaaaaaaa | 840 | |
| aaaaaaaaaa aaaaaaaaaa aaaaaaaaaa aaaaaaaaaa aaaaaaaaaa aaaaaaaaaa | 900 | |
| aaaaaaaaaa aaaaaaaaaa aaaaaaaaaa aa | 932 | |

<210> SEQ ID NO 13
<211> LENGTH: 997
<212> TYPE: RNA
<213> ORGANISM: Artificial
<220> FEATURE:
<223> OTHER INFORMATION: alpha(miR-17-5p)-tagBFP

<400> SEQUENCE: 13

| | | | | | |
|---|---|---|---|---|---|
| ggucagaucc | gcuaggaucc | cuaccugcac | uguaagcacu | uugagaucua | ccggucgcca | 60 |
| ccaugggauc | cagcgagcug | auuaaggaga | acaugcacau | gaagcuguac | auggagggca | 120 |
| ccguggacaa | ccaucacuuc | aagugcacau | ccgagggcga | aggcaagccc | uacgagggca | 180 |
| cccagaccau | gagaaucaag | guggucgagg | gcggcccucu | ccccuucgcc | uucgacaucc | 240 |
| uggcuacuag | cuuccucuac | ggcagcaaga | ccuucaucaa | ccacacccag | ggcauccccg | 300 |
| acuucuucaa | gcaguccuuc | ccugagggcu | ucacauggga | gagagucacc | acauacgaag | 360 |
| acggggggcgu | gcugaccgcu | acccaggaca | ccagccucca | ggacggcugc | cucaucuaca | 420 |
| acgucaagau | cagaggggug | aacuucacau | ccaacggccc | ugugaugcag | aagaaaacac | 480 |
| ucggcuggga | ggccuucacc | gagacgcugu | accccgcuga | cggcggccug | gaaggcagaa | 540 |
| acgacauggc | ccugaagcuc | gugggcggga | ccaucugau | cgcaaacauc | aagaccacau | 600 |
| auagauccaa | gaaacccgcu | aagaaccuca | agaugccugg | cgucuacuau | guggacuaca | 660 |
| gacuggaaag | aaucaaggag | gccaacaacg | agaccuacgu | cgagcagcac | gagguggcag | 720 |
| uggccagaua | cugcgaccuc | ccuagcaaac | uggggcacag | aucucauaug | caucucgagu | 780 |
| gauagucuag | accuucugcg | gggcuugccu | ucuggccaug | cccuucuucu | cucccuugca | 840 |
| ccuguaccuc | uuggucuuug | aauaaagccu | gaguaggaaa | aaaaaaaaa | aaaaaaaaa | 900 |
| aaaaaaaaa | aaaaaaaaa | aaaaaaaaa | aaaaaaaaa | aaaaaaaaa | aaaaaaaaa | 960 |
| aaaaaaaaa | aaaaaaaaa | aaaaaaaaa | aaaaaaa | | | 997 |

<210> SEQ ID NO 14
<211> LENGTH: 944
<212> TYPE: RNA
<213> ORGANISM: Artificial
<220> FEATURE:
<223> OTHER INFORMATION: alpha(miR-17-5p)-hdKeimaRed

<400> SEQUENCE: 14

| | | | | | |
|---|---|---|---|---|---|
| ggucagaucc | gcuaggaucc | cuaccugcac | uguaagcacu | uugagaucua | ccggucgcca | 60 |
| ccauggugag | cgugaucgcc | aagcagauga | ccuacaaggu | guacaugucc | ggcaccguga | 120 |
| acggccacua | cuucgaggug | gagggcgacg | gcaaggcaa | gcccuacgag | ggcgagcaga | 180 |
| ccgugaagcu | gaccgugacc | aagggcggcc | cccugcccuu | cgccugggac | auccuguccc | 240 |
| cccguuccca | guacggcagc | aucccccuuca | ccaaguaccc | cgaggacauc | cccgacuacg | 300 |
| ugaagcagag | cuuccccgag | ggcuacaccu | gggagaggac | caugaacuuc | gaggacggcg | 360 |
| ccgugugcac | cgugagcaac | gacuccagca | uccaggcaa | cugcuucauc | uacaacguga | 420 |
| agaucagcgg | caccaacuuc | cccccccaacg | gccccgugau | gcagaagaag | acccagggcu | 480 |
| gggagcccag | caccgagagg | cuguucgcca | gggacggaau | gcugaucggc | aacgacuaca | 540 |
| uggcccugaa | gcuggagggc | ggcggccacu | accugugcga | guucaagucc | accuacaagg | 600 |
| ccaagaagcc | cgugaggaug | cccggcuacc | acuacaucga | caggaagcug | gacgugacca | 660 |
| gccacaacag | ggacuacacc | uccguggagc | agugcgagau | cgccaucgcc | aggcacagcc | 720 |
| ugcugggcug | aaucuagacc | uucugcgggg | cuugccuucu | ggccaugccc | uucuucucuc | 780 |

-continued

| | |
|---|---|
| ccuugcaccu guaccucuug gucuuugaau aaagccugag uaggaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaa | 944 |

<210> SEQ ID NO 15
<211> LENGTH: 1023
<212> TYPE: RNA
<213> ORGANISM: Artificial
<220> FEATURE:
<223> OTHER INFORMATION: alpha(miR-92a-3p)-EGFP

<400> SEQUENCE: 15

| | |
|---|---|
| ggucagaucc gcuaggaucc acaggccggg acaagugcaa uaagaucuac cggucgccac | 60 |
| caugggaucc gugagcaagg gcgaggagcu guucaccggg guggugccca uccuggucga | 120 |
| gcuggacggc gacguaaacg gccacaaguu cagcgugucc ggcgagggcg agggcgaugc | 180 |
| caccuacggc aagcugaccc ugaaguucau cugcaccacc ggcaagcugc ccgugcccug | 240 |
| gcccacccuc gugaccaccc ugaccuacgg cgugcagugc uucagccgcu accccgacca | 300 |
| caugaagcag cacgacuucu ucaaguccgc caugcccgaa ggcuacaucc aggagcgcac | 360 |
| caucuucuuc aaggacgacg gcaacuacaa gacccgcgcc gaggugaagu ucgagggcga | 420 |
| cacccuggug aaccgcaucg agcugaaggg caucgacuuc aaggaggacg gcaacauccu | 480 |
| ggggcacaag cuggaguaca acuacaacag ccacaacguc uauaucaugg ccgacaagca | 540 |
| gaagaacggc aucaagguga acuucaagau ccgccacaac aucgaggacg gcagcgugca | 600 |
| gcucgccgac cacuaccagc agaacacccc caucggcgac ggccccgugc ugcugcccga | 660 |
| caaccacuac cugagcaccc aguccgcccu gagcaaagac cccaacgaga gcgcgauca | 720 |
| cauguccug cuggaguucg ugaccgccgc cgggaucacu cucggcaugg acgagcugua | 780 |
| caagagaucu cauaugcauc ucgagugaua gucuagaccu ucugcggggc uugccuucug | 840 |
| gccaugcccu ucuucucucc cuugcaccug uaccucuugg ucuuugaaua aagccugagu | 900 |
| aggaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaa | 1023 |

<210> SEQ ID NO 16
<211> LENGTH: 955
<212> TYPE: RNA
<213> ORGANISM: Artificial
<220> FEATURE:
<223> OTHER INFORMATION: alpha(miR-92a-3p)-hmAG1

<400> SEQUENCE: 16

| | |
|---|---|
| ggucagaucc gcuaggaucc acaggccggg acaagugcaa uaagaucuac cggucgccac | 60 |
| cauggugagc gugaucaagc ccgagaugaa gaucaagcug ugcaugaggg gcaccgugaa | 120 |
| cggccacaac uucgugaucg agggcgaggg caagggcaac cccuacgagg gcacccagau | 180 |
| ccuggaccug aacgugaccg agggcgcccc ccugcccuuc gccuacgaca uccugaccac | 240 |
| cguguuccag uacggcaaca gggccuucac caaguacccc gccgacaucc aggacuacuu | 300 |
| caagcagacc uuccccgagg cuaccacug ggagaggagc augaccuacg aggaccaggg | 360 |
| caucugcacc gccaccagca caucagcau gaggggcgac ugcuucuucu acgacaucag | 420 |
| guucgacggc accaacuucc cccccaacgg ccccgugaug cagaagaaga cccugaagug | 480 |
| ggagcccagc accgagaaga gugugugga ggacggcgug cugaagggcg acgugaacau | 540 |

```
gaggcugcug cuggagggcg gcggccacua caggugcgac uucaagacca ccuacaaggc    600
caagaaggag gugaggcugc ccgacgccca caagaucgac cacaggaucg agauccugaa    660
gcacgacaag gacuacaaca aggugaagcu guacgagaac gccgguggcc gguacuccau    720
gcugcccagc caggccaagu gaaucuagac cuucugcggg gcuugccuuc uggccaugcc    780
cuucuucucu cccuugcacc uguaccucuu ggucuuugaa uaaagccuga guaggaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaa                   955
```

<210> SEQ ID NO 17
<211> LENGTH: 995
<212> TYPE: RNA
<213> ORGANISM: Artificial
<220> FEATURE:
<223> OTHER INFORMATION: alpha(miR-92a-3p)-tagBFP

<400> SEQUENCE: 17

```
ggucagaucc gcuaggaucc acaggccggg acaagugcaa uaagaucuac cggucgccac     60
caugggaucc agcgagcuga uuaaggagaa caugcacaug aagcuguaca ugagagggcac   120 cguggacaac caucacuuca agugcacauc cgagggcgaa ggcaagcccu acgagggcac    180
ccagaccaug agaaucaagg uggucgaggg cggcccucuc cccuucgccu ucgacauccu    240
ggcuacuagc uuccucuacg gcagcaagac cuucaucaac cacacccagg caucccga     300 cuucuucaag caguccuucc cugagggcuu cacaugggag agaguacca cauacgaaga    360 cggggggcgug cugaccgcua cccaggacac cagccuccag gacggcugcc ucaucuacaa   420
cgucaagauc agaggggguga acuucacauc caacggcccu gugaugcaga gaaaacacu    480 cggcuggggag gccuucaccg agacgcugua ccccgcugac ggcggccugg aaggcagaaa    540
cgacauggcc cugaagcucg ugggcggag ccaucugauc gcaaacauca agaccacaua    600
uagauccaag aaacccgcua agaaccucaa gaugccuggc gucuacuaug uggacuacag    660
acuggaaaga aucaaggagg ccaacaacga gaccuacguc gagcagcacg agguggcagu    720
ggccagauac ugcgaccucc cuagcaaacu ggggcacaga ucucauaugc aucucgagug    780
auaucuagac cuucugcggg gcuugccuuc uggccaugcc cuucuucucu cccuugcacc    840
uguaccucuu ggucuuugaa uaaagccuga guaggaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaa                              995
```

<210> SEQ ID NO 18
<211> LENGTH: 943
<212> TYPE: RNA
<213> ORGANISM: Artificial
<220> FEATURE:
<223> OTHER INFORMATION: alpha(miR-92a-3p)-hdKeimaRed

<400> SEQUENCE: 18

```
ggucagaucc gcuaggaucc acaggccggg acaagugcaa uaagaucuac cggucgccac     60 caugugagc gugaucgcca agcagaugac cuacaaggug uacauguccg gcaccgugaa    120
cggccacuac uucgaggugg agggcgacgg caagggcaag cccuacgagg gcgagcagac    180
cgugaagcug accgugacca agggcggccc ccugcccuuc gccugggaca uccugucccc    240
ccuguuccag uacggcagca ucccccuucac caaguaccccc gaggacaucc ccgacuacgu    300
```

| | |
|---|---|
| gaagcagagc uuccccgagg gcuacaccug ggagaggacc augaacuucg aggacggcgc | 360 |
| cgugugcacc gugagcaacg acuccagcau ccagggcaac ugcuucaucu acaacgugaa | 420 |
| gaucagcggc accaacuucc ccccaacggc cccgugaug cagaagaaga cccagggcug | 480 |
| ggagcccagc accgagaggc uguucgccag ggacggaaug cugaucggca cgacuacau | 540 |
| ggcccugaag cuggagggcg gcggccacua ccugugcgag uucaagucca ccuacaaggc | 600 |
| caagaagccc gugaggaugc ccggcuacca cuacaucgac aggaagcugg acgugaccag | 660 |
| ccacaacagg gacuacaccu ccguggagca gugcgagauc gccaucgcca ggcacagccu | 720 |
| gcugggcuga aucuagaccu ucugcggggc uugccuucug ccaugcccu ucuucucucc | 780 |
| cuugcaccug uaccucuugg ucuuugaaua aagccgagu aggaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaa | 943 |

<210> SEQ ID NO 19
<211> LENGTH: 1019
<212> TYPE: RNA
<213> ORGANISM: Artificial
<220> FEATURE:
<223> OTHER INFORMATION: EGFP

<400> SEQUENCE: 19

| | |
|---|---|
| gggcgaauua agagagaaaa gaagaguaag aagaaauaua agacaccggu cgccaccaug | 60 |
| ggauccguga gcaagggcga ggagcuguuc accggggugg ugcccauccu ggucgagcug | 120 |
| gacggcgacg uaaacggcca caaguucagc guguccggcg agggcgaggg cgaugccacc | 180 |
| uacggcaagc ugacccugaa guucaucugc accaccggca agcugcccgu gcccuggccc | 240 |
| acccucguga ccaccцugac cuacggcgug cagugcuuca gccgcuaccc cgaccacaug | 300 |
| aagcagcacg acuucuucaa guccgccaug cccgaaggcu acguccagga gcgcaccauc | 360 |
| uucuucaagg acgacggcaa cuacaagacc cgcgccgagg ugaaguucga gggcgacacc | 420 |
| cuggugaacc gcaucgagcu gaagggcauc gacuucaagg aggacggcaa cauccugggg | 480 |
| cacaagcugg aguacaacua caacagccac aacgucuaua ucauggccga caagcagaag | 540 |
| aacggcauca aggugaacuu caagauccgc cacaacaucg aggacggcag cgugcagcuc | 600 |
| gccgaccacu accagcagaa cacccccauc ggcgacggcc ccgugcugcu gcccgacaac | 660 |
| cacuaccuga gcacccaguc cgcccugagc aaagacccca acgagaagcg cgaucacaug | 720 |
| guccugcugg aguucgugac cgccgccggg aucacucucg gcauggacga gcuguacaag | 780 |
| agaucucaua ugcaucucga gugauagucu agaccuucug cggggcuugc cuucuggcca | 840 |
| ugcccuucuu cucccccuug caccuguacc ucuggucuu ugaauaaagc cugaguagga | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaa | 1019 |

<210> SEQ ID NO 20
<211> LENGTH: 992
<212> TYPE: RNA
<213> ORGANISM: Artificial
<220> FEATURE:
<223> OTHER INFORMATION: tagBFP

<400> SEQUENCE: 20

| | |
|---|---|
| gggcgaauua agagagaaaa gaagaguaag aagaaauaua agacaccggu cgccaccaug | 60 |
| ggauccagcg agcugauuaa ggagaacaug cacaugaagc uguacaugga gggcaccgug | 120 |

```
gacaaccauc acuucaagug cacauccgag ggcgaaggca agcccuacga gggcacccag    180
accaugagaa ucaaggUggU cgagggcggc ccucucCCCu cgccuucga cauccuggcu     240 acuagcuucc ucuacggcag caagaccuuc aucaaccaca cccagggcau ccccgacuuc    300
uucaagcagu ccuccccuga gggcuucaca ugggagagag ucaccacaua cgaagacggg    360
ggcgugcuga ccgcuaccca ggacaccagc cuccaggacg cugccucau cuacaacguc    420 aagaucagag gggugaacuu cauccaaac ggcccuguga ugcagaagaa acacucggc     480 ugggaggccu ucaccgagac gcuguacccc gcugacggcg gccuggaagg cagaaacgac    540
auggcccuga gcucguggg cgggagccau cugaucgcaa acaucaagac cacauauaga    600
uccaagaaac ccgcuaagaa ccucaagaug ccuggcgucu acuaugugga cuacagacug    660
gaaagaauca aggaggccaa caacgagacc uacgucgagc agcacgaggu ggcaguggcc    720
agauacugcg accucccuag caaacugggg cacagaucuc auaugcaucu cgagugauag    780
ucuagaccuu cugcggggcu ugccuucugg ccaugcccuu cuucucuccc uugcaccugu    840
accucuuggu cuugaauaa agccgaguga ggaaaaaaaa aaaaaaaaaa aaaaaaaaa    900 aaaaaaaaa aaaaaaaaa aaaaaaaaa aaaaaaaaa aaaaaaaaa aaaaaaaaa        960 aaaaaaaaa aaaaaaaaa aaaaaaaaa aa                                     992
```

<210> SEQ ID NO 21
<211> LENGTH: 951
<212> TYPE: RNA
<213> ORGANISM: Artificial
<220> FEATURE:
<223> OTHER INFORMATION: hmAG1

<400> SEQUENCE: 21

```
gggcgaauua agagagaaaa gaagaguaag aagaaauaua agacaccggu cgccaccaug     60
gugagcguga ucaagcccga gaugaagauc aagcugugca ugaggggcac cgugaacggc    120
cacaacuucg ugaucgaggg cgagggcaag ggcaaccccu acgagggcac ccagauccug    180
gaccugaacg ugaccgaggg cgccccccug cccuucgccu acgacauccu gaccaccgug    240
uuccaguacg gcaacagggc cuucaccaag uaccccgccg acauccagga cuacuucaag    300
cagaccuucc ccgagggcua ccacugggag aggagcauga ccuacgagga ccagggcauc    360
ugcaccgcca ccagcaacau cagcaugagg ggcgacugcu ucuucuacga caucagguuc    420
gacggcacca acuuccccCC caacggcccc gugaugcaga agaagacccu gaagugggag    480
cccagcaccg agaagaugua cguggaggac ggcgugcuga agggcgacgu gaacaugagg    540
cugcugcugg agggcggcgg ccacuacagg ugcgacuuca agaccaccua caaggccaag    600
aaggaggUga ggcugcccga cgcccacaag aucgaccaca ggaucgagau ccugaagcac    660
gacaaggacu acaacaaggu gaagcuguac gagaacgccg uggccaggua cuccaugcug    720
cccagccagg ccaagugaau cuagaccuuc ugcggggcuu gccuucuggc caugcccuuc    780
uucucucCCu ugcaccugua ccucuuggUc uuugaauaaa gccgaguag gaaaaaaaaa    840 aaaaaaaaa aaaaaaaaa aaaaaaaaa aaaaaaaaa aaaaaaaaa aaaaaaaaa        900 aaaaaaaaa aaaaaaaaa aaaaaaaaa aaaaaaaaa aaaaaaaaa a                951
```

<210> SEQ ID NO 22
<211> LENGTH: 927
<212> TYPE: RNA
<213> ORGANISM: Artificial
<220> FEATURE:

<223> OTHER INFORMATION: hmKO2

<400> SEQUENCE: 22

| | | | | | |
|---|---|---|---|---|---|
| gggcgaauua | agagagaaaa | gaagaguaag | aagaaauaua | agacaccggu | cgccaccaug | 60 |
| gugaguguga | uuaaaccaga | gaugaagaug | agguacuaca | uggacggcuc | cgucaauggg | 120 |
| caugaguuca | caauugaagg | ugaaggcaca | ggcagaccuu | acgagggaca | ucaagagaug | 180 |
| acacuacgcg | ucacaauggc | cgagggcggg | ccaaugccuu | cgcguuuga | cuuaguguca | 240 |
| cacguguucu | guuacggcca | cagaguauuu | acuaaauauc | cagaagagau | accagacuau | 300 |
| uucaaacaag | cauuuccuga | aggccuguca | ugggaaggu | cguuggaguu | cgaagauggu | 360 |
| ggguccgcuu | cagucagugc | gcauauaagc | cuuagaggaa | acaccuucua | ccacaaaucc | 420 |
| aaauuuacug | ggguuaacuu | uccugccgau | gguccuauca | ugcaaaacca | aaguguugau | 480 |
| ugggagccau | caaccgagaa | aauuacugcc | agcgacggag | uucugaaggg | ugauguuacg | 540 |
| auguaccuaa | aacuugaagg | aggcggcaau | cacaaaugcc | aaaugaagac | uacuuacaag | 600 |
| gcggcaaaag | agauucuuga | aaugccagga | gaccauuaca | ucggccaucg | ccucgucagg | 660 |
| aaaaccgaag | gcaacauuac | ugagcaggua | gaagaugcag | uagcucauuc | cugaaucuag | 720 |
| accuucugcg | gggcuugccu | ucuggccaug | cccuucuucu | cucccuugca | ccuguaccuc | 780 |
| uuggucuuug | aauaaagccu | gaguaggaaa | aaaaaaaaa | aaaaaaaaaa | aaaaaaaaaa | 840 |
| aaaaaaaaaa | aaaaaaaaaa | aaaaaaaaaa | aaaaaaaaaa | aaaaaaaaaa | aaaaaaaaaa | 900 |
| aaaaaaaaa | aaaaaaaaaa | aaaaaaa | | | | 927 |

<210> SEQ ID NO 23
<211> LENGTH: 939
<212> TYPE: RNA
<213> ORGANISM: Artificial
<220> FEATURE:
<223> OTHER INFORMATION: hdKeimaRed

<400> SEQUENCE: 23

| | | | | | |
|---|---|---|---|---|---|
| gggcgaauua | agagagaaaa | gaagaguaag | aagaaauaua | agacaccggu | cgccaccaug | 60 |
| gugagcguga | ucgccaagca | gaugaccuac | aagguguaca | uguccggcac | cgugaacggc | 120 |
| cacuacuucg | agguggaggg | cgacggcaag | ggcaagcccu | acgagggcga | gcagaccgug | 180 |
| aagcugaccg | ugaccaaggg | cggcccccug | cccuucgccu | gggacauccu | guccccccug | 240 |
| uuccaguacg | gcagcauccc | cuucaccaag | uaccccgagg | acaucccgga | cuacgugaag | 300 |
| cagagcuucc | ccgagggcua | caccugggag | aggaccauga | acuucgagga | cggcgccgug | 360 |
| ugcaccguga | gcaacgacuc | cagcauccag | ggcaacugcu | ucaucuacaa | cgugaagauc | 420 |
| agcggcacca | acuuccccccc | caacggcccc | gugaugcaga | agaagacccca | gggcuggggag | 480 |
| cccagcaccg | agaggcuguu | cgccagggac | ggaaugcuga | ucggcaacga | cuacauggcc | 540 |
| cugaagcugg | agggcggcgg | ccacuaccug | ugcgaguuca | aguccaccua | caaggccaag | 600 |
| aagcccguga | ggaugcccgg | cuaccacuac | aucgacagga | gcuggacgu | gaccagccac | 660 |
| aacagggacu | acaccucccgu | ggagcagugc | gagaucgcca | ucgccaggca | cagccugcug | 720 |
| ggcugaaucu | agaccuucug | cggggcuugc | cuucuggcca | ugcccuucuu | cucucccuug | 780 |
| caccuguacc | ucuuggucuu | ugaauaaagc | cugaguagga | aaaaaaaaaa | aaaaaaaaaa | 840 |
| aaaaaaaaaa | aaaaaaaaaa | aaaaaaaaaa | aaaaaaaaaa | aaaaaaaaaa | aaaaaaaaaa | 900 |
| aaaaaaaaaa | aaaaaaaaaa | aaaaaaaaaa | aaaaaaaaa | | | 939 |

<210> SEQ ID NO 24
<211> LENGTH: 1005
<212> TYPE: RNA
<213> ORGANISM: Artificial
<220> FEATURE:
<223> OTHER INFORMATION: tagRFP (pSRT)

<400> SEQUENCE: 24

| | | | | |
|---|---|---|---|---|
| gggcgaauua agagagaaaa gaagaguaag aagaaauaua agagccacca ugggauccgu | 60 |
| gucuaagggc gaaagcucuga uuaaggagaa caugcacaug aagcuguaca uggagggcac | 120 |
| cgugaacaac caccacuuca agugcacauc cgagggcgaa ggcaagcccu acgagggcac | 180 |
| ccagaccaug agaaucaagg uggucgaggg cggcccucuc ccuucgccu ucgacauccu | 240 |
| ggcuaccagc uucauguacg gcagcagaac cuucaucaac cacacccagg gcaucccga | 300 |
| cuucuuuaag caguccuucc cugagggcuu cacaugggag agagucacca cauacgaaga | 360 |
| cggggggcgug cugaccgcua cccaggacac cagccuccag gacggcugcc ucaucuacaa | 420 |
| cgucaagauc agagggguga acuucccauc caacggcccu gugaugcaga gaaaaacacu | 480 |
| cggcugggag gccaacaccg agaugcugua ccccgcugac ggcggccugg aaggcagaag | 540 |
| cgacauggcc cugaagcucg uggggcgggg ccaccugauc ugcaacuuca agaccacaua | 600 |
| cagauccaag aaacccgcua agaaccucaa gaugcccggc gucuacuaug uggaccacag | 660 |
| acuggaaaga aucaaggagg ccgacaaaga gaccuacgcuc gagcagcacg agguggcugu | 720 |
| ggccagauac ugcgaccucc cuagcaaacu ggggcacaaa cuuaauagau cucauaugca | 780 |
| ucucgaguga uagucuagac cuucgcggg gcuugccuuc uggccaugcc cuucuucucu | 840 |
| cccuugcacc uguaccucuu ggucuuugaa uaaagccuga guaggaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaa | 1005 |

<210> SEQ ID NO 25
<211> LENGTH: 1143
<212> TYPE: RNA
<213> ORGANISM: Artificial
<220> FEATURE:
<223> OTHER INFORMATION: alpha(miR-24-3p)-hmAG1-M9

<400> SEQUENCE: 25

| | | | | |
|---|---|---|---|---|
| ggucagaucc gcuaggaucc cuguuccugc ugaacugagc caagaucuac cggucgccac | 60 |
| caugguga gc gugaucaagc cgagaugaa gaucaagcug ugcaugaggg gcaccgugaa | 120 |
| cggccacaac uucgugaucg agggcgaggg caagggcaac cccuacgagg gcacccagau | 180 |
| ccuggaccug aacgugaccg agggcgcccc ccugcccuuc gccuacgaca uccugaccac | 240 |
| cguguuccag uacggcaaca gggcuucac caaguacccc gccgacaucc aggacuacuu | 300 |
| caagcagacc uuccccgagg gcuaccacug ggagaggagc augaccuacg aggaccaggg | 360 |
| caucuggcacc gccaccagca acaucagcau gaggggcgac ugcuucuucu acgacaucag | 420 |
| guucgacggc accaacuucc cccccaacgg ccccgugaug cagaagaaga cccugaagug | 480 |
| ggagcccagc accgagaaga uguacgugga ggacggcgug cugaagggcg acgugaacau | 540 |
| gaggcugcug cuggagggcg gcggccacua caggugcgac uucaagacca ccuacaaggc | 600 |
| caagaaggag gugaggcugc ccgacgccca aagaucgac cacaggaucg agauccugaa | 660 |
| gcacgacaag gacuacaaca aggugaagcu guacgagaac gccgugggcca gguacccau | 720 |
| gcugcccagc caggccaaga gauccaauca gucuucaauu uuuggaccca ugaagggagg | 780 |

| aaauuuugga ggcagaagcu cuggccccua uggcgguggaa ggccaauacu uugcaaaacc | 840 |
| acgaaaccaa gguggcuaug gcgguuccag cagcagcagu agcuauggca guggcagaag | 900 |
| auuuagaucu cauaugcauc ucgagugaua gucuagaccu ucugcggggc uugccuucug | 960 |
| gccaugcccu ucuucucucc cuugcaccug uaccucuugg ucuuugaaua aagccugagu | 1020 |
| aggaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaa | 1143 |

<210> SEQ ID NO 26
<211> LENGTH: 1119
<212> TYPE: RNA
<213> ORGANISM: Artificial
<220> FEATURE:
<223> OTHER INFORMATION: alpha(miR-127-3p)-hmKO2-M9

<400> SEQUENCE: 26

| ggucagaucc gcuaggaucc agccaagcuc agacggaucc gaagaucuac cggucgccac | 60 |
| cauggugagu gugauuaaac cagagaugaa gaugagguac uacauggacg gcuccgucaa | 120 |
| ugggcaugag uucacaauug aaggugaagg cacaggcaga ccuuacgagg acaucaaga | 180 |
| gaugacacua cgcgucacaa uggccgaggg cgggccaaug ccuuucgcgu ugacuuagu | 240 |
| gucacacgug uucuguuacg gccacagagu auuuacuaaa uaccagaag agauaccaga | 300 |
| cuauuucaaa caagcauuuc cugaaggccu gucaugggaa aggucguugg aguucgaaga | 360 |
| uggugggucc gcuucaguca gugcgcauau aagccuuaga ggaaacaccu ucuaccacaa | 420 |
| auccaaauuu acuggggua acuuuccugc cgauggccu aucaugcaaa accaaagugu | 480 |
| ugauugggag ccaucaaccg agaaaauuac ugccagcgac ggaguucuga agggugaugu | 540 |
| uacgauguac cuaaaacuug aaggaggcgg caaucacaaa ugccaauga agacuacuua | 600 |
| caaggcggca aaagagauuc uugaaaugcc aggagaccau acaucggcc aucgccucgu | 660 |
| caggaaaacc gaaggcaaca uuacugagca gguagaagau gcaguagcuc auuccagauc | 720 |
| caaucagucu ucaaauuuug gacccaugaa ggaggaaau uuuggaggca gaagcucugg | 780 |
| ccccuauggc ggguggaggcc aauacuuugc aaaaccacga accaaggug gcuauggcgg | 840 |
| uuccagcagc agcaguagcu auggcagugg cagaagauuu agaucucaua ugcaucucga | 900 |
| gugauagucu agaccuucug cggggcuugc cuucuggcca ugcccuucuu cucucccuug | 960 |
| caccuguacc ucuuggucuu ugaauaaagc cugaguagga aaaaaaaaaa aaaaaaaaaa | 1020 |
| aaaaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaa | 1119 |

<210> SEQ ID NO 27
<211> LENGTH: 1162
<212> TYPE: RNA
<213> ORGANISM: Artificial
<220> FEATURE:
<223> OTHER INFORMATION: alpha(miR-17-5p)-tagBFP-M9

<400> SEQUENCE: 27

| ggucagaucc gcuaggaucc cuaccugcac uguaagcacu uugagaucua ccggucgcca | 60 |
| ccaugggauc cagcgagcug auuaaggaga acaugcacau gaagcuguac auggagggca | 120 |
| ccguggacaa ccaucacuuc aagugcacau ccgagggcga aggcaagccc uacgagggca | 180 |
| cccagaccau gagaaucaag guggucgagg gcggcccucu ccccuucgcc uucgacaucc | 240 |

```
uggcuacuag cuuccucuac ggcagcaaga ccuucaucaa ccacacccag ggcaucgccg    300
acuucuucaa gcaguccuuc ccugagggcu ucacauggga gagagucacc acauacgaag    360 acggggggcgu gcugaccgcu acccaggaca ccagccucca ggacggcugc cucaucuaca    420
acgucaagau cagaggggug aacuucacau ccaacggccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca    660
gacuggaaag aaucaaggag gccaacaacg agaccuacgu cgagcagcac gaggugggcag   720 uggccagaua cugcgaccuc ccuagcaaac uggggcacag auccaaucag ucuucaaauu    780
uuggacccau gaagggagga aauuuuggag gcagaagcuc uggcccccuau ggcgguggag    840 gccaauacuu ugcaaaacca cgaaaccaag guggcuaugg cgguuccagc agcagcagua    900
gcuauggcag uggcagaaga uuuagaucuc auaugcaucu cgagugauag ucuagaccuu    960
cugcggggcu ugccuucugg ccaugcccuu cuucucuccc uugcaccugu accucuuggu   1020
cuuugaauaa agccugagua ggaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aa                                           1162

<210> SEQ ID NO 28
<211> LENGTH: 1139
<212> TYPE: RNA
<213> ORGANISM: Artificial
<220> FEATURE:
<223> OTHER INFORMATION: hmAG1-M9

<400> SEQUENCE: 28
gggcgaauua agagagaaaa gaagaguaag aagaaauaua agacaccggu cgccaccaug     60
gugagcguga ucaagcccga gaugaagauc aagcugugca ugaggggcac cgugaacggc    120
cacaacuucg ugaucgaggg cgagggcaag ggcaaccccu acgagggcac ccagauccug    180
gaccugaacg ugaccgaggg cgcccccccug cccuucgccu acgacauccu gaccaccgug    240
uuccaguacg gcaacagggc cuucaccaag uaccccgccg acauccagga cuacuucaag    300
cagaccuucc ccgagggcua ccacugggag aggagcauga ccuacgagga ccagggcauc    360
ugcaccgcca ccagcaacau cagcaugagg ggcgacugcu ucuucuacga caucagguuc    420
gacggcacca acuuccccccc caacggcccc gugaugcaga agaagacccu gaaguggag     480 cccagcaccg agaagaugua cgugggaggac ggcgugcuga agggcgacgu gaacaugagg    540
cugcugcugg agggcggcgg ccacuacagg ugcgacuuca gaccaccua caaggccaag    600 aaggaggugga ggcugccga cgcccacaag aucgaccaca ggaucgagau ccugaagcac    660
gacaaggacu acaacaaggu gaagcuguac gagaacgccg uggccaggua uccaugcug    720 cccagccagg ccaagagauc caaucagucu ucaaauuuug acccaugaa ggggaggaaau    780 uuugaggca gaagccucugg ccccuaugcc gguggaggcc aauacuuugc aaaaccacga    840
aaccaaggug gcuauggcgg uuccagcagc agcaguagcu auggcaguug cagaagauuu    900
agaucucaua ugcaucucga gugauagucu agaccuucug cggggcuugc cuucuggcca    960
ugcccuucuu cucucccuug caccuguaccc ucuggucu ugaauaaagc cugaguagga   1020
aaaaaaaaaa aaaaaaaaaa aaaaaaaaaa aaaaaaaaaa aaaaaaaaaa aaaaaaaaaa   1080
```

```
                                             -continued aaaaaaaaaa aaaaaaaaaa aaaaaaaaaa aaaaaaaaaa aaaaaaaaaa aaaaaaaaa      1139

<210> SEQ ID NO 29
<211> LENGTH: 1115
<212> TYPE: RNA
<213> ORGANISM: Artificial
<220> FEATURE:
<223> OTHER INFORMATION: hmKO2-M9

<400> SEQUENCE: 29
gggcgaauua agagagaaaa gaagaguaag aagaaauaua agacaccggu cgccaccaug        60
gugaguguga uuaaaccaga gaugaagaug agguacuaca uggacggcuc cgucaauggg       120
caugaguuca caauugaagg ugaaggcaca ggcagaccuu acgagggaca ucaagagaug       180
acacuacgcg ucacaauggc cgagggcggg ccaaugccuu cgcguuuga cuuaguguca       240 cacguguucu guuacggcca cagaguauuu acuaaauauc cagaagagau accagacuau       300
uucaaacaag cauuuccuga aggccuguca ugggaaaggu cguuggaguu cgaagauggu       360 gggccgcuu cagucagugc gcauauaagc cuuagaggaa acaccuucua ccacaaauuc       420
aaauuuacug ggguuaacuu ccugccgau ggccuauca ugcaaaaacca aaguguugau        480 ugggagccau caaccgagaa aauuacugcc agcgacggaa uucugaaggg ugauguuacg       540
auguaccuaa aacuugaagg aggcggcaau cacaaaugcc aaaugaagac uacuuacaag       600
gcggcaaaag agauucuuga aaugccagga gaccauuaca ucggccaucg ccucgucagg       660 aaaccgaag gcaacauuac ugagcaggua gaagaugcag uagcucauuc cagauccaau       720
cagucuucaa auuuuggacc caugaaggga ggaaauuuug gaggcagaag cucuggcccc       780
uauggcggug gaggccaaua cuuugcaaaa ccacgaaacc aaggugggcua uggcgguucc       840 agcagcagca guagcuaugg cagucggcaga agauuuagau cucauaugca ucucgagugga     900 uagucuagac cuucugcggg gcuugccuuc uggccaugcc cuucuucucu cccuugcacc       960
uguaccucuu ggucuuugaa uaaagcccuga guaggaaaaa aaaaaaaaaa aaaaaaaaaa     1020
aaaaaaaaaa aaaaaaaaaa aaaaaaaaaa aaaaaaaaaa aaaaaaaaaa aaaaaaaaaa     1080
aaaaaaaaaa aaaaaaaaaa aaaaaaaaaa aaaaa                                 1115

<210> SEQ ID NO 30
<211> LENGTH: 1157
<212> TYPE: RNA
<213> ORGANISM: Artificial
<220> FEATURE:
<223> OTHER INFORMATION: tagBFP-M9

<400> SEQUENCE: 30
gggcgaauua agagagaaaa gaagaguaag aagaaauaua agacaccggu cgccaccaug        60
ggauccagcg agcugauuaa ggagaacaug cacaugaagc uguacaugga gggcaccgug       120
gacaaccauc acuucaagug cacauccgag ggcgaaggca gcccuacga gggcacccag        180 accaugagaa ucaaggguggu cgagggcggc ccucuccccu ucgccuucga cauccuggcu      240
acuagcuucc ucuacggcag caagaccuuc aucaaccaca cccagggcau ccccgacuuc       300
uucaagcagu ccuucccuga gggcuucaca ugggagagau caccacaua cgaagacggg       360 ggcgugcuga ccgcuacccca ggacaccagc cuccaggacg gcugccucau cuacaacguc      420
aagaucagag ggguaaacuu cacauccaac ggcccuguga ugcagaagaa aacacucggc      480
ugggaggccu ucaccgagac gcuguacccc gcgacggcg gccuggaagg cagaaacgac       540
auggcccuga agcucguggg gcgggagccau cugaucgcaa acaucaagac cacauauaga      600
```

| | | |
|---|---|---|
| uccaagaaac ccgcuaagaa ccucaagaug ccuggcgucu acuaugugga cuacagacug | 660 |
| gaaagaauca aggaggccaa caacgagacc uacgucgagc agcacgaggu ggcaguggcc | 720 |
| agauacugcg accucccuag caaacugggg cacagaucca aucagucuuc aaauuuugga | 780 |
| cccaugaagg gaggaaauuu uggaggcaga agcucuggcc ccuauggcgg uggaggccaa | 840 |
| uacuuugcaa aaccacgaaa ccaagguggc uauggcgguu ccagcagcag caguagcuau | 900 |
| ggcaguggca gaagauuuag aucucauaug caucucgagu gauagucuag accuucgcg | 960 |
| gggcuugccu ucuggccaug cccuucuucu cucccuugca ccuguaccuc uuggucuuug | 1020 |
| aauaaagccu gaguaggaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaa | 1157 |

<210> SEQ ID NO 31
<211> LENGTH: 1902
<212> TYPE: RNA
<213> ORGANISM: Artificial
<220> FEATURE:
<223> OTHER INFORMATION: CBG68luc

<400> SEQUENCE: 31

| | | |
|---|---|---|
| gggcgaauua agagagaaaa gaagaguaag aagaaauaua agacaccggu cgccaccaug | 60 |
| gugaaacgcg aaaagaacgu gaucuacggc ccagaaccac ugcauccacu ggaagaccuc | 120 |
| accgcuggug agaugcucuu ccgagcacug cguaaacaua gucaccccc ucaagcacuc | 180 |
| guggacgucg ugggagacga gagccucucc uacaagaauu uuucgaagc acugugcug | 240 |
| uuggcccaaa gccuccauaa uguggguac aaaaugaacg auguggugag cauuugugcu | 300 |
| gagaauaaca cucgcuucuu uauuccugua aucgcugcuu gguacaucgg caugauuguc | 360 |
| gccccuguga augaaucuua caucccagau gagcugugua agguuauggg uauuagcaaa | 420 |
| ccucaaaucg ucuuuacuac caaaaacauc uugaauaagg ucuggaagu ccagucucgu | 480 |
| acuaacuuca ucaaacgcau cauuauucug gauaccgucg aaaacaucca cggcugugag | 540 |
| agccucccua acuucaucuc ucguuacagc gauguaaua ucgcuaauuu caagcccuug | 600 |
| cauuuugauc cagucgagca aguggccgcu auuugugcu ccuccggcac cacugguuug | 660 |
| ccuaaaggug ucaugcagac ucaccagaau aucugugugc guugauccaa cgcucucgac | 720 |
| ccucgugugg guacucaauu gaucccuggc gugacugugc ugguguaucu gccuuucuuu | 780 |
| cacgccuuug uuucucuau uacccugggc uauucaugg ucggcuugcg ugucaucaug | 840 |
| uuucgucgcu ucgaccaaga agccuucuug aaggcuauuc aagacuacga ggugcguucc | 900 |
| gugaucaacg ucccuucagu cauuuuguuc cugagcaaau uccuuuggu ugacaaguau | 960 |
| gaucugagca gcuugcguga gcugugcugu ggcgcugcuc cuuggccaa agaaguggcc | 1020 |
| gaggucgcug cuaagcgucu gaaccucccu gguauccgcu gcgguuugg uuugacugag | 1080 |
| agcacuucug cuaacaucca uagcuugcga gacgaguuua gucugguag ccugggucgc | 1140 |
| gugacuccuc uuauggcugc aaagaucgcc gaccgugaga ccggcaaagc acugggccca | 1200 |
| aaucaagucg gugaauugug uauuaagggc ccuauggucu cuaaaggcua cgugaacaau | 1260 |
| guggaggcca cuaagaagc cauugaugau gauggcuggc uccauagcgg cgacuucggu | 1320 |
| uacuaugaug aggacgaaca cuucuaugug gucgaucgcu acaagaauu gauuaaguac | 1380 |
| aaaggcucuc aagucgcacc agccgaacug gaagaaauuu ugcugaagaa cccuuguauc | 1440 |

```
cgcgacgugg ccgucgugggu uaucccagac uuggaagcug gcgaguugcc uagcgccuuu   1500 gugguggaaac aacccggcaa ggagaucacu gcuaaggagg cuacgacua uuuggccgag   1560 cgcgugucuc acaccaaaua ucugcgugge ggcguccgcu ucgucgauuc uauuccacgc   1620
aacguuaccg guaagaucac ucguaaagag uugcugaage aacucccega aaaagcuggc   1680 ggcuaguaaa ucuagaccuu cugcggggcu ugccuucugg ccaugcccuu cuucucuccc   1740 uugcaccogu accucuuggu cuuugaauaa agccugagua ggaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aa                      1902
```

<210> SEQ ID NO 32
<211> LENGTH: 1906
<212> TYPE: RNA
<213> ORGANISM: Artificial
<220> FEATURE:
<223> OTHER INFORMATION: alpha(miR-1)-CBRluc

<400> SEQUENCE: 32

```
ggucagauce gcuaggauce auacauacuu cuuuacauuc caagaucuac cggucgccac    60
caugguaaag cgugagaaaa augucaucua uggcccugag ccucuccauc cuuuggagga   120
uuugacugcc ggcgaaaugc guuucgugc ucccgcaag cacucucauu gccucaagc     180 cuuggucgau ggguucggcg augaaucuuu gagcuacaag gaguuuuuug aggcaaccgu   240
cuugcuggcu cagucccucc acaauugugg cuacaagaug aacgacgucg uuaguaucug   300
ugcugaaaac aauaccceguu ucuucauuce agucaucgcc gcaugguaua ucggauugau   360
cguggcucca gucaacgaga gcuacauucc cgacgaacug uguaaagcua ugggguaucuc  420 uaagccacag auugucuuca ccacuaagaa uauucgaac aaaguccugg aagaccaaag    480
ccgcaccaac uuuauuaagc guaucaucau cuuggacacu guggagaaua uucacggaug   540
cgaaucuuug ccuaauuuca ucucucgcua uucagacggc aacaucgcaa cuuuaaaacc   600
acuccacuuc gacccugugg aacaaguugc agccauucug uuagcagcg uacuacugg     660 acucccaaag ggagucaug c agaccccauca aaaacauuugc gugcgucuga uccaugcucu  720 cgauccacge uacggcacuc agcugauucc uggugucacc gucuuggucu acuugccuuu   780
cuuccaugcu uucggcuuuc auauuacuuu ggguuacuuu auggucgguc uccgcgugau   840
uauguuccgc cguuuugauc aggaggcuuu cuugaaagce auccaagauu augaagucag   900
cagugucauc aacgugccua gcugauccu guuuugucu aagagcccac ucguggacaa   960
guacgacuug ucuucacugc gugaauugug uugcggugcc gcuccacugg cuaaggaggu   1020
cgcugaagug gccgccaaac gcuugaaucu ccaggauu cguguggcu ucggccucac    1080 cgaaucuacc agugcgauua uccagacucu cggggaugag uuuaagagcg cucuuuggg   1140 ccguccacu ccacucaugg cugcuaagau cgcugaucgc gaaacuggua aggcuuuggg   1200
cccgaaccaa gugggcgagc uguguaucaa aggcccuaug gugaagcaag guuaugucaa   1260
uaacguugaa gcuaccaagg aggccaucga cgacgacggc ugguugcauu cggugauuu    1320 uggauauuac gacgaagaug agcauuuuua cgucgggau cguucaaagg agcugaucaa    1380
auacaagggu agccagguug cuccagcuga guuggaggag auucuguuga aaauccaug    1440 cauucgcgau gucgcugugg ucggcauucc ugaucggag gccggcgaac ugccuucugc    1500 uuuucguuguc aagcagccug guacagaaau uaccgccaaa gaaguguaug auuaccggc    1560 ugaacgugug agccauacua aguacuugcg uggcggcgug cguuuuguug acuccauccc   1620
```

```
ucguaacgua acaggcaaaa uuacccgcaa ggagcuguug aaacaauugu uggugaaggc    1680
cggcgguuag uaauucuaga ccuucugcgg ggcuugccuu cuggccaugc ccuucuucuc    1740
ucccuugcac cuguaccucu uggucuuuga auaaagccug aguaggaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaa                   1906
```

<210> SEQ ID NO 33
<211> LENGTH: 1907
<212> TYPE: RNA
<213> ORGANISM: Artificial
<220> FEATURE:
<223> OTHER INFORMATION: alpha(miR-17-5p)-CBRluc

<400> SEQUENCE: 33

```
ggucagaucc gcuaggaucc cuaccugcac uguaagcacu uugagaucua ccggucgcca      60
ccaugguaaa gcgugagaaa aaugucaucu auggcccuga gcucuccau ccuuuggagg      120 auuugacugc cggcgaaaug cuguuucgug cucuccgcaa gcacucucau uugccucaag     180
ccuuggucga gugguggcggc gaugaaucuu ugagcuacaa ggaguuuuuu gaggcaaccg    240
ucuugcuggc ucagucccuc cacaauugug gcuacaagau gaacgacguc guuaguaucu    300
gugcugaaaa caauccccgu ucuucauuc cagucaucgc cgcauggauau aucgguauga    360 ucguggcucc agucaacgag agcuacauuc ccgacgaacu guguaaaguc auggguaucu    420
cuaagccaca gauugucuuc accacuaaga auauucugaa caaaguccug gaaguccaaa    480
gccgcaccaa cuuuauuaag cguaucauca ucuuggacac uguggagaau auucacgguu    540
gcgaaucuuu gccuaauuuc aucucucgcu auucagacgg caacaucgca aacuuuaaac    600
cacuccacuu cgacccugug gaacaauugg cagccauucu guguagcagc gguacuacug    660
gacucccaaa gggagucaug cagacccauc aaaacauuug cgugcgcucug auccaugcuc    720 ucgauccacg cuacggcacu cagcugauuc cuggugucac cgucugguc uacuugccuu    780 ucuuccaugc uuucggcuuu caauauuacu ugggguacuu uauggucggu ucccgcguga    840
uuauguuccg ccguuuugau caggaggcuu cuuugaaagc cauccaagau uaugaagucc    900
gcagugucau caacgugccu agcgugaucc uguuuuugcu aagagccca cucguggaca    960 aguacgacuu gucuucacug cgugaauugu guugcggugc cgcuccacug gcuaaggagg   1020
ucgcugaagu ggccgccaaa cgcuugaauc uuccagggau cguguggc uucggccuca    1080 ccgaaucuac cagugcgauu auccagacuc ucgggaugc guuuaagagc ggcucuuugg   1140
gccgugucac uccacucaug gcugcuaaga ucgcugaucg cgaaacuggu aaggcuuugg  1200
gcccgaacca aguggggcgag cuguguauca aggcccuau ggagcaag gguuaugca     1260 auaacguuga agcuaccaag gaggccaucg acgacgacgg cuggCugcau ucuggugauu   1320
uuggauauua cgacgaagau gagcauuuuu acgucgguggga ucguuacaag gagcugauca   1380
aaucaagggg uagccagguu gcuccagcug aguggaggga gauucuguug aaaaauccau   1440
gcauucgcga ugucgcugug ucggcauuc ugauucugga ggccggcgaa cugccuucug   1500
cuuucguugu caagcagccu gguacagaaa uuaccgccaa agaaguguau gauuaccugg  1560
cugaacgugu gagccauacu aaguacuugc guggcggcgu gcguuuguu gacuccaucc   1620 cucguaacgu acaggcaaaa auucccgca aggagcuguu gaaacaauug uuggugaagg  1680
ccggcgguua guauucuag accuucugcg gggcuugccu ucuggccaug cccuucuucu   1740
```

| | |
|---|---:|
| cucccuugca ccuguaccuc uuggucuuug aauaaagccu gaguaggaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaa aaaaaaa | 1907 |

<210> SEQ ID NO 34
<211> LENGTH: 1906
<212> TYPE: RNA
<213> ORGANISM: Artificial
<220> FEATURE:
<223> OTHER INFORMATION: alpha(miR-21-5p)-CBRluc

<400> SEQUENCE: 34

| | |
|---|---:|
| ggucagaucc gcuaggaucc ucaacaucag ucugauaagc uaagaucuac cggucgccac | 60 |
| cauguaaag cgugagaaaa augucaucua uggcccugag ccucuccauc cuuuggagga | 120 |
| uuugacugcc ggcgaaaugc cguuucgugc ucuccgcaag cacucucauu ugccucaagc | 180 |
| cuuggucgau guggucggcg augaaucuuu gagcuacaag gaguuuuuug aggcaaccgu | 240 |
| cuugcuggcu cagucccucc acaauugggg cuacaagaug aacgacgucg uuaguaucug | 300 |
| ugcugaaaac aauacccguu ucuucauucc agucaucgcc gcauguauau cgguaugau | 360 |
| cguggccuca gucaacgaga gcuacauucc cgacgaacug guaaaguca ugggauacuc | 420 |
| uaagccacag auugucuuca ccacuaagaa uauucugaac aaaguccugg aaguccaaag | 480 |
| ccgcaccaac uuuauuaagc guaucaucau cuuggacacu guggagaaua uucacguuug | 540 |
| cgaaucuuug ccuaauuuca ucucucgcua uucagacggc aacaucgcaa acuuuaaacc | 600 |
| acuccacuuc gacccugugg aacaaguugc agccauucug guagcagcg guacuacugg | 660 |
| acucccaaag ggagucaugc agacccauca aaacauuugc gugcgucuga uccaugcucu | 720 |
| cgauccacgc uacggcacuc agcugauucc uggugucacc gucuuggucu acuugccuuu | 780 |
| cuuccaugcu uucggcuuuc auauuacuuu ggguuacuuu auggucgguc uccgcgugau | 840 |
| uauguuccgc cguuuugauc aggaggcuuu cuugaaagcc auccaagauu augaagcccg | 900 |
| cagugucauc aacgugccua gcgugauccu guuuuugucu aagagcccac ucguggacaa | 960 |
| guacgacuuu cuucacugcg cugaauugu uugcggugcc gcuccacugg cuaaggaggu | 1020 |
| cgcugaagug gccgccaaac gcuugaaucu ccagggauu cguuguggcu ucggccucac | 1080 |
| cgaaucuacc agugcgauua uccagacucu cggggaugag uuuagagcg gcucuuuggg | 1140 |
| ccgugucacu ccacucaugg cugcuaagau cgcugaucgc gaaacgguaa aggcuuuggg | 1200 |
| cccgaaccaa gugggcgagc uguguaucaa aggcccuaug gugagcaagg guuaugucaa | 1260 |
| uaacguugaa gcuaccaagg aggccaucga cgacgacggc ugguugcauu cggugauuu | 1320 |
| uggauauuac gacgaagaug agcauuuuua cgucgggau cguuacaagg agcugaucaa | 1380 |
| auacaagggu agccagguug cuccagcuga guuggaggag auucuguuga aaauccaug | 1440 |
| cauucgcgau gucgcugugg ucggcauucc ugaucggag ccggcgaac ugccuucugc | 1500 |
| uuucguuguc aagcagccug guacagaaau uaccgccaaa gaaguguaug auuaccuggc | 1560 |
| ugaacgugug agccauacua aguacuugcg uggcggcgug cguuugguug acuccaucc | 1620 |
| ucguaacgua acaggcaaaa uuacccgcaa ggagcuguuu aaacaauugu ggugaaggc | 1680 |
| cggcggguuag uaauucuaga ccuucugcgg ggcuugccuu cuggccaugc ccuucuucuc | 1740 |
| ucccuugcac cuguaccucu uggucuuuga auaaagccug aguaggaaa aaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaa aaaaaa | 1906 |

<210> SEQ ID NO 35
<211> LENGTH: 1906
<212> TYPE: RNA
<213> ORGANISM: Artificial
<220> FEATURE:
<223> OTHER INFORMATION: alpha(miR-92a-3p)-CBRluc

<400> SEQUENCE: 35

| | | | | | |
|---|---|---|---|---|---|
| ggucagaucc | gcuaggaucc | acaggccggg | acaagugcaa | uaagaucuac | cggucgccac | 60 |
| caugguaaag | cgugagaaaa | augucaucua | uggcccugag | ccucuccauc | cuuuggagga | 120 |
| uuugacugcc | ggcgaaaugc | uguuucgugc | ucuccgcaag | cacucucauu | ugccucaagc | 180 |
| cuuggucgau | guggucggcg | augaaucuuu | gagcuacaag | gaguuuuuug | aggcaaccgu | 240 |
| cuugcuggcu | caguccucc | acaauugugg | cuacaagaug | aacgacgucg | uuaguaucug | 300 |
| ugcugaaaac | aauacccguu | ucuucauccc | agucaucgcc | gcaugguaua | ucgguaugau | 360 |
| cguggcaucca | gucaacgaga | gcuacauucc | cgacgaacug | uguaaaguca | ugggauaucuc | 420 |
| uaagccacag | auugucuuca | ccacuaagaa | uauucugaac | aaaguccugg | aaguccaaag | 480 |
| ccgcaccaac | uuuauuaagc | guacaucau | cuuggacacu | gggagaauaa | uucacgguug | 540 |
| cgaaucuuug | ccuaauuuca | ucucucgcua | uucagacggc | aacaucgcaa | acuuuaaacc | 600 |
| acuccacuuc | gacccugugg | aacaaguugc | agccauucug | uguagcagcg | guacuacugg | 660 |
| acucccaaag | ggagucaugc | agacccauca | aaacauuugc | gugcgucuga | uccaugcucu | 720 |
| cgauccacgc | uacggcacuc | agcugauucc | ugguguccacc | gucuggcucu | acuugccuuu | 780 |
| cuuccaugcu | uucggcuuuc | auauuacuuu | ggguuacuuu | auggucgguc | uccgcgugau | 840 |
| uauguuccgc | cguuuugauc | aggaggcuuu | cuugaaagcc | auccaagauu | augaagucccg | 900 |
| cagugucauc | aacgugccua | gcgugauccu | guuuuugucu | aagagcccac | ucguggacaa | 960 |
| guacgacuug | ucuucacugc | gugaauugu | uugcggugcc | gcuccacugg | cuaaggaggu | 1020 |
| cgcugaagug | gccgccaaac | gcuugaaucu | uccagggauu | cguguggcu | ucggccucac | 1080 |
| cgaaucuacc | agugcgauua | uccagacucu | cggggaugag | uuuaagagcg | gcucuuuggg | 1140 |
| ccgugucacu | ccacucaugg | cugcuaagau | cgcugaucgc | gaaacuggua | aggcuuuggg | 1200 |
| cccgaaccaa | guggggcgagc | uguguaucaa | aggcccuaug | gugagcaagg | guuaugucaa | 1260 |
| uaacguugaa | gcuaccaagg | aggccaucga | cgacgacgcc | ugguugcauu | cggugauuu | 1320 |
| uggauauuac | gacgaagaug | agcauuuuua | cgucgggau | cguuacaagg | agcugaucaa | 1380 |
| auacaagggu | agccagguug | ucccagcuga | guuggaggga | auucguuga | aaaauccaug | 1440 |
| cauucgcgau | gucgcugugg | ucggcauucc | ugaucggag | gccggcgaac | ugccuucugc | 1500 |
| uuucguuguc | aagcagccug | guacagaaau | uaccgccaaa | gaaguguaug | auuaccuggc | 1560 |
| ugaacgugug | agccauacua | aguacuugcg | uggcggcgug | cguuuguug | acuccaucc | 1620 |
| ucguaacgua | acaggcaaaa | uuacccgcaa | ggagcuguuu | aaacaauugu | ggugaaggc | 1680 |
| cggcgguuag | uaauucuaga | ccuucugcgg | ggcuugccuu | cuggccaugc | ccuucuucuc | 1740 |
| ucccuugcac | cuguaccucu | uggcuuuuga | auaaagccug | aguaggaaaa | aaaaaaaaaa | 1800 |
| aaaaaaaaaa | aaaaaaaaaa | aaaaaaaaaa | aaaaaaaaaa | aaaaaaaaaa | aaaaaaaaaa | 1860 |
| aaaaaaaaaa | aaaaaaaaaa | aaaaaaaaaa | aaaaaaaaaa | aaaaaa | | 1906 |

<210> SEQ ID NO 36
<211> LENGTH: 1906
<212> TYPE: RNA

<213> ORGANISM: Artificial
<220> FEATURE:
<223> OTHER INFORMATION: alpha(miR-24-3p)-CBRluc

<400> SEQUENCE: 36

```
ggucagaucc gcuaggaucc cuguuccugc ugaacugagc caagaucuac cggucgccac     60
caugguaaag cgugagaaaa augucaucua uggcccugag ccucuccauc cuuuggagga    120
uuugacugcc ggcgaaaugc uguuucgugc ucuccgcaag cacucucauu gccucaagc    180
cuuggucgau guggucggcg augaaucuuu gagcuacaag gaguuuuuug aggcaaccgu    240
cuugcuggcu cagucccucc acaauugugg cuacaagaug aacgacgucg uuaguaucug    300
ugcugaaaac aauacccguu ucuucauccc agucaucgcc gcaugguaua ucgguaugau    360
cguggcucca gucaacgaga gcuacauccc cgacgaacug uguaaaguca ugggguaucuc   420
uaagccacag auugucuuca ccacuaagaa uauucugaac aaaguccugg aaguccaaag    480
ccgcaccaac uuuauuaagc guaucaucau cuuggacacu guggagaaua uucacgguug    540
cgaaucuuug ccuaauuuca ucucucgcua uucagacggc aacaucgcaa acuuuaaacc    600
acuccacuuc gacccugugg aacaaguugc agccauucug uguagcagcg guacuacugg    660
acucccaaag ggagucaugc agacccauca aaacauuugc gugcgucuga uccaugcucu    720
cgauccacgc uacggcacuc agcgauuccc ugguguacc gucuuggucu acuugccuuu    780
cuuccaugcu uucggcuuuc auauuacuuu ggguuacuuu auggucgguc uccgcgugau    840
uauguuccgc cguuugauc aggaggcuuu cuugaaagcc auccaagauu augaaguccg    900
cagugucauc aacgugccua gcugauccu guuuugucu aagagcccac ucguggacaa     960
guacgacuug ucuucacugc gugaauugug uugcggugcc gcuccacugg cuaaggaggu   1020
cgcugaagug gccgccaaac gcuugaaucu uccagggauu cguuggcu ucggccucac    1080
cgaaucuacc agugcgauua uccagacucu cggggaugag uuuaagagcg cucuuuggg    1140
ccgucacu ccacucaugg cugcuaagau cgcugaucgc gaaacuggua aggcuuuggg     1200
cccgaaccaa guggggcgagc uguguaucaa aggcccuaug gugagcaagg guuaugucaa   1260
uaacguugaa gcuaccaagg aggccaucga cgacgacggc ugguugcauu cggugauuu    1320
uggauauuac gacgaagaug agcauuuuua cgucguggau cguuacaagg agcugaucaa   1380
auacaagggu agccagguug cuccagcuga guuggaggag auucuguuga aaaauccaug    1440
cauucgcgau gucgcugugg ucggcauucc ugaucuggag gccggcgaac ugccuucugc    1500
uuucguuguc aagcagccug guacagaaau uaccgccaaa gaaguguaug auuaccggc    1560
ugaacgugug agccauacua aguacuugcg uggcggcgug cguuugugu acuccaucc    1620
ucguaacgua acaggcaaaa uuacccgcaa ggagcguuu aaacaauugu ggguugaaggc   1680
cggcgguuag uaauucuaga ccuucugcgg ggcuugccuu cuggccaugc ccuucuucuc    1740
ucccuugcac cuguaccucu uggcuuuga auaaagccug aguaggaaaa aaaaaaaaa    1800
aaaaaaaaa aaaaaaaaaa aaaaaaaaa aaaaaaaaaa aaaaaaaaaa aaaaaaaaaa   1860
aaaaaaaaa aaaaaaaaaa aaaaaaaaa aaaaaaaaaa aaaaaa               1906
```

<210> SEQ ID NO 37
<211> LENGTH: 1906
<212> TYPE: RNA
<213> ORGANISM: Artificial
<220> FEATURE:
<223> OTHER INFORMATION: alpha(miR-127b-3p)-CBRluc

<400> SEQUENCE: 37

```
ggucagaucc gcuaggaucc agccaagcuc agacggaucc gaagaucuac cggucgccac      60 cauggugaaag cgugagaaaa augucaucua uggcccugag ccucuccauc cuuuggagga    120
uuugacugcc ggcgaaaugc uguuucgugc ucuccgcaag cacucucauu gccucaagc     180 cuuggucgau guggucggcg augaaucuuu gagcuacaag gaguuuuuug aggcaaccgu    240
cuugcuggcu caguccccuc acaauugugg cuacaagaug aacgacgucg uuaguaucug    300
ugcugaaaac aauacccguu ucuucauucc agucaucgcc gcaugguaua ucggguaugau 360 cguggcucca gucaacgaga gcuacauucc cgacgaacug uguaaaguca ugggguaucuc 420 uaagccacag auugucuuca ccacuaagaa uauucgaac aaaguccugg aaguccaaag    480
ccgcaccaac uuuauuaagc guaucaucau cuuggacacu guggagaaua uucacgguug    540
cgaaucuuug ccuaauuuca ucucucgcua uucagacggc aacaucgcaa acuuaaaacc    600
acuccacuuc gacccugugg aacaaguugc agccauucug guagcagcg guacuacugg    660 acucccaaag ggagucaugc agacccauca aaacauuugc gugcgucuga uccaugcucu    720
cgauccacgc uacggcacuc agcugauucc uggugucacc gucuuggucu acuugccuuu    780
cuuccaugcu uucggcuuuc auauuacuuu gggguuacuuu auggucgguc uccgcgugau    840
uauguuccgc cguuugauc aggaggcuuu cuugaaagcc auccaagauu augaaguccg    900
cagugucauc aacgugccua gcgugauccu guuuugucu aagagcccac ucgugggacaa    960 guacgacuug ucuucacugc gugaauugug uugcggugcc gcuccacugg cuaaggaggu 1020
cgcugaagug gccgccaaac gcuugaaucu ccaggaggauu cguguggcu ucggccucac  1080 cgaaucuacc agugcgauua uccagacucu cggggaaugag uuuaagagcg gcucuuuggg 1140
ccgugucacu ccacucaugg cugcuaagau cgcugaucgc gaaacuggua aggcuuuggg 1200
cccgaaccaa gugggcgagc uguguaucaa aggcccuaug gugagcaagg guuaugucaa 1260
uaacguugaa gcuaccaagg aggccaucga cgacgacggc ugguugcauu cggugauuu   1320 uggauauuac gacgaagaug agcauuuuua cgucguggau cguacaagg agcugaucaa  1380 auacaagggu agccagguug ccucagcuga guuggaggag auucuguuga aaaauccaug 1440
cauucgcgau gucgcugugg ucggcauuccc ugaucuggag gccggcgaac ugccuucugc 1500
uuucguuguc aagcagccug guacagaaau uaccgccaaa gaaguguauug auuaccuggc 1560 ugaacgugug agcauacua aguacuugcg uggcggcgug cguuuguug acuccauccc    1620 ucguaacgua acaggcaaaa uuacccgcaa ggagcuguug aaacaauuug uggugaaggc 1680 cggcggguuag uaauucuaga ccuucugcgg ggcuugccuu cuggccaugc ccuucuucuc 1740
ucccuugcac cuguaccucu uggucuuuga auaaagccug aguaggaaaa aaaaaaaaaaa 1800 aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaa               1906
```

<210> SEQ ID NO 38
<211> LENGTH: 1906
<212> TYPE: RNA
<213> ORGANISM: Artificial
<220> FEATURE:
<223> OTHER INFORMATION: alpha(miR-16-5p)-CBRluc

<400> SEQUENCE: 38

```
ggucagaucc gcuaggaucc cgccaauauu uacgugcugc uaagaucuac cggucgccac     60 cauggugaaag cgugagaaaa augucaucua uggcccugag ccucuccauc cuuuggagga   120
```

| | |
|---|---:|
| uuugacugcc ggcgaaaugc uguuucgugc ucuccgcaag cacucucauu ugccucaagc | 180 |
| cuuggucgau guggucggcg augaaucuuu gagcuacaag gaguuuuuug aggcaaccgu | 240 |
| cuugcuggcu cagucccucc acaauugugg cuacaagaug aacgacgucg uuaguaucug | 300 |
| ugcugaaaac aauacccguu ucuucauucc agucaucgcc gcaugguaua ucgguaugau | 360 |
| cguggcucca gucaacgaga gcuacauucc cgacgaacug uguaaaguca uggguaucuc | 420 |
| uaagccacag auugucuuca ccacuaagaa uauucgaac aaagcccugg aagcccaaag | 480 |
| ccgcaccaac uuuauuaagc guaucaucau cuuggacacu guggagaaua uucacgguug | 540 |
| cgaaucuuug ccuaauuuca ucucgcua uucagacggc aacaucgcaa acuuuaaacc | 600 |
| acuccacuuc gacccugugg aacaaguugc agccauucug uagcagcg uacuacugg | 660 |
| acucccaaag ggagucaugc agacccauca aaacauuugc gugcgucuga uccaugcucu | 720 |
| cgauccacgc uacggcacuc agcugauucc ugguguacc gucuuggucu acuugccuuu | 780 |
| cuuccaugcu uucggcuuuc auauuacuuu ggguuacuuu auggucgguc uccgcgugau | 840 |
| uauguuccgc cguuugauc aggaggcuuu cuugaaagcc auccaagauu augaagauccg | 900 |
| cagugucauc aacgugccua gcgugauccu guuuugucu aagagcccac ucgugacaa | 960 |
| guacgacuug ucuucacugc gugaauugug uugcggugcc gcuccacugg cuaaggaggu | 1020 |
| cgcugaagug ccgccaaac gcuugaaucu ccagggauu cguuguggcu ucggccucac | 1080 |
| cgaaucuacc agugcgauua ccagacucu cggggaugau uuuagagcg gcucuuggg | 1140 |
| ccgugucacu ccacucaugg cugcuaagau cgcugaucgc gaaacuggua aggcuuggg | 1200 |
| cccgaaccaa gugggcgagc uguguaucaa aggcccuaug gugagcaagg guuaugucaa | 1260 |
| uaacguugaa gcuaccaagg aggccaucga cgacgacggc ugguugcauu cuggugauuu | 1320 |
| uggauauuac gacgaagaug agcauuuuua cgucgugggau cguuacaagg agcugaucaa | 1380 |
| auacaagggu agccagguug cuccagcuga guugaggag auucguguga aaaauccaug | 1440 |
| cauucgcgau gucgcugugg ucggcauucc ugaucuggag gccggcgaac ugccuucugc | 1500 |
| uuucguuguc aagcagccug guacagaaau uaccgccaaa gaagguauag auuaccuggc | 1560 |
| ugaacgugug agccauacua aguacuuagcg uggcggcgug cguuugug acuccauccc | 1620 |
| ucguaacgua acaggcaaaa uuacccgcaa ggagcuguug aaacaauugu ggugaaggc | 1680 |
| cggcgguuag uaauucuaga ccuucugcgg ggcuugccuu cuggccaugc ccuucuucuc | 1740 |
| ucccuugcac cuguaccucu ggucuuuga auaaagccug aguaggaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaa | 1906 |

<210> SEQ ID NO 39
<211> LENGTH: 1906
<212> TYPE: RNA
<213> ORGANISM: Artificial
<220> FEATURE:
<223> OTHER INFORMATION: alpha(miR-203a)-CBRluc

<400> SEQUENCE: 39

| | |
|---|---:|
| ggucagaucc gcuaggaucc cuagugguccc uaaacauuuc acagaucuac cggucgccac | 60 |
| caugguaaag cgugagaaaa augucaucua uggcccugag ccucuccauc cuuuggagga | 120 |
| uuugacugcc ggcgaaaugc uguuucgugc ucuccgcaag cacucucauu ugccucaagc | 180 |
| cuuggucgau guggucggcg augaaucuuu gagcuacaag gaguuuuuug aggcaaccgu | 240 |
| cuugcuggcu cagucccucc acaauugugg cuacaagaug aacgacgucg uuaguaucug | 300 |

```
ugcugaaaac aauacccguu ucuucauucc agucaucgcc gcauggauaua ucgguaugau    360 cguggcucca gucaacgaga gcuacauccc cgacgaacug uguaaaguca uggguaucuc    420
uaagccacag auugucuuca ccacuaagaa uauucugaac aaaguccugg aaguccaaag    480
ccgcaccaac uuuauuaagc guaucaucau cuuggacacu guggagaaua uucacgguug    540
cgaaucuuug ccuaauuuca ucucucgcua uucagacggc aacaucgcaa acuuuaaacc    600
acuccacuuc gacccugugg aacaaguugc agccauucug guagcagcg guacuacugg    660 acucccaaag ggagucaugc agacccauca aaacauuugc gugcgucuga uccaugcucu    720
cgauccacgc uacggcacuc agcugauccc ugguguuacc gucuuggucu acuugccuuu    780
cuuccaugcu uucggcuuuc auauuacuuu ggguuacuuu augguucggc uccgcgugau    840
uauguuccgc cguuuugauc aggaggcuuu cuugaaagcc auccaagauu augaaguccg    900
cagugucauc aacgugccua gcgugauccu guuuugucu aagagcccac ucguggacaa    960
guacgacuug ucuucacugc gugaauugu uugcggugcc gcuccacugg cuaaggaggu   1020
cgcugaagug gccgccaaac gcuugaaucu uccagggauu cguguggcu ucggccucac    1080 cgaaucuacc agugcgauua uccagacucu cggggaugag uuuaagagcg gcucuuuggg   1140
ccgugucacu ccacucaugg cugcuaagau cgcugaucgc gaaacuggua aggcuuuggg   1200
cccgaaccaa gugggcgagc uguguaucaa aggcccuaug gugagcaagg guuaugucaa   1260
uaacguugaa gcuaccaagg aggccaucga cgacgacggc ugguugcauu cggugauuu    1320 uggauauuac gacgaagaug agcauuuuua cgucgugau cguuacaagg agcugaucaa   1380
auacaagggu agccagguug cuccagcuga guuggaggag auucuguuga aaauccaug   1440 cauucgcgau gucgcugugg ucggcauucc ugaucggag gccggcgaac ugccuucugc   1500
uuucguuguc aagcagccug guacagaaau uaccgccaaa gaaguguaug auuaccuggc   1560
ugaacgugug agccauacua aguacuugcg uggcggcgug cguuuuguug acuccauccc   1620
ucguaacgua acaggcaaaa uuacccgcaa ggagcuguug aaacaauugu uggugaaggc   1680
cggcgguuag uaauucuaga ccuucugcgg ggcuugccuu cuggccaugc ccuucuucuc   1740
ucccuugcac cuguacccu uggucuuuga auaaagccug aguaggaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaa                 1906

<210> SEQ ID NO 40
<211> LENGTH: 35
<212> TYPE: DNA
<213> ORGANISM: Artificial
<220> FEATURE:
<223> OTHER INFORMATION: FwdEGFP

<400> SEQUENCE: 40
caccggtcgc caccatggga tccgtgagca agggc                              35

<210> SEQ ID NO 41
<211> LENGTH: 45
<212> TYPE: DNA
<213> ORGANISM: Artificial
<220> FEATURE:
<223> OTHER INFORMATION: RevEGFP

<400> SEQUENCE: 41
gccccgcaga aggtctagac ctacttgtac agctcgtcca tgccg                   45
```

<210> SEQ ID NO 42
<211> LENGTH: 29
<212> TYPE: DNA
<213> ORGANISM: Artificial
<220> FEATURE:
<223> OTHER INFORMATION: FwdtagBFP

<400> SEQUENCE: 42
caccggtcgc caccatggga tccagcgag                                29

<210> SEQ ID NO 43
<211> LENGTH: 45
<212> TYPE: DNA
<213> ORGANISM: Artificial
<220> FEATURE:
<223> OTHER INFORMATION: RevtagBFP

<400> SEQUENCE: 43
gccccgcaga aggtctagac tatcactcga gatgcatatg agatc               45

<210> SEQ ID NO 44
<211> LENGTH: 36
<212> TYPE: DNA
<213> ORGANISM: Artificial
<220> FEATURE:
<223> OTHER INFORMATION: FwdhmAG1

<400> SEQUENCE: 44
caccggtcgc caccatggtg agcgtgatca agcccg                         36

<210> SEQ ID NO 45
<211> LENGTH: 39
<212> TYPE: DNA
<213> ORGANISM: Artificial
<220> FEATURE:
<223> OTHER INFORMATION: RevhmAG1

<400> SEQUENCE: 45
gccccgcaga aggtctagat tcacttggcc tggctgggc                      39

<210> SEQ ID NO 46
<211> LENGTH: 41
<212> TYPE: DNA
<213> ORGANISM: Artificial
<220> FEATURE:
<223> OTHER INFORMATION: FwdhmKO2

<400> SEQUENCE: 46
caccggtcgc caccatggtg agtgtgatta aaccagagat g                   41

<210> SEQ ID NO 47
<211> LENGTH: 50
<212> TYPE: DNA
<213> ORGANISM: Artificial
<220> FEATURE:
<223> OTHER INFORMATION: RevhmKO2

<400> SEQUENCE: 47
gccccgcaga aggtctagat tcaggaatga gctactgcat cttctacctg          50

<210> SEQ ID NO 48
<211> LENGTH: 35
<212> TYPE: DNA
<213> ORGANISM: Artificial
<220> FEATURE:
<223> OTHER INFORMATION: FwdhdKeimaRed

```
<400> SEQUENCE: 48
caccggtcgc caccatggtg agcgtgatcg ccaag                          35

<210> SEQ ID NO 49
<211> LENGTH: 39
<212> TYPE: DNA
<213> ORGANISM: Artificial
<220> FEATURE:
<223> OTHER INFORMATION: RevhdKeimaRed

<400> SEQUENCE: 49
gccccgcaga aggtctagat tcagcccagc aggctgtgc                      39

<210> SEQ ID NO 50
<211> LENGTH: 45
<212> TYPE: DNA
<213> ORGANISM: Artificial
<220> FEATURE:
<223> OTHER INFORMATION: RevM9

<400> SEQUENCE: 50
gccccgcaga aggtctagac tatcactcga gatgcatatg agatc               45

<210> SEQ ID NO 51
<211> LENGTH: 28
<212> TYPE: DNA
<213> ORGANISM: Artificial
<220> FEATURE:
<223> OTHER INFORMATION: T7Fwd5UTR

<400> SEQUENCE: 51
cagtgaattg taatacgact cactatag                                  28

<210> SEQ ID NO 52
<211> LENGTH: 37
<212> TYPE: DNA
<213> ORGANISM: Artificial
<220> FEATURE:
<223> OTHER INFORMATION: Rev5UTR

<400> SEQUENCE: 52
catggtggcg accggtgtct tatatttctt cttactc                        37

<210> SEQ ID NO 53
<211> LENGTH: 87
<212> TYPE: DNA
<213> ORGANISM: Artificial
<220> FEATURE:
<223> OTHER INFORMATION: temp5UTR

<400> SEQUENCE: 53
cagtgaattg taatacgact cactataggg cgaattaaga gagaaaagaa gagtaagaag   60
aaatataaga caccggtcgc caccatg                                      87

<210> SEQ ID NO 54
<211> LENGTH: 19
<212> TYPE: DNA
<213> ORGANISM: Artificial
<220> FEATURE:
<223> OTHER INFORMATION: Fwd3UTR

<400> SEQUENCE: 54
tctagacctt ctgcggggc                                            19
```

```
<210> SEQ ID NO 55
<211> LENGTH: 48
<212> TYPE: DNA
<213> ORGANISM: Artificial
<220> FEATURE:
<223> OTHER INFORMATION: Rev3UTR

<400> SEQUENCE: 55
tttttttttt tttttttttt cctactcagg ctttattcaa agaccaag           48

<210> SEQ ID NO 56
<211> LENGTH: 92
<212> TYPE: DNA
<213> ORGANISM: Artificial
<220> FEATURE:
<223> OTHER INFORMATION: temp3UTR

<400> SEQUENCE: 56
tctagacctt ctgcggggct tgccttctgg ccatgcccett cttctctccc ttgcacctgt    60
acctcttggt ctttgaataa agcctgagta gg                                  92

<210> SEQ ID NO 57
<211> LENGTH: 38
<212> TYPE: DNA
<213> ORGANISM: Artificial
<220> FEATURE:
<223> OTHER INFORMATION: T7FwdA

<400> SEQUENCE: 57
gctaatacga ctcactatag gtcagatccg ctaggatc                       38

<210> SEQ ID NO 58
<211> LENGTH: 39
<212> TYPE: DNA
<213> ORGANISM: Artificial
<220> FEATURE:
<223> OTHER INFORMATION: T7FwdB

<400> SEQUENCE: 58
gctaatacga ctcactatag gttccttaat cgcggatcc                      39

<210> SEQ ID NO 59
<211> LENGTH: 139
<212> TYPE: DNA
<213> ORGANISM: Artificial
<220> FEATURE:
<223> OTHER INFORMATION: Rev120A

<400> SEQUENCE: 59
tttttttttt tttttttttt tttttttttt tttttttttt tttttttttt tttttttttt    60
tttttttttt tttttttttt tttttttttt tttttttttt tttttttttt tttttttttt   120
cctactcagg ctttattca                                                139

<210> SEQ ID NO 60
<211> LENGTH: 60
<212> TYPE: DNA
<213> ORGANISM: Artificial
<220> FEATURE:
<223> OTHER INFORMATION: FwdMCS

<400> SEQUENCE: 60
gggatcccat ggtgtcgacc tgcagcatat gagctcctga attcgcccta tagtgagtcg    60
```

```
<210> SEQ ID NO 61
<211> LENGTH: 63
<212> TYPE: DNA
<213> ORGANISM: Artificial
<220> FEATURE:
<223> OTHER INFORMATION: RevMCS

<400> SEQUENCE: 61
gggagatctc atatgcatct cgagtgatag tctagacaag cttgagtatt ctatagtgtc      60
acc                                                                   63

<210> SEQ ID NO 62
<211> LENGTH: 43
<212> TYPE: DNA
<213> ORGANISM: Artificial
<220> FEATURE:
<223> OTHER INFORMATION: Code5UTR

<400> SEQUENCE: 62
aattaagaga gaaagaaga gtaagaagaa atataagagc cac                        43

<210> SEQ ID NO 63
<211> LENGTH: 43
<212> TYPE: DNA
<213> ORGANISM: Artificial
<220> FEATURE:
<223> OTHER INFORMATION: Comp5UTR

<400> SEQUENCE: 63
catggtggct cttatatttc ttcttactct tcttttctct ctt                       43

<210> SEQ ID NO 64
<211> LENGTH: 92
<212> TYPE: DNA
<213> ORGANISM: Artificial
<220> FEATURE:
<223> OTHER INFORMATION: Code3UTR

<400> SEQUENCE: 64
ctagaccttc tgcggggctt gccttctggc catgcccttc ttctctccct tgcacctgta      60
cctcttggtc tttgaataaa gcctgagtag ga                                   92

<210> SEQ ID NO 65
<211> LENGTH: 92
<212> TYPE: DNA
<213> ORGANISM: Artificial
<220> FEATURE:
<223> OTHER INFORMATION: Comp3UTR

<400> SEQUENCE: 65
agcttcctac tcaggcttta ttcaaagacc aagaggtaca ggtgcaaggg agagaagaag      60
ggcatggcca gaaggcaagc cccgcagaag gt                                   92

<210> SEQ ID NO 66
<211> LENGTH: 34
<212> TYPE: DNA
<213> ORGANISM: Artificial
<220> FEATURE:
<223> OTHER INFORMATION: CFwdtagRFP

<400> SEQUENCE: 66
gccaccatgg gatccgtgtc taagggcgaa gagc                                 34

<210> SEQ ID NO 67
```

```
<211> LENGTH: 30
<212> TYPE: DNA
<213> ORGANISM: Artificial
<220> FEATURE:
<223> OTHER INFORMATION: CRevtagRFP

<400> SEQUENCE: 67
gctcgagatc tattaagttt gtgccccagt                                     30

<210> SEQ ID NO 68
<211> LENGTH: 36
<212> TYPE: DNA
<213> ORGANISM: Artificial
<220> FEATURE:
<223> OTHER INFORMATION: CFwdtagBFP

<400> SEQUENCE: 68
gccaccatgg gatccagcga gctgattaag gagaac                              36

<210> SEQ ID NO 69
<211> LENGTH: 28
<212> TYPE: DNA
<213> ORGANISM: Artificial
<220> FEATURE:
<223> OTHER INFORMATION: CRevtagBFP

<400> SEQUENCE: 69
actcgagatc tgtgccccag tttgctag                                       28

<210> SEQ ID NO 70
<211> LENGTH: 34
<212> TYPE: DNA
<213> ORGANISM: Artificial
<220> FEATURE:
<223> OTHER INFORMATION: CFwdhmAG1

<400> SEQUENCE: 70
gccaccatgg gatccgtgag cgtgatcaag cccg                                34

<210> SEQ ID NO 71
<211> LENGTH: 26
<212> TYPE: DNA
<213> ORGANISM: Artificial
<220> FEATURE:
<223> OTHER INFORMATION: CRevhmAG1

<400> SEQUENCE: 71
tatgagatct cttggcctgg ctgggc                                         26

<210> SEQ ID NO 72
<211> LENGTH: 39
<212> TYPE: DNA
<213> ORGANISM: Artificial
<220> FEATURE:
<223> OTHER INFORMATION: CFwdhmKO2

<400> SEQUENCE: 72
gccaccatgg gatccgtgag tgtgattaaa ccagagatg                           39

<210> SEQ ID NO 73
<211> LENGTH: 37
<212> TYPE: DNA
<213> ORGANISM: Artificial
<220> FEATURE:
<223> OTHER INFORMATION: CRevhmKO2

<400> SEQUENCE: 73
```

```
tatgagatct ggaatgagct actgcatctt ctacctg                              37
```

<210> SEQ ID NO 74
<211> LENGTH: 38
<212> TYPE: DNA
<213> ORGANISM: Artificial
<220> FEATURE:
<223> OTHER INFORMATION: FwdM9

<400> SEQUENCE: 74

```
gagatccatg ggatccaatc agtcttcaaa ttttggac                             38
```

<210> SEQ ID NO 75
<211> LENGTH: 26
<212> TYPE: DNA
<213> ORGANISM: Artificial
<220> FEATURE:
<223> OTHER INFORMATION: RevSV40

<400> SEQUENCE: 75

```
ctttatttgt aaccattata agctgc                                          26
```

<210> SEQ ID NO 76
<211> LENGTH: 1023
<212> TYPE: RNA
<213> ORGANISM: Artificial
<220> FEATURE:
<223> OTHER INFORMATION: alpha(miR-16-5p)-EGFP

<400> SEQUENCE: 76

```
ggucagaucc gcuaggaucc cgccaauauu uacgugcugc uaagaucuac cggucgccac     60
caugggaucc gugagcaagg gcgaggagcu guucaccggg guggugccca uccuggucga    120
gcuggacggc gacguaaacg gccacaaguu cagcgugucc ggcgagggcg agggcgaugc    180
caccuacggc aagcugaccc ugaaguucau cugcaccacc ggcaagcugc ccgugcccug    240
gcccacccuc gugaccaccc ugaccuacgg cgugcagugc uucagccgcu accccgacca    300
caugaagcag cacgacuucu ucaaguccgc caugcccgaa ggcuacgucc aggagcgcac    360
caucuucuuc aaggacgacg gcaacuacaa gacccgcgcc gaggugaagu ucgagggcga    420
cacccugguk aaccgcaucg agcugaaggg caucgacuuc aaggaggacg gcaacauccu    480
ggggcacaag cuggaguaca acuacaacag ccacaacguc uauaucaugg ccgacaagca    540
gaagaacggc aucaagguga acuucaagau ccgccacaac aucgaggacg gcagcgugca    600
gcucgccgac cacuaccagc agaacacccc caucggcgac ggccccgugc ugcugcccga    660
caaccacuac cugagcaccc aguccgcccu gagcaaagac cccaacgaga gcgcgauca    720
caugguccug cuggaguucg ugaccgccgc cgggaucacu cucggcaugg acgagcugua    780
caagagaucu cauaugcauc ucgagugaua gucuagaccu ucugcggggc uugccuucug    840
gccaugcccu ucuucucucc cuugcaccug uaccucuugg ucuuugaaua aagccugagu    900
aggaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaa                                                                 1023
```

<210> SEQ ID NO 77
<211> LENGTH: 956
<212> TYPE: RNA
<213> ORGANISM: Artificial
<220> FEATURE:

<223> OTHER INFORMATION: alpha(miR-214-3p)-hmAG1

<400> SEQUENCE: 77

| | |
|---|---|
| gguuccgcga ucgcggaucc acugccuguc ugugccugcu guagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucgcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 78
<211> LENGTH: 956
<212> TYPE: RNA
<213> ORGANISM: Artificial
<220> FEATURE:
<223> OTHER INFORMATION: alpha(miR-127-3p)-hmAG1

<400> SEQUENCE: 78

| | |
|---|---|
| gguuccgcga ucgcggaucc agccaagcuc agacggaucc gaagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucgcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

```
<210> SEQ ID NO 79
<211> LENGTH: 956
<212> TYPE: RNA
<213> ORGANISM: Artificial
<220> FEATURE:
<223> OTHER INFORMATION: alpha(miR-24-3p)-hmAG1

<400> SEQUENCE: 79
gguuccgcga ucgcggaucc cguuccugc ugaacugagc caagaucaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc ccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acagggcgca cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956

<210> SEQ ID NO 80
<211> LENGTH: 956
<212> TYPE: RNA
<213> ORGANISM: Artificial
<220> FEATURE:
<223> OTHER INFORMATION: alpha(miR-16-5p)-hmAG1

<400> SEQUENCE: 80
gguuccgcga ucgcggaucc cgccaauauu uacgugcugc uaagaucaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc ccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acagggcgca cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
```

```
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956

<210> SEQ ID NO 81
<211> LENGTH: 956
<212> TYPE: RNA
<213> ORGANISM: Artificial
<220> FEATURE:
<223> OTHER INFORMATION: alpha(miR-21-5p)-hmAG1

<400> SEQUENCE: 81
gguuccgcga ucgcggaucc ucaacaucag ucugauaagc uaagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acagggugcg cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956

<210> SEQ ID NO 82
<211> LENGTH: 956
<212> TYPE: RNA
<213> ORGANISM: Artificial
<220> FEATURE:
<223> OTHER INFORMATION: alpha(miR-92a-3p)-hmAG1

<400> SEQUENCE: 82
gguuccgcga ucgcggaucc acaggccggg acaagugcaa uaagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
```

| | |
|---|---:|
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 83
<211> LENGTH: 956
<212> TYPE: RNA
<213> ORGANISM: Artificial
<220> FEATURE:
<223> OTHER INFORMATION: alpha(miR-17-5p)-hmAG1

<400> SEQUENCE: 83

| | |
|---|---:|
| gguuccgcga ucgcggaucc cuaccugcac uguaagcacu uugagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguccca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaaggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 84
<211> LENGTH: 956
<212> TYPE: RNA
<213> ORGANISM: Artificial
<220> FEATURE:
<223> OTHER INFORMATION: alpha(miR-339-5p)-hmAG1

<400> SEQUENCE: 84

| | |
|---|---:|
| gguuccgcga ucgcggaucc cgugagcucc uggaggacag ggaagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguccca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaaggc gacgugaaca | 540 |

| | |
|---|---|
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaa | 956 |

<210> SEQ ID NO 85
<211> LENGTH: 956
<212> TYPE: RNA
<213> ORGANISM: Artificial
<220> FEATURE:
<223> OTHER INFORMATION: alpha(miR-133a)-hmAG1

<400> SEQUENCE: 85

| | |
|---|---|
| gguuccgcga ucgcggaucc cagcugguug aaggggacca aaagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg gacgcgcu gcugagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaa | 956 |

<210> SEQ ID NO 86
<211> LENGTH: 956
<212> TYPE: RNA
<213> ORGANISM: Artificial
<220> FEATURE:
<223> OTHER INFORMATION: alpha(miR-17-3p)-hmAG1

<400> SEQUENCE: 86

| | |
|---|---|
| gguuccgcga ucgcggaucc cuacaagugc cuucacugca guagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |

```
gguucgacgg caccaacuuc cccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucgcgg ggcuugccuu cuggccaugc    780
ccuucuucuc ucccuugcac cuguaccucu ggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa       956
```

<210> SEQ ID NO 87
<211> LENGTH: 956
<212> TYPE: RNA
<213> ORGANISM: Artificial
<220> FEATURE:
<223> OTHER INFORMATION: alpha(miR-197-3p)-hmAG1

<400> SEQUENCE: 87

```
gguccgcga ucgcggaucc gcugggugga aagguggug aaagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucgcgg ggcuugccuu cuggccaugc    780
ccuucuucuc ucccuugcac cuguaccucu ggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa       956
```

<210> SEQ ID NO 88
<211> LENGTH: 956
<212> TYPE: RNA
<213> ORGANISM: Artificial
<220> FEATURE:
<223> OTHER INFORMATION: alpha(miR-224-5p)-hmAG1

<400> SEQUENCE: 88

```
gguccgcga ucgcggaucc aacggaacca cuagugacuu gagaucaaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
```

| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugagggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 89
<211> LENGTH: 956
<212> TYPE: RNA
<213> ORGANISM: Artificial
<220> FEATURE:
<223> OTHER INFORMATION: alpha(miR-365a-3p)-hmAG1

<400> SEQUENCE: 89

| gguuccgcga ucgcggaucc auaaggauuu uuaggggcau uaagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugagggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 90
<211> LENGTH: 956
<212> TYPE: RNA
<213> ORGANISM: Artificial
<220> FEATURE:
<223> OTHER INFORMATION: alpha(miR-331-3p)-hmAG1

<400> SEQUENCE: 90

| gguuccgcga ucgcggaucc uucuaggaua ggcccagggg cagaucaaca ccggucgcca | 60 |
| ccauggugag cgugaucaag cccgagauga agaucaagcu gugcaugagg ggcaccguga | 120 |

```
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugagggcga cugcuucuuc uacgacauca     420
gguucgacgg caccaacuuc cccccaacg gccccgugau gcagaagaag acccugaagu     480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 91
<211> LENGTH: 956
<212> TYPE: RNA
<213> ORGANISM: Artificial
<220> FEATURE:
<223> OTHER INFORMATION: alpha(miR-484)-hmAG1

<400> SEQUENCE: 91

```
gguuccgcga ucgcggaucc aucgggaggg gacugagccu gaagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugagggcga cugcuucuuc uacgacauca     420
gguucgacgg caccaacuuc cccccaacg gccccgugau gcagaagaag acccugaagu     480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 92
<211> LENGTH: 956
<212> TYPE: RNA
<213> ORGANISM: Artificial
<220> FEATURE:
<223> OTHER INFORMATION: alpha(miR-199a-5p)-hmAG1

<400> SEQUENCE: 92

```
gguuccgcga ucgcggaucc gaacagguag ucugaacacu gggagaucca ccggucgcca      60
ccaugugag cgugaucaag cccgagauga agaucaagcu gugcaugagg ggcaccguga     120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugagggcga cugcuucuuc uacgacauca     420
gguucgacgg caccaacuuc cccccaacg gccccgugau gcagaagaag acccugaagu     480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 93
<211> LENGTH: 956
<212> TYPE: RNA
<213> ORGANISM: Artificial
<220> FEATURE:
<223> OTHER INFORMATION: alpha(miR-370)-hmAG1

<400> SEQUENCE: 93

```
gguuccgcga ucgcggaucc accagguucc accccagcag gcagaucaca ccggucgcca    60
ccaugugag cgugaucaag cccgagauga agaucaagcu gugcaugagg ggcaccguga     120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugagggcga cugcuucuuc uacgacauca     420
gguucgacgg caccaacuuc cccccaacg gccccgugau gcagaagaag acccugaagu     480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 94
<211> LENGTH: 956

```
<212> TYPE: RNA
<213> ORGANISM: Artificial
<220> FEATURE:
<223> OTHER INFORMATION: alpha(miR-382-5p)-hmAG1

<400> SEQUENCE: 94
gguuccgcga ucgcggaucc cgaauccacc acgaacaacu ucagaucaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc ccugcccuu cgccuacgac auccugacca      240
ccguguccca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc cccccaacg gccccgugau gcagaagaag acccugaagu      480
gggagcccag caccgagaag auguacgugg aggacgcgu gcugaaggc gacgugaaca       540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucugcgg ggcuugccuu cuggccaugc     780
ccuucuucuc ucccuugcac cuguaccucu uggucuuuga auaaagccug aguaggaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaa        956

<210> SEQ ID NO 95
<211> LENGTH: 956
<212> TYPE: RNA
<213> ORGANISM: Artificial
<220> FEATURE:
<223> OTHER INFORMATION: alpha(miR-328)-hmAG1

<400> SEQUENCE: 95
gguuccgcga ucgcggaucc acggaagggc agagagggcc agagaucaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc ccugcccuu cgccuacgac auccugacca      240
ccguguccca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc cccccaacg gccccgugau gcagaagaag acccugaagu      480
gggagcccag caccgagaag auguacgugg aggacgcgu gcugaaggc gacgugaaca       540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucugcgg ggcuugccuu cuggccaugc     780
ccuucuucuc ucccuugcac cuguaccucu uggucuuuga auaaagccug aguaggaaaa     840
aaaaaaaaaa aaaaaaaaaa aaaaaaaaaa aaaaaaaaaa aaaaaaaaaa aaaaaaaaaa     900
```

```
aaaaaaaaaa aaaaaaaaaa aaaaaaaaaa aaaaaaaaaa aaaaaaaaaa aaaaaa      956
```

<210> SEQ ID NO 96
<211> LENGTH: 956
<212> TYPE: RNA
<213> ORGANISM: Artificial
<220> FEATURE:
<223> OTHER INFORMATION: alpha(miR-361-5p)-hmAG1

<400> SEQUENCE: 96

```
gguuccgcga ucgcggaucc guaccccugg agauucugau aaagaucaca ccggucgcca       60
ccauggugag cgugaucaag cccgagauga agaucaagcu gugcaugagg ggcaccguga      120
acggccacaa cuucgugauc gagggcgagg gcaagggcaa ccccuacgag ggcacccaga      180
uccuggaccu gaacgugacc gagggcgccc ccugcccuu cgccuacgac auccugacca       240
ccguguucca guacggcaac agggccuuca ccaaguaccc cgccgacauc caggacuacu      300
ucaagcagac cuuccccgag ggcuaccacu gggagaggag caugaccuac gaggaccagg      360
gcaucugcac cgccaccagc aacaucagca ugaggggcga cugcuucuuc uacgacauca      420
gguucgacgg caccaacuuc cccccaacg gccccgugau gcagaagaag acccugaagu       480
gggagcccag caccgagaag auguacgugg gaggacgcgu gcugaagggc gacgugaaca      540
ugaggcugcu gcuggagggc ggcggccacu acaggugcga cuucaagacc accuacaagg      600
ccaagaagga ggugaggcug cccgacgccc acaagaucga ccacaggauc gagauccuga      660
agcacgacaa ggacuacaac aaggugaagc uguacgagaa cgccguggcc agguacucca      720
ugcugcccag ccaggccaag ugaaucuaga ccuucgcgg ggcuugccuu cuggccaugc       780
ccuucuucuc ucccuugcac cuguaccucu ggucuuuga auaaagccug aguaggaaaa       840
aaaaaaaaaa aaaaaaaaaa aaaaaaaaaa aaaaaaaaaa aaaaaaaaaa aaaaaaaaaa      900
aaaaaaaaaa aaaaaaaaaa aaaaaaaaaa aaaaaaaaaa aaaaaaaaaa aaaaaa          956
```

<210> SEQ ID NO 97
<211> LENGTH: 956
<212> TYPE: RNA
<213> ORGANISM: Artificial
<220> FEATURE:
<223> OTHER INFORMATION: alpha(miR-486-5p)-hmAG1

<400> SEQUENCE: 97

```
gguuccgcga ucgcggaucc cucggggcag cucaguacag gaagaucaca ccggucgcca       60
ccauggugag cgugaucaag cccgagauga agaucaagcu gugcaugagg ggcaccguga      120
acggccacaa cuucgugauc gagggcgagg gcaagggcaa ccccuacgag ggcacccaga      180
uccuggaccu gaacgugacc gagggcgccc ccugcccuu cgccuacgac auccugacca       240
ccguguucca guacggcaac agggccuuca ccaaguaccc cgccgacauc caggacuacu      300
ucaagcagac cuuccccgag ggcuaccacu gggagaggag caugaccuac gaggaccagg      360
gcaucugcac cgccaccagc aacaucagca ugaggggcga cugcuucuuc uacgacauca      420
gguucgacgg caccaacuuc cccccaacg gccccgugau gcagaagaag acccugaagu       480
gggagcccag caccgagaag auguacgugg gaggacgcgu gcugaagggc gacgugaaca      540
ugaggcugcu gcuggagggc ggcggccacu acaggugcga cuucaagacc accuacaagg      600
ccaagaagga ggugaggcug cccgacgccc acaagaucga ccacaggauc gagauccuga      660
agcacgacaa ggacuacaac aaggugaagc uguacgagaa cgccguggcc agguacucca      720
ugcugcccag ccaggccaag ugaaucuaga ccuucgcgg ggcuugccuu cuggccaugc       780
```
ccuucuucuc ucccuugcac cguuaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956

<210> SEQ ID NO 98
<211> LENGTH: 956
<212> TYPE: RNA
<213> ORGANISM: Artificial
<220> FEATURE:
<223> OTHER INFORMATION: alpha(miR-450a-5p)-hmAG1

<400> SEQUENCE: 98
gguuccgcga ucgcggaucc auauuaggaa cacaucgcaa aaagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acagggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cguuaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956

<210> SEQ ID NO 99
<211> LENGTH: 956
<212> TYPE: RNA
<213> ORGANISM: Artificial
<220> FEATURE:
<223> OTHER INFORMATION: alpha(miR-7-5p)-hmAG1

<400> SEQUENCE: 99
gguuccgcga ucgcggaucc acaacaaaau cacuagucuu ccaagaucca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acagggugcga cuucaagacc accuacaagg    600

| | |
|---|---|
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

```
<210> SEQ ID NO 100
<211> LENGTH: 956
<212> TYPE: RNA
<213> ORGANISM: Artificial
<220> FEATURE:
<223> OTHER INFORMATION: alpha(miR-125b-5p)-hmAG1

<400> SEQUENCE: 100
```

| | |
|---|---|
| gguuccgcga ucgcggaucc ucacaaguua gggucucagg gaagaucaca ccggucgcca | 60 |
| ccauggugag cgugaucaag cccgagauga agaucaagcu ugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugagggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acagugugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

```
<210> SEQ ID NO 101
<211> LENGTH: 956
<212> TYPE: RNA
<213> ORGANISM: Artificial
<220> FEATURE:
<223> OTHER INFORMATION: alpha(miR-100-5p)-hmAG1

<400> SEQUENCE: 101
```

| | |
|---|---|
| gguuccgcga ucgcggaucc cacaaguucg gaucuacggg uuagaucaca ccggucgcca | 60 |
| ccauggugag cgugaucaag cccgagauga agaucaagcu ugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugagggggcga cugcuucuuc uacgacauca | 420 |
| gguucgacgg caccaacuuc cccccaacg gccccgugau gcagaagaag acccugaagu | 480 |

| | |
|---|---|
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucgcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 102
<211> LENGTH: 956
<212> TYPE: RNA
<213> ORGANISM: Artificial
<220> FEATURE:
<223> OTHER INFORMATION: alpha(miR-27a-3p)-hmAG1

<400> SEQUENCE: 102

| | |
|---|---|
| gguuccgcga ucgcggaucc gcggaacuua gccacuguga aagaucaaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucgcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 103
<211> LENGTH: 956
<212> TYPE: RNA
<213> ORGANISM: Artificial
<220> FEATURE:
<223> OTHER INFORMATION: alpha(let-7a-5p)-hmAG1

<400> SEQUENCE: 103

| | |
|---|---|
| gguuccgcga ucgcggaucc aacuauacaa ccuacuaccu caagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |

| | |
|---|---|
| ucaagcagac cuuccccgag ggcuaccacu gggagaggag caugaccuac gaggaccagg | 360 |
| gcaucugcac cgccaccagc aacaucagca ugagggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucgcgg ggcuugccuu cuggccaugc | 780 |
| ccuucuucuc ucccuugcac cuguaccucu ggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 104
<211> LENGTH: 956
<212> TYPE: RNA
<213> ORGANISM: Artificial
<220> FEATURE:
<223> OTHER INFORMATION: alpha(miR-191-5p)-hmAG1

<400> SEQUENCE: 104

| | |
|---|---|
| gguuccgcga ucgcggaucc cagcugcuuu ugggauuccg uugagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguccca guacggcaac agggccuuca ccaaguaccc cgcgacauc caggacuacu | 300 |
| ucaagcagac cuuccccgag ggcuaccacu gggagaggag caugaccuac gaggaccagg | 360 |
| gcaucugcac cgccaccagc aacaucagca ugagggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucgcgg ggcuugccuu cuggccaugc | 780 |
| ccuucuucuc ucccuugcac cuguaccucu ggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 105
<211> LENGTH: 956
<212> TYPE: RNA
<213> ORGANISM: Artificial
<220> FEATURE:
<223> OTHER INFORMATION: alpha(miR-19a-3p)-hmAG1

<400> SEQUENCE: 105

| | |
|---|---|
| gguuccgcga ucgcggaucc ucaguuuugc auagauuugc acaagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 | uccuggaccu gaacgugacc gagggcgccc cccugcccuu cgccuacgac auccugacca    240 ccguguucca guacggcaac agggccuuca ccaaguaccc cgccgacauc caggacuacu    300 ucaagcagac cuuccccgag ggcuaccacu gggagaggag caugaccuac gaggaccagg    360 gcaucugcac cgccaccagc aacaucagca ugaggggcga cugcuucuuc uacgacauca    420 gguucgacgg caccaacuuc cccccaacg gccccgugau gcagaagaag acccugaagu    480 gggagcccag caccgagaag auguacgugg aggacggcgu gcugaaggc gacgugaaca    540 ugaggcugcu gcuggagggc ggcggccacu acaggugcga cuucaagacc accuacaagg    600 ccaagaagga ggugaggcug cccgacgccc acaagaucga ccacaggauc gagauccuga    660 agcacgacaa ggacuacaac aaggugaagc uguacgagaa cgccguggcc agguacucca    720 ugcugcccag ccaggccaag ugaaucuaga ccuucgcgg ggcuugccuu cuggccaugc    780 ccuucuucuc ucccuugcac cuguaccucu ggucuuuga auaaagccug aguaggaaaa    840 aaaaaaaaaa aaaaaaaaaa aaaaaaaaaa aaaaaaaaaa aaaaaaaaaa aaaaaaaaaa    900 aaaaaaaaaa aaaaaaaaaa aaaaaaaaaa aaaaaaaaaa aaaaaa                  956

<210> SEQ ID NO 106
<211> LENGTH: 956
<212> TYPE: RNA
<213> ORGANISM: Artificial
<220> FEATURE:
<223> OTHER INFORMATION: alpha(miR-99b-5p)-hmAG1

<400> SEQUENCE: 106 gguccgcga ucgcggaucc cgcaaggucg guucuacggg ugagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu    480
gggagcccag caccgagaag auguacgugg aggacggcgu gcugaaggc gacgugaaca    540 ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucgcgg ggcuugccuu cuggccaugc    780
ccuucuucuc ucccuugcac cuguaccucu ggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaa                  956

<210> SEQ ID NO 107
<211> LENGTH: 956
<212> TYPE: RNA
<213> ORGANISM: Artificial
<220> FEATURE:
<223> OTHER INFORMATION: alpha(miR-193b-3p)-hmAG1

<400> SEQUENCE: 107

| | |
|---|---:|
| gguuccgcga ucgcggaucc agcgggacuu ugagggccag uuagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 108
<211> LENGTH: 956
<212> TYPE: RNA
<213> ORGANISM: Artificial
<220> FEATURE:
<223> OTHER INFORMATION: alpha(miR-342-3p)-hmAG1

<400> SEQUENCE: 108

| | |
|---|---:|
| gguccgcga ucgcggaucc acgggugcga uuucugugug agaagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 109
<211> LENGTH: 956
<212> TYPE: RNA
<213> ORGANISM: Artificial

```
<220> FEATURE:
<223> OTHER INFORMATION: alpha(miR-320-a)-hmAG1

<400> SEQUENCE: 109
gguuccgcga ucgcggaucc ucgcccucuc aacccagcuu uuagaucaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc cccugcccuu cgccuacgac auccugacca     240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc cccccaacg gccccgugau gcagaagaag cccugaagu      480 gggagcccag caccgagaag auguacgugg aggacggcgu gcugaagggc gacgugaaca     540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucugcgg ggcuugccuu cuggccaugc     780
ccuucuucuc ucccuugcac cuguaccucu uggucuuuga auaaagccug aguaggaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaa        956

<210> SEQ ID NO 110
<211> LENGTH: 956
<212> TYPE: RNA
<213> ORGANISM: Artificial
<220> FEATURE:
<223> OTHER INFORMATION: alpha(miR-93-5p)-hmAG1

<400> SEQUENCE: 110
gguuccgcga ucgcggaucc cuaccugcac gaacagcacu uugagaucca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc cccugcccuu cgccuacgac auccugacca     240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc cccccaacg gccccgugau gcagaagaag cccugaagu      480 gggagcccag caccgagaag auguacgugg aggacggcgu gcugaagggc gacgugaaca     540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucugcgg ggcuugccuu cuggccaugc     780
ccuucuucuc ucccuugcac cuguaccucu uggucuuuga auaaagccug aguaggaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaa        956
```

<210> SEQ ID NO 111
<211> LENGTH: 956
<212> TYPE: RNA
<213> ORGANISM: Artificial
<220> FEATURE:
<223> OTHER INFORMATION: alpha(miR-20a-5p)-hmAG1

<400> SEQUENCE: 111

| | |
|---|---|
| gguuccgcga ucgcggaucc uaccugcac auauaagcacu uuaagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acagguggcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 112
<211> LENGTH: 956
<212> TYPE: RNA
<213> ORGANISM: Artificial
<220> FEATURE:
<223> OTHER INFORMATION: alpha(miR-34a-5p)-hmAG1

<400> SEQUENCE: 112

| | |
|---|---|
| gguuccgcga ucgcggaucc acaaccagcu aagacacugc caagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acagguggcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |

```
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 113
<211> LENGTH: 956
<212> TYPE: RNA
<213> ORGANISM: Artificial
<220> FEATURE:
<223> OTHER INFORMATION: alpha(miR-22-3p)-hmAG1

<400> SEQUENCE: 113

```
gguuccgcga ucgcggaucc acaguucuuc aacuggcagc uuagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguccca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu ggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 114
<211> LENGTH: 956
<212> TYPE: RNA
<213> ORGANISM: Artificial
<220> FEATURE:
<223> OTHER INFORMATION: alpha(miR-143-3p)-hmAG1

<400> SEQUENCE: 114

```
gguuccgcga ucgcggaucc gagcuacagu gcuucaucuc aagaucaaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguccca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
```

| | |
|---|---|
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 115
<211> LENGTH: 956
<212> TYPE: RNA
<213> ORGANISM: Artificial
<220> FEATURE:
<223> OTHER INFORMATION: alpha(let-7i-5p)-hmAG1

<400> SEQUENCE: 115

| | |
|---|---|
| gguuccgcga ucgcggaucc aacagcacaa acuacuaccu caagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgcgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 116
<211> LENGTH: 956
<212> TYPE: RNA
<213> ORGANISM: Artificial
<220> FEATURE:
<223> OTHER INFORMATION: alpha(miR-106a-5p)-hmAG1

<400> SEQUENCE: 116

| | |
|---|---|
| gguuccgcga ucgcggaucc cuaccugcac uguaagcacu uuuagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgcgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |

| | |
|---|---|
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 117
<211> LENGTH: 956
<212> TYPE: RNA
<213> ORGANISM: Artificial
<220> FEATURE:
<223> OTHER INFORMATION: alpha(miR-145-5p)-hmAG1

<400> SEQUENCE: 117

| | |
|---|---|
| gguccgcga ucgcggaucc agggauuccu gggaaaacug gacagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccccaacg gccccgugau gcagaagaag acccugaagu | 480 |
| gggagcccag caccgagaag auguacgugg aggacgcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 118
<211> LENGTH: 956
<212> TYPE: RNA
<213> ORGANISM: Artificial
<220> FEATURE:
<223> OTHER INFORMATION: alpha(miR-10a-5p)-hmAG1

<400> SEQUENCE: 118

| | |
|---|---|
| gguccgcga ucgcggaucc cacaaauucg gaucuacagg guaagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc ccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |

-continued

| | |
|---|---|
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 119
<211> LENGTH: 956
<212> TYPE: RNA
<213> ORGANISM: Artificial
<220> FEATURE:
<223> OTHER INFORMATION: alpha(miR-423-3p)-hmAG1

<400> SEQUENCE: 119

| | |
|---|---|
| gguuccgcga ucgcggaucc acugagggc cucagaccga gcuagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acaggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 120
<211> LENGTH: 956
<212> TYPE: RNA
<213> ORGANISM: Artificial
<220> FEATURE:
<223> OTHER INFORMATION: alpha(miR-30a-3p)-hmAG1

<400> SEQUENCE: 120

| | |
|---|---|
| gguuccgcga ucgcggaucc gcugcaaaca uccgacugaa agagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |

-continued

```
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu     480
gggagcccag caccgagaag auguacgugg aggacggcgu gcugaagggc gacgugaaca    540
ugaggcugcu gcuggagggc ggcggccacu acagguggcga cuucaagacc accuacaagg   600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cguaccucu uggucuuuga auaaagccug aguaggaaaa     840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 121
<211> LENGTH: 956
<212> TYPE: RNA
<213> ORGANISM: Artificial
<220> FEATURE:
<223> OTHER INFORMATION: alpha(miR-151a-3p)-hmAG1

<400> SEQUENCE: 121

```
gguuccgcga ucgcggaucc ccucaaggag cuucagucua gagaucaaca ccggucgcca    60
ccauggugag cgugaucaag cccgagauga agaucaagcu ugcaugagg ggcaccguga    120 acggccacaa cuucgugauc gagggcgagg gcaagggcaa ccccuacgag ggcacccaga    180
uccuggaccu gaacgugacc gagggcgccc cccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu     480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cguaccucu uggucuuuga auaaagccug aguaggaaaa     840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 122
<211> LENGTH: 956
<212> TYPE: RNA
<213> ORGANISM: Artificial
<220> FEATURE:
<223> OTHER INFORMATION: alpha(miR-149-5p)-hmAG1

<400> SEQUENCE: 122

```
gguuccgcga ucgcggaucc gggagugaag acacggagcc agaagaucca ccggucgcca    60
```

```
ccauggugag cgugaucaag cccgagauga agaucaagcu gugcaugagg ggcaccguga      120
acggccacaa cuucgugauc gagggcgagg gcaagggcaa ccccuacgag ggcacccaga      180
uccuggaccu gaacgugacc gagggcgccc ccugcccuu cgccuacgac auccugacca       240
ccguguucca guacggcaac agggccuuca ccaaguaccc cgccgacauc caggacuacu      300
ucaagcagac cuuccccgag ggcuaccacu gggagaggag caugaccuac gaggaccagg      360
gcaucugcac cgccaccagc aacaucagca ugggggcga cugcuucuuc uacgacauca       420
gguucgacgg caccaacuuc cccccaacg gccccgugau gcagaagaag acccugaagu       480
gggagcccag caccgagaag auguacgugg aggacggcgu gcugaagggc gacgugaaca      540
ugaggcugcu gcuggagggc ggcggccacu acaggugcga cuucaagacc accuacaagg      600
ccaagaagga ggugaggcug cccgacgccc acaagaucga ccacaggauc gagauccuga      660
agcacgacaa ggacuacaac aaggugaagc uguacgagaa cgccguggcc agguacucca      720
ugcugcccag ccaggccaag ugaaucuaga ccuucgcgg ggcuugccuu cuggccaugc       780
ccuucuucuc ucccuugcac cuguaccucu uggucuuuga auaaagccug aguaggaaaa      840
aaaaaaaaaa aaaaaaaaaa aaaaaaaaaa aaaaaaaaaa aaaaaaaaaa aaaaaaaaaa      900
aaaaaaaaaa aaaaaaaaaa aaaaaaaaaa aaaaaaaaaa aaaaaaaaaa aaaaaa          956

<210> SEQ ID NO 123
<211> LENGTH: 956
<212> TYPE: RNA
<213> ORGANISM: Artificial
<220> FEATURE:
<223> OTHER INFORMATION: alpha(miR-296-5p)-hmAG1

<400> SEQUENCE: 123
gguuccgcga ucgcggaucc acaggauuga ggggggccc uagaucaaca ccggucgcca        60
ccauggugag cgugaucaag cccgagauga agaucaagcu gugcaugagg ggcaccguga      120
acggccacaa cuucgugauc gagggcgagg gcaagggcaa ccccuacgag ggcacccaga      180
uccuggaccu gaacgugacc gagggcgccc ccugcccuu cgccuacgac auccugacca       240
ccguguucca guacggcaac agggccuuca ccaaguaccc cgccgacauc caggacuacu      300
ucaagcagac cuuccccgag ggcuaccacu gggagaggag caugaccuac gaggaccagg      360
gcaucugcac cgccaccagc aacaucagca ugggggcga cugcuucuuc uacgacauca       420
gguucgacgg caccaacuuc cccccaacg gccccgugau gcagaagaag acccugaagu       480
gggagcccag caccgagaag auguacgugg aggacggcgu gcugaagggc gacgugaaca      540
ugaggcugcu gcuggagggc ggcggccacu acaggugcga cuucaagacc accuacaagg      600
ccaagaagga ggugaggcug cccgacgccc acaagaucga ccacaggauc gagauccuga      660
agcacgacaa ggacuacaac aaggugaagc uguacgagaa cgccguggcc agguacucca      720
ugcugcccag ccaggccaag ugaaucuaga ccuucgcgg ggcuugccuu cuggccaugc       780
ccuucuucuc ucccuugcac cuguaccucu uggucuuuga auaaagccug aguaggaaaa      840
aaaaaaaaaa aaaaaaaaaa aaaaaaaaaa aaaaaaaaaa aaaaaaaaaa aaaaaaaaaa      900
aaaaaaaaaa aaaaaaaaaa aaaaaaaaaa aaaaaaaaaa aaaaaaaaaa aaaaaa          956

<210> SEQ ID NO 124
<211> LENGTH: 956
<212> TYPE: RNA
<213> ORGANISM: Artificial
<220> FEATURE:
<223> OTHER INFORMATION: alpha(miR-324-3p)-hmAG1
```

<400> SEQUENCE: 124

```
gguuccgcga ucgcggaucc ccagcagcac cuggggcagu agaucaaaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc ccugcccuu cgccuacgac auccugacca      240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc cccccaacg gccccgugau gcagaagaag acccugaagu      480
gggagcccag caccgagaag auguacgugg aggacgcgu gcugaagggc gacgugaaca      540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucgcgg ggcuugccuu cuggccaugc      780
ccuucuucuc ucccuugcac cuguaccucu ggucuuuga auaaagccug aguaggaaaa     840
aaaaaaaaa aaaaaaaaa aaaaaaaaa aaaaaaaaa aaaaaaaaa aaaaaaaaa           900
aaaaaaaaa aaaaaaaaa aaaaaaaaa aaaaaaaaa aaaaaaaaa aaaaaa              956
```

<210> SEQ ID NO 125
<211> LENGTH: 956
<212> TYPE: RNA
<213> ORGANISM: Artificial
<220> FEATURE:
<223> OTHER INFORMATION: alpha(miR-26a-5p)-hmAG1

<400> SEQUENCE: 125

```
gguuccgcga ucgcggaucc agccuauccu ggauuacuug aaagaucaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc ccugcccuu cgccuacgac auccugacca      240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc cccccaacg gccccgugau gcagaagaag acccugaagu      480
gggagcccag caccgagaag auguacgugg aggacgcgu gcugaagggc gacgugaaca      540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucgcgg ggcuugccuu cuggccaugc      780
ccuucuucuc ucccuugcac cuguaccucu ggucuuuga auaaagccug aguaggaaaa     840
aaaaaaaaa aaaaaaaaa aaaaaaaaa aaaaaaaaa aaaaaaaaa aaaaaaaaa           900
aaaaaaaaa aaaaaaaaa aaaaaaaaa aaaaaaaaa aaaaaaaaa aaaaaa              956
```

<210> SEQ ID NO 126

```
<211> LENGTH: 956
<212> TYPE: RNA
<213> ORGANISM: Artificial
<220> FEATURE:
<223> OTHER INFORMATION: alpha(miR-106b-5p)-hmAG1

<400> SEQUENCE: 126
gguuccgcga ucgcggaucc aucugcacug ucagcacuuu aagaucaaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc cccugcccuu cgccuacgac auccugacca     240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc ccccccaacg gccccgugau gcagaagaag acccugaagu     480
gggagcccag caccgagaag auguacgugg aggacgcgcu gcugaagggc gacgugaaca     540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucgcgg ggcuugccuu cuggccaugc      780
ccuucuucuc ucccuugcac cuguaccucu ggucuuuga auaaagccug aguaggaaaa      840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaa         956

<210> SEQ ID NO 127
<211> LENGTH: 956
<212> TYPE: RNA
<213> ORGANISM: Artificial
<220> FEATURE:
<223> OTHER INFORMATION: alpha(miR-129-5p)-hmAG1

<400> SEQUENCE: 127
gguuccgcga ucgcggaucc gcaagcccag accgcaaaaa gagaucaaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc cccugcccuu cgccuacgac auccugacca     240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugaggggcga cugcuucuuc uacgacauca     420
gguucgacgg caccaacuuc ccccccaacg gccccgugau gcagaagaag acccugaagu     480
gggagcccag caccgagaag auguacgugg aggacgcgcu gcugaagggc gacgugaaca     540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccguggcc agguacucca     720
ugcugcccag ccaggccaag ugaaucuaga ccuucgcgg ggcuugccuu cuggccaugc      780
ccuucuucuc ucccuugcac cuguaccucu ggucuuuga auaaagccug aguaggaaaa      840
aaaaaaaaaa aaaaaaaaaa aaaaaaaaaa aaaaaaaaaa aaaaaaaaaa aaaaaaaaaa     900
```

```
aaaaaaaaaa aaaaaaaaaa aaaaaaaaaa aaaaaaaaaa aaaaaaaaaa aaaaaa          956
```

<210> SEQ ID NO 128
<211> LENGTH: 956
<212> TYPE: RNA
<213> ORGANISM: Artificial
<220> FEATURE:
<223> OTHER INFORMATION: alpha(let-7g-5p)-hmAG1

<400> SEQUENCE: 128

```
gguuccgcga ucgcggaucc aacuguacaa acuacuaccu caagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcca cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccgguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 129
<211> LENGTH: 956
<212> TYPE: RNA
<213> ORGANISM: Artificial
<220> FEATURE:
<223> OTHER INFORMATION: alpha(miR-212-3p)-hmAG1

<400> SEQUENCE: 129

```
gguuccgcga ucgcggaucc ggccgugacu ggagacuguu aagaucaaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccgguggcc agguacucca    720
```

| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 130
<211> LENGTH: 956
<212> TYPE: RNA
<213> ORGANISM: Artificial
<220> FEATURE:
<223> OTHER INFORMATION: alpha(miR-28-5p)-hmAG1

<400> SEQUENCE: 130

| gguuccgcga ucgcggaucc cucaauagac gugagcucc uuagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acagggcgca cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 131
<211> LENGTH: 956
<212> TYPE: RNA
<213> ORGANISM: Artificial
<220> FEATURE:
<223> OTHER INFORMATION: alpha(miR-186-5p)-hmAG1

<400> SEQUENCE: 131

| gguuccgcga ucgcggaucc agcccaaaag gagaauucuu ugagaucaca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugaggggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acagggcgca cuucaagacc accuacaagg | 600 |

```
ccaagaagga ggugaggcug cccgacgccc acaagaucga ccacaggauc gagauccuga    660
agcacgacaa ggacuacaac aaggugaagc uguacgagaa cgccgguggcc agguacucca   720 ugcugcccag ccaggccaag ugaaucuaga ccuucgcgg ggcuugccuu cuggccaugc     780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 132
<211> LENGTH: 956
<212> TYPE: RNA
<213> ORGANISM: Artificial
<220> FEATURE:
<223> OTHER INFORMATION: alpha(miR-155-5p)-hmAG1

<400> SEQUENCE: 132

```
gguuccgcga ucgcggaucc accccuauca cgauuagcau uaaagaucca ccggucgcca     60
ccauggugag cgugaucaag cccgagauga agaucaagcu gugcaugagg ggcaccguga    120
acggccacaa cuucgugauc gagggcgagg gcaaggcaa ccccuacgag ggcacccaga     180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu    480
gggagcccag caccgagaag auguacgugg aggacggcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccgguggcc agguacucca   720 ugcugcccag ccaggccaag ugaaucuaga ccuucgcgg ggcuugccuu cuggccaugc     780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaa        956
```

<210> SEQ ID NO 133
<211> LENGTH: 956
<212> TYPE: RNA
<213> ORGANISM: Artificial
<220> FEATURE:
<223> OTHER INFORMATION: alpha(miR-485-5p)-hmAG1

<400> SEQUENCE: 133

```
gguuccgcga ucgcggaucc gaauucauca cggccagccu cuagaucaca ccggucgcca     60
ccauggugag cgugaucaag cccgagauga agaucaagcu gugcaugagg ggcaccguga    120
acggccacaa cuucgugauc gagggcgagg gcaaggcaa ccccuacgag ggcacccaga     180
uccuggaccu gaacgugacc gagggcgccc ccugcccuu cgccuacgac auccugacca     240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
```

```
gguucgacgg caccaacuuc cccccaacg gccccgugau gcagaagaag acccugaagu    480
gggagcccag caccgagaag auguacgugg aggacggcgu gcugaaggc gacgugaaca    540 ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucgcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaa                  956
```

<210> SEQ ID NO 134
<211> LENGTH: 956
<212> TYPE: RNA
<213> ORGANISM: Artificial
<220> FEATURE:
<223> OTHER INFORMATION: alpha(miR-330-3p)-hmAG1

<400> SEQUENCE: 134

```
gguccgcga ucgcggaucc ucucugcagg ccgugugcuu ugcagaucca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccaacg gccccgugau gcagaagaag acccugaagu    480
gggagcccag caccgagaag auguacgugg aggacggcgu gcugaaggc gacgugaaca    540 ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucgcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaa                  956
```

<210> SEQ ID NO 135
<211> LENGTH: 956
<212> TYPE: RNA
<213> ORGANISM: Artificial
<220> FEATURE:
<223> OTHER INFORMATION: alpha(miR-345)-hmAG1

<400> SEQUENCE: 135

```
gguccgcga ucgcggaucc gagcccugga cuaggaguca gcagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca    240
ccguguucca guacggcaac agggccuuca ccaaguaccc cgccgacauc caggacuacu    300
```

```
ucaagcagac cuuccccgag ggcuaccacu gggagaggag caugaccuac gaggaccagg      360
gcaucugcac cgccaccagc aacaucagca ugaggggcga cugcuucuuc uacgacauca      420
gguucgacgg caccaacuuc cccccaacg gccccgugau gcagaagaag acccugaagu       480
gggagcccag caccgagaag auguacgugg aggacgcgu gcugaaggc gacgugaaca       540 ugaggcugcu gcuggagggc ggcggccacu acaggugcga cuucaagacc accuacaagg      600
ccaagaagga ggugaggcug cccgacgccc acaagaucga ccacaggauc gagauccuga      660
agcacgacaa ggacuacaac aaggugaagc uguacgagaa cgccgugggcc agguacucca     720 ugcugcccag ccaggccaag ugaaucuaga ccuucugcgg ggcuugccuu cuggccaugc      780
ccuucuucuc ucccuugcac cuguaccucu ggucuuuga auaaagccug aguaggaaaa       840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaa                    956
```

<210> SEQ ID NO 136
<211> LENGTH: 956
<212> TYPE: RNA
<213> ORGANISM: Artificial
<220> FEATURE:
<223> OTHER INFORMATION: alpha(miR-500a-3p)-hmAG1

<400> SEQUENCE: 136

```
gguuccgcga ucgcggaucc cagaauccuu gcccaggugc auagaucaca ccggucgcca       60
ccauggugag cgugaucaag cccgagauga agaucaagcu gugcaugagg ggcaccguga      120
acggccacaa cuucgugauc gagggcgagg gcaagggcaa ccccuacgag ggcacccaga     180
uccuggaccu gaacgugacc gagggcgccc ccugcccuu cgccuacgac auccugacca       240
ccguguucca guacggcaac agggccuuca ccaaguaccc cgccgacauc caggacuacu      300
ucaagcagac cuuccccgag ggcuaccacu gggagaggag caugaccuac gaggaccagg      360
gcaucugcac cgccaccagc aacaucagca ugaggggcga cugcuucuuc uacgacauca      420
gguucgacgg caccaacuuc cccccaacg gccccgugau gcagaagaag acccugaagu       480
gggagcccag caccgagaag auguacgugg aggacgcgu gcugaaggc gacgugaaca       540 ugaggcugcu gcuggagggc ggcggccacu acaggugcga cuucaagacc accuacaagg      600
ccaagaagga ggugaggcug cccgacgccc acaagaucga ccacaggauc gagauccuga      660
agcacgacaa ggacuacaac aaggugaagc uguacgagaa cgccgugggcc agguacucca     720 ugcugcccag ccaggccaag ugaaucuaga ccuucugcgg ggcuugccuu cuggccaugc      780
ccuucuucuc ucccuugcac cuguaccucu ggucuuuga auaaagccug aguaggaaaa       840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaa                    956
```

<210> SEQ ID NO 137
<211> LENGTH: 956
<212> TYPE: RNA
<213> ORGANISM: Artificial
<220> FEATURE:
<223> OTHER INFORMATION: alpha(miR-192-5p)-hmAG1

<400> SEQUENCE: 137

```
gguuccgcga ucgcggaucc ggcugucaau ucauaggguca gagaucaaca ccggucgcca      60
ccauggugag cgugaucaag cccgagauga agaucaagcu gugcaugagg ggcaccguga     120
```

| | |
|---|---|
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugagggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acagggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaa aaaaaaaaaa aaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

```
<210> SEQ ID NO 138
<211> LENGTH: 956
<212> TYPE: RNA
<213> ORGANISM: Artificial
<220> FEATURE:
<223> OTHER INFORMATION: alpha(miR-335-5p)-hmAG1

<400> SEQUENCE: 138
```

| | |
|---|---|
| gguccgcga ucgcggaucc acauuuuucg uuauugcucu ugaagaucca ccggucgcca | 60 |
| ccauggugag cgugaucaag cccgagauga agaucaagcu gugcaugagg ggcaccguga | 120 |
| acggccacaa cuucgugauc gagggcgagg gcaagggcaa ccccuacgag ggcacccaga | 180 |
| uccuggaccu gaacgugacc gagggcgccc cccugcccuu cgccuacgac auccugacca | 240 |
| ccguguucca guacggcaac agggccuuca ccaaguaccc cgccgacauc caggacuacu | 300 |
| ucaagcagac cuuccccgag ggcuaccacu gggagaggag caugaccuac gaggaccagg | 360 |
| gcaucugcac cgccaccagc aacaucagca ugagggcga cugcuucuuc uacgacauca | 420 |
| gguucgacgg caccaacuuc cccccaacg gccccgugau gcagaagaag acccugaagu | 480 |
| gggagcccag caccgagaag auguacgugg aggacggcgu gcugaagggc gacgugaaca | 540 |
| ugaggcugcu gcuggagggc ggcggccacu acagggugcga cuucaagacc accuacaagg | 600 |
| ccaagaagga ggugaggcug cccgacgccc acaagaucga ccacaggauc gagauccuga | 660 |
| agcacgacaa ggacuacaac aaggugaagc uguacgagaa cgccguggcc agguacucca | 720 |
| ugcugcccag ccaggccaag ugaaucuaga ccuucugcgg ggcuugccuu cuggccaugc | 780 |
| ccuucuucuc ucccuugcac cuguaccucu uggucuuuga auaaagccug aguaggaaaa | 840 |
| aaaaaaaaa aaaaaaaaaa aaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

```
<210> SEQ ID NO 139
<211> LENGTH: 956
<212> TYPE: RNA
<213> ORGANISM: Artificial
<220> FEATURE:
<223> OTHER INFORMATION: alpha(miR-140-5p)-hmAG1

<400> SEQUENCE: 139
```

```
gguuccgcga ucgcggaucc cuaccauagg guaaaaccac ugagaucaca ccggucgcca    60
ccauggugag cgugaucaag cccgagauga agaucaagcu gugcaugagg ggcaccguga   120
acggccacaa cuucgugauc gagggcgagg gcaagggcaa ccccuacgag ggcacccaga   180
uccuggaccu gaacgugacc gagggcgccc cccugcccuu cgccuacgac auccugacca   240
ccguguucca guacggcaac agggccuuca ccaaguaccc cgccgacauc caggacuacu   300
ucaagcagac cuuccccgag ggcuaccacu gggagaggag caugaccuac gaggaccagg   360
gcaucugcac cgccaccagc aacaucagca ugaggggcga cugcuucuuc uacgacauca   420
gguucgacgg caccaacuuc cccccaacg gccccgugau gcagaagaag acccugaagu   480
gggagcccag caccgagaag auguacgugg aggacggcgu gcugaagggc gacgugaaca   540
ugaggcugcu gcuggagggc ggcggccacu acaggugcga cuucaagacc accuacaagg   600
ccaagaagga ggugaggcug cccgacgccc acaagaucga ccacaggauc gagauccuga   660
agcacgacaa ggacuacaac aaggugaagc uguacgagaa cgccgguggcc agguacucca   720 ugcugcccag ccaggccaag ugaaucuaga ccuucgcgg ggcuugccuu cuggccaugc   780
ccuucuucuc ucccuugcac cuguaccucu uggucuuuga auaaagccug aguaggaaaa   840
aaaaaaaaaa aaaaaaaaaa aaaaaaaaaa aaaaaaaaaa aaaaaaaaaa aaaaaaaaaa   900
aaaaaaaaaa aaaaaaaaaa aaaaaaaaaa aaaaaaaaaa aaaaaaaa aaaaaa        956
```

<210> SEQ ID NO 140
<211> LENGTH: 956
<212> TYPE: RNA
<213> ORGANISM: Artificial
<220> FEATURE:
<223> OTHER INFORMATION: alpha(miR-18a-3p)-hmAG1

<400> SEQUENCE: 140

```
gguccgcga ucgcggaucc ccagaaggag cacuuagggc aguagaucca ccggucgcca    60
ccauggugag cgugaucaag cccgagauga agaucaagcu gugcaugagg ggcaccguga   120
acggccacaa cuucgugauc gagggcgagg gcaagggcaa ccccuacgag ggcacccaga   180
uccuggaccu gaacgugacc gagggcgccc cccugcccuu cgccuacgac auccugacca   240
ccguguucca guacggcaac agggccuuca ccaaguaccc cgccgacauc caggacuacu   300
ucaagcagac cuuccccgag ggcuaccacu gggagaggag caugaccuac gaggaccagg   360
gcaucugcac cgccaccagc aacaucagca ugaggggcga cugcuucuuc uacgacauca   420
gguucgacgg caccaacuuc cccccaacg gccccgugau gcagaagaag acccugaagu   480
gggagcccag caccgagaag auguacgugg aggacggcgu gcugaagggc gacgugaaca   540
ugaggcugcu gcuggagggc ggcggccacu acaggugcga cuucaagacc accuacaagg   600
ccaagaagga ggugaggcug cccgacgccc acaagaucga ccacaggauc gagauccuga   660
agcacgacaa ggacuacaac aaggugaagc uguacgagaa cgccgguggcc agguacucca   720 ugcugcccag ccaggccaag ugaaucuaga ccuucgcgg ggcuugccuu cuggccaugc   780
ccuucuucuc ucccuugcac cuguaccucu uggucuuuga auaaagccug aguaggaaaa   840
aaaaaaaaaa aaaaaaaaaa aaaaaaaaaa aaaaaaaaaa aaaaaaaaaa aaaaaaaaaa   900
aaaaaaaaaa aaaaaaaaaa aaaaaaaaaa aaaaaaaaaa aaaaaaaa aaaaaa        956
```

<210> SEQ ID NO 141
<211> LENGTH: 956
<212> TYPE: RNA

<213> ORGANISM: Artificial
<220> FEATURE:
<223> OTHER INFORMATION: alpha(miR-148a-3p)-hmAG1

<400> SEQUENCE: 141

```
gguuccgcga ucgcggaucc acaaaguucu guagugcacu gaagaucaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc ccugcccuu cgccuacgac auccugacca      240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugggggcga cugcuucuuc uacgacauca     420
gguucgacgg caccaacuuc cccccaacg gccccgugau gcagaagaag acccugaagu     480
gggagcccag caccgagaag auguacgugg aggacggcgu gcugaagggc gacgugaaca     540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccgguggcc agguacucca     720
ugcugcccag ccaggccaag ugaaucuaga ccuucgcgg ggcuugccuu cuggccaugc     780
ccuucuucuc ucccuugcac cuguaccucu uggucuuuga auaaagccug aguaggaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaa         956
```

<210> SEQ ID NO 142
<211> LENGTH: 956
<212> TYPE: RNA
<213> ORGANISM: Artificial
<220> FEATURE:
<223> OTHER INFORMATION: alpha(miR-124-3p)-hmAG1

<400> SEQUENCE: 142

```
gguuccgcga ucgcggaucc ggcauucacc gcgugccuua agaucaaaca ccggucgcca      60
ccauggugag cgugaucaag cccgagauga agaucaagcu gugcaugagg ggcaccguga     120
acggccacaa cuucgugauc gagggcgagg gcaagggcaa ccccuacgag ggcacccaga     180
uccuggaccu gaacgugacc gagggcgccc ccugcccuu cgccuacgac auccugacca      240
ccguguucca guacggcaac agggccuuca ccaaguaccc cgccgacauc caggacuacu     300
ucaagcagac cuuccccgag ggcuaccacu gggagaggag caugaccuac gaggaccagg     360
gcaucugcac cgccaccagc aacaucagca ugggggcga cugcuucuuc uacgacauca     420
gguucgacgg caccaacuuc cccccaacg gccccgugau gcagaagaag acccugaagu     480
gggagcccag caccgagaag auguacgugg aggacggcgu gcugaagggc gacgugaaca     540
ugaggcugcu gcuggagggc ggcggccacu acaggugcga cuucaagacc accuacaagg     600
ccaagaagga ggugaggcug cccgacgccc acaagaucga ccacaggauc gagauccuga     660
agcacgacaa ggacuacaac aaggugaagc uguacgagaa cgccgguggcc agguacucca     720
ugcugcccag ccaggccaag ugaaucuaga ccuucgcgg ggcuugccuu cuggccaugc     780
ccuucuucuc ucccuugcac cuguaccucu uggucuuuga auaaagccug aguaggaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaa         956
```

<210> SEQ ID NO 143
<211> LENGTH: 956
<212> TYPE: RNA
<213> ORGANISM: Artificial
<220> FEATURE:
<223> OTHER INFORMATION: alpha(miR-9-5p)-hmAG1

<400> SEQUENCE: 143

| | | | | | |
|---|---|---|---|---|---|
| gguuccgcga | ucgcggaucc | ucauacagcu | agauaaccaa | agaagaucca | ccggucgcca | 60 |
| ccauggugag | cgugaucaag | cccgagauga | agaucaagcu | gugcaugagg | ggcaccguga | 120 |
| acggccacaa | cuucgugauc | gagggcgagg | gcaagggcaa | ccccuacgag | ggcacccaga | 180 |
| uccuggaccu | gaacgugacc | gagggcgccc | cccugcccuu | cgccuacgac | auccugacca | 240 |
| ccguguccca | guacggcaac | agggccuuca | ccaaguaccc | cgccgacauc | caggacuacu | 300 |
| ucaagcagac | cuuccccgag | ggcuaccacu | gggagaggag | caugaccuac | gaggaccagg | 360 |
| gcaucugcac | cgccaccagc | aacaucagca | ugggggcga | cugcuucuuc | uacgacauca | 420 |
| gguucgacgg | caccaacuuc | cccccaacg | gccccgugau | gcagaagaag | acccugaagu | 480 |
| gggagcccag | caccgagaag | auguacgugg | aggacggcgu | gcugaagggc | gacgugaaca | 540 |
| ugaggcugcu | gcuggagggc | ggcggccacu | acaggugcga | cuucaagacc | accuacaagg | 600 |
| ccaagaagga | ggugaggcug | cccgacgccc | acaagaucga | ccacaggauc | gagauccuga | 660 |
| agcacgacaa | ggacuacaac | aaggugaagc | uguacgagaa | cgccguggcc | agguacucca | 720 |
| ugcugcccag | ccaggccaag | ugaaucuaga | ccuucgcgg | ggcuugccuu | cuggccaugc | 780 |
| ccuucuucuc | ucccuugcac | cuguaccucu | uggucuuuga | auaaagccug | aguaggaaaa | 840 |
| aaaaaaaaaa | aaaaaaaaaa | aaaaaaaaaa | aaaaaaaaaa | aaaaaaaaaa | aaaaaaaaaa | 900 |
| aaaaaaaaaa | aaaaaaaaaa | aaaaaaaaaa | aaaaaaaaaa | aaaaaaaaaa | aaaaaa | 956 |

<210> SEQ ID NO 144
<211> LENGTH: 956
<212> TYPE: RNA
<213> ORGANISM: Artificial
<220> FEATURE:
<223> OTHER INFORMATION: alpha(miR-1)-hmAG1

<400> SEQUENCE: 144

| | | | | | |
|---|---|---|---|---|---|
| gguuccgcga | ucgcggaucc | auacauacuu | cuuuacauuc | caagaucaca | ccggucgcca | 60 |
| ccauggugag | cgugaucaag | cccgagauga | agaucaagcu | gugcaugagg | ggcaccguga | 120 |
| acggccacaa | cuucgugauc | gagggcgagg | gcaagggcaa | ccccuacgag | ggcacccaga | 180 |
| uccuggaccu | gaacgugacc | gagggcgccc | cccugcccuu | cgccuacgac | auccugacca | 240 |
| ccguguccca | guacggcaac | agggccuuca | ccaaguaccc | cgccgacauc | caggacuacu | 300 |
| ucaagcagac | cuuccccgag | ggcuaccacu | gggagaggag | caugaccuac | gaggaccagg | 360 |
| gcaucugcac | cgccaccagc | aacaucagca | ugggggcga | cugcuucuuc | uacgacauca | 420 |
| gguucgacgg | caccaacuuc | cccccaacg | gccccgugau | gcagaagaag | acccugaagu | 480 |
| gggagcccag | caccgagaag | auguacgugg | aggacggcgu | gcugaagggc | gacgugaaca | 540 |
| ugaggcugcu | gcuggagggc | ggcggccacu | acaggugcga | cuucaagacc | accuacaagg | 600 |
| ccaagaagga | ggugaggcug | cccgacgccc | acaagaucga | ccacaggauc | gagauccuga | 660 |
| agcacgacaa | ggacuacaac | aaggugaagc | uguacgagaa | cgccguggcc | agguacucca | 720 |
| ugcugcccag | ccaggccaag | ugaaucuaga | ccuucgcgg | ggcuugccuu | cuggccaugc | 780 | ccuucuucuc ucccuugcac cuguaccucu uggucuuuga auaaagccug aguaggaaaa    840 aaaaaaaaaa aaaaaaaaaa aaaaaaaaaa aaaaaaaaaa aaaaaaaaaa aaaaaaaaaa    900 aaaaaaaaaa aaaaaaaaaa aaaaaaaaaa aaaaaaaaaa aaaaaa                   956

<210> SEQ ID NO 145
<211> LENGTH: 956
<212> TYPE: RNA
<213> ORGANISM: Artificial
<220> FEATURE:
<223> OTHER INFORMATION: alpha(miR-206)-hmAG1

<400> SEQUENCE: 145
gguuccgcga ucgcggaucc ccacacacuu ccuuacauuc caagaucaca ccggucgcca     60
ccauggugag cgugaucaag cccgagauga agaucaagcu gugcaugagg ggcaccguga    120
acggccacaa cuucgugauc gagggcgagg gcaagggcaa ccccuacgag ggcacccaga    180
uccuggaccu gaacgugacc gagggcgccc ccugcccuu cgccuacgac auccugacca    240
ccguguucca guacggcaac agggccuuca ccaaguaccc cgccgacauc caggacuacu    300
ucaagcagac cuuccccgag ggcuaccacu gggagaggag caugaccuac gaggaccagg    360
gcaucugcac cgccaccagc aacaucagca ugaggggcga cugcuucuuc uacgacauca    420
gguucgacgg caccaacuuc cccccccaacg gccccgugau gcagaagaag acccugaagu    480
gggagcccag caccgagaag auguacgugg aggacgcgu gcugaagggc gacgugaaca    540
ugaggcugcu gcuggagggc ggcggccacu acaggugcga cuucaagacc accuacaagg    600
ccaagaagga ggugaggcug cccgacgccc acaagaucga ccacaggauc gagauccuga    660
agcacgacaa ggacuacaac aaggugaagc uguacgagaa cgccguggcc agguacucca    720
ugcugcccag ccaggccaag ugaaucuaga ccuucugcgg ggcuugccuu cuggccaugc    780
ccuucuucuc ucccuugcac cuguaccucu uggucuuuga auaaagccug aguaggaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaa                   956

<210> SEQ ID NO 146
<211> LENGTH: 932
<212> TYPE: RNA
<213> ORGANISM: Artificial
<220> FEATURE:
<223> OTHER INFORMATION: alpha(miR-93-5p)-hmKO2

<400> SEQUENCE: 146
gguuccgcga ucgcggaucc cuaccugcac gaacagcacu uugagaucca ccggucgcca     60
ccauggugag ugugauuaaa ccagagauga agaugaggua cuacauggac ggcuccguca    120
augggcauga guucacaauu gaaggugaag gcacaggcag accuuacgag ggacaucaag    180
agaugacacu acgcgucaca auggccgagg gcggccaau gccuucgcg uuugacuuag    240 ugucacacgu guucuguuac ggccacagag uauuuacuaa auaccagaa gagauaccag    300 acuauuucaa acaagcauuu ccugaaggcc ugucauggga aggucguug gaguucgaag    360 augguggguc cgcuucaguc agugcgcaua uaagccuuag aggaaacacc uucuaccaca    420
aauccaaauu uacuggggu aacuuuccug ccgauggucc uaucaugcaa aaccaaagug    480 uugauugggea gccaucaacc gagaaaauua cugccagcga cggaguucug aagggugaug    540
uuacgaugua ccuaaaacuu gaaggaggcg gcaaucacaa augccaaaug aagacuacuu    600
acaaggcggc aaaagagauu cuugaaaugc caggagcca uuacaucggc caucgccucg    660

```
ucaggaaaac cgaaggcaac auuacugagc agguagaaga ugcaguagcu cauuccugaa    720
ucuagaccuu cugcggggcu ugccuucugg ccaugcccuu cuucucuccc uugcaccugu    780
accucuuggu cuuugaauaa agccgaguag gaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aa                                  932
```

<210> SEQ ID NO 147
<211> LENGTH: 932
<212> TYPE: RNA
<213> ORGANISM: Artificial
<220> FEATURE:
<223> OTHER INFORMATION: alpha(miR-145-5p)-hmKO2

<400> SEQUENCE: 147

```
gguuccgcga ucgcggaucc agggauuccu gggaaaacug acagauccca ccggucgcca    60
ccauggugag ugugauuaaa ccagagauga agaugaggua cuacauggac ggcuccguca    120
augggcauga guucacaauu gaaggugaag gcacaggcag accuuacgag ggacaucaag    180
agaugacacu acgcgucaca auggccgagg gcgggccaau gccuuucgcg uuugacuuag    240
ugucacacgu guucuguuac ggccacagag uauuuacuaa auaccagaaa gagauaccag    300
acuauuucaa acaagcauuu ccugaaggcc ugucauggga aggucguug gaguucgaag    360 augguggguc cgcuucaguc agugcgcaua uaagccuuag aggaaacacc uucuaccaca    420
aauccaaauu uacuggggu aacuuuccug ccgauggucc uaucaugcaa aaccaaagug    480
uugauuggga gccaucaacc gagaaaauua cugccagcga cggagauucug aagggugaug    540 uuacgaugua ccuaaaacuu gaaggaggcg gcaaucacaa augccaaaug aagacuacuu    600
acaaggcggc aaaagagauu cuugaaaugc caggagacca uuacaucggc caucgccucg    660
ucaggaaaac cgaaggcaac auuacugagc agguagaaga ugcaguagcu cauuccugaa    720
ucuagaccuu cugcggggcu ugccuucugg ccaugcccuu cuucucuccc uugcaccugu    780
accucuuggu cuuugaauaa agccgaguag gaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aa                                  932
```

<210> SEQ ID NO 148
<211> LENGTH: 932
<212> TYPE: RNA
<213> ORGANISM: Artificial
<220> FEATURE:
<223> OTHER INFORMATION: alpha(miR-26a-5p)-hmKO2

<400> SEQUENCE: 148

```
gguuccgcga ucgcggaucc agccuauccu ggauuacuug aaagaucaca ccggucgcca    60
ccauggugag ugugauuaaa ccagagauga agaugaggua cuacauggac ggcuccguca    120
augggcauga guucacaauu gaaggugaag gcacaggcag accuuacgag ggacaucaag    180
agaugacacu acgcgucaca auggccgagg gcgggccaau gccuuucgcg uuugacuuag    240
ugucacacgu guucuguuac ggccacagag uauuuacuaa auaccagaaa gagauaccag    300
acuauuucaa acaagcauuu ccugaaggcc ugucauggga aggucguug gaguucgaag    360 augguggguc cgcuucaguc agugcgcaua uaagccuuag aggaaacacc uucuaccaca    420
aauccaaauu uacuggggu aacuuuccug ccgauggucc uaucaugcaa aaccaaagug    480
```

```
uugauuggga gccaucaacc gagaaaauua cugccagcga cggaguucug aagggugaug    540
uuacgaugua ccuaaaacuu gaaggaggcg gcaaucacaa augccaaaug aagacuacuu    600
acaaggcggc aaagagauu cuugaaaugc caggagacca uuacaucggc caucgccucg    660
ucaggaaaac cgaaggcaac auuacugagc agguagaaga ugcaguagcu cauuccugaa    720
ucuagaccuu cugcggggcu ugccuucugg ccaugcccuu cuucucuccc uugcaccugu    780
accucuuggu cuugaauaa agccugagua ggaaaaaaaa aaaaaaaaa aaaaaaaaa       840 aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aa                                  932

<210> SEQ ID NO 149
<211> LENGTH: 997
<212> TYPE: RNA
<213> ORGANISM: Artificial
<220> FEATURE:
<223> OTHER INFORMATION: alpha(miR-125b-5p)-tagBFP

<400> SEQUENCE: 149
gguuccgcga ucgcggaucc ucacaaguua gggucucagg gaagaucaca ccgucgcca     60 ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggcccucu ccccuucgcc uucgacaucc    240
uggcuacuag cuuccucuac ggcagcaaga ccuucaucaa ccacacccag ggcaucccog    300 acuucuucaa gcaguccuuc ccugagggcu ucauuggga gagagucacc acauacgaag    360
acgggggcgu gcugaccgcu acccaggaca ccagccucca ggacggcugc cucaucuaca    420
acgucaagau cagaggggug aacuucacau ccaacgcccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca    660
gacuggaaag aaucaaggag gccaacaacg agaccuacgu cgagcagcac gagguggcag    720
uggccagaua cugcgaccuc ccuagcaaac ugggggcacag aucucauaug caucucgagu    780
gauagucuag accuucugcg gggcuugccu ucuggccaug cccuucucu cucccuugca    840 ccuguaccuc uuggucuuug aauaaagccu gaguaggaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaa                            997

<210> SEQ ID NO 150
<211> LENGTH: 997
<212> TYPE: RNA
<213> ORGANISM: Artificial
<220> FEATURE:
<223> OTHER INFORMATION: alpha(miR-93-5p)-tagBFP

<400> SEQUENCE: 150
gguuccgcga ucgcggaucc cuaccugcac gaacagcacu uugagaucca ccgucgcca     60 ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggcccucu ccccuucgcc uucgacaucc    240
uggcuacuag cuuccucuac ggcagcaaga ccuucaucaa ccacacccag ggcaucccog    300
```

```
acuucuucaa gcaguccuuc ccugagggcu ucacauggga gagagucacc acauacgaag    360 acggggcgu gcugaccgcu acccaggaca ccagccucca ggacggcugc cucaucuaca     420
acgucaagau cagaggggug aacuucacau ccaacggccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca    660
gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                             997
```

<210> SEQ ID NO 151
<211> LENGTH: 997
<212> TYPE: RNA
<213> ORGANISM: Artificial
<220> FEATURE:
<223> OTHER INFORMATION: alpha(miR-145-5p)-tagBFP

<400> SEQUENCE: 151

```
gguuccgcga ucgcggaucc agggauuccu gggaaaacug acagauccca ccggucgcca    60
ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggcccucu ccccuucgcc uucgacaucc    240
uggcuacuag cuuccucuac ggcagcaaga ccuucaucaa ccacacccag ggcauccccg    300
acuucuucaa gcaguccuuc ccugagggcu ucacauggga gagagucacc acauacgaag    360 acggggcgu gcugaccgcu acccaggaca ccagccucca ggacggcugc cucaucuaca     420
acgucaagau cagaggggug aacuucacau ccaacggccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca    660
gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                             997
```

<210> SEQ ID NO 152
<211> LENGTH: 997
<212> TYPE: RNA
<213> ORGANISM: Artificial
<220> FEATURE:
<223> OTHER INFORMATION: alpha(miR-26a-5p)-tagBFP

<400> SEQUENCE: 152

```
gguuccgcga ucgcggaucc agccuauccu ggauuacuug aaagaucaca ccggucgcca      60
ccaugggauc cagcgagcug auuaaggaga acaugcacau gaagcuguac auggagggca     120
ccguggacaa ccaucacuuc aagugcacau ccgagggcga aggcaagccc uacgagggca     180
cccagaccau gagaaucaag guggucgagg gcggcccucu ccccuucgcc uucgacaucc     240
uggcuacuag cuuccucuac ggcagcaaga ccuucaucaa ccacacccag ggcaucccog     300
acuucuucaa gcaguccuuc ccugagggcu ucacauggga gagagucacc acauacgaag     360
acggggcgu gcugaccgcu acccaggaca ccagccucca ggacggcugc cucaucuaca      420
acgucaagau cagaggggug aacuucacau ccaacggccc ugugaugcag aagaaaacac     480
ucggcuggga ggccuucacc gagacgcugu accccgcuga cggcggccug gaaggcagaa     540
acgacauggc ccugaagcuc gugggcggga gccaucugau cgcaaacauc aagaccacau     600
auagauccaa gaaacccgcu aagaaccuca agaugccugg cgucuacuau guggacuaca     660
gacuggaaag aaucaaggag gccaacaacg agaccuacgu cgagcagcac gagguggcag     720
uggccagaua cugcgaccuc ccuagcaaac uggggcacag aucucauaug caucucgagu     780
gauagucuag accuucugcg gggcuugccu ucuggccaug cccuucuucu cucccuugca     840
ccuguaccuc uuggucuuug aauaaagccu gaguaggaaa aaaaaaaaa aaaaaaaaa      900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaa                              997

<210> SEQ ID NO 153
<211> LENGTH: 944
<212> TYPE: RNA
<213> ORGANISM: Artificial
<220> FEATURE:
<223> OTHER INFORMATION: alpha(miR-125b-5p)-hdKeimaRed

<400> SEQUENCE: 153 gguccgcga ucgcggaucc ucacaaguua gggucucagg gaagaucaca ccggucgcca       60
ccauggugag cgugaucgcc aagcagauga ccuacaaggu guacaugucc ggcaccguga     120
acggccacua cuucgaggug gagggcgacg gcaagggcaa gcccuacgag ggcgagcaga     180
ccgugaagcu gaccgugacc aagggcggcc ccugcccuu cgccugggac auccugaccc      240
cccguuccca guacgcagc uccccuuca ccaaguaccc cgaggacauc cccgacuacg        300
ugaagcagag cuuccccgag ggcuacaccu gggagaggac caugaacuuc gaggacggcg     360
ccgugugcac cgugagcaac gacuccagca uccaggccaa cugcuucauc uacaacguga     420
agaucagcgg caccaacuuc cccccaacg gccccgugau gcagaagaag acccagggcu      480
gggagcccag caccgagagg cuguucgcca gggacggaau gcugaucggc aacgacuaca     540
uggcccugaa gcuggagggc ggcggccacu accgugcga guucaagucc accacaagg       600
ccaagaagcc cgugaggaug cccggcuacc acuacaucga caggaagcug gacgugacca     660
gccacaacag ggacuacacc uccgugggagc agugcgagau cgccaucgcc aggcacagcc   720
ugcugggcug aaucuagacc uucugcgggg cuugccuucu ggccaugccc uucuucucuc     780
ccuugcaccu guaccucuug gucuuugau aaagccugag uaggaaaaaa aaaaaaaaaa      840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaa                      944

<210> SEQ ID NO 154
<211> LENGTH: 944
```

```
<212> TYPE: RNA
<213> ORGANISM: Artificial
<220> FEATURE:
<223> OTHER INFORMATION: alpha(miR-93-5p)-hdKeimaRed

<400> SEQUENCE: 154
gguuccgcga ucgcggaucc cuaccugcac aacagcacu uugagaucca ccggucgcca      60
ccauggugag cgugaucgcc aagcagauga ccuacaaggu guacaugucc ggcaccguga     120
acggccacua cuucgaggug gagggcgacg gcaaggcaa gcccuacgag ggcgagcaga     180
ccgugaagcu gaccgugacc aagggcggcc ccugcccuu cgccugggac auccugcccc     240
cccuguucca guacggcagc auccccuuca ccaaguaccc cgaggacauc cccgacuacg     300
ugaagcagag cuuccccgag ggcuacaccu gggagaggac caugaacuuc gaggacggcg     360
ccgugugcac cgugagcaac gacuccagca uccagggcaa cugcuucauc uacaacguga     420
agaucagcgg caccaacuuc cccccaacg gccccgugau gcagaagaag acccagggcu     480
gggagcccag caccgagagg cuguuccgca ggacggaau gcugaucggc aacgacuaca     540
uggcccugaa gcuggagggc ggcggccacu accugugcga guucaagucc accuacaagg     600
ccaagaagcc cgugaggaug cccggcuacc acuacaucga caggaagcug gacgugacca     660
gccacaacag ggacuacacc uccguggagc agugcgagau cgccaucgcc aggcacagcc     720
ugcugggcug aaucuagacc uucugcgggg cuugccuucu ggccaugccc uucuucucuc     780
ccuugcaccu guaccucuug gucuuugaau aaagccugag uaggaaaaaa aaaaaaaaaa     840 aaaaaaaaa aaaaaaaaaa aaaaaaaaaa aaaaaaaaaa aaaaaaaaaa aaaaaaaaaa     900 aaaaaaaaa aaaaaaaaaa aaaaaaaaaa aaaaaaaaaa aaaa                     944

<210> SEQ ID NO 155
<211> LENGTH: 944
<212> TYPE: RNA
<213> ORGANISM: Artificial
<220> FEATURE:
<223> OTHER INFORMATION: alpha(miR-145-5p)-hdKeimaRed

<400> SEQUENCE: 155
gguuccgcga ucgcggaucc agggauuccu gggaaaacug acagaucca ccggucgcca      60 ccauggugag cgugaucgcc aagcagauga ccuacaaggu guacaugucc ggcaccguga     120
acggccacua cuucgaggug gagggcgacg gcaaggcaa gcccuacgag ggcgagcaga     180
ccgugaagcu gaccgugacc aagggcggcc ccugcccuu cgccugggac auccugcccc     240
cccuguucca guacggcagc auccccuuca ccaaguaccc cgaggacauc cccgacuacg     300
ugaagcagag cuuccccgag ggcuacaccu gggagaggac caugaacuuc gaggacggcg     360
ccgugugcac cgugagcaac gacuccagca uccagggcaa cugcuucauc uacaacguga     420
agaucagcgg caccaacuuc cccccaacg gccccgugau gcagaagaag acccagggcu     480
gggagcccag caccgagagg cuguuccgca ggacggaau gcugaucggc aacgacuaca     540
uggcccugaa gcuggagggc ggcggccacu accugugcga guucaagucc accuacaagg     600
ccaagaagcc cgugaggaug cccggcuacc acuacaucga caggaagcug gacgugacca     660
gccacaacag ggacuacacc uccguggagc agugcgagau cgccaucgcc aggcacagcc     720
ugcugggcug aaucuagacc uucugcgggg cuugccuucu ggccaugccc uucuucucuc     780
ccuugcaccu guaccucuug gucuuugaau aaagccugag uaggaaaaaa aaaaaaaaaa     840 aaaaaaaaa aaaaaaaaaa aaaaaaaaaa aaaaaaaaaa aaaaaaaaaa aaaaaaaaaa     900
```

<210> SEQ ID NO 156
<211> LENGTH: 944
<212> TYPE: RNA
<213> ORGANISM: Artificial
<220> FEATURE:
<223> OTHER INFORMATION: alpha(miR-26a-5p)-hdKeimaRed

<400> SEQUENCE: 156

```
gguuccgcga ucgcggaucc agccuauccu ggauuacuug aaagaucaca ccggucgcca      60
ccauggugag cgugaucgcc aagcagauga ccuacaaggu guacaugucc ggcaccguga     120
acggccacua cuucgaggug gagggcgacg gcaagggcaa gcccuacgag ggcgagcaga     180
ccgugaagcu gaccgugacc aagggcggcc ccugcccuu cgccugggac auccugcccc     240
cccuguucca guacggcagc auccccuuca ccaaguaccc cgaggacauc cccgacuacg     300
ugaagcagag cuuccccgag ggcuacaccu gggagaggac caugaacuuc gaggacggcg     360
ccgugugcac cgugagcaac gacuccagca uccagggcaa cugcuucauc uacaacguga     420
agaucagcgg caccaacuuc cccccaacg gccccgugau gcagaagaag acccagggcu     480
gggagcccag caccgagagg cuguucgcca gggacgaau gcugaucggc aacgacuaca     540
uggcccugaa gcuggagggc ggcggccacu accugugcga guucaagucc accuacaagg     600
ccaagaagcc cgugaggaug cccggcuacc acuacaucga caggaagcug gacgugacca     660
gccacaacag ggacuacacc uccguggagc agugcgagau cgccaucgcc aggcacagcc     720
ugcugggcug aaucuagacc uucugcgggg cuugccuucu ggccaugccc ucuucucuc     780
ccuugcaccu guaccucuug gucuuugaau aaagccugag uaggaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaa                       944
```

<210> SEQ ID NO 157
<211> LENGTH: 932
<212> TYPE: RNA
<213> ORGANISM: Artificial
<220> FEATURE:
<223> OTHER INFORMATION: alpha(miR-16-5p)-hmKO2

<400> SEQUENCE: 157

```
gguuccgcga ucgcggaucc cgccaauauu uacgugcugc uaagaucaca ccggucgcca      60
ccauggugag ugugauuaaa ccagagauga agaugaggua cuacauggac ggcuccguca     120
augggcauga guucacaauu gaaggugaag gcacaggcag accuuacgag ggacaucaag     180
agaugacacu acgcgucaca auggccgagg gcggggccaau gccuucgcg uuugacuuag     240
ugucacacgu guucuguuac ggccacagag uauuuacuaa auaccagaa gagauaccag     300
acuauuucaa acaagcauuu ccugaaggcc ugucaugggc aaggucguug gaguucgaag     360
auggugggguc cgcuucaguc agugcgcaua uaagccuuag aggaaacacc uucuaccaca     420
aauccaaauu uacugggguu aacuuuccug ccgauggucc uaucaugcaa aaccaaagug     480
uugauuggga gccaucaacc gagaaaauua cugccagcga cggaguucug aagggugaug     540
uuacgaugua ccuaaaacuu gaaggaggcg gcaaucacaa augccaaaug aagacuacuu     600
acaaggcggc aaaagagauu cugaaaaugc caggagacca uuacaucgca caucgccucg     660
ucaggaaaac cgaaggcaac auuacugagc agguagaaga ugcaguagcu cauuccgaa      720
ucuagaccuu cugcggggcu ugccuucugg ccaugcccuu cuucucucc uugcaccugu     780
```

```
accucuuggu cuuugaauaa agccugagua ggaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aa                                  932
```

<210> SEQ ID NO 158
<211> LENGTH: 932
<212> TYPE: RNA
<213> ORGANISM: Artificial
<220> FEATURE:
<223> OTHER INFORMATION: alpha(miR-17-5p)-hmKO2

<400> SEQUENCE: 158

```
gguuccgcga ucgcggaucc cuaccugcac guaagcacu uugagaucca ccggucgcca     60
ccauggugag ugugauuaaa ccagagauga agaugaggua cuacauggac ggcuccguca   120
augggcauga guucacaauu gaaggugaag gcacaggcag accuuacgag ggacaucaag   180
agaugacacu acgcgucaca auggccgagg gcgggccaau gccuuucgcg uuugacuuag   240 ugcacacgu guucuguuac ggccacagag uauuuacuaa auaccagaa gagauaccag    300 acuauuucaa acaagcauuu ccugaaggcc ugucauggga aaggucguug gaguucgaag   360
auggugdguc cgcuucaguc agugcgcaua uaagccuuag aggaaacacc uucuaccaca   420
aauccaaauu uacuggggu aacuuuccug ccgauggucc uaucaugcaa aaccaaagug   480
uugauuggga gccaucaacc gagaaaauua cugccagcga cggagauucug aagggugaug   540 uuacgaugua ccuaaaacuu gaaggaggcg gcaaucacaa augccaaaug aagacuacuu   600
acaaggcggc aaaagagauu cuugaaaugc caggagacca uuacaucggc caucgccucg   660
ucaggaaaac cgaaggcaac auuacugagc agguagaaga ugcaguagcu cauuccugaa   720
ucuagaccuu cugcggggcu ugccuucugg ccaugcccuu cuucucuccc uugcaccugu   780
accucuuggu cuuugaauaa agccugagua ggaaaaaaaa aaaaaaaaaa aaaaaaaaaa   840
aaaaaaaaaa aaaaaaaaaa aaaaaaaaaa aaaaaaaaaa aaaaaaaaaa aaaaaaaaaa   900
aaaaaaaaaa aaaaaaaaaa aaaaaaaaaa aa                                 932
```

<210> SEQ ID NO 159
<211> LENGTH: 932
<212> TYPE: RNA
<213> ORGANISM: Artificial
<220> FEATURE:
<223> OTHER INFORMATION: alpha(miR-21-5p)-hmKO2

<400> SEQUENCE: 159

```
gguuccgcga ucgcggaucc ucaacaucag ucugauaagc uaagaucaca ccggucgcca    60
ccauggugag ugugauuaaa ccagagauga agaugaggua cuacauggac ggcuccguca   120
augggcauga guucacaauu gaaggugaag gcacaggcag accuuacgag ggacaucaag   180
agaugacacu acgcgucaca auggccgagg gcgggccaau gccuuucgcg uuugacuuag   240 ugcacacgu guucuguuac ggccacagag uauuuacuaa auaccagaa gagauaccag    300 acuauuucaa acaagcauuu ccugaaggcc ugucauggga aaggucguug gaguucgaag   360
augguggguc cgcuucaguc agugcgcaua uaagccuuag aggaaacacc uucuaccaca   420
aauccaaauu uacuggggu aacuuuccug ccgauggucc uaucaugcaa aaccaaagug   480
uugauuggga gccaucaacc gagaaaauua cugccagcga cggagauucug aagggugaug   540 uuacgaugua ccuaaaacuu gaaggaggcg gcaaucacaa augccaaaug aagacuacuu   600
```

| | |
|---|---|
| acaaggcggc aaaagagauu cuugaaaugc caggagacca uuacaucggc caucgccucg | 660 |
| ucaggaaaac cgaaggcaac auuacugagc agguagaaga ugcaguagcu cauuccugaa | 720 |
| ucuagaccuu cugcggggcu ugccuucugg ccaugcccuu cuucucuccc uugcaccugu | 780 |
| accucuuggu cuuugaauaa agccugagua ggaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aa | 932 |

```
<210> SEQ ID NO 160
<211> LENGTH: 932
<212> TYPE: RNA
<213> ORGANISM: Artificial
<220> FEATURE:
<223> OTHER INFORMATION: alpha(miR-27a-3p)-hmKO2

<400> SEQUENCE: 160
```

| | |
|---|---|
| gguuccgcga ucgcggaucc gcggaacuua gccacuguga aagaucaaca ccggucgcca | 60 |
| ccauggugag ugugauuaaa ccagagauga agaugaggua cuacauggac ggcuccguca | 120 |
| augggcauga guucacaauu gaaggugaag gcacaggcag accuuacgag ggacaucaag | 180 |
| agaugacacu acgcgucaca auggccgagg gcgggccaau gccuucgcg uuugacuuag | 240 |
| ugucacacgu guucuguuac ggccacagag uauuuacuaa auauccagaa gagauaccag | 300 |
| acuauuucaa acaagcauuu ccugaaggcc ugucauggga aaggucguug gaguucgaag | 360 |
| auggugggguc cgcuucaguc agugcgcaua uaagccuuag aggaaacacc uucuaccaca | 420 |
| aauccaaauu uacuggggu aacuuuccug ccgauggucc uaucaugcaa aaccaaagug | 480 |
| uugauuggga gccaucaacc gagaaaauua cugccagcga cggaguucug aagggugaug | 540 |
| uuacgaugua ccuaaaacuu gaaggaggcg gcaaucacaa augccaaaug aagacuacuu | 600 |
| acaaggcggc aaaagagauu cuugaaaugc caggagacca uuacaucggc caucgccucg | 660 |
| ucaggaaaac cgaaggcaac auuacugagc agguagaaga ugcaguagcu cauuccugaa | 720 |
| ucuagaccuu cugcggggcu ugccuucugg ccaugcccuu cuucucuccc uugcaccugu | 780 |
| accucuuggu cuuugaauaa agccugagua ggaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aa | 932 |

```
<210> SEQ ID NO 161
<211> LENGTH: 932
<212> TYPE: RNA
<213> ORGANISM: Artificial
<220> FEATURE:
<223> OTHER INFORMATION: alpha(miR-20a-5p)-hmKO2

<400> SEQUENCE: 161
```

| | |
|---|---|
| gguuccgcga ucgcggaucc cuaccugcac uauaagcacu uuaagauccha ccggucgcca | 60 |
| ccauggugag ugugauuaaa ccagagauga agaugaggua cuacauggac ggcuccguca | 120 |
| augggcauga guucacaauu gaaggugaag gcacaggcag accuuacgag ggacaucaag | 180 |
| agaugacacu acgcgucaca auggccgagg gcgggccaau gccuucgcg uuugacuuag | 240 |
| ugucacacgu guucuguuac ggccacagag uauuuacuaa auauccagaa gagauaccag | 300 |
| acuauuucaa acaagcauuu ccugaaggcc ugucauggga aaggucguug gaguucgaag | 360 |
| augguggguc cgcuucaguc agugcgcaua uaagccuuag aggaaacacc uucuaccaca | 420 |
| aauccaaauu uacuggggu aacuuuccug ccgauggucc uaucaugcaa aaccaaagug | 480 |

```
uugauuggga gccaucaacc gagaaaauua cugccagcga cggaguucug aagggugaug    540
uuacgaugua ccuaaaacuu gaaggaggcg gcaaucacaa augccaaaug aagacuacuu    600
acaaggcggc aaaagagauu cuugaaaugc caggagacca uuacaucggc caucgccucg    660
ucaggaaaac cgaaggcaac auuacugagc agguagaaga ugcaguagcu cauuccugaa    720
ucuagaccuu cugcggggcu ugccuucugg ccaugcccuu cuucucuccc uugcaccugu    780
accucuuggu cuuugaauaa agccgaguag gaaaaaaaa aaaaaaaaaa aaaaaaaaa     840 aaaaaaaaaa aaaaaaaaaa aaaaaaaaaa aaaaaaaaa aaaaaaaaaa aaaaaaaaaa    900
aaaaaaaaaa aaaaaaaaaa aaaaaaaaaa aa                                932
```

<210> SEQ ID NO 162
<211> LENGTH: 932
<212> TYPE: RNA
<213> ORGANISM: Artificial
<220> FEATURE:
<223> OTHER INFORMATION: alpha(miR-106a-5p)-hmKO2

<400> SEQUENCE: 162

```
gguuccgcga ucgcggaucc cuaccugcac uguaagcacu uuuagaucca ccggucgcca    60
ccauggugag ugugauuaaa ccagagauga agaugaggua cuacauggac ggcuccguca    120
augggcauga guucacaauu gaaggugaag gcacaggcag accuuacgag ggacaucaag    180
agaugacacu acgcgucaca auggccgagg gcgggccaau gccuucgcg uuugacuuag    240 ugucacacgu guucuguuac ggccacagag uauuuacuaa auauccagaa gagauaccag    300
acuauuucaa acaagcauuu ccugaaggcc ugucauggga aaggucguug gaguucgaag    360 auggugggic cgcuucaguc agugcgcaua uaagccuuag aggaaacacc uucuaccaca    420
aauccaaauu uacgggguu aacuuuccug ccgauggucc uaucaugcaa aaccaaagug    480
uugauuggga gccaucaacc gagaaaauua cugccagcga cggaguucug aagggugaug    540
uuacgaugua ccuaaaacuu gaaggaggcg gcaaucacaa augccaaaug aagacuacuu    600
acaaggcggc aaaagagauu cuugaaaugc caggagacca uuacaucggc caucgccucg    660
ucaggaaaac cgaaggcaac auuacugagc agguagaaga ugcaguagcu cauuccugaa    720
ucuagaccuu cugcggggcu ugccuucugg ccaugcccuu cuucucuccc uugcaccugu    780
accucuuggu cuuugaauaa agccgaguag gaaaaaaaa aaaaaaaaaa aaaaaaaaa     840 aaaaaaaaaa aaaaaaaaaa aaaaaaaaaa aaaaaaaaa aaaaaaaaaa aaaaaaaaaa    900
aaaaaaaaaa aaaaaaaaaa aaaaaaaaaa aa                                932
```

<210> SEQ ID NO 163
<211> LENGTH: 932
<212> TYPE: RNA
<213> ORGANISM: Artificial
<220> FEATURE:
<223> OTHER INFORMATION: alpha(miR-143-3p)-hmKO2

<400> SEQUENCE: 163

```
gguuccgcga ucgcggaucc gagcuacagu gcuucaucuc aagaucaaca ccggucgcca    60
ccauggugag ugugauuaaa ccagagauga agaugaggua cuacauggac ggcuccguca    120
augggcauga guucacaauu gaaggugaag gcacaggcag accuuacgag ggacaucaag    180
agaugacacu acgcgucaca auggccgagg gcgggccaau gccuucgcg uuugacuuag    240 ugucacacgu guucuguuac ggccacagag uauuuacuaa auauccagaa gagauaccag    300
```

| | |
|---|---|
| acuauuucaa acaagcauuu ccugaaggcc ugucauggga aaggucguug gaguucgaag | 360 |
| augguggguc cgcuucaguc agugcgcaua uaagccuuag aggaaacacc uucuaccaca | 420 |
| aauccaaauu uacuggggau aacuuuccug ccgauggucc uaucaugcaa aaccaaagug | 480 |
| uugauuggga gccaucaacc gagaaaauua cugccagcga cggaguucug aagggugaug | 540 |
| uuacgaugua ccuaaaacuu gaaggaggcg gcaaucacaa augccaaaug aagacuacuu | 600 |
| acaaggcggc aaaagagauu cuugaaaugc caggagacca uuacaucggc caucgccucg | 660 |
| ucaggaaaac cgaaggcaac auuacugagc agguagaaga ugcaguagcu cauuccugaa | 720 |
| ucuagaccuu cugcggggcu ugccuucugg ccaugcccuu cuucucuccc uugcaccugu | 780 |
| accucuuggu cuuugaauaa agccugagua ggaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aa | 932 |

<210> SEQ ID NO 164
<211> LENGTH: 932
<212> TYPE: RNA
<213> ORGANISM: Artificial
<220> FEATURE:
<223> OTHER INFORMATION: alpha(let-7i-5p)-hmKO2

<400> SEQUENCE: 164

| | |
|---|---|
| gguuccgcga ucgcggaucc aacagcacaa acuacuaccu caagaucaca ccggucgcca | 60 |
| ccauggugag ugugauuaaa ccagagauga agaugaggua cuacauggac ggcuccguca | 120 |
| augggcauga guucacaauu gaaggugaag gcacaggcag accuacgag ggacaucaag | 180 |
| agaugacacu acgcgucaca auggccgagg gcgggccaau gccuucgcg uuugacuuag | 240 |
| ugucacacgu guucuguuac ggccacagag uauuuacuaa auaccagaa gagauaccag | 300 |
| acuauuucaa acaagcauuu ccugaaggcc ugucauggga aaggucguug gaguucgaag | 360 |
| augguggguc cgcuucaguc agugcgcaua uaagccuuag aggaaacacc uucuaccaca | 420 |
| aauccaaauu uacuggggau aacuuuccug ccgauggucc uaucaugcaa aaccaaagug | 480 |
| uugauuggga gccaucaacc gagaaaauua cugccagcga cggaguucug aagggugaug | 540 |
| uuacgaugua ccuaaaacuu gaaggaggcg gcaaucacaa augccaaaug aagacuacuu | 600 |
| acaaggcggc aaaagagauu cuugaaaugc caggagacca uuacaucggc caucgccucg | 660 |
| ucaggaaaac cgaaggcaac auuacugagc agguagaaga ugcaguagcu cauuccugaa | 720 |
| ucuagaccuu cugcggggcu ugccuucugg ccaugcccuu cuucucuccc uugcaccugu | 780 |
| accucuuggu cuuugaauaa agccugagua ggaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aa | 932 |

<210> SEQ ID NO 165
<211> LENGTH: 932
<212> TYPE: RNA
<213> ORGANISM: Artificial
<220> FEATURE:
<223> OTHER INFORMATION: alpha(miR-125b-5p)-hmKO2

<400> SEQUENCE: 165

| | |
|---|---|
| gguuccgcga ucgcggaucc ucacaaguua gggucucagg gaagaucaca ccggucgcca | 60 |
| ccauggugag ugugauuaaa ccagagauga agaugaggua cuacauggac ggcuccguca | 120 |
| augggcauga guucacaauu gaaggugaag gcacaggcag accuacgag ggacaucaag | 180 |

| agaugacacu | acgcgucaca | auggccgagg | gcgggccaau | gccuuucgcg | uuugacuuag | 240 |
| ugucacacgu | guucuguuac | ggccacagag | uauuuacuaa | auauccagaa | gagauaccag | 300 |
| acuauuucaa | acaagcauuu | ccugaaggcc | ugucauggga | aaggucguug | gaguucgaag | 360 |
| auggugdggc | cgcuucaguc | agugcgcaua | uaagccuuag | aggaaacacc | uucuaccaca | 420 |
| aauccaaauu | uacugggguu | aacuuuccug | ccgaugguce | uaucaugcaa | aaccaaagug | 480 |
| uugauuggga | gccaucaacc | gagaaaauua | cugccagcga | cggaguucug | aagggugaug | 540 |
| uuacgaugua | ccuaaaacuu | gaaggaggcg | gcaaucacaa | augccaaaug | aagacuacuu | 600 |
| acaaggcggc | aaaagagauu | cuugaaaugc | caggagacca | uuacaucggc | caucgccucg | 660 |
| ucaggaaaac | cgaaggcaac | auuacugagc | agguagaaga | ugcaguagcu | cauuccugaa | 720 |
| ucuagaccuu | cugcggggcu | ugccuucugg | ccaugcccuu | cuucucuccc | uugcaccugu | 780 |
| accucuuggu | cuuugaauaa | agccugagua | ggaaaaaaaa | aaaaaaaaaa | aaaaaaaaaa | 840 |
| aaaaaaaaaa | aaaaaaaaaa | aaaaaaaaaa | aaaaaaaaaa | aaaaaaaaaa | aaaaaaaaaa | 900 |
| aaaaaaaaaa | aaaaaaaaaa | aaaaaaaaaa | aa | | | 932 |

<210> SEQ ID NO 166
<211> LENGTH: 997
<212> TYPE: RNA
<213> ORGANISM: Artificial
<220> FEATURE:
<223> OTHER INFORMATION: alpha(miR-16-5p)-tagBFP

<400> SEQUENCE: 166

| gguuccgcga | ucgcggaucc | cgccaauauu | uacgugcugc | uaagaucaca | ccggucgcca | 60 |
| ccaugggauc | cagcgagcug | auuaaggaga | acaugcacau | gaagcuguac | auggagggca | 120 |
| ccguggacaa | ccaucacuuc | aagugcacau | ccgagggcga | aggcaagccc | uacgagggca | 180 |
| cccagaccau | gagaaucaag | gugguecgagg | gcggcccucu | ccccuucgcc | uucgacaucc | 240 |
| uggcuacuag | cuuccucuac | ggcagcaaga | ccuucaucaa | ccacacccag | ggcauccccg | 300 |
| acuucuucaa | gcagucccuu | ccugagggcu | ucacauggga | gagagucacc | acauacgaag | 360 |
| acgggggcgu | gcugaccgcu | acccaggaca | ccagccucca | ggacggcugc | cucaucuaca | 420 |
| acgucaagau | cagagggggug | aacuucacau | ccaacggccc | ugugaugcag | aagaaaacac | 480 |
| ucggcuggga | ggccuucacc | gagacgcugu | accccgcuga | cggcggccug | gaaggcagaa | 540 |
| acgacauggc | ccugaagcuc | gugggcggga | gccaucugau | cgcaaacauc | aagaccacau | 600 |
| auagauccaa | gaaacccgcu | aagaaccuca | agaugccugg | cgucuacuau | guggacuaca | 660 |
| gacuggaaag | aaucaaggag | gccaacaacg | agaccuacgu | cgagcagcac | gagguggcag | 720 |
| uggccagaua | cugcgaccuc | ccuagcaaac | ugggcacag | aucucauaug | caucucgagu | 780 |
| gauagucuag | accuucugcg | gggcuugccu | ucuggccaug | cccuucuucu | cucccuugca | 840 |
| ccuguaccuc | uuggucuuug | aauaaagccu | gaguaggaaa | aaaaaaaaaa | aaaaaaaaa | 900 |
| aaaaaaaaaa | aaaaaaaaaa | aaaaaaaaaa | aaaaaaaaaa | aaaaaaaaaa | aaaaaaaaaa | 960 |
| aaaaaaaaaa | aaaaaaaaaa | aaaaaaaaaa | aaaaaaa | | | 997 |

<210> SEQ ID NO 167
<211> LENGTH: 997
<212> TYPE: RNA
<213> ORGANISM: Artificial
<220> FEATURE:
<223> OTHER INFORMATION: alpha(miR-17-5p)-tagBFP

<400> SEQUENCE: 167

```
gguuccgcga ucgcggaucc cuaccugcac uguaagcacu uugagaucca ccggucgcca      60
ccaugggauc cagcgagcug auuaaggaga acaugcacau gaagcuguac auggagggca     120
ccguggacaa ccaucacuuc aagugcacau ccgagggcga aggcaagccc uacgagggca     180
cccagaccau gagaaucaag guggucgagg gcggcccucu ccccuucgcc uucgacaucc     240
uggcuacuag cuuccucuac ggcagcaaga ccuucaucaa ccacacccag ggcauccccg     300
acuucuucaa gcaguccuuc ccugagggcu ucacauggga gagagucacc acaucgaag      360
acggggggcgu gcugaccgcu acccaggaca ccagccucca ggacggcugc cucaucuaca    420
acgucaagau cagagggggug aacuucacau ccaacggccc ugugaugcag aagaaaacac    480
ucggcuggga ggccuucacc gagacgcugu accccgcuga cggcggccug gaaggcagaa     540
acgacauggc ccugaagcuc gugggcggga gccaucugau cgcaaacauc aagaccacau     600
auagauccaa gaaacccgcu aagaaccuca agaugccugg cgucuacuau guggacuaca    660
gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaa aaaaaaaaaa aaaaaa                                997
```

<210> SEQ ID NO 168
<211> LENGTH: 997
<212> TYPE: RNA
<213> ORGANISM: Artificial
<220> FEATURE:
<223> OTHER INFORMATION: alpha(miR-21-5p)-tagBFP

<400> SEQUENCE: 168

```
gguuccgcga ucgcggaucc ucaacaucag ucugauaagc uaagaucaca ccggucgcca     60
ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggcccucu ccccuucgcc uucgacaucc    240
uggcuacuag cuuccucuac ggcagcaaga ccuucaucaa ccacacccag ggcauccccg    300
acuucuucaa gcaguccuuc ccugagggcu ucacauggga gagagucacc acaucgaag     360
acggggggcgu gcugaccgcu acccaggaca ccagccucca ggacggcugc cucaucuaca   420
acgucaagau cagagggggug aacuucacau ccaacggccc ugugaugcag aagaaaacac   480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca   660
gacuggaaag aaucaaggag gccaacaacg agaccuacgu cgagcagcac gagguggcag   720
uggccagaua cugcgaccuc ccuagcaaac uggggcacag aucucauaug caucucgagu   780
gauagucuag accuucugcg gggcuugccu ucuggccaug cccuucuucu cucccuugca   840
ccuguaccuc uuggucuuug aauaaagccu gaguaggaaa aaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaa aaaaaaaaaa aaaaaa                               997
```

<210> SEQ ID NO 169
<211> LENGTH: 997
<212> TYPE: RNA
<213> ORGANISM: Artificial
<220> FEATURE:
<223> OTHER INFORMATION: alpha(miR-27a-3p)-tagBFP

<400> SEQUENCE: 169

| | | | | | |
|---|---|---|---|---|---|
| gguuccgcga | ucgcggaucc | gcggaacuua | gccacuguga | aagaucaaca | ccggucgcca | 60 |
| ccaugggauc | cagcgagcug | auuaaggaga | acaugcacau | gaagcuguac | auggagggca | 120 |
| ccguggacaa | ccaucacuuc | aagugcacau | ccgagggcga | aggcaagccc | uacgagggca | 180 |
| cccagaccau | gagaaucaag | guggucgagg | gcggcccucu | ccccuucgcc | uucgacaucc | 240 |
| uggcuacuag | cuuccucuac | ggcagcaaga | ccuucaucaa | ccacacccag | ggcaucccCg | 300 |
| acuucuucaa | gcagccuuc | ccugagggcu | ucacauggga | gagagucacc | acaucgaag | 360 |
| acggggGcgu | gcugaccgcu | acccaggaca | ccagccucca | ggacggcugc | cucaucuaca | 420 |
| acgucaagau | cagaggggug | aacuucacau | ccaacggccc | ugugaugcag | aagaaaacac | 480 |
| ucggcuggga | ggccuucacc | gagacgcugu | accccgcuga | cggcggccug | gaaggcagaa | 540 |
| acgacauggc | ccugaagcuc | gugggcggga | gccaucugau | cgcaaacauc | aagaccacau | 600 |
| auagauccaa | gaaacccgcu | aagaaccuca | agaugccugg | cgucuacuau | guggacuaca | 660 |
| gacuggaaag | aaucaaggag | gccaacaacg | agaccuacgu | cgagcagcac | gagguggcag | 720 |
| uggccagaua | cugcgaccuc | ccuagcaaac | uggggcacag | aucucauaug | caucucgagu | 780 |
| gauagucuag | accuucugcg | gggcuugccu | ucuggccaug | cccuucuucu | cucccuugca | 840 |
| ccuguaccuc | uuggucuuug | aauaaagccu | gaguaggaaa | aaaaaaaaa | aaaaaaaaa | 900 |
| aaaaaaaaa | aaaaaaaaa | aaaaaaaaa | aaaaaaaaa | aaaaaaaaa | aaaaaaaaa | 960 |
| aaaaaaaaa | aaaaaaaaa | aaaaaaaaa | aaaaaaa | | | 997 |

<210> SEQ ID NO 170
<211> LENGTH: 997
<212> TYPE: RNA
<213> ORGANISM: Artificial
<220> FEATURE:
<223> OTHER INFORMATION: alpha(miR-20a-5p)-tagBFP

<400> SEQUENCE: 170

| | | | | | |
|---|---|---|---|---|---|
| gguuccgcga | ucgcggaucc | cuaccugcac | uauaagcacu | uuaagaucca | ccggucgcca | 60 |
| ccaugggauc | cagcgagcug | auuaaggaga | acaugcacau | gaagcuguac | auggagggca | 120 |
| ccguggacaa | ccaucacuuc | aagugcacau | ccgagggcga | aggcaagccc | uacgagggca | 180 |
| cccagaccau | gagaaucaag | guggucgagg | gcggcccucu | ccccuucgcc | uucgacaucc | 240 |
| uggcuacuag | cuuccucuac | ggcagcaaga | ccuucaucaa | ccacacccag | ggcaucccCg | 300 |
| acuucuucaa | gcagccuuc | ccugagggcu | ucacauggga | gagagucacc | acaucgaag | 360 |
| acggggGcgu | gcugaccgcu | acccaggaca | ccagccucca | ggacggcugc | cucaucuaca | 420 |
| acgucaagau | cagaggggug | aacuucacau | ccaacggccc | ugugaugcag | aagaaaacac | 480 |
| ucggcuggga | ggccuucacc | gagacgcugu | accccgcuga | cggcggccug | gaaggcagaa | 540 |
| acgacauggc | ccugaagcuc | gugggcggga | gccaucugau | cgcaaacauc | aagaccacau | 600 |
| auagauccaa | gaaacccgcu | aagaaccuca | agaugccugg | cgucuacuau | guggacuaca | 660 |
| gacuggaaag | aaucaaggag | gccaacaacg | agaccuacgu | cgagcagcac | gagguggcag | 720 |

| | |
|---|---|
| uggccagaua cugcgaccuc ccuagcaaac uggggcacag aucucauaug caucucgagu | 780 |
| gauagucuag accuucugcg gggcuugccu ucuggccaug cccuucuucu cucccuugca | 840 |
| ccuguaccuc uuggucuuug aauaaagccu gaguaggaaa aaaaaaaaa aaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaa | 997 |

<210> SEQ ID NO 171
<211> LENGTH: 997
<212> TYPE: RNA
<213> ORGANISM: Artificial
<220> FEATURE:
<223> OTHER INFORMATION: alpha(miR-106a-5p)-tagBFP

<400> SEQUENCE: 171

| | |
|---|---|
| gguuccgcga ucgcggaucc cuaccugcac uguaagcacu uuuagaucca ccggucgcca | 60 |
| ccaugggauc cagcgagcug auuaaggaga acaugcacau gaagcuguac auggagggca | 120 |
| ccguggacaa ccaucacuuc aagugcacau ccgagggcga aggcaagccc uacgagggca | 180 |
| cccagaccau gagaaucaag guggucgagg gcggcccucu ccccuucgcc uucgacaucc | 240 |
| uggcuacuag cuuccucuac ggcagcaaga ccuucaucaa ccacacccag ggcauccccg | 300 |
| acuucuucaa gcagucccuuc ccugagggcu ucacauggga gagagucacc acauacgaag | 360 |
| acgggggcgu gcugaccgcu acccaggaca ccagccucca ggacggcugc cucaucuaca | 420 |
| acgucaagau cagaggggug aacuucacau ccaacggccc ugugaugcag aagaaaacac | 480 |
| ucggcuggga ggccuucacc gagacgcugu accccgcuga cggcggccug gaaggcagaa | 540 |
| acgacauggc ccugaagcuc gugggcggga gccaucugau cgcaaacauc aagaccacau | 600 |
| auagauccaa gaaacccgcu aagaaccuca agaugccugg cgucuacuau guggacuaca | 660 |
| gacuggaaag aaucaaggag gccaacaacg agaccuacgu cgagcagcac gagguggcag | 720 |
| uggccagaua cugcgaccuc ccuagcaaac uggggcacag aucucauaug caucucgagu | 780 |
| gauagucuag accuucugcg gggcuugccu ucuggccaug cccuucuucu cucccuugca | 840 |
| ccuguaccuc uuggucuuug aauaaagccu gaguaggaaa aaaaaaaaa aaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaa | 997 |

<210> SEQ ID NO 172
<211> LENGTH: 997
<212> TYPE: RNA
<213> ORGANISM: Artificial
<220> FEATURE:
<223> OTHER INFORMATION: alpha(miR-143-3p)-tagBFP

<400> SEQUENCE: 172

| | |
|---|---|
| gguuccgcga ucgcggaucc gagcuacagu gcuucaucuc aagaucaaca ccggucgcca | 60 |
| ccaugggauc cagcgagcug auuaaggaga acaugcacau gaagcuguac auggagggca | 120 |
| ccguggacaa ccaucacuuc aagugcacau ccgagggcga aggcaagccc uacgagggca | 180 |
| cccagaccau gagaaucaag guggucgagg gcggcccucu ccccuucgcc uucgacaucc | 240 |
| uggcuacuag cuuccucuac ggcagcaaga ccuucaucaa ccacacccag ggcauccccg | 300 |
| acuucuucaa gcagucccuuc ccugagggcu ucacauggga gagagucacc acauacgaag | 360 |
| acgggggcgu gcugaccgcu acccaggaca ccagccucca ggacggcugc cucaucuaca | 420 |
| acgucaagau cagaggggug aacuucacau ccaacggccc ugugaugcag aagaaaacac | 480 |

```
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca    660
gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucgcg gggcuugccu ucuggccaug cccuucuucu ucccuugca    840 ccuguaccuc uuggucuuug aauaaagccu gaguaggaaa aaaaaaaaa aaaaaaaaa    900 aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                            997
```

<210> SEQ ID NO 173
<211> LENGTH: 997
<212> TYPE: RNA
<213> ORGANISM: Artificial
<220> FEATURE:
<223> OTHER INFORMATION: alpha(let-7i-5p)-tagBFP

<400> SEQUENCE: 173

```
gguccgcga ucgcggaucc aacagcacaa acuacuaccu caagaucaca ccggucgcca    60
ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggccucu ccccuucgcc uucgacaucc    240
uggcuacuag cuuccucuac ggcagcaaga ccuucaucaa ccacacccag ggcauccccg    300
acuucuucaa gcaguccuuc ccugagggcu ucacauggga gagagucacc acauacgaag    360 acggggggcgu gcugaccgcu acccaggaca ccagccucca ggacggcugc cucaucuaca    420
acgucaagau cagaggggug aacuucacau ccaacggccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca    660
gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucgcg gggcuugccu ucuggccaug cccuucuucu ucccuugca    840 ccuguaccuc uuggucuuug aauaaagccu gaguaggaaa aaaaaaaaa aaaaaaaaa    900 aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                            997
```

<210> SEQ ID NO 174
<211> LENGTH: 944
<212> TYPE: RNA
<213> ORGANISM: Artificial
<220> FEATURE:
<223> OTHER INFORMATION: alpha(miR-16-5p)-hdKeimaRed

<400> SEQUENCE: 174

```
gguccgcga ucgcggaucc cgccaauauu uacgugcugc uaagaucaca ccggucgcca    60
ccauggugag cgugaucgcc aagcagauga ccuacaaggu guacaugucc ggcaccguga    120
acggccacua cuucgaggug gagggcgacg gcaagggcaa gcccuacgag ggcgagcaga    180
```

| | |
|---|---|
| ccgugaagcu gaccgugacc aagggcggcc cccugcccuu cgccugggac auccuguccc | 240 |
| cccuguucca guacggcagc auccccuuca ccaaguaccc cgaggacauc cccgacuacg | 300 |
| ugaagcagag cuuccccgag ggcuacaccu gggagaggac caugaacuuc gaggacggcg | 360 |
| ccgugugcac cgugagcaac gacuccagca uccagggcaa cugcuucauc uacaacguga | 420 |
| agaucagcgg caccaacuuc cccccaacg gccccgugau gcagaagaag acccagggcu | 480 |
| gggagcccag caccgagagg cuguucgcca ggacggaau gcugaucggc aacgacuaca | 540 |
| uggcccugaa gcuggagggc ggcggccacu accugugcga guucaagucc accacaagg | 600 |
| ccaagaagcc cgugaggaug cccggcuacc acuacaucga caggaagcug gacgugacca | 660 |
| gccacaacag ggacuacacc uccguggagc agugcgagau cgccaucgcc aggcacagcc | 720 |
| ugcugggcug aaucuagacc uucugcgggg cuugccuucu ggccaugccc uucuucucuc | 780 |
| ccuugcaccu guaccucuug gucuuugaau aaagccugag uaggaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaa | 944 |

<210> SEQ ID NO 175
<211> LENGTH: 944
<212> TYPE: RNA
<213> ORGANISM: Artificial
<220> FEATURE:
<223> OTHER INFORMATION: alpha(miR-17-5p)-hdKeimaRed

<400> SEQUENCE: 175

| | |
|---|---|
| gguuccgcga ucgcggaucc cuaccugcac uguaagcacu uugagaucca ccggucgcca | 60 |
| ccauggugag cgugaucgcc aagcagauga ccuacaaggu guacaugucc ggcaccguga | 120 |
| acggccacua cuucgaggug gagggcgacg gcaagggcaa gcccuacgag ggcgagcaga | 180 |
| ccgugaagcu gaccgugacc aagggcggcc cccugcccuu cgccugggac auccuguccc | 240 |
| cccuguucca guacggcagc auccccuuca ccaaguaccc cgaggacauc cccgacuacg | 300 |
| ugaagcagag cuuccccgag ggcuacaccu gggagaggac caugaacuuc gaggacggcg | 360 |
| ccgugugcac cgugagcaac gacuccagca uccagggcaa cugcuucauc uacaacguga | 420 |
| agaucagcgg caccaacuuc cccccaacg gccccgugau gcagaagaag acccagggcu | 480 |
| gggagcccag caccgagagg cuguucgcca ggacggaau gcugaucggc aacgacuaca | 540 |
| uggcccugaa gcuggagggc ggcggccacu accugugcga guucaagucc accacaagg | 600 |
| ccaagaagcc cgugaggaug cccggcuacc acuacaucga caggaagcug gacgugacca | 660 |
| gccacaacag ggacuacacc uccguggagc agugcgagau cgccaucgcc aggcacagcc | 720 |
| ugcugggcug aaucuagacc uucugcgggg cuugccuucu ggccaugccc uucuucucuc | 780 |
| ccuugcaccu guaccucuug gucuuugaau aaagccugag uaggaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaa | 944 |

<210> SEQ ID NO 176
<211> LENGTH: 944
<212> TYPE: RNA
<213> ORGANISM: Artificial
<220> FEATURE:
<223> OTHER INFORMATION: alpha(miR-21-5p)-hdKeimaRed

<400> SEQUENCE: 176

| | |
|---|---|
| gguuccgcga ucgcggaucc ucaacaucag ucugauaagc uaagaucaca ccggucgcca | 60 |

```
ccauggugag cgugaucgcc aagcagauga ccuacaaggu guacaugucc ggcaccguga      120
acggccacua cuucgaggug gagggcgacg gcaagggcaa gcccuacgag ggcgagcaga      180
ccgugaagcu gaccgugacc aagggcggcc cccugcccuu cgccugggac auccugsccc     240
cccuguucca guacggcagc auccccuuca ccaaguaccc cgaggacauc cccgacuacg      300
ugaagcagag cuuccccgag ggcuacaccu gggagaggac caugaacuuc gaggacggcg      360
ccgugugcac cgugagcaac gacuccagca uccagggcaa cugcuucauc uacaacguga      420
agaucagcgg caccaacuuc cccccaacg gccccgugau gcagaagaag acccagggcu      480
gggagcccag caccgagagg cuguucgcca gggacgaaau gcugaucggc aacgacuaca      540
uggcccugaa gcuggagggc ggcggccacu accgugcga guucaaguc accuacaagg       600 ccaagaagcc cgugaggaug cccggcuacc acuacaucga caggaagcug gacgugacca      660
gccacaacag ggacuacacc uccguggagc agugcgagau cgccaucgcc aggcacagcc      720
ugcugggcug aaucuagacc uucucgcggg cuugccuucu ggccaugccc uucuucucuc     780
ccuugcaccu guaccucuug gucuuugaau aaagccugag uaggaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaa                     944
```

<210> SEQ ID NO 177
<211> LENGTH: 944
<212> TYPE: RNA
<213> ORGANISM: Artificial
<220> FEATURE:
<223> OTHER INFORMATION: alpha(miR-27a-3p)-hdKeimaRed

<400> SEQUENCE: 177

```
gguuccgcga ucgcggaucc gcggaacuua gccacuguga aagaucaaca ccggucgcca       60
ccauggugag cgugaucgcc aagcagauga ccuacaaggu guacaugucc ggcaccguga      120
acggccacua cuucgaggug gagggcgacg gcaagggcaa gcccuacgag ggcgagcaga      180
ccgugaagcu gaccgugacc aagggcggcc cccugcccuu cgccugggac auccugsccc     240
cccuguucca guacggcagc auccccuuca ccaaguaccc cgaggacauc cccgacuacg      300
ugaagcagag cuuccccgag ggcuacaccu gggagaggac caugaacuuc gaggacggcg      360
ccgugugcac cgugagcaac gacuccagca uccagggcaa cugcuucauc uacaacguga      420
agaucagcgg caccaacuuc cccccaacg gccccgugau gcagaagaag acccagggcu      480
gggagcccag caccgagagg cuguucgcca gggacgaaau gcugaucggc aacgacuaca      540
uggcccugaa gcuggagggc ggcggccacu accgugcga guucaaguc accuacaagg       600 ccaagaagcc cgugaggaug cccggcuacc acuacaucga caggaagcug gacgugacca      660
gccacaacag ggacuacacc uccguggagc agugcgagau cgccaucgcc aggcacagcc      720
ugcugggcug aaucuagacc uucucgcggg cuugccuucu ggccaugccc uucuucucuc     780
ccuugcaccu guaccucuug gucuuugaau aaagccugag uaggaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaa                     944
```

<210> SEQ ID NO 178
<211> LENGTH: 944
<212> TYPE: RNA
<213> ORGANISM: Artificial
<220> FEATURE:

<223> OTHER INFORMATION: alpha(miR-20a-5p)-hdKeimaRed

<400> SEQUENCE: 178

| | | |
|---|---|---|
| gguuccgcga ucgcggaucc cuaccugcac uauaagcacu uuaagaucca ccggucgcca | 60 | |
| ccauggugag cgugaucgcc aagcagauga ccuacaaggu guacaugucc ggcaccguga | 120 | |
| acggccacua cuucgaggug gagggcgacg gcaagggcaa gcccuacgag ggcgagcaga | 180 | |
| ccgugaagcu gaccgugacc aagggcggcc ccugcccuu cgccgggac auccugnccc | 240 | |
| cccuguucca guacggcagc auccccuuca ccaaguaccc cgaggacauc cccgacuacg | 300 | |
| ugaagcagag cuuccccgag ggcuacaccu gggagaggac caugaacuuc gaggacggcg | 360 | |
| ccgugugcac cgugagcaac gacuccagca uccagggcaa cugcuucauc uacaacguga | 420 | |
| agaucagcgg caccaacuuc cccccaacg gccccgugau gcagaagaag acccagggcu | 480 | |
| gggagcccag caccgagagg cuguucgcca gggacggaau gcugaucggc aacgacuaca | 540 | |
| uggcccugaa gcuggagggc ggcggccacu accugugcga guucaagucc accuacaagg | 600 | |
| ccaagaagcc cgugaggaug cccggcuacc acuacaucga caggaagcug gacgugacca | 660 | |
| gccacaacag ggacuacacc uccgugggagc agugcgagau cgccaucgcc aggcacagcc | 720 | |
| ugcugggcug aaucuagacc uucugcgggg cuugccuucu ggccaugccc uucuucucuc | 780 | |
| ccuugcaccu guaccucuug gucuuugaau aaagccugag uaggaaaaaa aaaaaaaaaa | 840 | |
| aaaaaaaaaa aaaaaaaaaa aaaaaaaaaa aaaaaaaaaa aaaaaaaaaa aaaaaaaaaa | 900 | |
| aaaaaaaaaa aaaaaaaaaa aaaaaaaaaa aaaaaaaaaa aaaa | 944 | |

<210> SEQ ID NO 179
<211> LENGTH: 944
<212> TYPE: RNA
<213> ORGANISM: Artificial
<220> FEATURE:
<223> OTHER INFORMATION: alpha(miR-106a-5p)-hdKeimaRed

<400> SEQUENCE: 179

| | | |
|---|---|---|
| gguuccgcga ucgcggaucc cuaccugcac uguaagcacu uuuagaucca ccggucgcca | 60 | |
| ccauggugag cgugaucgcc aagcagauga ccuacaaggu guacaugucc ggcaccguga | 120 | |
| acggccacua cuucgaggug gagggcgacg gcaagggcaa gcccuacgag ggcgagcaga | 180 | |
| ccgugaagcu gaccgugacc aagggcggcc ccugcccuu cgccgggac auccugnccc | 240 | |
| cccuguucca guacggcagc auccccuuca ccaaguaccc cgaggacauc cccgacuacg | 300 | |
| ugaagcagag cuuccccgag ggcuacaccu gggagaggac caugaacuuc gaggacggcg | 360 | |
| ccgugugcac cgugagcaac gacuccagca uccagggcaa cugcuucauc uacaacguga | 420 | |
| agaucagcgg caccaacuuc cccccaacg gccccgugau gcagaagaag acccagggcu | 480 | |
| gggagcccag caccgagagg cuguucgcca gggacggaau gcugaucggc aacgacuaca | 540 | |
| uggcccugaa gcuggagggc ggcggccacu accugugcga guucaagucc accuacaagg | 600 | |
| ccaagaagcc cgugaggaug cccggcuacc acuacaucga caggaagcug gacgugacca | 660 | |
| gccacaacag ggacuacacc uccgugggagc agugcgagau cgccaucgcc aggcacagcc | 720 | |
| ugcugggcug aaucuagacc uucugcgggg cuugccuucu ggccaugccc uucuucucuc | 780 | |
| ccuugcaccu guaccucuug gucuuugaau aaagccugag uaggaaaaaa aaaaaaaaaa | 840 | |
| aaaaaaaaaa aaaaaaaaaa aaaaaaaaaa aaaaaaaaaa aaaaaaaaaa aaaaaaaaaa | 900 | |
| aaaaaaaaaa aaaaaaaaaa aaaaaaaaaa aaaaaaaaaa aaaa | 944 | |

```
<210> SEQ ID NO 180
<211> LENGTH: 944
<212> TYPE: RNA
<213> ORGANISM: Artificial
<220> FEATURE:
<223> OTHER INFORMATION: alpha(miR-143-3p)-hdKeimaRed

<400> SEQUENCE: 180
gguuccgcga ucgcggaucc gagcuacagu gcuucaucuc aagaucaaca ccggucgcca    60
ccauggugag cgugaucgcc aagcagauga ccuacaaggu guacaugucc ggcaccguga   120
acggccacua cuucgaggug gagggcgacg gcaagggcaa gcccuacgag ggcgagcaga   180
ccgugaagcu gaccgugacc aagggcggcc cccugcccuu cgccgggac auccugucc    240 cccuguucca guacggcagc aucccuuca ccaaguaccc cgaggacauc cccgacuacg    300
ugaagcagag cuuccccgag ggcuacaccu gggagaggac caugaacuuc gaggacggcg   360
ccgugugcac cgugagcaac gacuccagca uccagggcaa cugcuucauc uacaacguga   420
agaucagcgg caccaacuuc cccccaacg gccccgugau gcagaagaag acccagggcu    480
gggagcccag caccgagagg cuguucgcca gggacggaau gcugaucggc aacgacuaca   540
uggcccugaa gcuggagggc ggcggccacu accugugcga guucaagucc accuacaagg   600
ccaagaagcc cgugaggaug cccggcuacc acuacaucga caggaagcug gacgugacca   660
gccacaacag ggacuacacc uccguggagc agugcgagau cgccaucgcc aggcacagcc   720
ugcugggcug aaucuagacc uucugcgggg cuugccuucu ggccaugccc uucuucucuc   780
ccuugcaccu guaccucuug gucuuugaau aaagccugag uaggaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaa                    944

<210> SEQ ID NO 181
<211> LENGTH: 944
<212> TYPE: RNA
<213> ORGANISM: Artificial
<220> FEATURE:
<223> OTHER INFORMATION: alpha(let-7i-5p)-hdKeimaRed

<400> SEQUENCE: 181
gguuccgcga ucgcggaucc aacagcacaa acuacuaccu caagaucaca ccggucgcca    60
ccauggugag cgugaucgcc aagcagauga ccuacaaggu guacaugucc ggcaccguga   120
acggccacua cuucgaggug gagggcgacg gcaagggcaa gcccuacgag ggcgagcaga   180
ccgugaagcu gaccgugacc aagggcggcc cccugcccuu cgccgggac auccugucc    240 cccuguucca guacggcagc aucccuuca ccaaguaccc cgaggacauc cccgacuacg    300
ugaagcagag cuuccccgag ggcuacaccu gggagaggac caugaacuuc gaggacggcg   360
ccgugugcac cgugagcaac gacuccagca uccagggcaa cugcuucauc uacaacguga   420
agaucagcgg caccaacuuc cccccaacg gccccgugau gcagaagaag acccagggcu    480
gggagcccag caccgagagg cuguucgcca gggacggaau gcugaucggc aacgacuaca   540
uggcccugaa gcuggagggc ggcggccacu accugugcga guucaagucc accuacaagg   600
ccaagaagcc cgugaggaug cccggcuacc acuacaucga caggaagcug gacgugacca   660
gccacaacag ggacuacacc uccguggagc agugcgagau cgccaucgcc aggcacagcc   720
ugcugggcug aaucuagacc uucugcgggg cuugccuucu ggccaugccc uucuucucuc   780
ccuugcaccu guaccucuug gucuuugaau aaagccugag uaggaaaaaa aaaaaaaaaa    840
```

```
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaa                     944
```

<210> SEQ ID NO 182
<211> LENGTH: 34
<212> TYPE: DNA
<213> ORGANISM: Artificial
<220> FEATURE:
<223> OTHER INFORMATION: 5Tmi133a_Afwd

<400> SEQUENCE: 182

```
gatcccagct ggttgaaggg gaccaaaaga tcta                                34
```

<210> SEQ ID NO 183
<211> LENGTH: 34
<212> TYPE: DNA
<213> ORGANISM: Artificial
<220> FEATURE:
<223> OTHER INFORMATION: 5Tmi133a_Arev

<400> SEQUENCE: 183

```
ccggtagatc ttttggtccc cttcaaccag ctgg                                34
```

<210> SEQ ID NO 184
<211> LENGTH: 34
<212> TYPE: DNA
<213> ORGANISM: Artificial
<220> FEATURE:
<223> OTHER INFORMATION: 5Tmi17_3_Afwd

<400> SEQUENCE: 184

```
gatccctaca agtgccttca ctgcagtaga tcta                                34
```

<210> SEQ ID NO 185
<211> LENGTH: 34
<212> TYPE: DNA
<213> ORGANISM: Artificial
<220> FEATURE:
<223> OTHER INFORMATION: 5Tmi17_3_Arev

<400> SEQUENCE: 185

```
ccggtagatc tactgcagtg aaggcacttg tagg                                34
```

<210> SEQ ID NO 186
<211> LENGTH: 35
<212> TYPE: DNA
<213> ORGANISM: Artificial
<220> FEATURE:
<223> OTHER INFORMATION: 5Tmi17_5_Afwd

<400> SEQUENCE: 186

```
gatccctacc tgcactgtaa gcactttgag atcta                               35
```

<210> SEQ ID NO 187
<211> LENGTH: 35
<212> TYPE: DNA
<213> ORGANISM: Artificial
<220> FEATURE:
<223> OTHER INFORMATION: 5Tmi17_5_Arev

<400> SEQUENCE: 187

```
ccggtagatc tcaaagtgct tacagtgcag gtagg                               35
```

<210> SEQ ID NO 188
<211> LENGTH: 34

```
<212> TYPE: DNA
<213> ORGANISM: Artificial
<220> FEATURE:
<223> OTHER INFORMATION: 5Tmi1_Afwd

<400> SEQUENCE: 188
gatccataca tacttcttta cattccaaga tcta                              34

<210> SEQ ID NO 189
<211> LENGTH: 34
<212> TYPE: DNA
<213> ORGANISM: Artificial
<220> FEATURE:
<223> OTHER INFORMATION: 5Tmi1_Arev

<400> SEQUENCE: 189
ccggtagatc ttggaatgta agaagtatg tatg                               34

<210> SEQ ID NO 190
<211> LENGTH: 34
<212> TYPE: DNA
<213> ORGANISM: Artificial
<220> FEATURE:
<223> OTHER INFORMATION: 5Tmi206_Afwd

<400> SEQUENCE: 190
gatccccaca cacttcctta cattccaaga tcta                              34

<210> SEQ ID NO 191
<211> LENGTH: 34
<212> TYPE: DNA
<213> ORGANISM: Artificial
<220> FEATURE:
<223> OTHER INFORMATION: 5Tmi206_Arev

<400> SEQUENCE: 191
ccggtagatc ttggaatgta aggaagtgtg tggg                              34

<210> SEQ ID NO 192
<211> LENGTH: 34
<212> TYPE: DNA
<213> ORGANISM: Artificial
<220> FEATURE:
<223> OTHER INFORMATION: 5Tmi21_Afwd

<400> SEQUENCE: 192
gatcctcaac atcagtctga taagctaaga tcta                              34

<210> SEQ ID NO 193
<211> LENGTH: 34
<212> TYPE: DNA
<213> ORGANISM: Artificial
<220> FEATURE:
<223> OTHER INFORMATION: 5Tmi21_Arev

<400> SEQUENCE: 193
ccggtagatc ttagcttatc agactgatgt tgag                              34

<210> SEQ ID NO 194
<211> LENGTH: 68
<212> TYPE: DNA
<213> ORGANISM: Artificial
<220> FEATURE:
<223> OTHER INFORMATION: 5Tmi367_Afwd

<400> SEQUENCE: 194
```

```
gatcctcacc attgctaaag tgcaattaga tctaccggta gatctaattg cactttagca    60
atggtgag                                                             68
```

<210> SEQ ID NO 195
<211> LENGTH: 34
<212> TYPE: DNA
<213> ORGANISM: Artificial
<220> FEATURE:
<223> OTHER INFORMATION: 5Tmi367_Arev

<400> SEQUENCE: 195

```
ccggtagatc taattgcact ttagcaatgg tgag                                34
```

<210> SEQ ID NO 196
<211> LENGTH: 34
<212> TYPE: DNA
<213> ORGANISM: Artificial
<220> FEATURE:
<223> OTHER INFORMATION: 5Tmi373_5_Afwd

<400> SEQUENCE: 196

```
gatccggaaa gcgcccccat tttgagtaga tcta                                34
```

<210> SEQ ID NO 197
<211> LENGTH: 34
<212> TYPE: DNA
<213> ORGANISM: Artificial
<220> FEATURE:
<223> OTHER INFORMATION: 5Tmi373_5_Arev

<400> SEQUENCE: 197

```
ccggtagatc tactcaaaat gggggcgctt tccg                                34
```

<210> SEQ ID NO 198
<211> LENGTH: 76
<212> TYPE: DNA
<213> ORGANISM: Artificial
<220> FEATURE:
<223> OTHER INFORMATION: 5UTR-T92a-3p

<400> SEQUENCE: 198

```
cgactcacta taggtcagat ccgctaggat ccacaggccg ggacaagtgc aataagatct    60
accggtcgcc accatg                                                    76
```

<210> SEQ ID NO 199
<211> LENGTH: 76
<212> TYPE: DNA
<213> ORGANISM: Artificial
<220> FEATURE:
<223> OTHER INFORMATION: 5UTR-T16-5p

<400> SEQUENCE: 199

```
cgactcacta taggtcagat ccgctaggat cccgccaata tttacgtgct gctaagatct    60
accggtcgcc accatg                                                    76
```

<210> SEQ ID NO 200
<211> LENGTH: 76
<212> TYPE: DNA
<213> ORGANISM: Artificial
<220> FEATURE:
<223> OTHER INFORMATION: 5UTR-T197-3p

<400> SEQUENCE: 200

```
cgactcacta taggtcagat ccgctaggat ccgctgggtg gagaaggtgg tgaaagatct    60
```
accggtcgcc accatg 76

<210> SEQ ID NO 201
<211> LENGTH: 76
<212> TYPE: DNA
<213> ORGANISM: Artificial
<220> FEATURE:
<223> OTHER INFORMATION: 5UTR-T24-3p

<400> SEQUENCE: 201
cgactcacta taggtcagat ccgctaggat ccctgttcct gctgaactga gccaagatct 60
accggtcgcc accatg 76

<210> SEQ ID NO 202
<211> LENGTH: 77
<212> TYPE: DNA
<213> ORGANISM: Artificial
<220> FEATURE:
<223> OTHER INFORMATION: 5UTR-T339-5p

<400> SEQUENCE: 202
cgactcacta taggtcagat ccgctaggat cccgtgagct cctggaggac agggaagatc 60
taccggtcgc caccatg 77

<210> SEQ ID NO 203
<211> LENGTH: 75
<212> TYPE: DNA
<213> ORGANISM: Artificial
<220> FEATURE:
<223> OTHER INFORMATION: 5UTR-T224-5p

<400> SEQUENCE: 203
cgactcacta taggtcagat ccgctaggat ccaacggaac cactagtgac ttgagatcta 60
ccggtcgcca ccatg 75

<210> SEQ ID NO 204
<211> LENGTH: 76
<212> TYPE: DNA
<213> ORGANISM: Artificial
<220> FEATURE:
<223> OTHER INFORMATION: 5UTR-T127-3p

<400> SEQUENCE: 204
cgactcacta taggtcagat ccgctaggat ccagccaagc tcagacggat ccgaagatct 60
accggtcgcc accatg 76

<210> SEQ ID NO 205
<211> LENGTH: 76
<212> TYPE: DNA
<213> ORGANISM: Artificial
<220> FEATURE:
<223> OTHER INFORMATION: 5UTR-T365a-3p

<400> SEQUENCE: 205
cgactcacta taggtcagat ccgctaggat ccataaggat ttttaggggc attaagatct 60
accggtcgcc accatg 76

<210> SEQ ID NO 206
<211> LENGTH: 76
<212> TYPE: DNA
<213> ORGANISM: Artificial
<220> FEATURE:

```
<223> OTHER INFORMATION: 5UTR-T183-5p

<400> SEQUENCE: 206
cgactcacta taggtcagat ccgctaggat ccagtgaatt ctaccagtgc cataagatct    60
accggtcgcc accatg                                                    76

<210> SEQ ID NO 207
<211> LENGTH: 75
<212> TYPE: DNA
<213> ORGANISM: Artificial
<220> FEATURE:
<223> OTHER INFORMATION: 5UTR-T331-3p

<400> SEQUENCE: 207
cgactcacta taggtcagat ccgctaggat ccttctagga taggcccagg ggcagatcta    60
ccggtcgcca ccatg                                                     75

<210> SEQ ID NO 208
<211> LENGTH: 76
<212> TYPE: DNA
<213> ORGANISM: Artificial
<220> FEATURE:
<223> OTHER INFORMATION: 5UTR-T203a

<400> SEQUENCE: 208
cgactcacta taggtcagat ccgctaggat ccctagtggt cctaaacatt tcacagatct    60
accggtcgcc accatg                                                    76

<210> SEQ ID NO 209
<211> LENGTH: 76
<212> TYPE: DNA
<213> ORGANISM: Artificial
<220> FEATURE:
<223> OTHER INFORMATION: 5UTR-T214-3p

<400> SEQUENCE: 209
cgactcacta taggtcagat ccgctaggat ccactgcctg tctgtgcctg ctgtagatct    60
accggtcgcc accatg                                                    76

<210> SEQ ID NO 210
<211> LENGTH: 148
<212> TYPE: DNA
<213> ORGANISM: Artificial
<220> FEATURE:
<223> OTHER INFORMATION: 3UTRtemp_4xT21-5p

<400> SEQUENCE: 210
cctactcagg ctttattcac gcggccgcgt agcttatcag actgatgttg agtagcttat    60
cagactgatg ttgagtagct tatcagactg atgttgagta gcttatcaga ctgatgttga   120
cagctcgtcg ccccgcagaa ggtctaga                                      148

<210> SEQ ID NO 211
<211> LENGTH: 148
<212> TYPE: DNA
<213> ORGANISM: Artificial
<220> FEATURE:
<223> OTHER INFORMATION: 3UTRtemp_4xT17-5p

<400> SEQUENCE: 211
cctactcagg ctttattcac gcggccgcca aagtgcttac agtgcaggta gcaaagtgct    60
tacagtgcag gtagcaaagt gcttacagtg caggtagcaa agtgcttaca gtgcaggtag   120
```

```
cagctcgtcg ccccgcagaa ggtctaga                                         148

<210> SEQ ID NO 212
<211> LENGTH: 145
<212> TYPE: DNA
<213> ORGANISM: Artificial
<220> FEATURE:
<223> OTHER INFORMATION: Rev120A-2

<400> SEQUENCE: 212
tttttttttt tttttttttt tttttttttt tttttttttt tttttttttt tttttttttt      60
tttttttttt tttttttttt tttttttttt tttttttttt tttttttttt tttttttttt     120
cctactcagg ctttattcac gcggc                                           145
```

METHOD FOR DETERMINING DESIRED CELL TYPE USING EXPRESSION OF MIRNA AS INDICATOR

RELATED APPLICATIONS

This application is a 35 U.S.C. § 371 national phase application of PCT Application PCT/JP2015/050467 filed Jan. 9, 2015, which claims priority to Japanese Application No. 2014-003726 filed Jan. 10, 2014, The entire contents of each are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-323_ST25.txt, 226,704 bytes in size, generated on Jul. 7, 2016, and filed via EFS-Web, is provided in lieu of a paper copy. This Sequence Listing is hereby incorporated by reference into the specification for its disclosures.

FIELD AND BACKGROUND OF THE INVENTION

The present invention relates to a method for distinguishing a desired cell type using the expression of miRNA as an indicator.

The tissues or organs of a multicellular organism are composed of many types of cells. The human body is composed of approximately 60 trillion ($6 \times 10^{13}$) cells, and there are 411 cell types known, even if only mature cells are considered. With regard to these cells, not only a technique of analyzing the function of each cell, but also a technique of distinguishing or identifying a cell type in preparation of cells for medical application has become important.

In order to identify a cell, a means for detecting a ligand that is specifically expressed on a cell surface, using an antibody, has been generally known. However, in order to detect intracellular information using an antibody, it is necessary to immobilize a target cell and/or to allow the cell to permeate through a membrane. Thus, detection using an antibody has been problematic in that it cannot be applied to fractionation of living cells. In addition, a receptor capable of specifying a cell is not necessarily present on the cell surface. Moreover, a means for classifying one factor into two factors, positive/negative (negative or positive) (i.e., a qualitative classification means), such as ligand detection using an antibody, has been problematic in that detectable combinations are limited, and thus, it is difficult to carry out a refined classification.

As a method for more specifically classifying cells, that is, as a method for quantitatively classifying cells, for example, the profiling of cells based on multivariate measurement using a microarray, next-generation sequencing, etc. has been known. In these methods, with regard to an intracellular molecule such as a protein or RNA, many types of molecules are simultaneously subjected to a quantitative measurement, or are subjected to statistical analysis such as multivariate analysis, so that the cells can be quantitatively classified. However, since the measured cells are destroyed, this method is problematic in that it is impossible to measure cells in a live state.

As a target that can be an indicator for identifying cells, microRNA (hereinafter referred to as "miRNA") has attracted attention. As a means for detecting miRNA in living cells, a reporter assay, which is carried out by introducing a reporter construct comprising DNA or a virus into cells, has been used. However, by such a method, it is likely that the reporter construct will be incorporated into the genome of a host cell and remain. Thus, the cells identified by this method will cause problems in medical application. Moreover, detection of miRNA according to the conventional reporter assay has been directed to searching for the target gene of the miRNA, and it has not been used to identify cells.

SUMMARY OF INVENTION

Technical Problem

It has been desired to develop a method for distinguishing cells, with high accuracy in a live state.

Solution to Problem

The present inventors have found that a desired cell type can be distinguished from a cell group comprising two or more types of cells by quantitatively obtaining information regarding the expression of miRNA in living cells, using mRNA having a specific structure, thereby completing the present invention.

Specifically, according to one embodiment, the present invention relates to a method for distinguishing a desired cell type from a cell group comprising two or more types of cells, using the expression of miRNA as an indicator, wherein the method comprises the following steps:
(1) a step of introducing mRNA comprising a first marker gene operably linked to the target sequence of miRNA used as an indicator into a cell group; and
(2) a step of distinguishing a cell type, using the translation level of the first marker gene as an indicator.

In the method, the step (1) is preferably a step of simultaneously introducing the target sequence of miRNA used as an indicator and two or more mRNAs comprising different first marker genes into cells.

In the method, the desired cell type is preferably a cell type in which the expression level of miRNA used as an indicator is low, and the step (2) is preferably a step of distinguishing a cell type in which the translation level of the first marker gene is high.

In the method, the desired cell type is preferably a cell type in which the expression level of miRNA used as an indicator is high, and the step (2) is preferably a step of distinguishing a cell type in which the translation level of the first marker gene is low.

In the mRNA used in the method, the target sequence of the miRNA is preferably linked to the 5'-terminal side of the first marker gene.

In the method, the determination is preferably carried out using a flow cytometer.

In the method, the determination is preferably carried out using an image analyzer.

It is preferable that the method further comprise a step of screening for miRNA used as an indicator, which is specific to the cell type, before the step (1).

Moreover, according to another aspect, the present invention relates to a kit for distinguishing a cell, which comprises mRNA comprising a first marker gene operably linked to the target sequence of miRNA used as an indicator.

Advantageous Effects of Invention

According to the present invention, by utilizing, as an indicator, the activity of miRNA that is intracellular information, a cell type can be distinguished with high resolution. Since the method according to the present invention can be applied in a live state, it is particularly advantageous in that cells can be used for various intended uses, in particular, for medical use, after completion of the determination. Moreover, since the method of the present invention can be carried out by introducing mRNA into a group of cells and this mRNA is decomposed with a half-life of approximately 1 day and is promptly removed from the inside of the cell, the present method does not cause problems such that viral infection or DNA remaining in the cells would give damage to the genome. Furthermore, the method of the present invention is also advantageous in a simple detection method using a cytometer. In particular, by introducing the synthesized mRNA into cells, a detection error in the activity used as an indicator could be reduced, separation ability could be improved, and it becomes possible to carry out high-accuracy determination. As an effective application of the present invention, for example, upon differentiation of pluripotent stem cells into specific cells, a desired cell type is distinguished from pluripotent stem cells with desired properties, or from a cell group obtained by inducing differentiation from the pluripotent stem cells, so that the desired cells can be classified, isolated or selectively eliminated.

Further, even in a case in which there is only a slight difference in terms of the expression of miRNA used as an indicator among a plurality of cell types comprised in a cell group, for example, even in a case in which the difference is approximately 1.5-fold or less, the method of the present invention is able to distinguish these cells from one another by using two mRNAs comprising first marker genes operably linked to the target sequences of at least two miRNAs used as indicators. This is based on the findings that the activity ratio of reporter proteins expressed from two co-introduced mRNAs is constant in a cell population and has little variation. Further, by increasing the types of such co-introduced mRNAs, it becomes possible to distinguish a larger number of cells based on a larger number of indicators.

BRIEF DESCRIPTION OF DRAWINGS

FIG. 1 is a view schematically describing the technique of the present invention whereby two different types of cells are separated on a dot plot plane of flow cytometry, and a conventional technique.

FIG. 3B includes histograms showing the ratio of two fluorescence signals and graphs showing the cumulative curve of two types of miRNA-responsive reporter mRNAs.

FIG. 4 includes a series of views showing the two-dimensional separation or three-dimensional separation of existing cell lines using three types of or four types of miRNA-responsive reporter mRNAs.

FIG. 9A includes a series of views showing the two-dimensional separation of two types of cell lines using two types of miRNA-responsive reporter mRNAs.

FIG. 9B includes a series of views showing the two-dimensional separation of two types of cell lines using two types of miRNA-responsive reporter mRNAs.

FIG. 11A is a view showing two-dimensional separation using three types of miRNA-responsive reporter mRNAs according to flow cytometry and imaging cytometry.

FIG. 11B is a view showing two-dimensional separation using miRNA-responsive reporter mRNAs linked to three types of nuclear localization signal genes according to flow cytometry and imaging cytometry.

FIG. 13 is a view showing the results obtained by screening for miRNA-responsive reporter mRNA used for separation of NHLF in Example 10, and the results obtained by analyzing separation of the cell population NHLF, using an mRNA set responding to miRNA having a high positive correlation to the cell population NHLF, or using an miRNA set that does not have such a high positive correlation.

FIG. 15 is a view schematically showing the results assumed in a case in which there is a distribution of two miRNA activities in a certain cell group, when the certain cell group has assumed to incorporate the same amount of mRNA as the other.

FIG. 17(*b*) is a view showing the results of a flow cytometric analysis, in a case in which control mRNA (hmAG1-M9) and miRNA-responsive reporter mRNA (α(miR-145-5p)-hmKO2-M9) have been co-introduced into IMR-90 without TGF-β1 stimulation (−TGF-β1: green) or with TGF-β1 stimulation (+TGF-β1: violet).

DESCRIPTION OF EMBODIMENTS

Figure 2A:
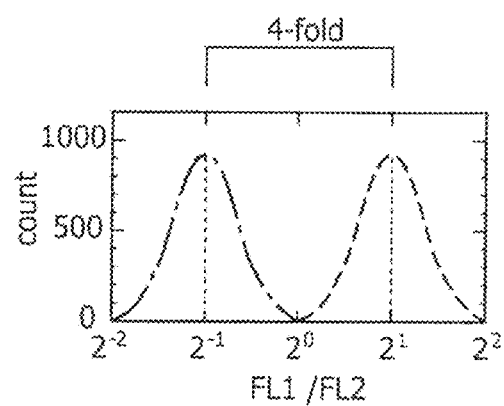
FIG. 2 includes histograms showing a signal rate obtained in a case in which miRNA-responsive reporter mRNA or control mRNA is introduced into two different types of cell types.

Hereinafter, the present invention will be described in detail in the following embodiments. However, the scope of the present invention is not intended to be limited to these embodiments.

According to a first embodiment the present invention relates to a method for distinguishing a desired cell type from a cell group comprising two or more types of cells, using the expression of miRNA as an indicator. The determination method according to the present embodiment comprises the following steps:
(1) a step of introducing mRNA comprising a first marker gene operably linked to the target sequence of miRNA used as an indicator into a cell group; and
(2) a step of distinguishing a cell type, using the translation level of the fast marker gene as an indicator.

The cell group used as a target in the determination method of the present invention is a cell group comprising two or more types of cells. This cell group may be either a cell group collected from multicellular organism species, or a cell group obtained by culturing isolated cells. The cell group is particularly a cell group comprising two or more types of somatic cells collected from mammals (e.g. a human, a mouse, a monkey, a swine, a rat, etc.), or a cell group obtained by culturing cells isolated from mammals or mammalian cell lines. Examples of the somatic cells include keratinizing epithelial cells (e.g. keratinized epidermal cells), mucosal epithelial cells (e.g. epithelial cells on a tongue surface layer), exocrine epithelial cells (e.g. mammary gland cells), hormone secreting cells (e.g. adrenomedullary cells), cells for metabolism/storage (e.g. liver cells), inner luminal epithelial cells constituting a boundary surface (e.g. type I alveolar cells), inner luminal epithelial cells in the inner chain tube (e.g. vascular endothelial cells), cells having cilia with transport ability (e.g. respiratory tract epithelial cells), cells for extracellular matrix secretion (e.g. fibroblasts), contractile cells (e.g. smooth muscle cells), cells of blood and immune system (e.g. T lymphocytes), cells regarding senses (e.g. rod cells), autonomic nervous system neurons (e.g. cholinergic neurons), cells supporting sensory organs and peripheral neurons (e.g. satellite cells), nerve cells and glial cells in the central nervous system (e.g. astroglial cells), pigment cells (e.g. retinal pigment epithelial cells), and the progenitor cells thereof (tissue progenitor cells). The degree of differentiation of cells, the age of an animal from which cells are collected, etc. are not particularly limited. Both undifferentiated progenitor cells (including somatic stem cells) and finally differentiated mature cells can be used as a source of somatic cells in the present invention. Herein, examples of the undifferentiated progenitor cells include tissue stem cells (somatic stem cells) such as neural stem cells, hematopoietic stem cells, mesenchymal stem cells, or dental pulp stem cells. In the present invention, the type of mammal as a source, from which somatic cells are collected, is not particularly limited, and it is preferably a human. In addition, a preferred cell group is a cell group, in which artificial operations are performed on prophase somatic cells after collection of the cells, and it may be a cell group that includes undesired cells. Thus, the cell group is, for example, a cell group comprising iPS cells prepared from the somatic cells, or a cell group obtained after differentiation of pluripotent stem cells such as ES cells or iPS cells, which may include differentiated cells other than desired cells. In the present embodiment, the cell group as a determination target is preferably in a survival state. In the present invention, the expression "cells in a survival state" is used to mean cells in a state in which they maintain metabolic capacity. The present invention is advantageous in that, after cells have been subjected to the method of the present invention and the determination method has been then terminated, the cells remain alive without losing their original properties, and can be used in the subsequent intended use, in particular, while maintaining division capacity.

In the method of the present invention, the "desired cell type" to be distinguished means a group of cells, which is classified from other cell types, using the expression of miRNA as an indicator. In particular, the desired cell type means a certain group of cells having common properties, in terms of miRNA activity, which will be described in detail later. In the present invention, such a certain group of cells, which is classified from other cell types, using miRNA as an indicator, is also referred to as "homologous cells." The desired cell type distinguished by the method of the present invention may be one type, or two or more types, for example, three types, four types, five types, six types, seven types, or eight types or more. Theoretically, the distinguish-possible cell type is not limited, and according to the present invention, 100 or more types of cells can be distinguished simultaneously.

In the present invention, the expression "to distinguish a desired cell type" is used to mean that the detectable signal information of desired specific one or more cell types, which are different from other cell types, is presented from a cell group comprising two or more types of cells, and in particular, that visually recognizable information is presented. It is to be noted that the visually recognizable information is not limited to emission of visual signals directly from cells, but it also includes information obtained by converting signals emitted from cells to visually recognizable information, using numerical values, charts, images, etc. Thus, the visually recognizable information means information visually recognizable by one skilled in the art. In the present description, the term "distinguish" may include the meanings that, after completion of the determination, the desired cell type is recognized, the desired cell type is distinguished, the desired cell type is identified, the desired cell type is classified, the desired cell type is isolated, undesired cell types are removed, the life or death of the desired cell type is distinguished, specific biological signals are detected or quantified in the desired cell type, and the desired cell type is fractionated based on specific physical or chemical signals. In the present invention, determination whereby a cell group, which has been unknown to comprise two or more types of cells, is distinguished to comprise different cell types by the method of the present invention, is also considered to be one aspect of determination of a desired cell type.

An aspect, in winch a desired cell type is distinguished from a cell group comprising two or more types of cells, using the expression of miRNA as an indicator, includes the aforementioned various determination aspects, and also, this aspect is divided into a case in which the attribute regarding the "cell group comprising two or more types of cells" has previously been known to a certain extent, and a case in which there is no information regarding the attribute of the cell group.

The case in which the attribute regarding the cell group has previously been known to a certain extent means a case in which cell types comprised in the cell group have previously been specified to a certain extent by another method or the like. For example, there is a case in which specific cell types comprised in a specific cell group have previously been analyzed and predicted by the classification method using an antibody, or an Omics analysis/profiling method that is the profiling of cells based on multivariate measurement using a microarray, next-generation sequencing or the like, which have been described above as prior art techniques. Even in such a case, determination of a desired cell type in a live state by the method of the present invention is useful.

On the other hand, even in a case in which there is no information regarding the attribute of a cell group, the present invention is applicable.

There is a case in which a screening method applied in a step of screening for miRNA used as an indicator is different between the former case and the latter case. Such a screening step may be comprised as an optional pre-step in the method of the present invention. Details for the screening step will be described later.

In the method of the present invention, messenger RNA (mRNA) comprising a first marker gene operably linked to the target sequence of miRNA used as an indicator (hereinafter also referred to as "miRNA target sequence") is used. In such mRNA, when specific miRNA is present, translation of the first marker gene is regulated depending on the abundance of such miRNA. Preferably, this is mRNA, in which when specific miRNA is present, the amount of a protein translated from the first marker gene (hereinafter referred to as a "marker protein") is reduced by suppressing the translation of the first marker gene depending on the abundance of the miRNA.

The "expression of miRNA" in the present invention means that miRNA, in which mature miRNA interacts with a plurality of predetermined proteins to form an RNA-induced silencing complex (RISC), is present. The "mature miRNA" is single-stranded RNA (20 to 25 nucleotides), and it is generated from pre-miRNA as a result of extranuclear cleavage by Dicer, whereas the "pre-miRNA" is generated from pri-mRNA, which is single-stranded RNA transcribed from DNA by partial cleavage by an intranuclear enzyme called Drosha. The miRNA used in the present invention is selected from at least 10,000 or more types of miRNAs, as appropriate. More specifically, the present miRNA is selected, as appropriate, from miRNAs registered in database information (e.g., www.mirbase.org/ or www.microrna.org/), and/or miRNAs described in reference information stored in the database. That is to say, in the present invention, the miRNA used as an indicator is not limited to specific miRNA. The miRNA used as an indicator can be appropriately selected, depending on the properties of a cell type to be distinguished by the method of the present invention. Moreover, in particular, one miRNA or a combination of multiple miRNAs, which is expressed at a high level (high activity) in some cells and which is expressed at a low level (low activity) in other cells in a cell group as a determination target, is preferably selected. This is because separation accuracy can be further increased. Such miRNA or such a combination of multiple miRNAs can be selected by the after-mentioned screening method. Such miRNA used as an indicator is not limited to the miRNAs that had been specified at the time of filing of the present application, but it also includes all miRNAs, the presence and function will be specified in the future.

The miRNA target sequence means a sequence capable of specifically binding to the miRNA used as an indicator. For instance, the miRNA target sequence is preferably a sequence completely complementary to the miRNA used as an indicator. Otherwise, as long as the miRNA target sequence is recognizable by miRNA, it may also have a mismatch with the completely complementary sequence. The mismatch with the sequence completely complementary to the miRNA may be generally a mismatch, which is recognizable by the miRNA in a desired cell, and it is considered that there may be a mismatch of approximately 40% to 50% with regard to the original function of the cell in a living body. Such a mismatch is not particularly limited, and it is, for example, a mismatch of 1%, 5%, 10%, 20%, 30% or 40% of 1 nucleotide, 2 nucleotides, 3 nucleotides, 4 nucleotides, 5 nucleotides, 6 nucleotides, 7 nucleotides, 8 nucleotides, 9 nucleotides, 10 nucleotides or the entire recognition sequence. In addition, in particular, as with the miRNA target sequence on mRNA comprised by a cell, the target sequence may comprise a large number of mismatches in a portion other than a seed region, namely, in a region on the 5'-terminal side in the target sequence, which corresponds to approximately 16 nucleotides on the 3'-terminal side of miRNA. The seed region may not comprise such mismatches, or may comprise a mismatch of 1 nucleotide, 2 nucleotides, or 3 nucleotides.

The first marker gene is a gene encoding any given protein, which is translated in a cell, functions as a marker, and enables determination of a cell type. The protein, which is translated in a cell and is able to function as a marker, may be, for example, a protein, which can be visualized by fluorescence, luminescence or color development, or by supporting such fluorescence, luminescence or color development, and can be quantified. Examples of the fluorescent protein include: blue fluorescent proteins such as Sirius or EBFP; cyan fluorescent proteins such as mTurquoise, TagCFP, AmCyan, mTFP1, MidoriishiCyan, or CFP; green fluorescent proteins such as TurboGFP, AcGFP, TagGFP, Azami-Green (e.g. hmAG1), ZsGreen, EmGFP, EGFP, GFP2, or HyPer; yellow fluorescent proteins such as TagYFP, EYFP, Venus, VFP, PhiVFP, PhiYFP-m, TurboYFP, Zs Yellow, or mBanana; orange fluorescent proteins such as KusabiraOrange (e.g. hmKO2) or mOrange; red fluorescent proteins such as TurboRFP, DsRed-Express, DsRed2, TagRFP, DsRed-Monomer, AsRed2, or mStrawberry; and near infrared fluorescent proteins such as TurboFP602, mRFP1, JRed, KillerRed, mCherry, HeRed, KeimaRed (e.g. hdKeimaRed), mRasberry, or mPlum, but examples of the fluorescent protein are not limited thereto.

An example of the luminescent protein is aequorin, but examples are not limited thereto. In addition, examples of the protein supporting fluorescence, luminescence or color development include enzymes decomposing fluorescence, luminescence or color development precursors, such as luciferase, phosphatase, peroxidase, or β lactamase, but examples of this protein are not limited thereto. In the present invention, when the protein supporting fluorescence, luminescence or color development is used as a first marker gene, determination of a desired cell is carried out by allowing a cell to come into contact with a corresponding precursor, or by introducing such a corresponding precursor into a cell.

Other examples of the protein capable of functioning as a marker in a cell include proteins, which have a direct influence on the junction of cells. Specific examples of such a protein include a cell growth protein, a cell killing protein, a cell signaling factor, a drug resistance gene, a transcriptional regulator, a translational regulator, a differentiation regulator, a reprogramming inducer, an RNA-binding protein factor, a chromatin control factor, and a membrane protein, but examples of the protein are not limited thereto. For example, the cell growth protein allows only cells, in which the protein has been expressed, to grow, and then specifies growing cells, so that it functions as a marker. The cell killing protein causes cell death to cells, in which the protein has been expressed, and kills cells themselves that comprise or do not comprise specific miRNA, so that it functions as a marker for showing the life or death of the cells. The cell signaling factor functions as a marker, when cells, in which the factor has been expressed, emit specific biological signals, and these signals are then specified. Examples of the cell killing protein include Bax and Bim. As an example, the translational regulator recognizes the three-dimensional structure of specific RNA and binds thereto, and it thereby regulates translation of another mRNA into a protein, so that it functions as a marker. Examples of the translational regulator include 5R1,5R2 (Nat Struct Biol. 1998 July; 5(7):543-6), B2 (Nat Struct Mol Biol. 2005 November; 12(11):952-7), Fox-1 (EMBO J. 2006 Jan. 11; 25(1):163-73.), GLD-1 (J Mol Biol. 2005 Feb. 11; 346(1): 91-104.), Hfq (EMBO J. 2004 Jan. 28; 23(2):396-405), HuD (Nat Struct Biol. 2001 February; 8(2):141-5.), SRP19 (RNA. 2005 July; 11(7):1043-50), L1 (Nat. Struct Biol. 2003 February; 10(2):104-8.), L11 (Nat Struct Biol. 2000 October; 7(10):834-7.), L18 (Biochem. J. 2002 Mar. 15; 362(Pt 3):553-60), L20 (J Biol Chem. 2003 Sep. 19; 278 (38):36522-30.), L23 (J Biomol NMR. 2003 June; 26(2): 131-7), L25 (EMBO J. 1999 Nov. 15; 18(22):6508-21.), L30 (Nat Struct Biol. 1999 December; 6(12):1081-3.), LicT (EMBO J. 2002 Apr. 15; 21(8):1987-97.), MS2 coat (FEBS J. 2006 April; 273(7):1463-75.), Nova-2 (Cell. 2000 Feb. 4; 100(3):323-32), Nucleocapsid (J Mol Biol. 2000 Aug. 11; 301(2):491-511.), Nucleolin (EMBO J. 2000 Dec. 15; 19(24):6870-81.), p19 (Cell. 2003 Dec. 26; 115(7):799-811), L7Ae (RNA. 2005 August; 11(8):1992-200.), PAZ (PiWi Argonaut and Zwille (Nat Struct Biol. 2003 December; 10(12):1026-32.), RnaseIII (Cell. 2006 Jan. 27; 124(2):355-66), RR1-38 (Nat Struct Biol. 1998 July; 5(7):543-6.), S15 (EMBO J. 2003 Apr. 15; 22(8):1898-908.), S4 (J Biol Chem. 1979 Mar. 25; 254(6): 1775-7.), S8 (J Mol Biol. 2001 Aug. 10; 311(2):311-24.), SacY (EMBO J. 1997 Aug. 15; 16(16): 5019-29.), SmpB (J Biochem (Tokyo). 2005 December; 138(6):729-39), snRNP U1A (Nat Struct Biol. 2000 October; 7(10):834-7.), SRP54 (RNA. 2005 July; 11(7):1043-50), Tat (Nucleic Acids Res. 1996 Oct. 15; 24(20):3974-81.), ThrRS (Nat Struct Biol. 2002 May; 9(5):343-7.); TIS11d (Nat Struct Mol Biol. 2004 March; 11(3):257-64.), Virp1 (Nucleic Acids Res. 2003 Oct. 13; 31(19); 5534-43.), Vts1P (Nat Struct Mol Biol. 2006 February; 13(2):177-8.), and λN (Cell. 1998 Apr. 17; 93(2):289-99.). Among these, more preferred translational regulators are MS2 coat and L7Ae.

In the present invention, the first marker gene may comprise a gene encoding a localization signal. Examples of such a localisation signal include a nuclear localization signal, a cell membrane localization signal, a mitochondrial localization signal, and a protein secretion signal. Specific examples include a classical nuclear localization sequence (NLS), an M9 sequence, a mitochondrial target sequence (MTS), and an endoplasmic reticulum localization sequence, but examples are not limited thereto. Such a localization signal is particularly advantageous when the determination step in the method of the present invention is carried out on an image, in the after-mentioned imaging cytometry or the like.

In the present invention, when the translational regulator is used as a marker, mRNA having a second marker gene for which translation is regulated by the translational regulator is simultaneously introduced into a cell. An example of such mRNA having a second marker gene for which translation is regulated by the protein is mRNA having a second marker gene sequence operably linked to an RNA sequence, to which the protein capable of regulating the translation can bind. A specific example of such mRNA is mRNA disclosed in WO2009/066757 or WO2014/014122. The disclosures of these publications are all incorporated herein by reference. One skilled in the art could appropriately select mRNA having a second marker gene for which translation is regulated by a protein, which can be preferably used in the method of the present invention, by referring to the aforementioned publications. In the present invention, the same first marker genes as those described above can be used as second marker genes.

The mRNA used in the method of the present invention comprises a first marker gene operably linked to the target sequence of miRNA used as an indicator. In the description of the present invention, such mRNA is also referred to as "miRNA-responsive reporter mRNA. In the present invention, the phrase "a first marker gene is operably linked to the target sequence of miRNA" means that at least one miRNA target sequence is comprised in the 5'-UTR and 3'-UTR of an open reading frame encoding the first marker gene (including an initiation codon), and/or in the open reading frame. The mRNA preferably comprises, in the direction from the 5'-terminus to the 3'-terminus, a Cap structure (7-methylguanosine 5'-phosphate), an open reading frame encoding the first marker gene, and poly(A) tail, and also comprises, in the 5'-UTR, in the 3'-UTR and/or in the open reading frame, at least one miRNA target sequence. The position of the miRNA target sequence in the mRNA may be either 5'-UTR or 3'-UTR, or may also be in the open reading frame (on the 3'-terminal side of the initiation codon). Otherwise, the mRNA may comprise miRNA target sequences in all of these positions. Accordingly, the number of miRNA target sequences may be 1, 2, 3, 4, 5, 6, 7, 8, or more.

Preferably, one miRNA target sequence is present in the 5'-UTR. This is because it can achieve efficient translational inhibition. At this time, the number of nucleotides and the type of nucleotides between the cap structure and the miRNA target sequence may be freely distinguished, as long as they do not include AUG serving as an initiation codon and do not constitute a stem structure or a steric structure. For instance, the cap structure and the miRNA target sequence can be designed, such that the number of nucleotides between the cap structure and the miRNA target sequence can be 0 to 50 nucleotides, and preferably 10 to 30 nucleotides. Moreover, the number of nucleotides and the type of nucleotides between the miRNA target sequence and the initiation codon may be freely distinguished, as long as they do not constitute a stem structure or a steric structure. The miRNA target sequence and the initiation codon can be designed, such that the number of nucleotides between the miRNA target sequence and the initiation codon is 0 to 50 nucleotides, and preferably 10 to 30 nucleotides. It has been confirmed that translational inhibition can be achieved, even if four miRNA target sequences are present in the 3'-UTR.

The miRNA-responsive reporter mRNA preferably comprises modified nucleotides such as pseudo uridine and 5-methylcytidine, instead of ordinary uridine and cytidine. This is because of reduction in cytotoxicity. Such modified nucleotides can be positioned independently or as a part of the mRNA, in both cases of uridine and cytidine. In the case of being comprised as a part, the nucleotides can be positioned randomly at any given ratio.

After the sequence of the miRNA-responsive reporter mRNA has been distinguished as described above, one skilled in the art is able to synthesize the miRNA-responsive reporter mRNA according to any existing genetic engineering method. In particular, the miRNA-responsive reporter mRNA can be obtained according to an in vitro transcription synthesis method, using template DNA comprising a promoter sequence as a template.

There is a case in which only one type of miRNA-responsive reporter mRNA is used, or there is another case in which two or more types of, for example, three types, four types, five types, six types, seven types, or eight types or more of miRNA-responsive reporter mRNAs are used, depending on the purpose of determination, a target, or the activity of miRNA used as an indicator. For example, in the case of using two or more types of miRNA-responsive reporter mRNAs, it is desirable that both miRNA target sequences and first marker genes comprised in individual miRNA-responsive reporter mRNAs be different from one another. In addition, in the case of using two or more types of miRNA-responsive reporter mRNAs, the number of miRNA target sequences comprised in the miRNA-responsive reporter mRNA, the distance of the miRNA target sequence from the 5'-terminus, and other structural characteristics of the miRNA-responsive reporter mRNA may be different among individual miRNA-responsive reporter mRNAs.

In the present invention, in the step of introducing miRNA-responsive reporter mRNA into a cell (hereinafter referred to as an "introduction step"), one or more types of miRNA-responsive reporter mRNAs are directly introduced into cells included in a cell group, by applying a lipofection method, a liposome method, an electroporation method, a calcium phosphate co-precipitation method, a DEAE dextran method, a microinjection method, a gene gun method, etc. In the case of introduction of two or more different types of miRNA-responsive reporter mRNAs, or in the case of using miRNA-responsive reporter mRNA and mRNA used as a control (hereinafter also referred to as "control mRNA"), a plurality of mRNAs are preferably co-introduced into a cell group. This is because the ratio of the activities of marker proteins expressed from the thus co-introduced two or more mRNAs is constant in a cell population. At this time, the amount of miRNA-responsive reporter mRNA introduced is different, depending on the type of a cell group, into which the mRNA is introduced, the type of the introduced mRNA, a method of introducing the mRNA, and the types of introduction reagents. In order to achieve a desired translation level, one skilled in the art can appropriately select these conditions. Herein, the term "control mRNA" is used to mean mRNA, which does not have a miRNA target site and encodes a marker gene that is different from the first marker gene encoded by the miRNA-responsive reporter mRNA. Also regarding the amount of the control mRNA introduced, one skilled in the art can appropriately select the aforementioned conditions to achieve a desired translation level.

When the miRNA-responsive reporter mRNA is introduced into a cell, the translation level of the first marker gene encoded by the miRNA-responsive reporter mRNA is regulated, for example, the translation level is suppressed, if certain miRNA is present as RISC in the cell. Such regulation of the translation level is quantitatively carried out depending on miRNA activity. In contrast, if the certain miRNA is not present in the cell, or if the certain miRNA is not present as RISC, the translation level of the first marker gene encoded by the miRNA-responsive reporter mRNA is not suppressed. Accordingly, the translation level of the first marker gene is different between a cell in which the certain miRNA is present as RISC and a cell in which it is not present. It is to be noted that, in the present description, the case in which the certain miRNA is present as RISC is also referred to as a "case in which miRNA activity is present." On the other hand, control mRNA expresses a marker protein, regardless of miRNA activity. This is because, even if such control mRNA is introduced into a cell, translation is not regulated depending on the expression level of miRNA, since the miRNA target sequence is not present therein.

Subsequently, a step of distinguishing a cell, using the translation level of the first marker gene as an indicator (hereinafter also referred to as a "determination step"), is carried out. In the determination step, a cell is distinguished based on the aforementioned translation level of the first marker gene. That is, this step can be a step of distinguishing the desired cell type that is a cell in which the expression level of the miRNA used as an indicator is low and the translation level of the first marker gene is high, and/or a step of distinguishing a desired cell type that is a cell in which the expression level of the miRNA used as an indicator is high and the translation level of the first marker gene is low. Such a cell in which the expression level of the miRNA used as an indicator is low, or a cell in which the expression level of the miRNA used as an indicator is high, can be distinguished by obtaining the ratio of the translation levels of the first marker genes among cells belonging to a cell group comprising two or more types of cells. Herein, when a translational regulator is used as a first marker gene, a cell is distinguished based on the translation level of a second marker gene that has been simultaneously introduced into the cell. By utilizing the aforementioned mRNA having a second marker gene for which translation is suppressed by a first marker gene, the translation level of the second marker gene, is proportional to the expression level of the miRNA used as an indicator. Specifically, in a case in winch the desired cell type is a cell in which the expression level of the miRNA used as an indicator is low, a cell in which the translation level of the second marker gene is low is distinguished. On the other hand, in a case in which the desired cell type is a cell in which the expression level of the miRNA used as an indicator is high, a cell in which the translation level of the second marker gene is high is distinguished. Accordingly, when a cell killing protein is used as a second marker gene, for example, a cell in which the expression level of the miRNA used as an indicator is high can be specifically induced to undergo cell death, and can be eliminated.

Specifically, the determination step can be carried out by detecting signals from a marker protein, employing a predetermined detection apparatus. Examples of the detection apparatus include a flow cytometer, an imaging cytometer, a fluorescence microscope, a luminescence microscope, and a CCD camera, but examples are not limited thereto. As such a detection apparatus, one skilled in the an can use a suitable apparatus, depending on a marker protein and the aspect of determination. For instance, when the marker protein is a fluorescent protein or a luminescent protein, it is possible to quantify the marker protein using a detection apparatus such as a flow cytometer, an imaging cytometer, a fluorescence microscope or a CCD camera. When the marker protein is a protein supporting fluorescence, luminescence or color development, a method of quantifying the marker protein using a detection apparatus such as a luminescence microscope, a CCD camera or a luminometer can be applied. When the marker protein is a membrane localization protein, a method of quantifying the marker protein using a detection reagent specific to a cell surface protein, such as an antibody, and the aforementioned detection apparatus, can be applied, and also, a method of isolating cells without performing the process of quantifying the marker protein, such as a magnetic cell separation device (MACS), can be applied. When the marker protein is a drug resistance gene, a method, which comprises detecting the expression of the first marker gene by administration of a drug and then isolating living cells, can be applied.

An example of a preferred detection method, which is applied when the marker protein is a fluorescent protein, is flow cytometry. In the flow cytometry, the intensity of light emitted from a fluorescent protein, luciferase, that is a marker protein translated in each cell, can be provided as information for determination. Hereafter, the aspect of determination of a cell type, in which flow cytometry is applied and one or more miRNA-responsive reporter mRNAs are used, will be described in several cases.

[a. Separation Based on Expression Intensity, in which miRNA-Responsive Reporter mRNA is Used]

According to one aspect of the present invention, only one type of miRNA-responsive reporter mRNA is used. Referring to FIG. 1(a) for example, the values of fluorescence intensity obtained in the case of introducing only one type of miRNA-responsive reporter mRNA into a desired cell group have an inverted V-shaped distribution, as shown on the paper, outside of the graph plane. This is because there is a variation in the number of mRNAs introduced into individual cells in the target cell group. For example, when translation from miRNA-responsive reporter mRNA is suppressed depending on the miRNA activity in a desired cell, such an inverted V-shaped distribution of desired cells is moved to the left. When the distribution of the fluorescence intensity values obtained from the desired cell group is not overlapped with the distribution of the fluorescence intensity values obtained from another cell group, the desired cell group can be separated from the other cell group by separating only those having specific fluorescence intensity values, and thus, can be distinguished. Otherwise, as shown on the paper of FIG. 1(a), even if the distribution of the fluorescence intensity values is overlapped with another distribution, a region on the edge with no overlapping of the distributions is distinguished, and cells can be separated.

[b. One-Dimensional Separation, in which miRNA-Responsive Reporter mRNA and Control mRNA are Used]

According to one aspect of the present invention, only one type of miRNA-responsive reporter mRNA is used, and control mRNA can be co-introduced into a cell. It can be said that translation of the first marker gene in the control mRNA is constant depending on the type of a cell, without being affected by miRNA. The control mRNA can be designed and prepared in the same manner as that for the miRNA-responsive reporter mRNA, with the exception that the control mRNA does not have a miRNA target site. In the present description, the term "dimension" is used to mean a "dimension" regarding the translation ratio of marker genes, and in particular, the ratio of the measured fluorescence intensity values.

In the present invention, when the miRNA-responsive reporter mRNA and the control mRNA are co-introduced, the ratio of the activities of marker proteins expressed from the two types of mRNAs is found to be constant in a cell population and has a small variation. Accordingly, by obtaining the ratio of the fluorescence intensities of marker proteins expressed from the two types of mRNAs, the expression ratio of specific mRNA in each cell can be obtained.

The expression ratio of marker proteins is almost constant among homologous cells, but there is a certain amount of variation. This is because of the following reasons.

(1) There is a slight variation in terms of miRNA expression level even among homologous cells.

(2) There is also variation in terms of the reaction rate of the expressed miRNA with the co-introduced mRNA.

(3) There is also variation in terms of the cell introduction ratio of the co-introduced two mRNAs.

Consequently, there is a case in which a certain extent of difference is generated in terms of the expression ratio of marker proteins, even among homologous cells. In the case of measurement by flow cytometry, such homologous cells are distributed in a belt shape having a certain width, in a dot plot in which the expression intensity of a marker protein encoded by the miRNA-responsive reporter mRNA is set on the X-axis and the expression intensity of a marker protein encoded by the control mRNA is set on the Y-axis. This width is caused by the aforementioned variation. When a plurality of belt-shaped plots corresponding to the number of different cell types appear and these are separated, these cells can be distinguished. As an example, in a case in which the measurement is carried out by flow cytometry in the determination step, in a dot plot in which the expression intensity of a first marker protein encoded by a first miRNA-responsive reporter mRNA is set on the X-axis and the expression intensity of a second marker protein encoded by a second miRNA-responsive reporter mRNA is set on the Y-axis, the homologous cells are distributed in a belt shape having a certain width. Such an aspect is schematically shown in FIG. 1(a). In FIG. 1(a), three belt-shaped plot groups are present. On the paper, the belt-shaped plots in the upper left and the lower right indicate two different types of cell groups, which have been distinguished on a dot plot plane by co-introduction of two types of miRNA-responsive reporter mRNAs. The belt-shaped plot in the center schematically shows the expression intensity of a marker protein when only the control mRNA is introduced into the same cell group as that described above for a control experiment, and two different types of cell groups cannot be distinguished on the dot plot plane.

In the separation shown in FIG. 1(a), a case in which a first miRNA-responsive reporter mRNA that targets miRNA (a) and a second miRNA-responsive reporter mRNA that targets miRNA (b) are used for example, will be described. When cell A and cell B are classified using these mRNAs, separation ability becomes high, if miRNA (a) is highly expressed (high activity) in the cell A and miRNA (b) is highly expressed (high activity) in the cell B. In other words, separation ability becomes high, if the translation of miRNA (a)-responsive mRNA is suppressed in the cell A and the translation of miRNA (b)-responsive mRNA is suppressed in the cell B. In FIG. 1(a), the arrow going from right to left along the X-axis in the figure and the arrow going from up to down along the Y-axis on the paper each indicate translation inhibition in the different direction. When it is assumed that regarding the first miRNA-responsive reporter mRNA, the translation inhibition of the cell A is α-fold (α>1) stronger than the cell B, and regarding the second miRNA-responsive reporter mRNA, the translation inhibition of the cell B is β-fold (β<1) stronger than the cell A, the cell A can be distinguished from the cell B on the dot plot of flow cytometry, if α×β is approximately 1.9-fold or more. If it is preferably 2.0-fold or more, and more preferably 2.5-fold or more, the cell A can be more clearly distinguished from the cell B. In another aspect, determination can be carried out by developing a histogram based on the ratio of two fluorescence values obtained from two mRNAs (e.g. the lower left histogram of FIG. 1(a)). By performing determination using such a ratio, a difference in the mRNA introduction efficiency among cells can be canceled.

The resolution of the cell type in such an aspect will be further described. FIG. 2 is a view schematically showing the principle of the present invention by which the cell type A is distinguished from the cell type B with high resolution. In the aforementioned FIG. 1(a), when fluorescence intensity is observed in a plurality of different miRNA-responsive reporter mRNAs, those fluorescence intensities are observed in the form of separated belts on the dot plot of flow cytometry. This demonstrates that the ratio of a plurality of fluorescence intensity values (lower left of FIG. 1(a)) gives a better separation. That is to say, when two types of mRNAs are introduced, two types of fluorescence intensity values can be measured, and one type of fluorescence intensity ratio can be obtained. Thus, the target cells are distributed one-dimensionally (on a number line of fluorescence intensity ratio) and are separated. FIG. 2(a) is a histogram showing a signal rate obtained when miRNA-responsive reporter mRNA and control mRNA are each introduced into two different cell groups A and B. Herein, a case in which the width of the distribution of fluorescence intensity ratio, namely, the width of a belt shown on a dot plot is 4-fold is assumed. Referring to FIG. 2(a), it is found that if there is a difference of 4-fold between the cells A and B, in terms of the translational efficiency of the miRNA-responsive reporter mRNA obtained as a quantitative ratio of marker proteins (i.e., the activity of the miRNA), it is possible to separate the two types of cell groups from each other on the histogram.

[c. One-Dimensional Separation Using Two Types of miRNA-Responsive Reporter mRNAs]

Figure 2B:
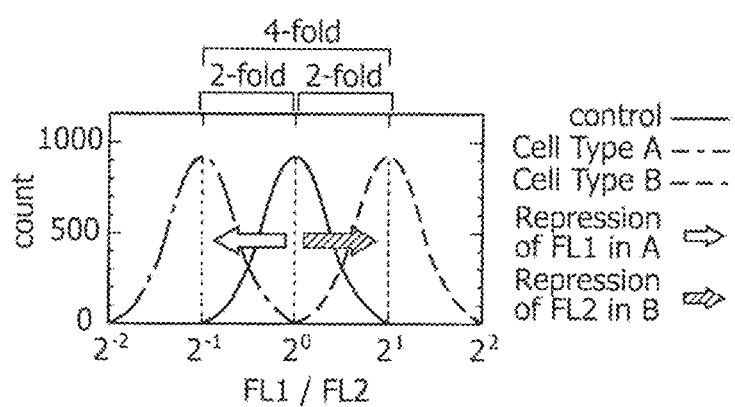

In another aspect of the present invention, two or more types of miRNA-responsive reporter mRNAs are preferably co-introduced into cells. This is because the separation ability of cells can be enhanced by using two or more types of miRNA-responsive reporter mRNAs. FIG. 2(b) is a schematic view describing the present embodiment, which enables high resolution even in a case in which there is merely a slight difference in terms of translational efficiency. That is, it is demonstrated that, even if they are a first miRNA-responsive mRNA (fluorescence intensity FL1 obtained by flow cytometry), which has merely a difference in translational efficiency of approximately 2-fold in comparison to control mRNA when it is introduced into the cell A, and a second miRNA-responsive mRNA (fluorescence intensity FL2 obtained by flow cytometry), which has merely a difference in translational efficiency of approximately 2-fold in comparison to control mRNA when it is introduced into the cell B, it is possible to sufficiently separate the cells from each other by using these two types of miRNA-responsive reporter mRNAs. Herein, when it is assumed that regarding the first miRNA-responsive reporter mRNA, the translational inhibition of the cell A is α-fold (α>1) stronger than that of the cell B, and that regarding the second miRNA-responsive reporter mRNA, the translational inhibition of the cell B is β-fold (β>1) stronger than that of the cell A, it is considered that the cell A can be separated from the cell B, if the integrated value of α×β is greater than the distribution width of the certain cell type shown in FIG. 2 (in this figure, 4-fold as an example). The exemplified 4-fold width is considered to be a case in which a relatively wide width could be generated, that is, the case of high level of difficulty.

Referring to FIG. 2(b), in the case of α>1 and β<1, a cell population moves in the same direction. In the figure, β corresponding to the right arrow (β>1) faces to the left in the case of β<1. For example, in this figure, even if the cell A moves to the left by 8-fold at α=8 and the cell B moves to the left by 2-fold at β=0.5, a width of 4-fold remains between the cells (integrated value: 8×0.5), and thus, the two cells are separated from each other. In this case, however, the separation becomes better, not when the second miRNA-responsive reporter mRNA, but reporter mRNA that does not respond to miRNA (β=1) is used (integrated value: 8×1).

On the other hand, upon considering separation of cells using a ratio histogram (FIG. 2), if certain miRNA-responsive mRNA is used, the peak of a cell population is not only shifted to the right and left, but the width of the cell population is also changed. For separation of cells, the entire distribution of cells is shifted to the right and left until it exceeds "the width of cell distribution." However, the shift amount (difference) of the entire distribution is distinguished by the integrated value of αβ. Meanwhile, such a width of cell distribution is widened or narrowed also by a combination of two types of miRNA-responsive mRNAs (see Example 10 and FIG. 15). As such, it is assumed that there is a case in which the narrowing of the distribution width while sacrificing the entire shift amount is advantageous for separation of cells.

When cells are to be separated according to a prior art technique using two types of antibodies binding to different fluorochromes and a cell surface antigen, if fluorescence intensity is measured by flow cytometry in the same manner as that described above, a dot plot as schematically shown in FIG. 1(c) is obtained. That is, there are many overlapped portions between the cell A and the cell B, and thus, it is impossible to separate these cells from each other with high accuracy. In contrast, by using miRNA-responsive reporter mRNA, and further, by using a combination of two or more types of miRNA-responsive mRNA such that, as described above, translational efficiency can be relatively suppressed in the aforementioned cells and it can be relatively increased in other cells, resolution can be enhanced.

[d. Two-Dimensional Separation Using Three Types of miRNA-Responsive Reporter mRNAs]

Moreover, by using three or more types of miRNA-responsive reporter mRNAs and co-introducing them into a plurality of cells, separation ability can be further enhanced based on the same principle as that described above. For instance, by introducing three types of mRNAs, three types of fluorescence intensity values can be measured, and two types of fluorescence intensity ratios can be obtained. Hence, target cells are two-dimensionally distributed (on a plane of fluorescence intensity ratio) and are separated. As an example, a case in which a first miRNA-responsive reporter mRNA targeting miRNA (a), a second miRNA-responsive reporter mRNA targeting miRNA (b), and a third miRNA-responsive reporter mRNA targeting miRNA (c) are co-introduced into two different types of cells A and B, will be described. The expression intensity of a first marker protein encoded by the first miRNA-responsive reporter mRNA measured by flow cytometry is defined as FL1; the expression intensity of a second marker protein encoded by the second miRNA-responsive reporter mRNA measured by flow cytometry is defined as FL2; and the expression intensity of a third marker protein encoded by the third miRNA-responsive reporter mRNA measured by flow cytometry is defined as FL3. When FL1/FL3 and FL2/FL3 are set on the X-axis and Y-axis, respectively, and a dot plot is produced, homologous cells appear not in the shape of a belt, but in the shape of a mass. Such an aspect is schematically shown in FIG. 1(b). Two masses existing on a dotted line going from upper left to lower right on the paper in FIG. 1(b) indicate dot plot masses observed by not using the third miRNA-responsive reporter mRNAs, but using control mRNA that does not respond to any miRNA. It can also be said that this indicates sections obtained by cutting the plane of FIG. 1(a) with a large arrow going from upper left to lower right on the paper. In contrast, it is found that as a result of co-introduction of the third miRNA-responsive reporter mRNA and the subsequent translational regulation that has been performed in a further different direction depending on a difference in the activity of miRNA (c), two masses existing on the dotted line are translationally regulated in each different directions (upper right and lower left on the paper), and thus, that the cell A can be more clearly separated from the cell B on the dot plot plane. Also, when two-dimensional separation is carried out using three types of miRNA-responsive reporter mRNAs, identical separation results can be obtained, although the fluorescence intensity of any one of the three types of miRNA-responsive reporter mRNAs is set at FL3 in the aforementioned calculation.

According to the two-dimensional separation using three types of miRNA-responsive reporter mRNAs, it becomes possible to distinguish and separate 25 types to 60 types or more of different cells, in which the miRNA active state is different in a 2-fold unit. As described above, this is because, theoretically, two types of cells can be distinguished from each other on the dot plot of flow cytometry, if the integrated value of translational efficiency of two types of miRNA-responsive reporter mRNAs is 1.9-fold or more in two types of cells. Accordingly, the two-dimensional separation using three types of miRNA-responsive reporter mRNAs can be practically used for determination of cell type. For example, if there may be cells in which the active state of certain miRNA has a difference of 5 stages (by 2-fold), it is considered that two types of miRNA-responsive mRNAs and one type of control mRNA are simultaneously introduced into the cells, so that 5×5=25 types of cells can be separated from one another. Using three types of miRNA-responsive reporter mRNA, 5×5×5=125 types of cells can be separated from one another by calculation. However, in practice, since there is overlap, approximately 61 types of cells can be separated. This is shown in Example 2 and FIG. 4(f).

[e. Three-Dimensional Separation Using Four Types of miRNA-Responsive Reporter mRNAs]

In the same manner as the aforementioned aspect d, it is also possible to carry out three-dimensional separation using four types of miRNA-responsive reporter mRNAs. That is to say, if four types of mRNAs are introduced into cells, four types of fluorescence intensity values can be measured, and three types of fluorescence intensity ratios can be obtained. Thus, target cells are three-dimensionally distributed (in the space of the fluorescence intensity ratio), and are separated from one another. As an example, a case in which a first miRNA-responsive reporter mRNA targeting miRNA (a), a second miRNA-responsive reporter mRNA targeting miRNA (b), a third miRNA-responsive reporter mRNA targeting miRNA (c), and a fourth miRNA-responsive reporter mRNA targeting miRNA (d) are co-introduced into two different types of cells A and B, will be described. The expression intensity of a first marker protein encoded by the first miRNA-responsive reporter mRNA measured by flow cytometry is defined as FL1; the expression intensity of a second marker protein encoded by the second miRNA-responsive reporter mRNA measured by flow cytometry is defined as FL2; the expression intensity of a third marker protein encoded by the third miRNA-responsive reporter mRNA measured by flow cytometry is defined as FL3; and the expression intensity of a fourth marker protein encoded by the fourth miRNA-responsive reporter mRNA measured by flow cytometry is defined as FL4. When FL1/FL4, FL2/FL4, and FL3/FL4 are set at X-axis, Y-axis, and Z-axis, respectively, and a dot plot is produced, homologous cells are each distributed in the form of a mass in a three dimensional space.

Furthermore, a higher dimensional separation is theoretically possible, and if (n+1) types of different miRNA-responsive reporter mRNAs are used, (n+1) types of fluorescence intensity values can be measured, and an n type of fluorescence intensity ratios can be obtained. As a result, it becomes possible to separate multiple types of cells from one another in an n-dimensional space. In this case as well, it is necessary that both a miRNA target sequence and a first marker gene be different in (n+1) types of miRNA-responsive reporter mRNAs. In particular, in the case of separation using fluorescence intensity, an n type of marker proteins need to have a detectably different wavelength region.

An example of another detection method applied in the determination step of the present invention is imaging cytometry. Such imaging cytometry can be carried out using an image analyzer. The image analyzer is able to obtain information regarding a change over time of the translation level of a first marker gene in a cell, and is excellent in terms of imaging and visualization, and is also able to improve the analysis amount per unit time. In addition, the image analyzer is advantageous in that it can be applied to analysis including the morphological or positional information of cells, and identification of cells that targets cells adhering to a culture vessel or a cell group organized in a planar or steric manner.

Even in the case of using such an image analyzer, the fluorescence intensity ratios obtained from two or more types of miRNA-responsive reporter mRNAs are shown in the form of a dot plot on a plane, so that different cell types can be separated from one another, and the aforementioned aspects a to d can be carried out.

Further, by image processing, the fluorescence intensity ratios of cells are converted to color information, so that a determination step that can be more visually utilized can be created. Specifically, a plurality of miRNA-responsive reporter mRNAs are designed such that they comprise a sequence encoding a nuclear localization signal, such as M9. Thereby, a marker protein is translated such that it is fused with the nuclear localization signal in a cell, and the marker protein is localized in the nucleus of the cell, so that a clearer fluorescence image of cells can be obtained.

The method of the present invention preferably comprises a step of screening for miRNA used as an indicator, as an optional pre-step. In the screening step, one or more miRNAs having different activities in multiple types of cells, which are comprised or are predicted to be comprised in a "cell group comprising two or more types of cells" as a measurement target, are selected. This is because the aforementioned desired resolution is achieved. In particular, when cell types comprised in a cell group have previously been known to a certain extent, one miRNA, which is highly expressed (high activity) in a cell A and is expressed at a low level in another cell B, is selected. When two or more types of miRNAs used as indicators are selected, a combination of mRNAs, namely, a combination of miRNA (a), which is expressed at a high level (high activity) in a cell A and is expressed at a low level (low activity) in another cell B, and miRNA (b), which is expressed at a low level (low activity) in a cell A and is expressed at a high level (high activity) in another cell B, is selected. Then, miRNA target sequences are distinguished in miRNA-responsive reporter mRNAs, based on one or two or more miRNAs distinguished in such a step.

When cells comprised in a cell group ore available as each isolated cells (e.g. cells A and cells B), the screening step can be carried out by a method comprising the following three steps. That is, in a first step, multiple types of miRNAs selected from a miRNA library are screened. For example, with regard to 60 to 70 types of miRNAs, miRNA-responsive reporter mRNA, which targets each miRNA and encodes an identical fluorescent protein, is prepared. Thereafter, each miRNA-responsive reporter mRNA and control mRNA encoding another fluorescent protein are co-introduced into each of existing cells A and B, and translational efficiency (a marker protein translated from the control mRNA/a marker protein translated from the miRNA-responsive reporter mRNA) is then measured.

In a second step, from the values of translational efficiency measured in the first step, 2 types, 3 types, or 4 types are combined with one another, and a vector constituted from those values is defined as each coordinate vector for the cell A and the cell B (e.g. XY coordinate, XYZ coordinate, or any given n-dimensional coordinate (wherein n represents an integer of 4 or greater)), and the distance between the cells in the ordinate is then calculated. When three or more types of existing cells are comprised, the shortest distance, among the distances between all types of two cells comprised, is calculated.

In a third step, two types, three types, or four types of miRNAs, which increase the distance between cells that has been calculated in the second step, are defined as target sequences, and one set of miRNA-responsive reporter mRNAs each encoding different fluorescent protein genes are prepared. The one set of miRNA-responsive reporter mRNAs are co-introduced into each of the cells A and B or into three or more types of cells, and separation ability is then tested. Among a plurality of sets, those from which the test results that the fluorescence ratio distributions of individual cells have appeared in each different regions and there has been small overlap among the distributions have been obtained, are preferably used in the subsequent introduction step and determination step.

On the other hand, in the case of a cell group regarding which a separation method different from the present invention has been known, the following operation is further needed: separation according to a different method is simultaneously carried out in the first step of the screening step, and the translational efficiency of each separated cell, namely, the value of miRNA activity is measured. Examples of such a separation method different from the present invention include: a method, which comprises immobilizing cells upon separation, performing membrane permeation, and detecting an intracellular factor using tin antibody, and a method which comprises previously modifying a gene even it is a living cell, and using a cell used for the purpose of the screening step (a reporter line, etc.). However, examples of the separation method different from the present invention are not limited thereto. The second step and the third step can be carried out in the same manners as those described above. The present screening method will be demonstrated in Example 9.

When multiple types of cells comprised in the "cell group comprising two or more types of cells" as a measurement target are unknown, the aforementioned screening step can be converted to the following screening step including the following first to fourth steps. In a first step, the miRNA activity value in the cell group is measured, and at the same time, a distribution of the miRNA activities of individual cells in the cell group is obtained. As a result, multiple types of miRNAs exhibiting a wide distribution of miRNA activities are selected. For example, it is preferable to select 6 to 10 types of miRNAs.

In a second step, a combination set of two types, three types, or fourth types of miRNAs is prepared from the miRNAs selected in the first step. In the second step, one set of miRNA-responsive reporter mRNAs, which targets two types, three types, or fourth types of miRNAs comprised in the one set, as target sequences, and encodes different fluorescent protein genes, is prepared.

In a third step, one set of miRNA-responsive reporter mRNAs, which is constituted with the two types, three types, or four types of miRNA-responsive reporter mRNAs prepared in the second step, is co-introduced into a cell group, and the correlation among miRNA activities in the cell group is then analyzed.

In a fourth step, one set of miRNA-responsive reporter mRNAs constituted with two types, three types, or four types of miRNA-responsive reporter mRNAs have been prepared again based on the correlation of miRNA activities analyzed in the third step, and the mRNAs are then co-introduced into the cell group to test separation ability. Among a plurality of sets, those, from which the test results that a distribution of fluorescence ratios in the cell group has been separated into two types, three types, four types, or more types of populations have been obtained, are preferably used in the subsequent introduction step and determination step. When such multiple types of cells comprised in the "cell group comprising two or more types of cells" are unknown, it can be said that the determination method of the present invention is a method of giving the definitions of a new cell type. The present screening method will be demonstrated in Examples 10 and 11.

As another optional pre-step, the present method may comprise a step of synthesizing miRNA-responsive reporter mRNA. In such a synthesis step, after miRNA used as an indicator or a combination of such miRNAs has been distinguished in the screening step, miRNA-responsive reporter mRNA or a combination of miRNA-responsive reporter mRNAs, which comprises miRNA target sequences that target them, is synthesized.

In addition, as a further optional step, the present method may comprise a step of separating cells after completion of the determination step.

In the aforementioned description, as a specific example of distinguishing cells, cases in each of which flow cytometry or imaging cytometry is applied in the determination step have been described. However, the present invention is not limited to the aforementioned aspects, and determination can be carried out theoretically in various aspects.

According to another aspect, the present invention relates to a kit for distinguishing a cell type, which comprises at least one type of miRNA-responsive reporter mRNA or a combination of two or more types of miRNA-responsive reporter mRNAs, and further comprises an optionally selected control mRNA. Such a kit may be prepared by enclosing the above-described miRNA-responsive reporter mRNA or combination of two or more types of miRNA-responsive reporter mRNAs in a preservable vessel or the like. Moreover, the present kit may comprise instructions regarding the use method thereof.

EXAMPLES

Hereinafter, the present invention will be described more in detail in the following Examples. However, these Examples are not intended to limit, the scope of the present invention.
[Construction of Plasmid]
An IVT template for control tag RFP mRNA (SEQ ID NO: 24) (template DNA used for the synthesis of mRNA) was amplified from the plasmid pSRT-tagRFP according to PCR, using a primer set, T7Fwd5UTR and Rev120A. First, using a primer set, FwdMCS and RevMCS, the multicloning site of pGEM T-easy (Promega) was modified according to PCR-based site directed mutagenesis, so as to obtain a pAM empty vector. Subsequently, a DNA fragment prepared by digesting pCDFDuet-1 (Novagen) with NheI and AgeI was blunt-ended, and the resulting fragment was then inserted into a DNA fragment prepared by digesting pAM with DraI to prepare a pSM empty vector. Subsequently, in order to prepare a pSRT empty vector, a pair of oligo DNAs, Code 5UTR and Comp 5UTR, were annealed, and the resultant was then inserted into the EcoRI-NcoI site. Then, the annealed Code 3UTR and Comp 3UTR were inserted into a XbaI-HindIII site (or "fragment"). Finally, the coding sequence of tagRFP was amplified according to PCR using a suitable primer set, it was then digested with NcoI and BglII, and it was then inserted into the NcoI and BglII site of pSRT to obtain pSRT-tagRFP.

In order to fuse M9 as a nuclear localization signal with a fluorescent protein, the coding regions of hmAG1, hmKO2, and tagBFP were amplified using a suitable primer set, and the tagRFP region of pSRT-tagRFP was then substituted. Subsequently, the M9 sequence was amplified using a primer set, FwdM9 and RevSV40, from p4LambdaN22-3mEGFP-M9 (Reference [4]), it was then digested with BamHI and BglII, and it was then inserted into the BglII site. The sequences of primers and oligonucleotides are shown in the following Table 1.

TABLE 1

| name | sequence (5' to 3') | Seq ID No. |
|---|---|---|
| FwdEGFP | CACCGGTCGCCACCATGGGATCCGTGAGCAAGGGC | 40 |
| RevEGFP | GCCCCGCAGAAGGTCTAGACCTACTTGTACAGCTCGTCCATGCCG | 41 |
| FwdtagBFP | CACCGGTCGCCACCATGGGATCCAGCGAG | 42 |
| RevtagBFP | GCCCCGCAGAAGGTCTAGACTATCACTCGAGATGCATATGAGATC | 43 |
| FwdhmAG1 | CACCGGTCGCCACCATGGTGAGCGTGATCAAGCCCG | 44 |
| RevhmAG1 | GCCCCGCAGAAGGTCTAGATTCACTTGGCCTGGCTGGGC | 45 |
| FwdhmKO2 | CACCGGTCGCCACCATGGTGAGTGTGATTAAACCAGAGATG | 46 |
| RevhmKO2 | GCCCCGCAGAAGGTCTAGATTCAGGAATGAGCTACTGCATCTTCTACCTG | 47 |
| FwdhdKeimaRed | CACCGGTCGCCACCATGGTGAGCGTGATCGCCAAG | 48 |
| RevhdKeimaRed | GCCCCGCAGAAGGTCTAGATTCAGCCCAGCAGGCTGTGC | 49 |
| RevM9 | GCCCCGCAGAAGGTCTAGACTATCACTCGAGATGCATATGAGATC | 50 |
| T7Fwd5UTR | CAGTGAATTGTAATACGACTCACTATAG | 51 |
| Rev5UTR | CATGGTGGCGACCGGTGTCTTATATTTCTTCTTACTC | 52 |
| temp5UTR | CAGTGAATTGTAATACGACTCACTATAGGGCGAATTAAGAGAGAAAGAAGAGTAAGAAGAAATATAAGACACCGGTCGCCACCATG | 53 |
| Fwd3UTR | TCTAGACCTTCTGCGGGGC | 54 |
| Rev3UTR | TTTTTTTTTTTTTTTTTTTTCCTACTCAGGCTTTATTCAAAGACCAAG | 55 |
| temp3UTR | TCTAGACCTTCTGCGGGGCTTGCCTTCTGGCCATGCCCTTCTTCTCTCCCTTGCACCTGTACCTGTACCTCTTGGTCTTTGAATAAAGCCTGAGTAGG | 56 |
| T7FwdA | GCTAATACGACTCACTATAGGTCAGATCCGCTAGGATC | 57 |

TABLE 1-continued

| name | sequence (5' to 3') | Seq ID No. |
|---|---|---|
| T7FwdB | GCTAATACGACTCACTATAGGTTCCTTAATCGCGGATCC | 58 |
| Rev120A | TTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTCCTACTCAGGCTTTATTCA | 59 |
| FwdMCS | GGGATCCCATGGTGTCGACCTGCAGCATATGAGCTCCTGAATTCGCCCTATAGTGAGTCG | 60 |
| RevMCS | GGGAGATCTCATATGCATCTCGAGTGATAGTCTAGACAAGCTTGAGTATTCTATAGTGTCACC | 61 |
| Code5UTR | AATTAAGAGAGAAAAGAAGAGTAAGAAGAAATATAAGAGCCAC | 62 |
| Comp5UTR | CATGGTGGCTCTTATATTTCTTCTTACTCTTCTTTTCTCTCTT | 63 |
| Code3UTR | CTAGACCTTCTGCGGGGCTTGCCTTCTGGCCATGCCCTTCTTCTCTCCCTTGCACCTGTACCTCTTGGTCTTTGAATAAAGCCTGAGTAGGA | 64 |
| Comp3UTR | AGCTTCCTACTCAGGCTTTATTCAAAGACCAAGAGGTACAGGTGCAAGGGAGAGAAGAAGGGCATGGCCAGAAGGCAAGCCCCGCAGAAGGT | 65 |

| name | sequence (5' to 3') | Seq ID No. |
|---|---|---|
| CFwdtagRFP | GCCACCATGGGATCCGTGTCTAAGGGCGAAGAGC | 66 |
| CRevtagRFP | GCTCGGAGATCTATTAAGTTTGTGCCCCAGT | 67 |
| CFwdtagBFP | GCCACCATGGGATCCAGCCAGCTGATTAAGGAGAAC | 68 |
| CRevtagBFP | ACTCGAGATCTGTGCCCCAGTTTGCTAG | 69 |
| CFwdhmAG1 | GCCACCATGGGATCCGTGAGCGTGATCAAGCCCG | 70 |
| CRevhmAG1 | TATGAGATCTCTTGGCCTGGCTGGGC | 71 |
| CFwdhmKO2 | GCCACCATGGGATCCGTGAGTGTGATTAAACCAGAGATG | 72 |
| CRevhmKO2 | TATGAGATCTGGAATGAGCTACTGCATCTTCTACCTG | 73 |
| FwdM9 | GAGATCCATGGGATCCAATCAGTCTTCAAATTTTGGAC | 74 |
| RevSV40 | CTTTATTTGTAACCATTATAAGCTGC | 75 |
| Rev120A-2 | TTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTCCTACTCAGGCTTTATTCACGCGGC | 212 |

[Construction of IVT Template DNA]

The protein coding region and control 5'UTR and 3'UTR sequences of the fluorescent protein were amplified according to PCR using suitable primers from plasmids or oligo DNAs. Several 5'UTR fragments were generated from plasmids. The pair of DNA fragments shown in Table 2 was annealed, and was then inserted into the BamHI-AgeI site of 18nt-2xFr15-ECFP (Reference [3]). Subsequently, using a primer set, T7FwdA and Rev5UTR, 5'UTR was amplified.

TABLE 2

| miRNA | | Primer | |
|---|---|---|---|
| name | ID | name | Sequence ID |
| hsa-miR-133a | MIMAT0000427 | 5Tmi133a_Afwd/5Tmi133a_Arev | 182/183 |
| hsa-miR-17-3p | MIMAT0000071 | 5Tmi17_3_Afwd/5Tmi17_3_Arev | 184/185 |
| hsa-miR-17-5p | MIMAT0000070 | 5Tmi17_5_Afwd/5Tmi17_5_Arev | 186/187 |
| hsa-miR-1 | MIMAT0000416 | 5Tmi1_Afwd/5Tmi1_Arev | 188/189 |
| hsa-miR-206 | MIMAT0000462 | 5Tmi206_Afwd/5Tmi206_Arev | 190/191 |
| hsa-miR-21-5p | MIMAT0000076 | 5Tmi21_Afwd/5Tmi21_Arev | 192/193 |
| hsa-miR-367-3p | MIMAT0000719 | 5Tmi367_Afwd/5Tmi367_Arev | 194/195 |
| hsa-miR-373-5p | MIMAT0000725 | 5Tmi373_5_Afwd/5Tmi373_5_Arev | 196/197 |

TABLE 3

| miRNA | | Primer | |
|---|---|---|---|
| name | ID | name | Sequence ID |
| hsa-miR-92a-3p | MIMAT0000092 | 5UTR-T92a-3p | 198 |
| hsa-miR-16-5p | MIMAT0000069 | 5UTR-T16-5p | 199 |
| hsa-miR-197-3p | MIMAT0000227 | 5UTR-T197-3p | 200 |
| hsa-miR-24-3p | MIMAT0000080 | 5UTR-T24-3p | 201 |

TABLE 3-continued

| miRNA | | Primer | |
|---|---|---|---|
| name | ID | name | Sequence ID |
| hsa-miR-339-5p | MIMAT0000764 | 5UTR-T339-5p | 202 |
| hsa-miR-224-5p | MIMAT0000281 | 5UTR-T224-5p | 203 |
| hsa-miR-127-3p | MIMAT0000446 | 5UTR-T127-3p | 204 |
| hsa-miR-365a-3p | MIMAT0000710 | 5UTR-T365a-3p | 205 |
| hsa-miR-183-5p | MIMAT0000261 | 5UTR-T183-5p | 206 |
| hsa-miR-331-3p | MIMAT0000760 | 5UTR-T331-3p | 207 |
| hsa-miR-203a | MIMAT0000264 | 5UTR-T203a | 208 |
| hsa-miR-214-3p | MIMAT0000271 | 5UTR-T214-3p | 209 |

TABLE 4

| miRNA | | Primer | |
|---|---|---|---|
| name | ID | name | Sequence ID |
| hsa-miR-17-5p | MIMAT0000070 | 3UTRtemp_4xT21-5p | 210 |
| hsa-miR-21-5p | MIMAT0000076 | 3UTRtemp_4xT17-5p | 211 |

In order to generate an IVT template, a 5'-UTR fragment and a 3'-UTR fragment (10 pmol each) and 50 ng of the protein coding region of a reporter protein were amplified according to PCR using the primer set, T7FwdA and Rev120A, shown in Table 2, and they are then linked to one another. Other 5'-UTR fragments shown in Table 3 were synthesized from oligo DNAs, and the synthesized fragments were then added to second PCR, instead of the 5' UTR fragment produced in the PCR. In order to prepare control mRNA or a screening library, T7Fwd5UTR or T7FwdB was used instead of T7FwdA in the second PCR. As an IVT template of mRNA comprising 4 copies of miRNA target sequences in the 3'-UTR, the oligo DNA shown in Table 4 was used instead of the PCR fragment of the 3'-UTR, and using Rev120A-2 instead of Rev120A, the fragments were amplified according to PCR and were then linked to one another. The PCR product was purified using MinElute PCR purification kit (QIAGEN) according to the instructions of the manufacturer. Before the purification, the PCR product amplified from the plasmid was digested with Dpn I (Toyobo) at 37° C. for 30 minutes. The sequences of primers are shown in Table 1.

[Synthesis and Generation of mRNA]

The miRNA-responsive reporter mRNA was prepared using MegaScript T7 kit (Ambion) according to modified protocols (see Reference [1] as described below). In this reaction, pseudo uridine-5'-triphosphate and 5-methylcytidine-5'-triphosphate (TriLink BioTechnologies) were used, instead of uridine triphosphate and cytidine triphosphate, respectively. Before the IVT reaction (the synthesis of mRNA), guanosine-5'-triphosphate was 5-fold diluted with Anti Reverse Cap Analog (New England Biolabs). The reaction mixture was incubated at 37° C. for 4 hours, and TURBO DNase (Ambion) was then added to the resultant. Thereafter, the thus obtained mixture was further incubated at 37° C. for 30 minutes. Thereafter, the obtained mRNA was purified with FavorPrep Blood/Cultured Cells total RNA extraction column (Favorgen Biotech), and the resultant was then incubated at 37° C. for 30 minutes, using Antarctic Phosphatase (Mew England Biolabs). Thereafter, the resultant was further purified using RNeasy MiniElute Cleanup Kit (QIAGEN).

[Screening for miRNA-Responsive mRNA]

Screening for miRNA-responsive mRNA was carried out by three steps. In a first step, miRNA-responsive reporter hmAG1 mRNA and control hmKO2 mRNA were co-introduced, and eight miRNAs, the activities of which largely differed depending on the types of the cells, were selected. In a second step, a combination table of four miRNA-responsive reporter mRNAs was produced, and was then tested. In this combination table, all types of two combinations could be encompassed, such that a pair of any two miRNAs selected from the eight miRNAs could be selected from four types of marker fluorescent proteins. In a third step, four miRNA-responsive reporter mRNAs were newly combined with one another, and several sets were then tested.

[Cell Culture]

HeLa cells and MCF-7 cells were cultured in Dulbecco's modified Eagle's medium (DMEM)-F12 comprising 10% Fetal Bovine Serum (FBS) and 1% Antibiotic Antimycotic Solution (Sigma), and in RPMI 1640, respectively. 293FT cells (Invitrogen) were allowed to grow in DMEM, to which 10% FBS, 2 mM L-Glutamine (Invitrogen), 0.1 mM Non-Essential Amino Acids (Invitrogen), 1 mM Sodium Pyruvate (Sigma) and 0.5% Penicillin-Streptomycin (Invitrogen) had been added. In an experiment in which cells were mixed, individual types of cells were prepared in the same medium as that for the HeLa cells, and the same numbers of cells were mixed with one another and were seeded.

IMR-90 cells (ATCC) were in Eagle's basal medium, to which 10% FBS and 1% Penicillin-Streptomycin-Glutamine (Gibco) had been added, on a gelatin-coated plate. Normal human lung fibroblasts (NHLF; Lonza) were cultured according to the instructions of the manufacturer. IMR-90 within 20 passages and NHLF within 10 passages were used. In order to allow IMR-90 cells to differentiate in vitro, these cells were kept in a starved state in a low-serum medium (0.01% FBS) for 48 hours, and were then stimulated in the low-serum medium in the presence or absence of 10 ng/mL human TGF-β1 (derived from mammals; PeproTech) for 24 hours. Subsequently, the resulting cells were transfected with the above designed and prepared miRNA-responsive reporter mRNA. Four hours after the transfection, the medium was exchanged with the one used in the transfection.

[Transfection with miRNA-Responsive Reporter mRNA]

Cultured cells (HeLa, 293FT, MCF-7, and IMR-90) were seeded on a 24-well plate, and on the following day, the synthesized mRNA was introduced therein. NHLF was seeded on a 24-well plate, and on the same day, the synthesized mRNA was introduced therein. Such introduction was carried out using 1 μL of StemFect (Stemgent) according to the instructions of the manufacturer. For the measurement of translational efficiency, reporter EGFP mRNA responding to each different type of miRNA and control tagRFP (Evrogen) mRNA (each 100 ng) were co-introduced into each cell. However, in an experiment regarding a comparison of the designing of mRNAs (Example 3 and FIG. 6), translational efficiency was distinguished in the presence of 2 pmol mirVana miRNA inhibitor (Applied Biosciences).

In an inhibitor assay, 0.1 to 1 pmol miRNA inhibitor, or 25 to 200 ng of reporter mRNA (comprising a click beetle luciferase CBRlue (Promega) gene in the ORF and having the same 5'-UTR as that of reporter EGFP) was co-introduced, together with two reporter mRNAs. Twenty-four hours after the introduction, the cells were measured by a flow cytometry method using Accuri C6 (BD Biosciences). The fluorescence intensity ratio of two types of reporter proteins in each cell was calculated, and was then plotted. The translational efficiency was distinguished by dividing the average intensity of EGFP responding to miRNA by the average intensity of control tag RFP measured by flow cytometry.

In order to separate cells using two miRNA-responsive reporter mRNAs, 100 ng of reporter mRNA expressing EGFP, and 125 ng of reporter mRNA expressing hmKO2 (Amalgaam) were co-introduced, into cells or a mixture thereof. In the first screening for IMR-90 cells, the cells were transfected with 50 ng of reporter hmAG1 (Amalgaam) mRNA and 80 ng of control hmKO2 mRNA. With regard to the differentiated IMR-90 cells and NHLF cells, hmAG1 mRNA and hmKO2 mRNAs were used at 2-fold. In the case of co-introduction of three mRNAs, 40 ng of hmAG1 mRNA, 10 ng of hmKO2 mRNA, and 200 ng of tagBFP (Evrogen) mRNA were used, in the case of co-introduction of four mRNAs, 250 ng of hdKeimaRed (Amalgaam) mRNA was used, as well as the aforementioned three mRNAs. CBG68luc mRNA (SEQ ID NO: 31) was used to dilute hmAG1 mRNA, hmKO2 mRNA, and tapBFP mRNA. The medium was exchanged 4 hours after the transfection.

[Flow Cytometry]

Twenty-hour hours after the transfection, the cells were separated from the culture dish, and they were then passed through a mesh and were analyzed by flow cytometry. For the analysis of co-introduction of two mRNAs, Accuri C6 (BD Biosciences) equipped with FL1 (530/30 nm) and FL2 (585/40 nm) filters was employed. For the analysis of co-introduction of three mRNAs or four mRNAs, FACSAria (BD Biosciences) was employed. hmAG1, hmKO2, tagBFP and hdKeimaRed were detected with blue laser (488 nm) comprising an FITC filter (530/30 nm), and analyzed with green laser (561 nm) comprising PE filter (585/42 nm), violet laser (405 nm) comprising Pacific Blue filter (450/40 nm), and violet laser comprising Qdot 605 filter (610/20 nm), respectively. Dead cells and debris were removed by front and lateral light scattering signals, in the measurement of translational efficiency, the intensity of EGFP and the intensity of tagRFP were corrected based on the spectral matrix obtained from the data set of cells translated with EGFP or tagRFP (Reference [5]). The translational efficiency was defined as a value obtained by dividing the average intensity of the corrected EGFP signals by the average intensity of the corrected tagRFP signals.

[Imaging Cytometry]

The reporter fluorescent protein was fused with the nuclear localization signal M9 on the C-terminal side, so that the co-introduced cells were clarified. Twenty-four hours after introduction of three mRNAs, using IN Cell Analyzer 6000 (GE Healthcare), the bright field image and fluorescence image of the cells were obtained. The fluorescence signals of hmAG1, hmKO2 and tagBFP were measured using blue laser comprising an FTTC filter, green laser comprising a DsRed filter, and UV laser comprising a DAPI filter, respectively. The obtained images were analyzed using Cell Profiler (Reference [2]). First, the nucleus was identified in the average images of three fluorescence channels. Subsequently, as with flow cytometry, the hmKO2 signals and the tagBFP signals were divided by the hmAG1 signals in every pixel. Then, the geometric mean rate in each nucleus was obtained. The images were edited using ImageJ (manufactured by The National Institutes of Health (NIH)).

Figure 3A:
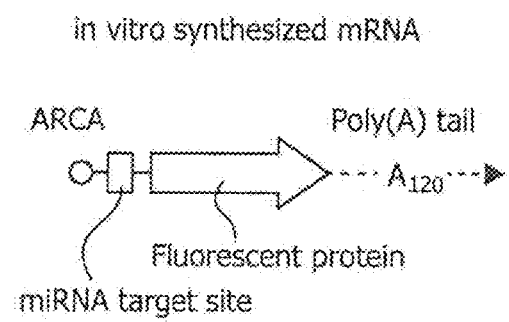
FIG. 3A includes a series of views showing the two-dimensional separation of existing cell lines using one or two types of miRNA-responsive reporter mRNAs.
Figure 3A:
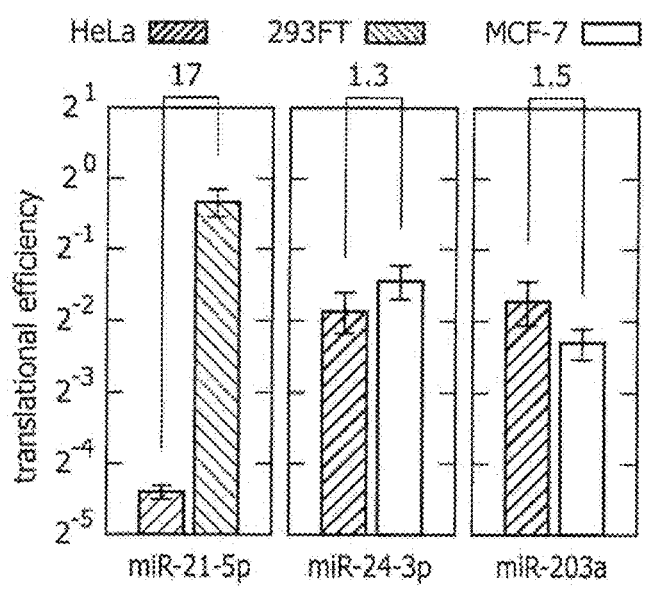
Figure 3A:
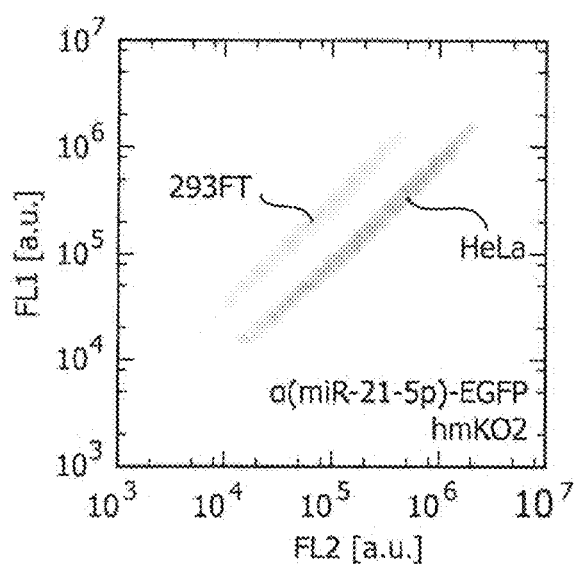
Figure 3A:
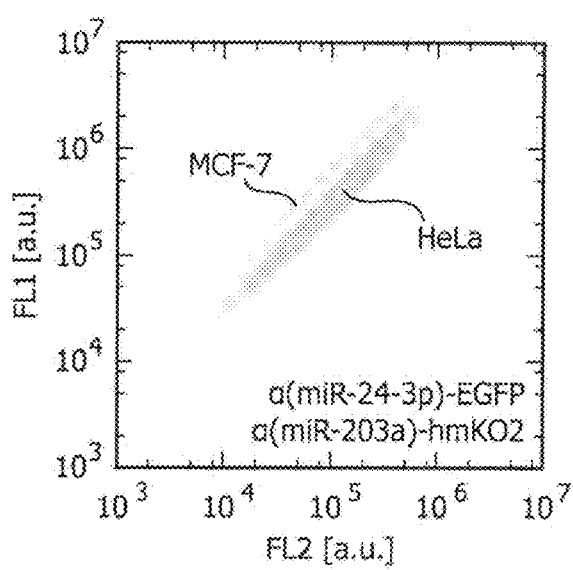

Example 1: One-Dimensional Separation of Existing Cell Lines, Using miRNA-Responsive Reporter mRNA One-dimensional separation of existing cell lines was carried out using one or two types of miRNA-responsive reporter mRNAs. The results are shown in FIG. 3. FIG. 3(a) is a schematic view showing in vitro synthesized miRNA-responsive reporter mRNA used in the present Example. In the direction from the 5'-terminus on the left side to the 3'-terminus on the right side on the paper, ARCA (gap structure analog), a miRNA target sequence, a gene encoding a fluorescent protein, and poly(A) tail are positioned. The ARCA, the miRNA target sequence, and the initiation codon were designed, such that the ARCA could be separated from the miRNA target sequence by approximately 20 nucleotides, and the miRNA target sequence could also be separated from the initiation codon by approximately 20 nucleotides.

FIG. 3(b) is a graph showing a comparison in translational efficiency, when three types of miRNA-responsive reporter mRNAs were each introduced into three types of cell lines. A gene encoding EGFP was used as a marker gene in all cases, and miR-21-5p, miR-24-3p and miR-203a were used as miRNA target sequences, respectively. With regard to the three types of miRNA-responsive reporter mRNAs ($\alpha$(miR-21-5p)-EGFP (SEQ ID NO: 1), $\alpha$(miR-24-3p)-EGFP (SEQ ID NO: 3), and $\alpha$(miR-203a)-EGFP (SEQ ID NO: 5)), 100 ng of each mRNA, together with 100 ng of control tagRFP mRNA (SEQ ID NO: 24), was directly co-introduced into HeLa, 293FT and MCF-7 cells. Translational efficiency was distinguished by dividing the average intensity of EGFP by the average intensity of tagRFP according to a flow cytometric measurement 24 hours after the co-introduction. The numerical value in the upper portion of each graph column indicates the magnification of translational efficiency among the individual cell lines. The error bar indicates an average±standard deviation (n=3).

Figure 3C:
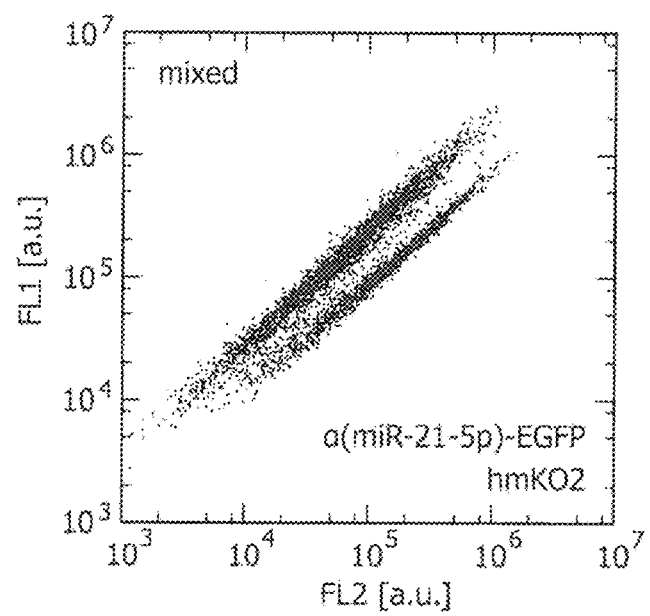
FIG. 3C includes views showing the two-dimensional separation of a mixture of two types of existing cell lines using one or two types of miRNA-responsive reporter mRNAs, and histograms showing the ratio of two fluorescence signals.
Figure 3C:
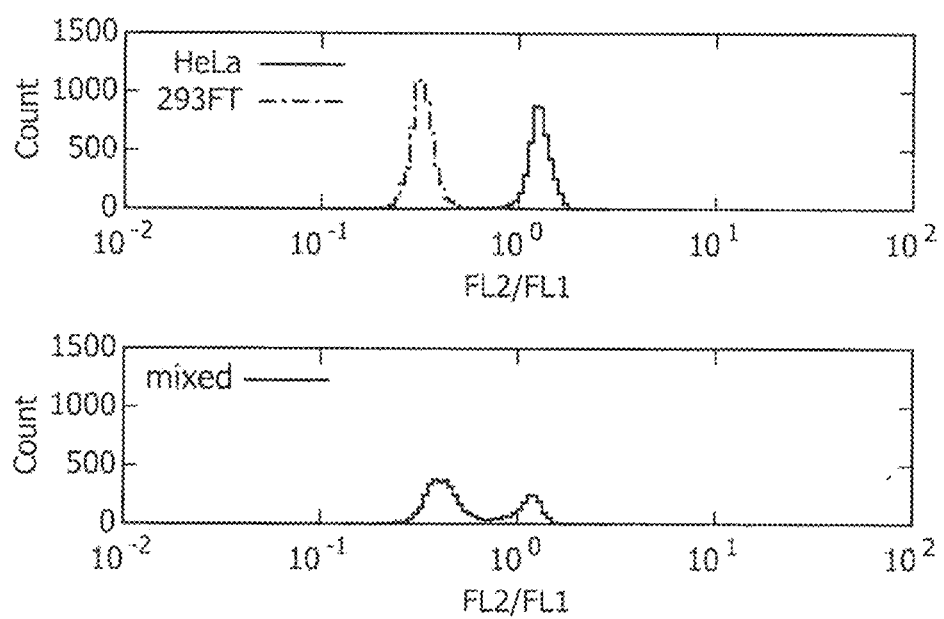

FIG. 3(c) is a dot plot showing the measurement results obtained 24 hours after the co-introduction of miR-21-5p-responsive EGFP mRNA and control hmKO2 mRNA (SEQ ID NO: 22) into each of HeLa cells and 293FT cells. On the other hand, FIG. 3(f) is a dot plot showing the measurement results obtained 24 hours after the co-introduction of the same mRNAs as those described above into a mixture of HeLa cells and 293FT cells. The measurement was carried out using Accuri C6 flow cytometer, and the test was independently performed three times. Representative results were shown in the figure. From the fluorescence intensify ratio reflecting a difference in miRNA activity, it is found that the two types of cell lines were apparently separated from each other.

FIG. 3(d) is a dot plot showing the measurement results obtained 24 hours after the co-introduction of miR-24-3p-responsive EGFP mRNA and miR-203a-responsive hmKO2 mRNA (SEQ ID NO: 6) into each of HeLa cells and MFC-7 cells. On the other hand, FIG. 3(h) is a dot plot showing the measurement results obtained 24 hours after the co-introduction of the same mRNAs as those described above into a mixture of HeLa cells and MFC-7 cells. Referring to FIG. 3(b), it is found that the activities of these miRNAs were slightly and reversely different in the two cell lines. Referring to FIGS. 3(d) and (h), it is found that the two types of cell lines were clearly separated from each other, using such a slight difference in the activity.

FIG. 3(e) includes histograms showing the ratio of two fluorescence signals. A set of miRNA-responsive reporter mRNA/control mRNA (EGFP mRNA (SEQ ID NO: 19) or hmKO2 mRNA (SEQ ID NO: 22)) shown in each histogram was co-introduced into HeLa cells, MCF-7 cells, and a mixture thereof. The cumulative frequency of the fluorescence ratio of cells, into which the two types of miRNA-responsive reporter mRNAs have been introduced, is shown in the lowest column. In addition, FIG. 3(g) includes histograms showing the ratio of two fluorescence signals in the dot plot shown in each of FIG. 3(c) and FIG. 3(f).

Example 2: Cell Separation in a Higher-Dimensional Space

Cell separation was carried out using three types of or four types of miRNA-responsive reporter mRNAs. First, three types of miRNA-responsive reporter mRNAs, α(miR-34-3p)-EGFP, α(miR-127-3p)-EGFP (SEQ ID NO: 7), α(miR-17-5p)-EGFP (SEQ ID NO: 9) and α(miR-92a-3p)-EGFP (SEQ ID NO: 15), where measured in terms of translational efficiency in HeLa, 293FT, and MCF-7 cells. The results are shown in FIGS. 4(a) and (d). The numerical value at the top of each column indicates the translational efficiency ratio of two types out of the three types of cell lines. The error bars each indicate a mean value±standard deviation (n=3).

The results obtained by performing two-dimensional separation using three types of miRNA-responsive reporter mRNAs (α(miR-24-3p)-hmAG1 (SEQ ID NO: 4), α(miR-127-3p)-hmKO2 (SEQ ID NO: 8) and α(miR-17-5p)-tagBFP (SEQ ID NO: 13)) are shown in FIG. 4(b). Three types of miRNA-responsive reporter mRNAs were each independently co-introduced into three types of cell lines, and twenty-four hours later, the results were analyzed by FACSAria. The data of flow cytometry were plotted regarding two ratios. The two ratios indicate a value obtained by dividing the hmKO2 intensity by the hmAG1 intensity, and a value obtained by dividing the tagBFP intensity by the hmAG1 intensity. The densities of the HeLa cells, 293FT cells and MCF-7 cells, which involved co-introduction of the mRNAs, were plotted on the plane. With regard to the colored density plots, the densities of 293FT cells, HeLa cells and MCF-7 cells were indicated with red, green and blue channels, respectively, and the obtained images were then overlapped, and the colored density plots were produced as negative images thereof.

The results obtained by performing two-dimensional separation on a sample prepared by mixing three types of cells, using three types of miRNA-responsive reporter mRNAs, are shown in FIG. 4(c). The data of flow cytometry were plotted regarding two ratios.

Three-dimensional separation was carried out using four types of miRNA-responsive reporter mRNAs. Four types of control mRNAs, hmAG1 mRNA (SEQ ID NO: 21), hmKO2 mRNA (SEQ ID NO: 22), tagBFP mRNA (SEQ ID NO: 20) and hdKeimaRed mRNA (SEQ ID NO: 23), were co-introduced into each of HeLa, 293FT, MCF-7, and a mixture thereof. On the other hand, four types of miRNA-responsive reporter mRNAs, α(miR-24-3p)-hmAG1, α(miR-127-3p)-hmKO2, α(miR-92-3p)-tagBFP (SEQ ID NO: 17) and α(miR-17-5p)-hdKeimaRed (SEQ ID NO: 14), were co-introduced into each of HeLa, 293FT, MCF-7, and a mixture thereof. Twenty-four hours after the introduction, a flow cytometric analysis was carried out. The results obtained by performing three-dimensional separation using four types of miRNA-responsive reporter mRNAs are shown in FIG. 4(e). After completion of the measurement by flow cytometry, geometric means of three ratios, that is, a value obtained by dividing the hmKO2 intensity by the hmAG1 intensity, a value obtained by dividing the tagBFP intensity by the hmAG1 intensity, and a value obtained by dividing the hdKeimaRed intensity by the hmAG1 intensity were calculated and were then plotted. The error bar indicates a geometric mean±geometric standard deviation in each axis (n=5900 to 7300).

Figure 5A:
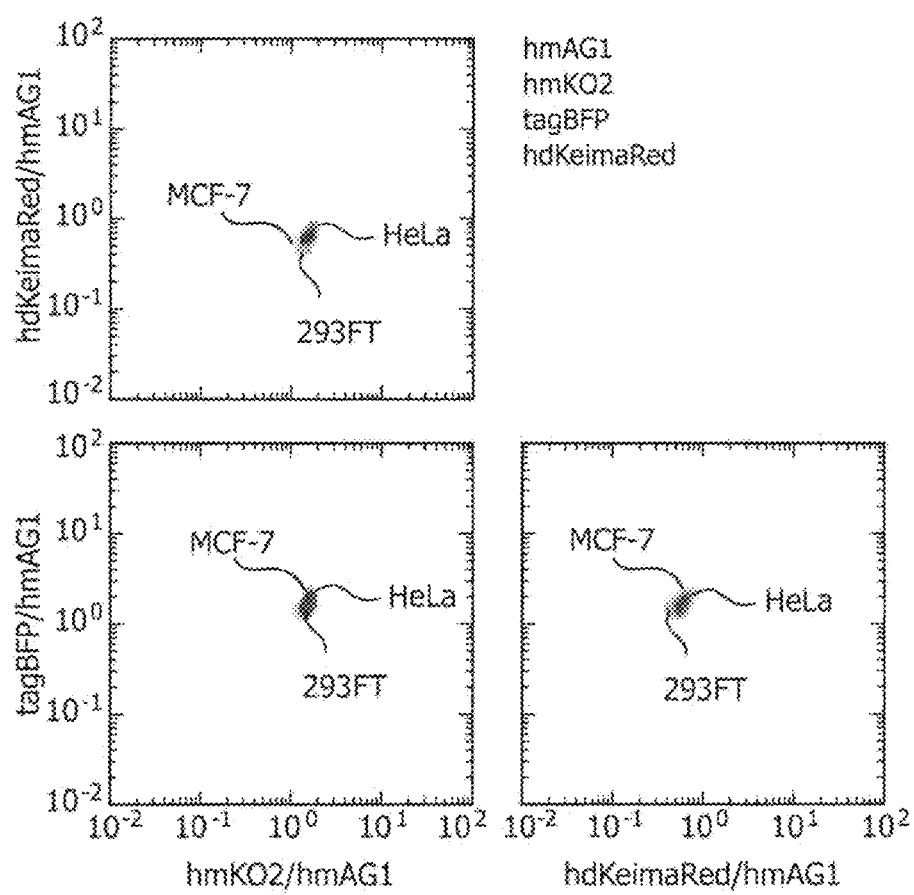
FIG. 5A includes a series of views showing the three-dimensional separation of three types of cell lines using four types of control mRNAs.
Figure 5A:
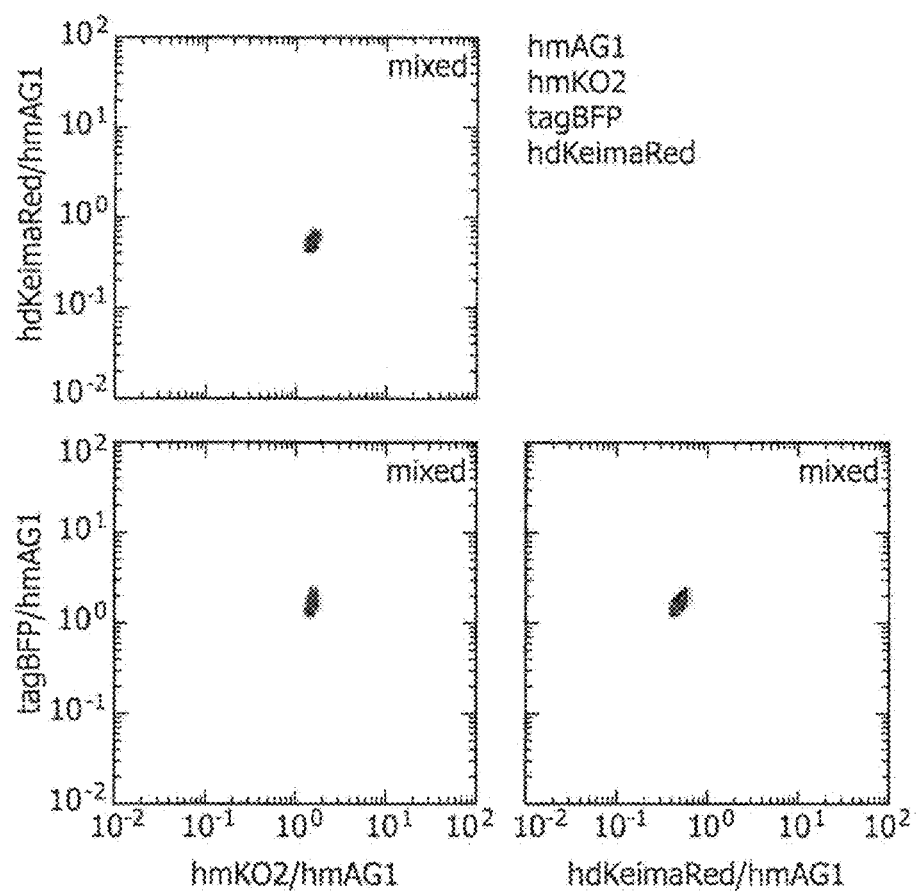
Figure 5B:
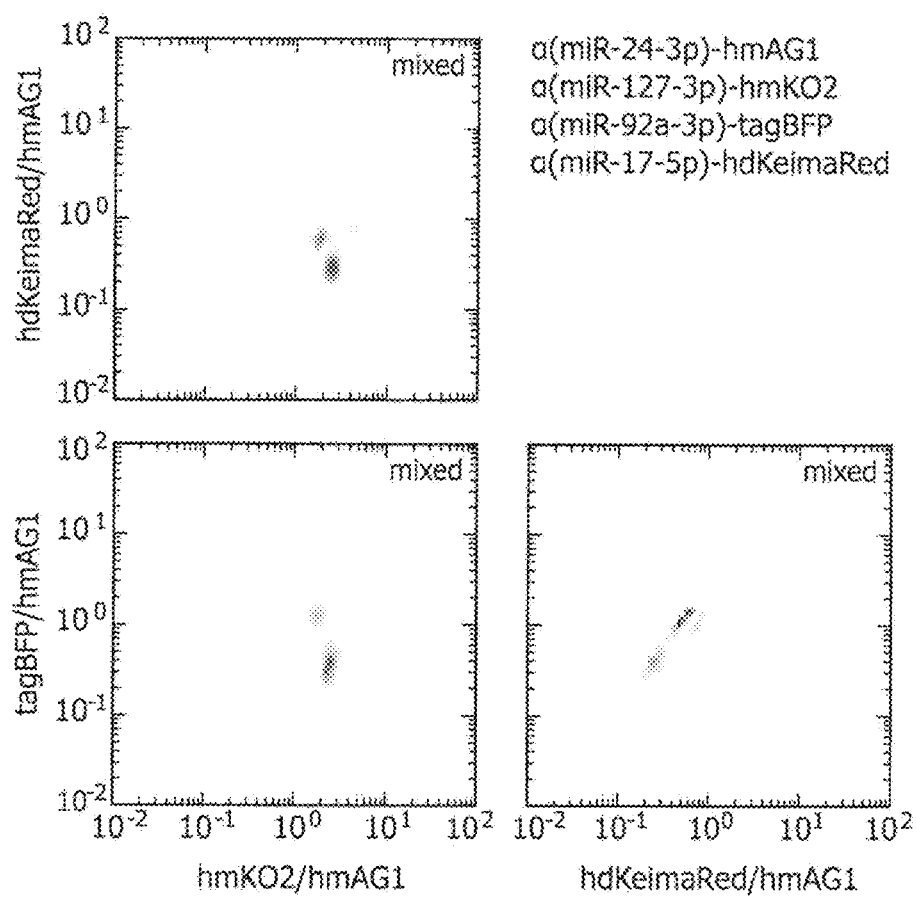
FIG. 5B includes a series of views showing the three-dimensional separation of three types of cell lines using four types of miRNA-responsive reporter mRNAs.

The cell density was plotted on three planes vertical to three axes, and the fluorescence intensities of hmKO2, tagBFP and hdKeimaRed were each divided by the fluorescence intensity of hmAG1. The density plot is shown in FIG. 5, FIG. 5 shows representative results obtained from three independent experiments. From FIGS. 5A(a) and (b), it is found that, even referring to any plane plot, the three types of cell lines, into which the four types of control mRNAs had been co-introduced, could not be separated from one another. On the other hand, from FIG. 5(c), it is found that the three types of cell lines, into which the four types of miRNA-responsive reporter mRNAs had been co-introduced, could be apparently separated from one another in all of the planar dot plots. Moreover, from FIG. 5(d), cell separation can also be confirmed in a mixture of the three types of cell lines by visual observation. That is to say, it becomes possible to perform determination capable of separating a mixture of cell lines into three types of cell lines.

Control mRNAs having no miRNA target sequences, namely, hmAG1 mRNA, hmKO2 mRNA, and tagBFP mRNA were each diluted to 5 stages of dilutions by 2-fold, and these dilutions were then combined in various ways and were then co-introduced into HeLa cells. Density plots obtained from 46 types of independent introduction results are shown in FIG. 4(f). Set A is a group comprising dot plots obtained from 4 stages of 2-fold dilutions, and Set B is a group comprising dot plots obtained from 5 stages of 2-fold dilutions. Detailed introduction conditions are shown in Table 5A and Table 5B. This experiment, in which a plurality of control mRNAs were diluted to various concentrations, demonstrates various miRNA-responsive reporter mRNAs that may be generated by miRNA activity in cells. That is, it is suggested that, theoretically, focusing on three types of miRNAs, when the activity of each miRNA is assumed to be different with 4 stages by 2-fold (wherein at maximum $4^3=64$ cell types can be assumed), the cells can be separated into at maximum 37 types by using three types of miRNA-responsive reporter mRNAs. In addition, it is also suggested that cells can be separated by the same method as that described above, even in a case in which the activity of miRNA is different with 5 stages (by 2-fold) (in such a case, at maximum $5^3=125$ cell types can be assumed, and the cells can be separated into at maximum 61 types using three types of miRNA-responsive reporter mRNAs).

TABLE 5A

| | Dilution factor | | | hmKO2/hmAG1 | | tagBFP/hmAG1 | |
|---|---|---|---|---|---|---|---|
| Set | hmAG1 (40 ng) | hmKO2 (10 ng) | tagBFP (200 ng) | mean | 90% interval | mean | 90% interval |
| A | 1 | 1 | 1 | 1.574 | 2.245 | 2.965 | 1.973 |
| A | 1 | 1 | 2 | 1.442 | 2.280 | 1.401 | 2.008 |
| A | 1 | 1 | 4 | 1.660 | 2.593 | 0.787 | 1.975 |
| A | 1 | 1 | 8 | 1.603 | 2.377 | 0.383 | 1.937 |
| A | 1 | 2 | 1 | 0.929 | 1.940 | 2.806 | 1.886 |
| A | 1 | 2 | 2 | 0.878 | 2.426 | 1.386 | 1.953 |
| A | 1 | 2 | 4 | 0.952 | 2.304 | 0.753 | 2.007 |
| A | 1 | 2 | 8 | 0.897 | 2.235 | 0.365 | 1.987 |
| A | 1 | 4 | 1 | 0.472 | 2.787 | 2.825 | 2.047 |
| A | 1 | 4 | 2 | 0.469 | 2.382 | 1.447 | 2.057 |
| A | 1 | 4 | 4 | 0.517 | 2.737 | 0.793 | 1.966 |
| A | 1 | 4 | 8 | 0.459 | 2.197 | 0.341 | 1.995 |
| A | 1 | 8 | 1 | 0.277 | 2.710 | 2.968 | 1.971 |
| A | 1 | 8 | 2 | 0.298 | 3.082 | 1.545 | 2.088 |
| A | 1 | 8 | 4 | 0.272 | 3.230 | 0.710 | 2.019 |
| A | 1 | 8 | 8 | 0.284 | 3.086 | 0.389 | 2.045 |
| A | 1 | 1 | 1 | 9.564 | 2.687 | 15.421 | 2.587 |
| A | 1 | 1 | 2 | 9.031 | 2.431 | 7.598 | 2.502 |

TABLE 5A-continued

| Set | Dilution factor | | | hmKO2/hmAG1 | | tagBFP/hmAG1 | |
| --- | --- | --- | --- | --- | --- | --- | --- |
| | hmAG1 (40 ng) | hmKO2 (10 ng) | tagBFP (200 ng) | mean | 90% interval | mean | 90% interval |
| A | 1 | 1 | 4 | 10.809 | 2.433 | 4.166 | 2.415 |
| A | 1 | 1 | 8 | 9.647 | 2.328 | 2.012 | 2.268 |
| A | 8 | 2 | 1 | 6.004 | 2.009 | 15.804 | 3.018 |
| A | 8 | 2 | 2 | 5.903 | 2.027 | 7.718 | 3.157 |
| A | 8 | 2 | 4 | 6.581 | 2.071 | 3.819 | 2.898 |
| A | 8 | 2 | 8 | 5.832 | 2.078 | 2.093 | 2.396 |
| A | 8 | 4 | 1 | 3.380 | 2.131 | 15.611 | 3.568 |
| A | 8 | 4 | 2 | 3.166 | 1.987 | 8.567 | 2.789 |
| A | 8 | 4 | 4 | 3.244 | 2.051 | 4.150 | 2.758 |
| A | 8 | 4 | 8 | 3.219 | 1.951 | 2.196 | 2.360 |
| A | 8 | 8 | 1 | 1.709 | 2.336 | 16.277 | 2.502 |
| A | 8 | 8 | 2 | 1.648 | 2.164 | 8.270 | 2.441 |
| A | 8 | 8 | 4 | 1.720 | 2.145 | 4.311 | 2.393 |
| A | 8 | 8 | 8 | 1.881 | 2.247 | 2.196 | 2.532 |
| A | 2 | 1 | 8 | 2.897 | 1.663 | 0.614 | 2.026 |
| A | 2 | 8 | 1 | 0.543 | 2.981 | 4.638 | 2.142 |

TABLE 5B

| Set | Dilution factor | | | hmKO2/hmAG1 | | tagBFP/hmAG1 | |
| --- | --- | --- | --- | --- | --- | --- | --- |
| | hmAG1 (40 ng) | hmKO2 (10 ng) | tagBFP (200 ng) | mean | 90% interval | mean | 90% interval |
| A | 4 | 1 | 8 | 5.279 | 1.723 | 1.092 | 2.057 |
| A | 4 | 2 | 8 | 3.291 | 1.736 | 1.203 | 2.139 |
| A | 4 | 8 | 1 | 1.020 | 2.603 | 9.637 | 2.382 |
| A | 4 | 8 | 2 | 0.992 | 2.511 | 4.675 | 2.360 |
| B | 1 | 1 | 16 | 1.742 | 1.657 | 0.199 | 2.062 |
| B | 1 | 16 | 1 | 0.193 | 5.100 | 2.857 | 2.129 |
| B | 1 | 16 | 16 | 0.203 | 4.997 | 0.219 | 2.162 |
| B | 16 | 1 | 16 | 16.047 | 2.784 | 1.610 | 2.336 |
| B | 16 | 16 | 1 | 2.006 | 2.553 | 29.087 | 4.669 |
| B | 16 | 1 | 1 | 15.916 | 2.640 | 25.754 | 3.660 |
| B | 4 | 16 | 1 | 0.636 | 4.540 | 8.858 | 2.585 |
| B | 4 | 1 | 16 | 5.799 | 1.675 | 0.631 | 2.042 |

*mean: geometric mean
*90% interval: fold-change

Example 3: Insertion of miRNA Target Sequence and Translational Efficiency

Figure 6:
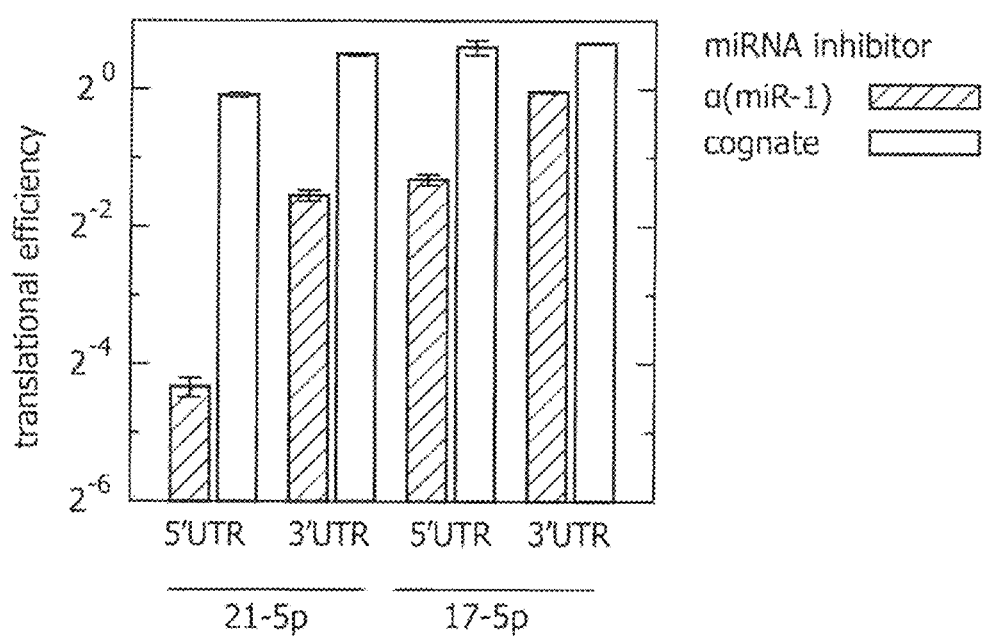
FIG. 6 is a view showing the influence of the insertion site of a miRNA target sequence upon the translational efficiency of miRNA-responsive reporter mRNA.

The position of a miRNA target sequence in reporter miRNA-responsive reporter mRNA was examined. That is, miRNA-responsive reporter mRNA (α(miR-21-5p)-EGFP (SEQ ID NO: 1)) in which one perfect complementary sequence of miR-21-5p that is the target site of miR-21-5p is present in the 5'UTR, and miRNA-responsive reporter mRNA (EGFP-4xα(4xmiR-21-5p) (SEQ ID NO: 2)) in which four perfect complementary sequences of miR-21-5p are present in the 3'UTR, were prepared. The thus prepared mRNAs were examined in terms of translational efficiency. Likewise, miRNA-responsive reporter mRNA (α(miR-17-5p)-EGFP (SEQ ID NO: 9)) in which one perfect complementary sequence of miR-17-5p that is the target site of miR17-5p is present in the 5'UTR, and miRNA-responsive reporter mRNA (EGFP-4xα(4xmiR-17-5p) (SEQ ID NO: 10)) in which four perfect complementary sequences of miR-17-5p are present in the 3'UTR, were prepared. The thus prepared mRNAs were examined in terms of translational efficiency. The translational efficiency of each reporter mRNA was measured in the presence of an inhibiting agent, (inhibitor) to miRNA, to which the reporter mRNA responded. An inhibitor to miR-1 was used as a negative control. The concentration of such an inhibitor was set at 2 pmol. The error bars each indicate a mean value±standard deviation (n=2). The results are shown in FIG. 6.

Example 4: Activity of miRNA-Responsive Reporter mRNA as miRNA Inhibitor

Figure 7A:
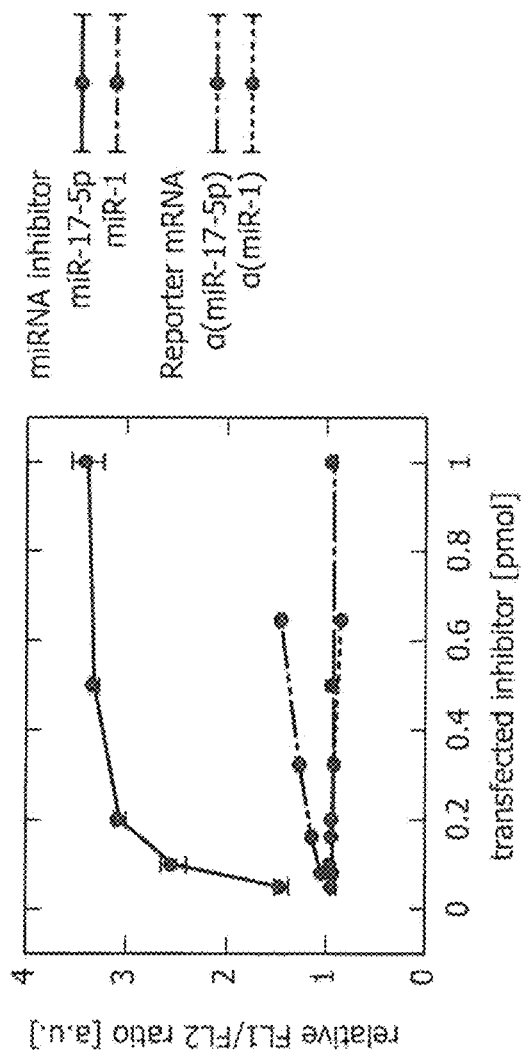
FIG. 7 is a view showing that miRNA-responsive reporter mRNA does not have inhibitory effects on intracellular miRNA activity.

An experiment was carried out to verify a difference between a commercially available miRNA inhibitor and miRNA-responsive reporter mRNA. The translational efficiency of α(miR-17-5p)-EGFP responding to the same miR-17-5p in HeLa cells was measured in the presence of a commercially available miRNA inhibitor or miR-17-5p-responsive reporter mRNA (α(miR-17-5p)-CBRLuc (SEQ ID NO: 33); it does not exhibit fluorescence because it is a luciferase gene). An inhibitor to miR-1 and luciferase mRNA (α(miR-1)-CBRLuc (SEQ ID NO: 32)) responding to miR-1 were used as negative controls. The results are shown in FIG. 7(a). The error bars each indicate a mean value±standard deviation (n=3). From these results, it is found that miRNA-responsive reporter mRNA hardly functions as a miRNA inhibitor.

It was confirmed that reporter mRNAs (luciferase) responding to six other types of miRNAs (that is, α(miR-21-5p)-CBRluc: SEQ ID NO: 34, α(miR-92a-3p)-CBRluc: SEQ ID NO: 35, α(miR-24-3p)-CBRluc: SEQ ID NO: 36, α(miR-127b-3p)-CBRluc: SEQ ID NO: 37, α(miR-16-5p)-CBRluc: SEQ ID NO: 38, and α(miR-203a)-CBRluc: SEQ ID NO: 39) do not function as miRNA inhibitors.

Figure 7B:
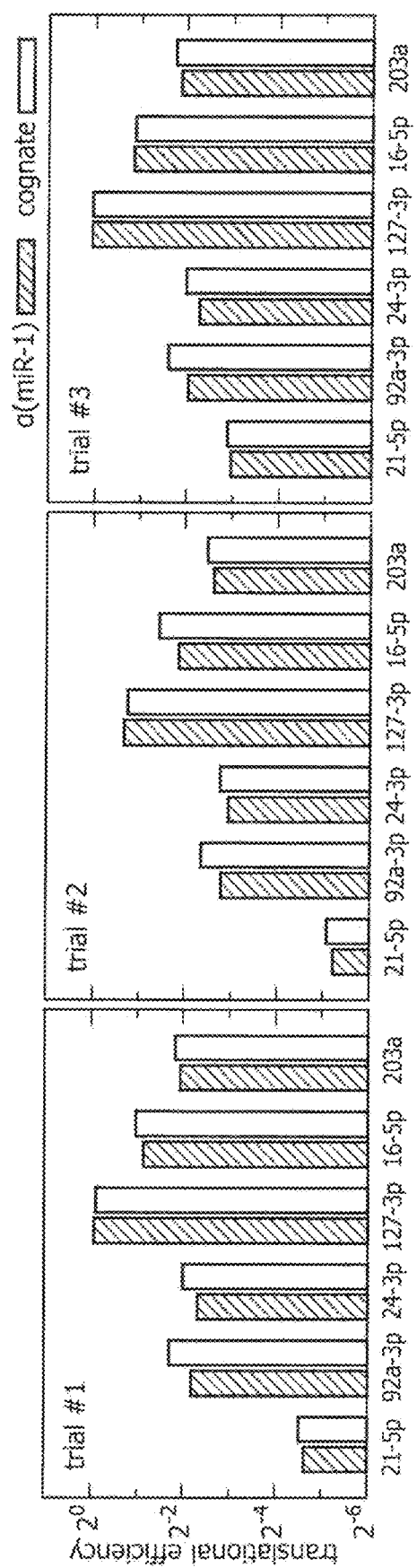

The activity of each miRNA was measured using EGFP reporter mRNA responding to the miRNA. At this time, miR-1 (negative control) or luciferase reporter mRNA responding to the same miRNA was introduced. The results obtained from testing 3 times are shown in FIG. 7(b).

Figure 8A:
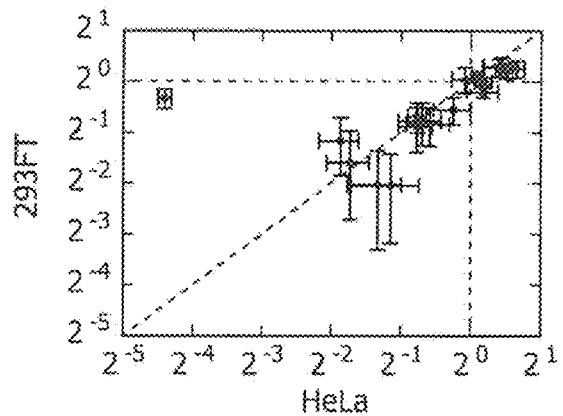
FIG. 8 includes graphs showing the translational efficiency of the selected 20 types of miRNA-responsive reporter mRNAs in three types of cell lines.
Figure 8B:
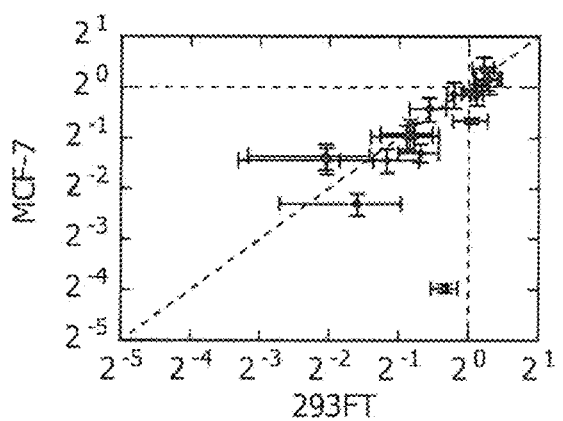
Figure 8C:
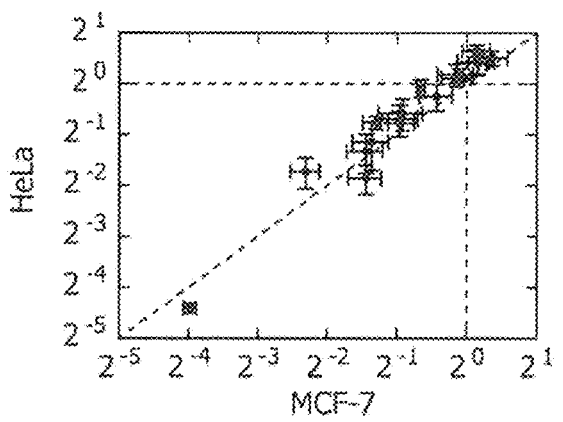

Example 5: Translational Efficiency of miRNA-Responsive Reporter mRNA in Three Types of Cell Lines Twenty types of miRNA-responsive reporter mRNAs were introduced into each of three types of cell lines, and the translational efficiency ratio was then examined. FIG. 8 includes graphs showing the translational efficiency of these 20 types of miRNA-responsive reporter mRNAs in the three types of cell lines. FIG. 8(a) shows a comparison made between HeLa and 293FT, FIG. 8(b) shows a comparison made between 293FT and MCF-7, and FIG. 8(c) shows a comparison made between MCF-7 and HeLa. The error bars each indicate a mean value±standard deviation (n=3). Using the value of translational efficiency obtained from the present results, a vector was configured with this value. In this case, the distance between cells in the possible coordinate was calculated, and a combination of miRNA-responsive reporter mRNAs used in other Examples was selected.

Figure 9C:
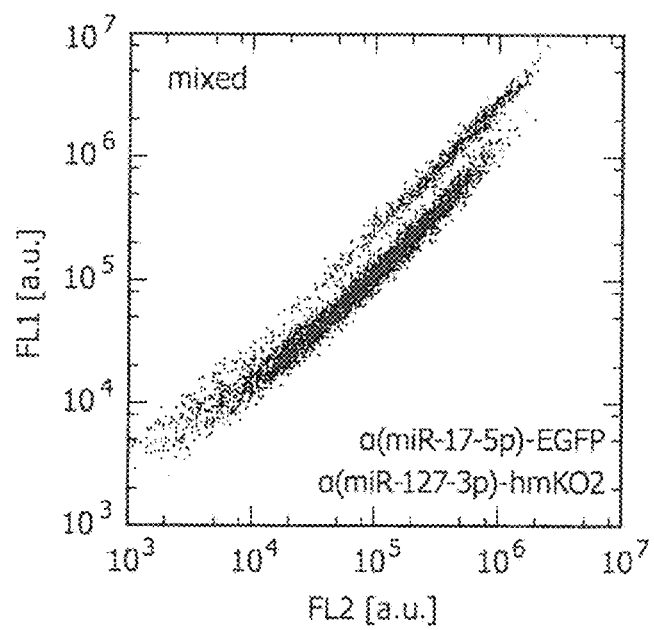
FIG. 9C is a view showing the two-dimensional separation of a mixture of two types of cell lines using two types of miRNA-responsive reporter mRNAs.
Figure 9C:
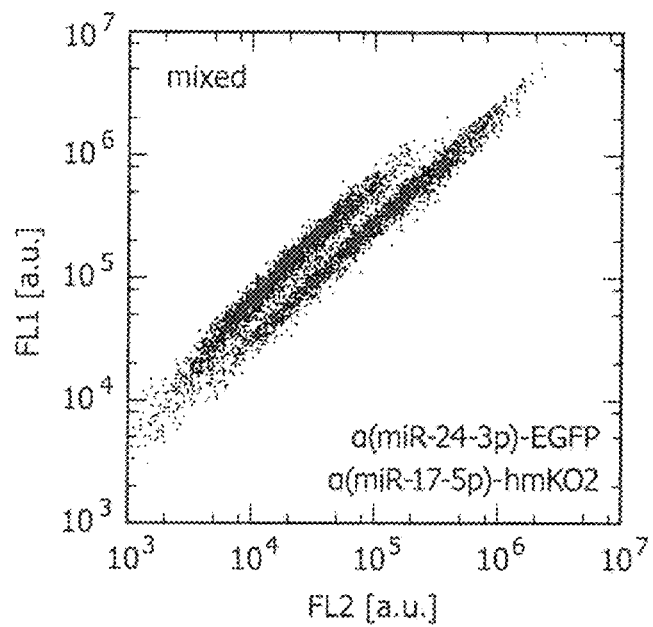

Example 6: One-Dimensional Separation Using Two Types of miRNA-Responsive Reporter mRNAs One dimensional separation of cells was carried out using two types of miRNA-responsive reporter mRNAs, based on the fluorescence intensity ratio of two types of cell lines, in the same manner as that of Example 1. A series of results is shown in FIG. 9. The results show that, even in two types of cell lines, in which the transcriptional efficiency of certain miRNA-responsive reporter mRNA, that is, the miRNA activity was 2-fold or less, 293FT could be separated from HeLa, or 293FT could be separated from MCF-7. The error bars each indicate a mean value±standard deviation (n=3).

In order to examine the activities of miR-24-3p and miR-17-5p in 293FT cells and HeLa cells, translational efficiency was measured. For the measurement, α(miR-24-3p)-EGFP and α(miR-17-5p)-EGFP were used. The results are shown in FIG. 9(a). The numerical value at the top of each column indicates the ratio of translational efficiency. Into 293FT cells, HeLa cells and a mixture thereof, α(miR-24-3p)-EGFP and α(miR-17-5p)-hmKO2 (SEQ ID NO: 12) were co-introduced, and 24 hours after the introduction, a flow cytometric analysis was carried out. As control mRNAs, EGFP and hmKO2 were used. FIG. 9(b) shows the results of dot plotting. From the figure, it is found that the 293FT cells could be distinguished from the HeLa cells as different belt-shaped plots. Moreover, FIG. 9(g) shows the same dot plotting as that described above, regarding a mixture of 293FT and HeLa. From these results, it is found that the two types of cells could be observed separately, even if a mixture of these cells was measured. FIG. 9(c) shows histograms regarding signal ratio. A set of miRNA-responsive reporter mRNA/control mRNA, as shown in each histogram, was co-introduced into each cell line. The ratio of two types of fluorescence signals, which had been measured by flow cytometry, was calculated, and was then plotted. The cumulative frequency of cells, into which two types of miRNA-responsive reporter mRNAs were introduced, is shown in the lowest column of FIG. 9(c).

Likewise, in order to examine the activities of miR-17-5p and miR-127-3p in 293FT cells and MCF-7 cells, translational efficiency was measured. For the measurement, α(miR-17-5p)-EGFP and α(miR-127-3p)-EGFP were used. The results are shown in FIG. 9(d). The numerical value at the top of each column indicates the ratio of translational efficiency. Into 293FT cells, MCF-7 cells and a mixture thereof, α(miR-17-5p)-EGFP and α(miR-127-3p)-hmKO2 were co-introduced, and 24 hours after the introduction, a flow cytometric analysis was carried out. As control mRNAs, EGFP and hmKO2 were used. FIG. 9(e) shows the results of dot plotting. It is found that the 293FT cells could be distinguished from the MCF-7 cells as different belt-shaped plots. Moreover, FIG. 9(h) shows the same dot plotting as that described above, regarding a mixture of 293FT and MCF-7. From these results, it is found that the two types of cells could be observed separately, even if a mixture of these cells was measured. FIG. 9(f) shows histograms regarding signal ratio. A set of miRNA-responsive reporter mRNA/control mRNA, as shown in each histogram, was co-introduced into each cell line. The ratio of two types of fluorescence signals, which had been measured by flow cytometry, was calculated, and was then plotted. The cumulative frequency of cells, into which two types of miRNA-responsive reporter mRNAs were introduced, is shown in the lowest column of FIG. 9(f).

Figure 10A:
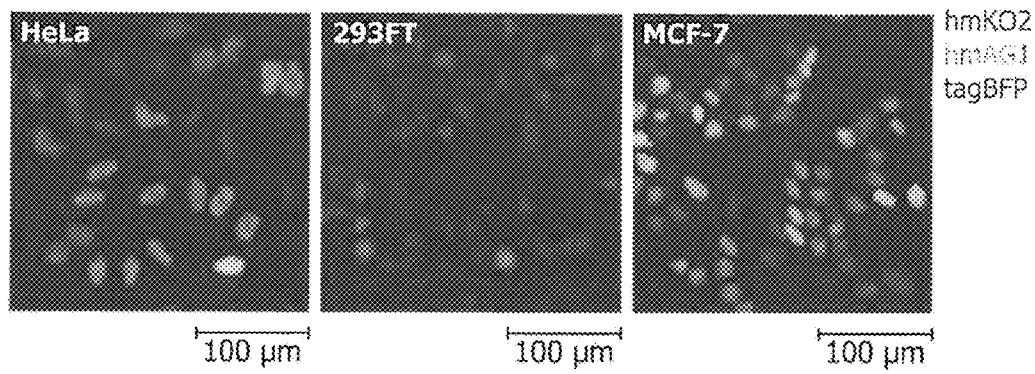
FIG. 10 is a view showing the colored images of cells and the two-dimensional separation of existing cell lines, in a determination method using an imaging analyzer.
Figure 10B:
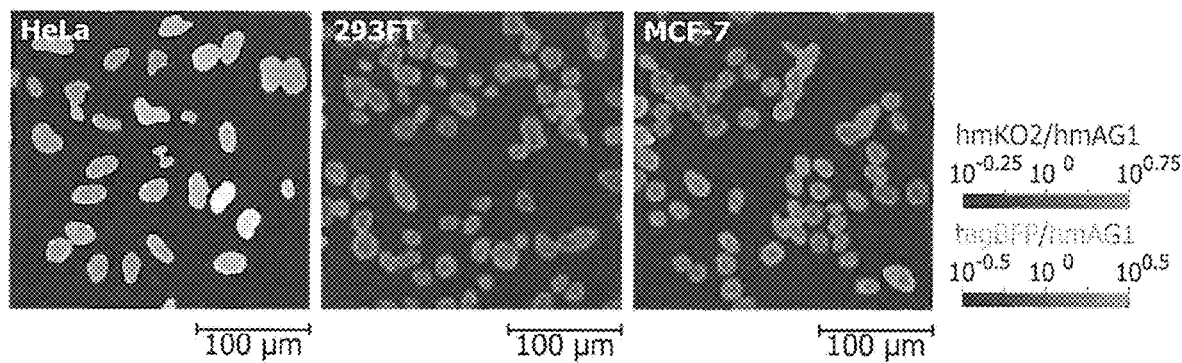
Figure 10C:
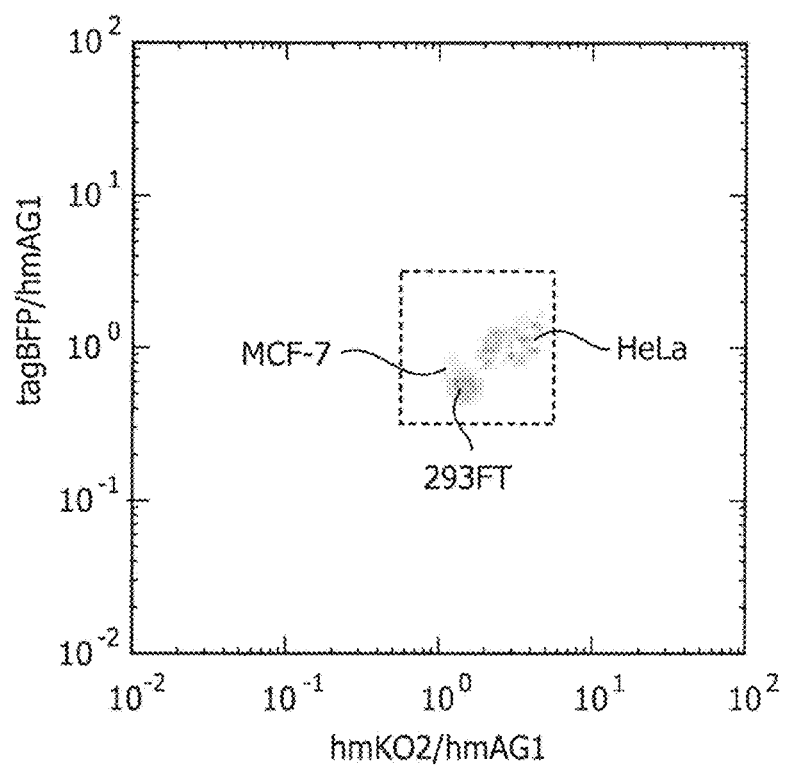

Example 7: Co-Introduction of Three Types of miRNA-Responsive Reporter mRNAs, in which Reporter Fluorescent Protein is Linked to Nuclear Localization Signal Into HeLa, 293FT and MCF-7 cells, three types of miRNA-responsive reporter mRNAs expressing nuclear localized fluorescent proteins, namely, 40 ng of α(miR-24-3p)-hmAG1-M9 (SEQ ID NO: 25), 10 ng of α(miR-127-3p)-hmKO2-M9 (SEQ ID NO: 26), and 200 ng of α(miR-17-5p)-tagBFP-M9 (SEQ ID NO: 27) were co-introduced. Twenty-four hours after the introduction, an imaging cytometric analysis was carried out. FIG. 10(a) shows the fluorescence images of the introduced cells. In the figure, . . . indicates 100 µm. The hmKO2, hmAG1, and tagBFP were indicated with red, green and blue channels, respectively. From FIG. 10(a), it is found that there is a variation in intensity, depending on the nucleus. FIG. 10(b) shows the results obtained by subjecting the measured data of the same target as that in FIG. 10(a) to pseudo-color processing using two ratios. The nucleus was removed from the cells involving co-introduction, and fluorescence intensity in each pixel was then analyzed. The ratio obtained by dividing the fluorescence signals of hmKO2 by the fluorescence signals of hmAG1, and the ratio obtained by dividing the fluorescence signals of tagBFP by the fluorescence signals of hmAG1, were normalized from the ranges of 10-0.25 to 100.75 and 10-0.5 to 100.5, to result in 0 to 1, respectively, and the ratios were then indicated with violet color and green color, respectively. FIG. 10(c) shows the density plotting of these ratios.

Example 8: Two-Dimensional Separation by Flow Cytometry and Imaging Cytometry, Using Three Types of miRNA-Responsive Reporter mRNAs Into each of HeLa, 293FT, MCF-7, and a mixture thereof, three types of control mRNAs, hmAG1, hmKO2 and tagBFP were co-introduced. In addition, into HeLa, 293FT, MCF-7, and a mixture thereof, three types of control mRNAs, in which a reporter fluorescent protein was linked to a nuclear localization signal, namely, hmAG1-M9 (SEQ ID NO: 28), hmKO2-M9 (SEQ ID NO: 29) and tagBFP-M9 (SEQ ID NO: 30) were co-introduced. Likewise, into each of HeLa, 293FT, MCF-7, and a mixture thereof, three types of miRNA-responsive reporter mRNAs, α(miR-24-3p)-hmAG1, α(miR-127-3p)-hmKO2 and α(miR-92-3p)-tagBFP were co-introduced. Also, into each of HeLa, 293FT, MCF-7, and a mixture thereof, three types of miRNA-responsive reporter mRNAs, in which a reporter fluorescent protein was linked to a nuclear localization signal, that is, α(miR-24-3p)-hmAG1-M9, α(miR-127-3p)-hmKO2-M9 and α(miR-92-3p)-tagBFP-M9 were co-introduced. Twenty-four hours after these introductions, a flow cytometric analysis and an imaging cytometric analysis were carried out. Representative results obtained from three independent experiments are shown in FIG. 11.

The flow cytometric analysis results of HeLa cells, 293FT cells, MCF-7 cells, and a mixture thereof, into which the three types of control mRNAs were introduced, are shown in FIG. 11(a), and the imaging cytometry results thereof are shown in FIG. 11(c). Moreover, the flow cytometric analysts results of HeLa cells, 293FT cells, MCF-7 cells, and a mixture thereof, into which the three types of control mRNAs, in which a reporter fluorescent protein was linked to a nuclear localization signal, were co-introduced, are shown in FIG. 11(e), and the imaging cytometry results thereof are shown in FIG. 11(g). From all of these results, it is found that cells could not be separated from one another.

The flow cytometric analysis results of HeLa cells, 293FT cells, MCF-7 cells, and a mixture thereof, into which the three types of miRNA-responsive reporter mRNAs were introduced, are shown in FIG. 11(b), and the imaging cytometry results thereof are shown in FIG. 11(d). Moreover, the flow cytometric analysis results of HeLa cells, 293FT cells, MCF-7 cells, and a mixture thereof, into which the three types of miRNA-responsive reporter mRNAs, in which a reporter fluorescent protein was linked to a nuclear localization signal, were co-introduced, are shown in FIG.

11(f), and the imaging cytometry results thereof are shown in FIG. 11(h). When the three types of miRNA-responsive reporter mRNAs were introduced into the three types of cells, the cells could be separated from one another, either by flow cytometry or by imaging cytometry. Since an independent plot group could be observed even in a mixture of cells, it is found that it is possible to separate the three types of cells from one another. Furthermore, even in a case in which the three types of miRNA-responsive reporter mRNAs, in which a reporter fluorescent protein was linked to a nuclear localization signal, were used, the same results as those described above were obtained.

Example 9: Separation of Fibroblast Lines Using miRNA-Responsive Reporter mRNA

An experiment was carried out to distinguish not only cell lines from different origins, but also differences in conditions of identical cell lines. Herein, IMR-90 cells were focused on as representative normal human cells. It has been known that IMR-90, which is in a resting state, tends to differentiate to smooth muscle by receiving TGF stimulation. Sixty-seven types of miRNAs, which had been confirmed to be expressed in IMR-90 and do not comprise CAU, were selected, and a library of miRNA-responsive reporter mRNAs expressing hmAG1 as a reporter protein was then produced (SEQ ID NOS: 77 to 143). Each mRNA, together with control hmKO2 mRNA, was introduced into IMR-90, and a flow cytometric analysis was then carried out.

Figure 12A:
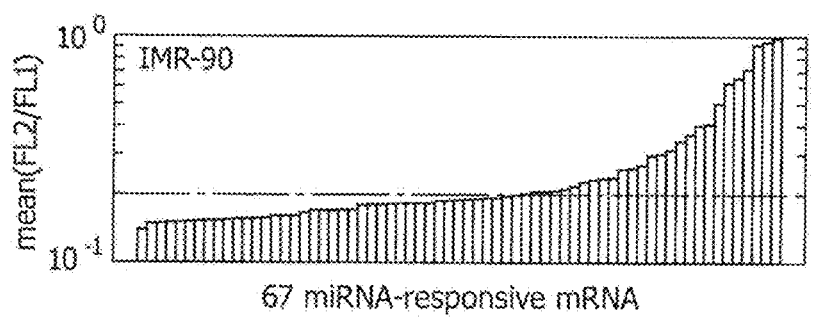
FIG. 12A is a view showing the results obtained by screening for miRNA-responsive reporter mRNA used for separation of IMR-90 in Example 9, and the results of a flow cytometric analysis in which miRNA-responsive reporter mRNAs have been co-introduced into IMR-90 with or without TGF stimulation.
Figure 12A:
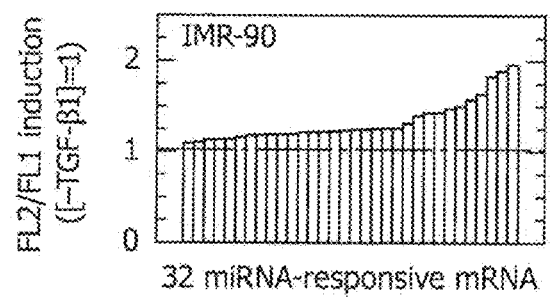
Figure 12A:
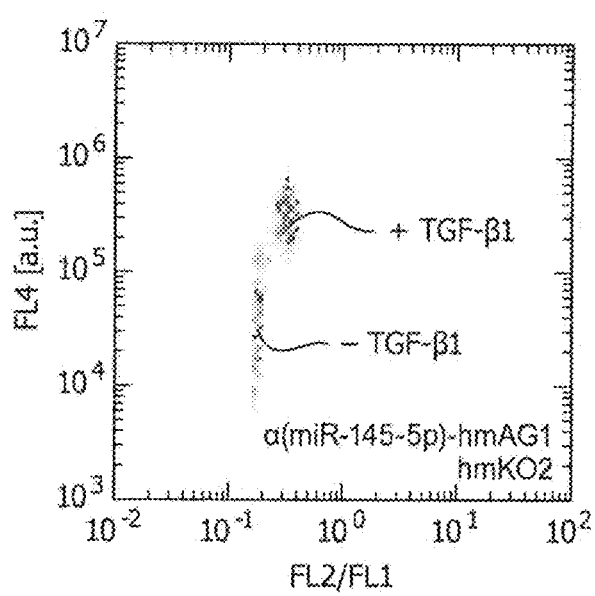

Subsequently, a first screening was carried out, and 26 miRNA-responsive mRNAs, which were active in IMR-90, were obtained. The results are shown in FIG. 12A(a). In FIG. 12A(a), mRNAs having an average fluorescence ratio (FL2/FL1) of 0.199 or more were distinguished to have activity (whereas in the case of mRNA that does not respond to control miRNA, it is 0.198). From the 26 miRNAs, two types of mRNAs having high similarity to each other were omitted, and the remaining 24 miRNA-responsive mRNAs were extracted.

Further, miRNA-responsive reporter mRNAs responding to two miRNAs highly associated with muscle differentiation were produced (SEQ ID NOS: 144 and 145). To these two mRNAs, the above extracted 24 mRNAs, and 6 mRNAs, the activity of which was not observed in the above section and which responded to miRNA associated with TGF signals or muscle differentiation, were gathered, and a total of 32 mRNAs were subjected to a second screening for searching for miRNA, the activity of which was changed before and after TGF-β1 stimulation to IMR-90. IMR-90 was left in a starved state for 2 days, and was then stimulated with 10 ng/mL TGF-β1. On the following day, mRNA was introduced into the cells, and further, on the day following the introduction, a flow cytometric analysis was carried out. The results obtained by searching for the total of 32 types of miRNAs are shown in FIG. 12A(b). The miRNA-responsive mRNA (α(miR-145-5p)-hmAG1) (SEQ ID NO: 117), which had the highest activity in FIG. 12A(h), was used in the subsequent experiment.

Imaging cytometry was carried out as follows. IMR-90, with or without TGF stimulation, was simultaneously stained with miRNA-responsive mRNA (a pair of α(miR-145-5p)-hmAG1 and hmKO2) and an anti-αSMA antibody.

Differentiation induction and the immunostaining of IMR-90 after introduction of mRNA were carried out by the following methods. One day after the co-introduction of mRNA, a medium and Cytofix Fixation Buffer (BD Biosciences) in an amount equal to the medium were added to the cells, followed by leaving them to rest at 37° C. for 10 minutes, so that the cells were immobilized. Subsequently, the resulting cells were washed with Pharmingen Stain Buffer (FBS, BD Biosciences), and were then left to rest in Phosflow Perm Buffer III (BD Biosciences) on ice for 30 minutes, so that the permeation treatment of the cell membrane was carried out. After washing, the resulting cells were left to rest in Blocking One (Nakalai Tesque, Inc.) on ice for 30 minutes. Thereafter, the cells were stained with an anti-αSMA antibody, which had been 200-fold diluted with Pharmingen Stain Buffer (FBS) comprising 10% Blocking One, at room temperature for 30 minutes. After washing, the resulting cells were stained with Hoechist 33342 (Life Technologies). The thus-stained cells were analyzed using IN Cell Analyzer 6000.

Flow cytometry on intracellular factors was carried out as follows. After completion of differentiation induction and introduction of mRNA, IMR-90 was peeled from the culture plate. The cells were immobilized and were then subjected to membrane permeation, using the aforementioned Cytofix Fixation Buffer and Phosflow Perm Buffer III, according to the instruction manual.

After completion of the membrane permeation, the cells were blocked with Blocking One, and were then stained with a 100-fold diluted anti-αSMA antibody at room temperature for 30 minutes, in the same manner as that described above. After completion of the staining, the cells were washed and were then subjected to a flow cytometric analysis.

The results of the flow cytometric analysis are shown in FIG. 12A(c) in the form of a density plot. From the results shown in FIG. 2A(c), a difference in the differentiation conditions of the cells of the same type could be distinguished, by using α(145-5p)-hmAG1, FIG. 12B(d) shows the same experimental results as those described above in the form of histograms. Herein, the results obtained by introduction of a pair of control mRNAs are shown with the solid line and the dashed line. In the case of applying an antibody staining method of the prior art, cells need to be immobilized, and as shown in the histograms, the width of distribution was wide and there were many overlapping portions. On the other hand, in the case of applying the method of the present invention, it was demonstrated that living cells can be directly used, and thus, that the width of distribution is narrow and sufficient determination can be carried out.

A similar experiment was carried out using a nuclear localized reporter protein, and imaging cytometry was then carried out. The results are shown in FIG. 12C(f). Herein, an image analysis was carried out, the fluorescence ratio (hmKO2/hmAG1) per pixel was then calculated, and it was then indicated in green in the picture. The fluorescence intensity from the antibody was indicated in magenta. The same experimental results as those described above are shown in FIG. 12B(e) in the form of histograms. Herein also, the results obtained by introduction of a pair of control mRNAs are shown with the solid line and the dashed line.

Figure 12B:
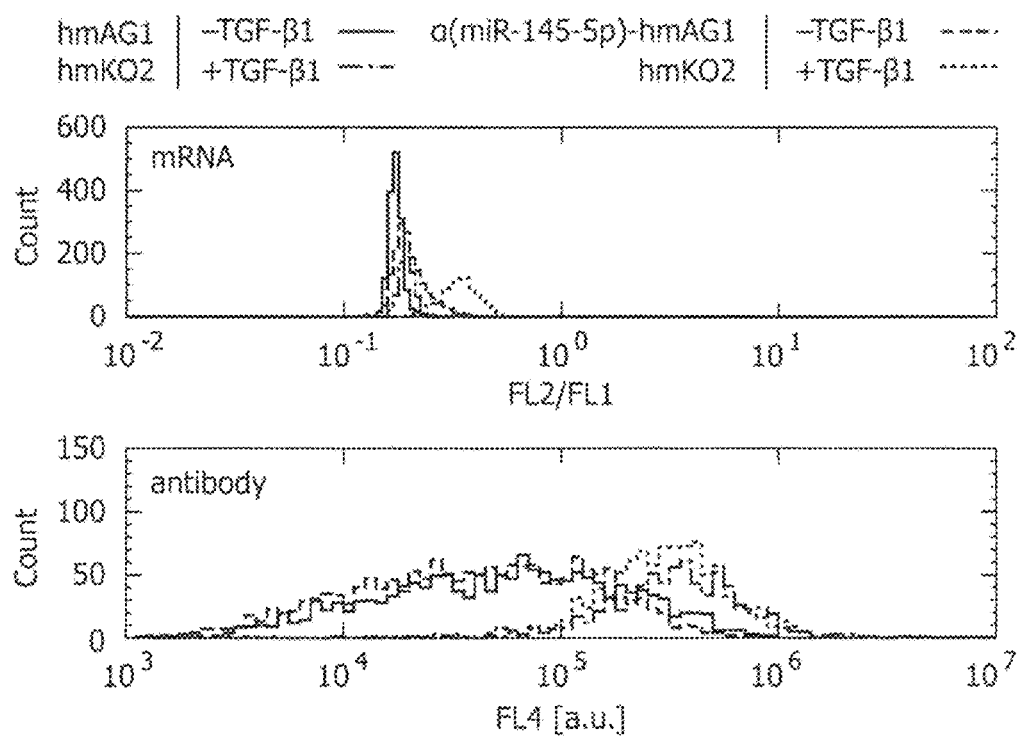
FIG. 12B is a view showing the results of FIG. 12A(c) and FIG. 12C(f) in the form of histograms.
Figure 12B:
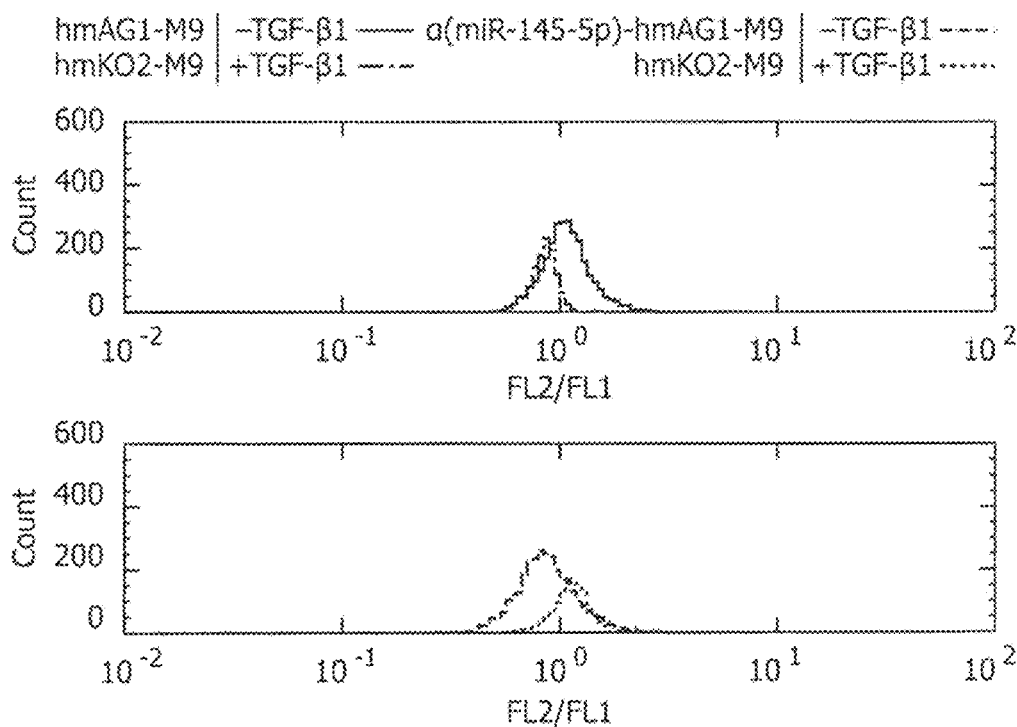
Figure 12C:
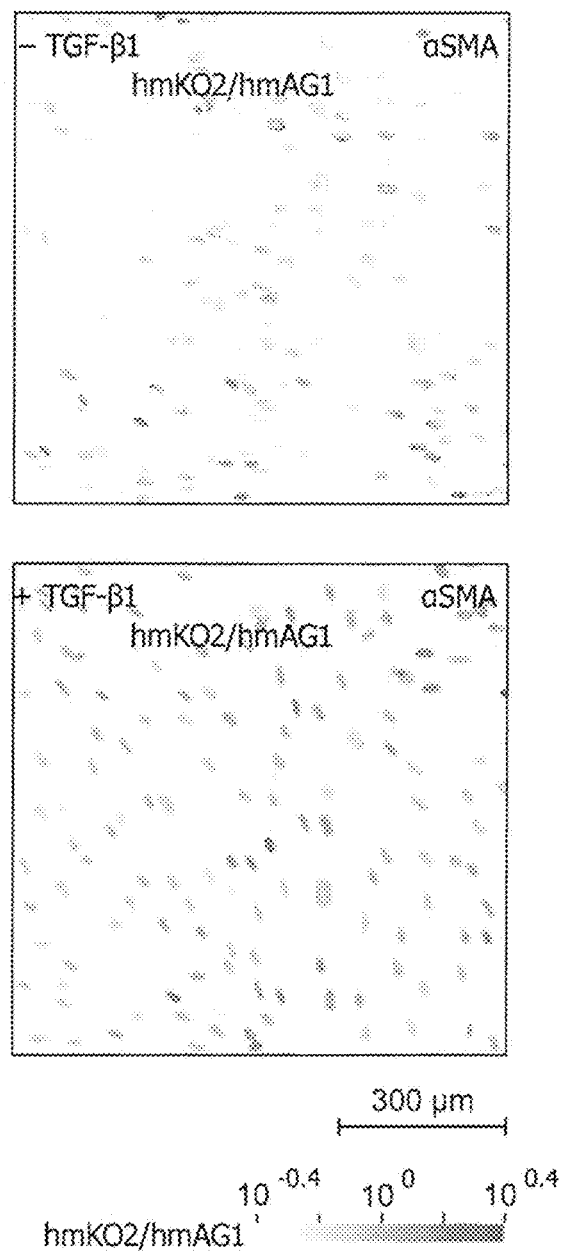
FIG. 12C is a view showing the results of an imaging cytometric analysis in a case in which miRNA-responsive reporter mRNAs for expressing nuclear localized reporter proteins have been co-introduced into IMR-90 with or without TGF stimulation.

The results shown in FIG. 12B(e) and FIG. 12C(f) demonstrated that when the mRNA of the present invention is used, the quantitative ratio of a nuclear localized protein is different between the case of the presence of TGF-β1 stimulation and the case of the absence of such stimulation. It was also found that these results are highly matched with the results obtained by the flow cytometric analysis shown in FIG. 12B(d).

Figure 17A:
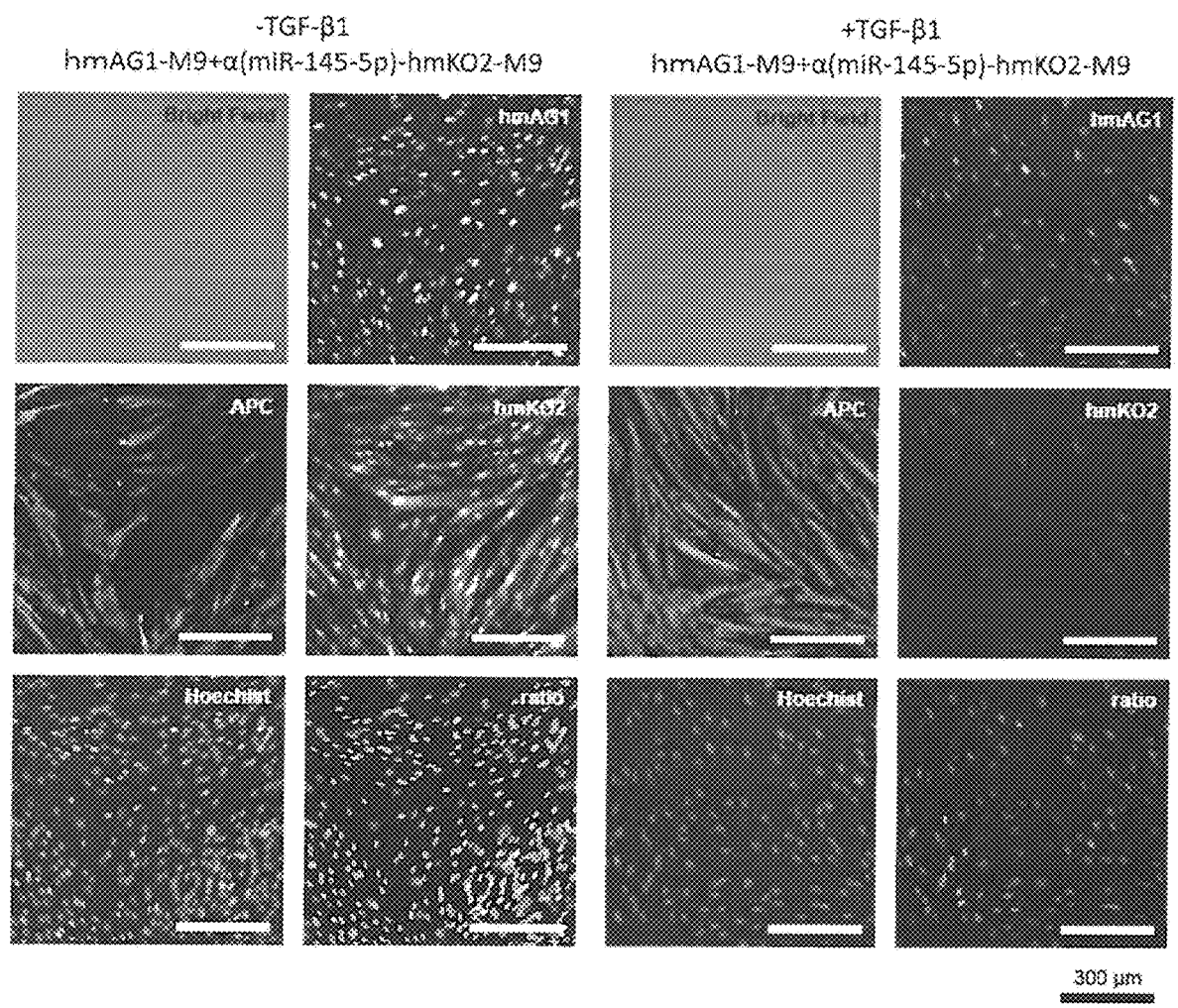
FIG. 17(*a*) is a view showing the results of an imaging cytometric analysis in a case in which control miRNA (hmAG1-M9) and miRNA-responsive reporter mRNA (α(miR-145-5p)-hmKO2-M9) have been co-introduced into IMR-90 without TGF-β1 stimulation (−TGF-β1; left view) or with TGF-β1 stimulation (+TFG-β1; right view). In the figure, Bright Field indicates a phase-contrast image; hmAG1 indicates the fluorescence image of hmAG1; APC indicates the stained image of αSMA antibody; hmKO2 indicates the fluorescence image of hmKO2; Hoechist indicates a nuclear-stained image; and ratio indicates an overlapped fluorescence image.
Figure 17B:
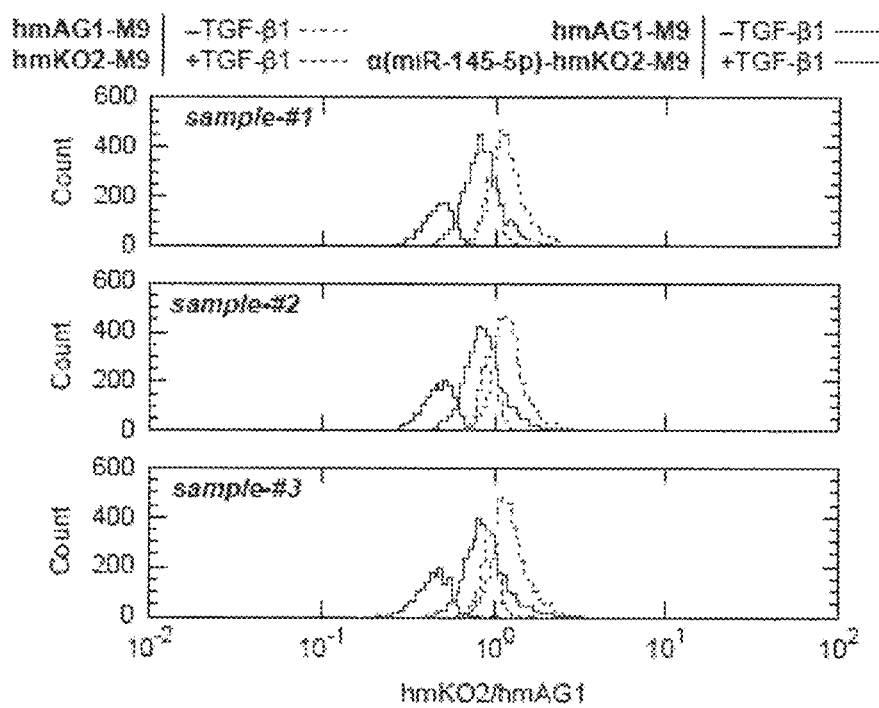

Moreover, the combination of the reporter proteins of miRNA-responsive mRNAs was changed, and the same analysis as that described above was carried out using a pair of α(miR-145-5p)-hmKO2 and hmAG1. The results of imaging cytometry are shown in FIG. 17(a), and the results of flow cytometry are shown in FIG. 17(b). As a result, it was confirmed that the expression of miR-145-5p in SMA-positive cells is increased by muscle differentiation with the addition of TGF-β1, as in the case of using the aforementioned pair of α(miR-145-5p)-hmAG1 and hmKO2, and that the expression of the corresponding reporter protein is decreased.

As described above, it was demonstrated that the present invention is able to discriminate living cells, not depending on the type of a reporter protein.

Example 10: Discrimination of Cell Population of Primary Culture (NHLF), Using miRNA-Responsive Reporter mRNA Using the same library of 67 miRNAs as described above, not the miRNA activity of the established cells, but the miRNA activity of a population of the primary cultured cells (NHLF) of human normal lung fibroblasts was examined. FIG. 13(a) shows the strategy of searching for mRNA for selecting cells (for clarifying the mixing state of cells). In a first screening, the activity of miRNA was detected, and 8 miRNAs were selected from the 67 miRNAs. In a second screening, the 8 miRNAs were combined with reporter proteins, and 56 sets of reporter mRNAs were searched.

Using the same library of 67 types of miRNA-responsive reporter mRNAs as that for IMR-90, the activity of miRNA in the primary cultured cells (NHLF) of human normal lung fibroblasts was searched. The results are shown in FIG. 13A(b). Herein, in particular, the peak width (90% interval) of the fluorescence ratio created by cell populations, into which mRNA had been introduced, was analyzed, and 8 miRNAs having a large peak width (i.e. miR-16-5p, miR-17-5p, miR-21-5p, miR-27a-3p, miR-20a-5p, miR-106a-5p, miR-143-3p, and let-7i-5p) were selected.

activity was distributed more broadly in the cell population, and thus, it was a more heterogeneous population.

FIG. 13(c) shows a combination table used for a second screening. The numbers 1 to 8 indicate 8 types of miRNAs, and in this experiment, the numbers 1 to 8 successively indicate miR-16-5p, miR-17-5p, miR-21-5p, miR-27a-3p, miR-20a-5p, miR-106a-5p, miR-143-3p, and let-7i-5p. In the table, the row (h), the column (i), and two-digit numbers (j, k) in each square indicate miRNA numbers, to which hmAG1, hmKO2, tagBFP, and hdKeimaRed respond, respectively. According to this table, it is found that all combinations of reporter proteins can be encompassed regarding a combination of any two miRNAs.

Subsequently, the correlation of these miRNA activities was obtained. Regarding each combination of miRNAs, a pair of reporter mRNAs responding to the miRNAs (SEQ ID NOS: 114, 81, 114, 102, 80, 111, 83, 116, and 157 to 181) was introduced into NHLF, and the peak width (90% interval) of the fluorescence ratio created by the cell population was then analyzed. A mean value of the values obtained from the following 6 types of combinations was obtained. For example, in the case of miR-143-3p and miR-21-5p, the combinations are as follows:

(A) α(miR-143-3p)-hmAG1 (SEQ ID NO: 114)+α(miR-21-5p)-hmKO2 (SEQ ID NO: 159), (B) α(miR-143-3p)-hmAG1+α(miR-21-5p)-tagBFP (SEQ ID NO: 168), (C) α(miR-143-3p)-hmAG1+α(miR-21-5p)-hdKeimaRed (SEQ ID NO: 176), (D) α(miR-21-5p)-hmAG1 (SEQ ID NO: 81)+α(miR-143-3p)-hmKO2 (SEQ ID NO: 163), (E) α(miR-21-5p)-hmAG1+α(miR-143-3p)-tagBFP (SEQ ID NO: 172), and (F) α(miR-21-5p)-hmAG1+α(miR-143-3p)-hdKeimaRed (SEQ ID NO: 180).

This peak width is shown in the following Table 6 as a relative value to the peak width obtained by the same analysis when control mRNA has been introduced into cells.

TABLE 6

| | relative 90% interval | | | | | | | |
|---|---|---|---|---|---|---|---|---|
| | miR-143-3p | miR-21-5p | let-7i-5p | miR-27a-3p | miR-16-5p | miR-20a-5p | miR-17-5p | miR-106a-5p |
| miR-143-3p | | 2.77 | 1.90 | 1.87 | 2.17 | 2.32 | 2.22 | 2.34 |
| miR-21-5p | | | 1.38 | 1.43 | 1.53 | 1.59 | 1.84 | 1.76 |
| let-7i-5p | | | | 1.12 | 1.24 | 1.42 | 1.49 | 1.52 |
| miR-27a-3p | | | | | 1.18 | 1.41 | 1.37 | 1.43 |
| miR-16-5p | | | | | | 1.19 | 1.21 | 1.18 |
| miR-20a-5p | | | | | | | 0.96 | 0.91 |
| miR-17-5p | | | | | | | | 0.97 |
| miR-106a-5p | | | | | | | | |

Figure 14A:
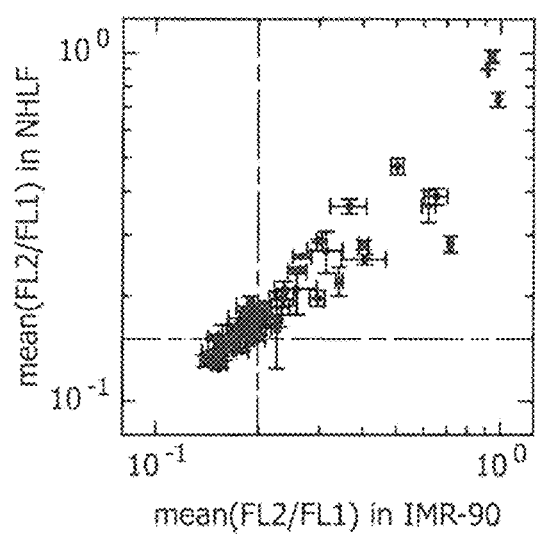
FIG. 14 is a view showing the results obtained by comparing the result of a first screening between the cell line (IMR-90) and primary cultured cells (NHLF).
Figure 14B:
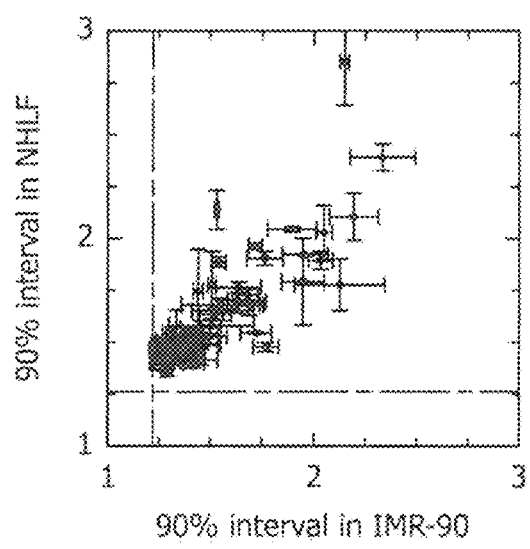

FIGS. 14(a) and (b) show the results obtained by comparing the results of the first screening between the cell line (IMR-90) and the primary cultured cells (NHLF). FIGS. 14(a) and (b) both show the results regarding the 67 types of miRNA-responsive reporter mRNAs. That is, FIG. 14(a) shows the comparison of fluorescence ratio, that is, the comparison of peak position, whereas FIG. 14(b) shows the comparison of 90% interval, that is, the comparison of peak width. In both of the figures, a mean value from screening experiments conducted twice and a standard deviation are indicated as an error bar. From FIGS. 14(a) and (b), it was demonstrated that the mean value of miRNA activity was the same as that of the established IMR-90, but that the miRNA From this Table, it is found that a functional relationship can be found between miRNAs in the target cell population. For example, there is a negative correlation between the functions of miRNA having large values, such as a combination of miR-143-3p and miR-21-5p. That is, in this case, the activity of miR-21-5p is low in cells in which the activity of miR-143-3p is high, and the activity of miR-21-5p is low in cells in which the activity of miR-143-3p is low. On the other hand, there is a positive correlation between the functions of miRNAs having small values. It was demonstrated that, in fact, miR-17, miR-20a and miR-106a, which form a miR-17 precursor family, exhibit a high positive correlation in terms of activity.

The reason the relationship in terms of miRNA activity is clarified will be described using FIG. 15. FIG. 15 is a view schematically showing assumed results obtained when a certain cell group has incorporated equal amounts of mRNAs and there is a distribution of two miRNA activities in the cell group. FIG. 15(a) shows that the peak of the fluorescence ratio becomes narrow when two miRNA activities positively correlate with each other. FIG. 15(b) shows that the peak of the fluorescence ratio becomes wide when two miRNA activities negatively correlate with each other. FIG. 15(c) shows that an intermediate width peak can be formed when two miRNA activities do not correlate with each other.

FIG. 13(d) shows the results obtained by performing a separation analysts on NHLF, using reporter mRNAs (α(miR-106a-5p)-hmAG1 (SEQ ID NO: 116), α(miR-21-5p)-hmKO2 (SEQ ID NO: 159), and α(miR-143-3p)-tag-BFP) responding to three miRNAs, which have negatively correlated, or have not correlated with one another, in terms of miRNA activity. A cell population, into which the mRNAs have been introduced, is shown in the form of the density distribution of the fluorescence ratio.

FIG. 13(e) shows the results obtained by performing a separation analysis on NHLF, using reporter mRNAs (α(miR-20a-5p)-hmAG1 (SEQ ID NO: 111), α(miR-17-5p)-hmKO2 (SEQ ID NO: 12), and α(miR-106a-5p)-tag-BFP (SEQ ID NO: 171)) responding to three miRNAs, which have positively correlated with one another, in terms of miRNA activity. A cell population, into which the mRNAs have been introduced, is shown in the form of the density distribution of the fluorescence ratio.

As demonstrated in FIGS. 13(d) and (e), even in a case in which the target is an identical cell population, the cells are indicated as an extremely homogeneous cell population (f), if an mRNA set for such miRNAs having high positive correlation is used. In contrast, if another miRNA set is used, the heterogeneity of the cells was observed (e). As such, miRNA-responsive mRNAs to be used can be selected, depending on the purpose of distinguishing desired cells. For example, in this case, in a case in which NHLF is considered to be desired cells and NHLF is distinguished from other cells, by using an mRNA set for miRNAs having high positive correlation, the desired cells can be narrowed to a cell population with a narrow width (a specific cell population). When a wide variety of NHLF cells are considered to be a cell population comprising desired cells and the desired cells are separated and fractionated from the cell population, by using an mRNA set for miRNAs having high negative correlation, a desired portion can be collected from the widely distributed cells.

Example 11: Determination of Cell Population of IMR-90, Using miRNA-Responsive Reporter mRNA The same second screening as that for NHLF was carried out on the established fibroblasts, IMR-90. In this experiment, the numbers 1 to 8, which show the miRNAs shown in FIG. 13(C), successively indicate miR-16-5p, miR-17-5p, miR-125b-5p, miR-93-5p, miR-20a-5p, miR-106a-5p, miR-145-5p, and miR-26a-5p. Regarding each miRNA combination, a pair of reporter mRNAs responding to the miRNAs (SEQ ID NO: 117, 100, 125, 80, 157, 166, 174, 83, 167, 158, 175, 111, 161, 170, 178, 110, 116, 162, 171, 179, and 146 to 156) was introduced into IMR-90, and the peak width (90% interval) of the fluorescence ratio created by the cell population was analyzed. This peak width is shown in the following Table 7 as a relative value to the peak width obtained by the same analysis when control mRNA has been introduced into cells.

TABLE 7

| | relative 90% interval | | | | | | | |
|---|---|---|---|---|---|---|---|---|
| | miR-145-5p | miR-125b-5p | miR-26a-5p | miR-16-5p | miR-17-5p | miR-20a-5p | miR-93-5p | miR-106a-5p |
| miR-145-5p | | 0.87 | 0.93 | 1.16 | 1.32 | 1.24 | 1.06 | 1.26 |
| miR-125b-5p | | | 0.88 | 1.13 | 1.16 | 1.13 | 1.06 | 1.18 |
| miR-26a-5p | | | | 1.26 | 1.28 | 1.39 | 1.25 | 1.39 |
| miR-16-5p | | | | | 1.11 | 1.08 | 1.03 | 1.02 |
| miR-17-5p | | | | | | 0.87 | 0.89 | 0.93 |
| miR-20a-5p | | | | | | | 0.76 | 0.82 |
| miR-93-5p | | | | | | | | 0.77 |
| miR-106a-5p | | | | | | | | |

Figure 16:
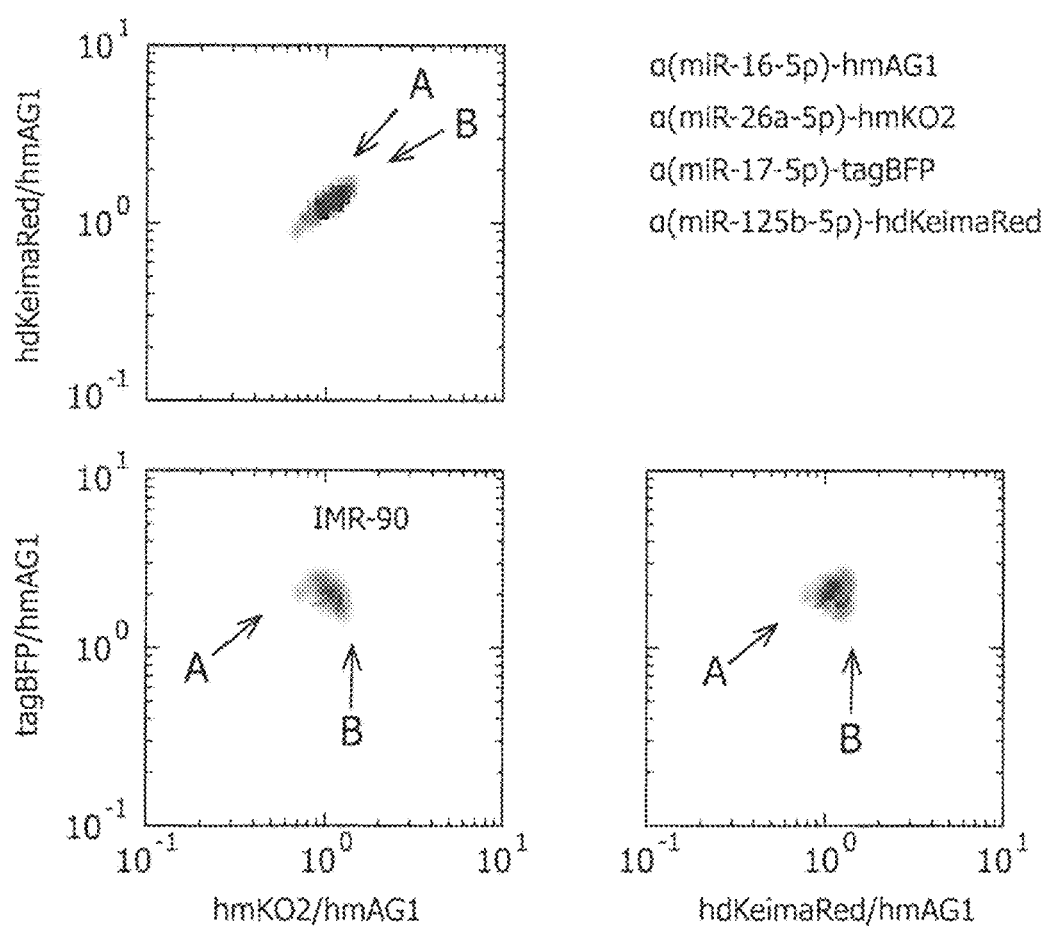
FIG. 16 is a view showing the results obtained by co-introducing four types of miRNA-responsive mRNAs, which have been selected based on the results of a second screening, into IMR-90, wherein the results are shown in the form of a three-dimensional density plot.

FIG. 16 shows the results obtained by selecting four types of miRNA-responsive mRNAs (α(miR-16-5p)-hmAG1 (SEQ ID NO: 80), α(miR-26a-5p)-hmKO2 (SEQ ID NO: 148), α(miR-17-5p)-tagBFP (SEQ ID NO: 167), and α(miR-125b-5p)-hdKeimaRed (SEQ ID NO: 153) based on the results of the second screening, and then co-introducing the four types of miRNA-responsive mRNAs into IMR-90, wherein the results are shown in the form of a three-dimensional density plot. As indicated with the arrows A and B shown in the figure, it has been found that the IMR-90 is separated into two cell groups.

REFERENCES

[1] Highly efficient reprogramming to pluripotency and directed differentiation of human cells with synthetic modified mRNA.

Warren, L., Manos P D., Ahfeldt T., Loh Y H., Li H., Lau F., Ebina W., Mandal P K., Smith Z D., Meissner A., Daley G Q., Brack A S., Collins J J., Cowan C., Schlaeger T M., Rossi D J.

Cell Stem Cell, 7(5):618-30, 2010

[2] Improved structure, function and compatibility for Cell-Profiler: modular high-throughput image analysis software.
Kamentsky L., Jones T R., Fraser A., Bray M A., Logan D J., Madden K L., Ljosa V., Rueden C., Eliceiri E W., Carpenter A E.
Bioinformatics, 27(8): 1179-80, 2011
[3] Quantitative and simultaneous translational control of distinct mammalian mRNAs.
Endo K., Stapleton J A., Hayashi K., Saito H., Inoue T.
Nucleic Acids Res, 41(13):e135, 2013
[4] LambdaN-GFP: an RNA reporter system for live-cell imaging.
Daigle N., Ellenberg J. Nat Methods, 4(8):633-6, 2007

[5] New approaches to fluorescence compensation and visualization of FACS data.
Tung J W., Parks D R., Moore W A., Herzenberg L A., Herzenberg L A.
Clin Immunol, 110(3):277-83, 2004
[6] MicroRNA profiling reveals two distinct p53-related human pluripotent stem cell states.
Neveu P., Kye M J., Qi S., Buchholz D E., Clegg D O., Sahin M., Park I H., Kim K S., Daley G Q., Kornblum H I., Shraiman B I., Kosik K S.
Cell Stem Cell, 7(6):671-81, 2010

The invention claimed is:

1. A method for distinguishing a desired cell type from a cell group comprising two or more types of cells, using the expression of miRNA as an indicator, wherein the method comprises the following steps:
   (1) a step of introducing a reporter mRNA comprising a Cap structure or Cap analogue, a nucleic acid sequence encoding a marker protein operably linked to a target sequence of miRNA into a cell group, and a polyA tail, wherein the reporter mRNA is introduced into the cell group in a form of a synthetic RNA molecule without using a virus vector construct or DNA vector construct, and wherein the target sequence of miRNA is linked to the 5'-terminal side of the nucleic acid sequence encoding the marker protein; and
   (2) a step of distinguishing the desired cell type, using a translation level of the marker protein.

2. The method according to claim 1, wherein the reporter mRNA further comprises a target sequence of miRNA linked to the 3' terminal side of the nucleic acid sequence encoding the marker protein.

3. The method according to claim 1, wherein the step of distinguishing the desired cell type is carried out using a flow cytometer.

4. The method according to claim 1, wherein the step of distinguishing the desired cell type is carried out using an image analyzer.

5. The method according to claim 1, which further comprises a step of screening for miRNA used as an indicator before the step (1).

6. The method according to claim 1, further comprising a step of introducing a control mRNA comprising a Cap structure or Cap analogue, a nucleic acid sequence encoding a control marker protein and a polyA tail into the cell group, wherein the control mRNA does not include a target sequence of miRNA and the control marker protein is different from the marker protein of the reporter mRNA.

7. The method according to claim 6, wherein the marker protein of the reporter mRNA and the control marker protein are a fluorescence protein, and
   the step of distinguishing comprises:
   a step of measuring a fluorescence intensity of the marker protein of the reporter mRNA and the control marker protein; and
   a step of calculating a ratio of the fluorescence intensity of the marker protein of the reporter mRNA to that of the control marker protein to obtain translational efficiency.

8. The method according to claim 1, wherein the marker protein comprises a cell growth protein, a cell killing protein, a cell signaling factor, a drug resistance protein, a transcriptional regulator, a translational regulator, a differentiation regulator, a reprogramming inducer, an RNA-binding protein factor, a chromatin control factor, or a membrane protein.

9. A method for distinguishing a desired cell type from a cell group comprising two or more types of cells, using the expression of miRNA as an indicator, wherein the method comprises the following steps:
   (1) a step of simultaneously introducing two or more reporter mRNAs into a cell group, wherein the two or more reporter mRNAs comprise a Cap structure or Cap analogue, a nucleic acid sequence encoding a marker protein gene operably linked to a target sequence of miRNA and a poly A tail; wherein the target sequence of miRNA is linked to the 5'-terminal side of the nucleic acid sequence encoding the marker protein; and wherein the two or more reporter mRNAs each comprise a different target sequence and a different nucleic acid sequence encoding a different marker protein, and the two or more mRNAs are introduced into the cell group in a form of a synthetic RNA molecule without using a virus vector construct or DNA vector construct; and
   (2) a step of distinguishing the desired cell type, using a translation level of the marker protein.

10. The method according to claim 9, wherein the marker protein comprises a cell growth protein, a cell killing protein, a cell signaling factor, a drug resistance protein, a transcriptional regulator, a translational regulator, a differentiation regulator, a reprogramming inducer, an RNA-binding protein factor, a chromatin control factor, or a membrane protein.

11. The method according to claim 9, wherein the reporter mRNA further comprises a target sequence of miRNA linked to the 3' terminal side of the nucleic acid sequence encoding the marker protein.

12. The kit according to claim 11, wherein the reporter mRNA further comprises a target sequence of miRNA linked to the 3'-terminal side of the nucleic acid sequence encoding a marker protein.

13. The method according to claim 9, wherein the step of distinguishing the desired cell type is carried out using a flow cytometer.

14. The method according to claim 9, wherein the step of distinguishing the desired cell type is carried out using an image analyzer.

15. The method according to claim 9, which further comprises a step of screening for miRNA used as an indicator before the step (1).

16. The method according to claim 9, further comprising a step of introducing a control mRNA comprising a Cap structure or Cap analogue, a nucleic acid sequence encoding a control marker protein and a polyA tail into the cell group, wherein the control mRNA does not include a target sequence of miRNA and the control marker protein is different from the marker protein of the reporter mRNA.

17. The method according to claim 16, wherein the marker protein of the reporter mRNA and the control marker protein are a fluorescence protein, and the step of distinguishing comprises:
a step of measuring a fluorescence intensity of the marker protein of the reporter mRNA and the control marker protein; and
a step of calculating a ratio of the fluorescence intensity of the marker protein of the reporter mRNA to that of the control marker protein to obtain translational efficiency.

18. A kit for distinguishing a cell, which comprises:
(a) one or more reporter mRNA comprising a Cap structure or Cap analogue, a nucleic acid sequence encoding a marker protein operably linked to a target sequence of miRNA and a polyA tail, wherein the target sequence of miRNA is linked to the 5'-terminal side of the nucleic acid sequence encoding the marker protein, with the proviso that when two or more reporter mRNAs are present, the two or more reporter mRNAs each comprise a different target sequence and a different nucleic acid sequence encoding a different marker protein; and
(b) a control mRNA comprising a Cap structure or Cap analogue, a nucleic acid sequence encoding a control marker protein and a polyA tail, wherein the control mRNA does not include a target sequence of miRNA and the control marker protein is different from the marker protein of the reporter mRNA.

19. The kit according to claim 18, wherein the marker protein comprises a cell growth protein, a cell killing protein, a cell signaling factor, a drug resistance protein, a transcriptional regulator, a translational regulator, a differentiation regulator, a reprogramming inducer, an RNA-binding protein factor, a chromatin control factor, or a membrane protein.

20. The kit according to claim 18, wherein the reporter mRNA further comprises a target sequence of miRNA linked to the 3'-terminal side of the nucleic acid sequence encoding a marker protein.

21. A kit for distinguishing a cell, which comprises:
two or more reporter mRNAs comprising a Cap structure or Cap analogue, a nucleic acid sequence encoding a marker protein operably linked to a target sequence of miRNA and a polyA tail, wherein the target sequence of miRNA is linked to the 5'-terminal side of the nucleic acid sequence encoding the marker protein, and wherein the two or more reporter mRNAs each comprise a different target sequence and a different nucleic acid sequence encoding a different marker protein.

22. The kit according to claim 21, wherein the marker protein comprises a cell growth protein, a cell killing protein, a cell signaling factor, a drug resistance protein, a transcriptional regulator, a translational regulator, a differentiation regulator, a reprogramming inducer, an RNA-binding protein factor, a chromatin control factor, or a membrane protein.

23. The kit according to claim 21, wherein the reporter mRNA further comprises a target sequence of miRNA linked to the 3'-terminal side of the nucleic acid sequence encoding a marker protein.

24. A kit for distinguishing a cell, which comprises:
one or more reporter mRNA comprising a Cap structure or Cap analogue, a nucleic acid sequence encoding a marker protein operably linked to a target sequence of miRNA, and a polyA tail, wherein the target sequence of miRNA is linked to the 5'-terminal side of the nucleic acid sequence encoding the marker protein.

* * * * *

UNITED STATES PATENT AND TRADEMARK OFFICE
CERTIFICATE OF CORRECTION

PATENT NO. : 10,590,492 B2
APPLICATION NO. : 15/110503
DATED : March 17, 2020
INVENTOR(S) : Saito et al.

It is certified that error appears in the above-identified patent and that said Letters Patent is hereby corrected as shown below:

In the Specification

Column 8, Line 54: Please correct "VFP, PhiVFP" to read -- YFP, PhiYFP --

Column 15, Line 11: Please correct "($\beta<1$)" to read -- ($\beta>1$) --

Column 25, Line 56: Please correct "TURBO DNasc" to read -- TURBO DNase --

Column 26, Line 60: Please correct "CBRlue" to read -- CBRluc --

Column 27, Line 14: Please correct "used, in" to read -- used. In --

Column 27, Line 51: Please correct "FTTC" to read -- FITC --

Signed and Sealed this
Eleventh Day of August, 2020

Andrei Iancu
*Director of the United States Patent and Trademark Office*